(12) United States Patent
Tudan et al.

(10) Patent No.: US 7,378,098 B2
(45) Date of Patent: May 27, 2008

(54) CXC CHEMOKINE RECEPTOR 4 AGONIST PEPTIDES

(75) Inventors: Christopher R. Tudan, Vancouver (CA); Ahmed Merzouk, Richmond (CA); Lakhdar Arab, Vancouver (CA); Geeta Saxena, Vancouver (CA); Connie J. Eaves, Vancouver (CA); Johanne Cashman, Vancouver (CA); Ian Clark-Lewis, Vancouver (CA); Hassan Salari, Delta (CA)

(73) Assignees: The University of British Columbia, Vancouver, B.C.; Chemokine Therapeutics Corporation, Vancouver, B.C.

( * ) Notice: Subject to any disclaimer, the term of this patent is extended or adjusted under 35 U.S.C. 154(b) by 328 days.

(21) Appl. No.: 10/086,177

(22) Filed: Feb. 26, 2002
(Under 37 CFR 1.47)

(65) Prior Publication Data
US 2003/0148940 A1    Aug. 7, 2003

Related U.S. Application Data

(63) Continuation-in-part of application No. 09/835,107, filed on Apr. 12, 2001, now abandoned.

(60) Provisional application No. 60/232,425, filed on Sep. 14, 2000.

(30) Foreign Application Priority Data
Apr. 12, 2000    (CA) .................................. 2305036
Feb. 23, 2001    (CA) .................................. 2335109

(51) Int. Cl.
A61K 38/18        (2006.01)
C07K 14/475       (2006.01)
G01N 33/53        (2006.01)
A61K 31/7088      (2006.01)

(52) U.S. Cl. .................. 424/185.1; 530/300; 530/324; 514/2; 514/12

(58) Field of Classification Search ................ 530/300, 530/317, 321, 323, 324; 514/2, 12; 424/192.1
See application file for complete search history.

(56) References Cited

U.S. PATENT DOCUMENTS

| | | | |
|---|---|---|---|
| 2,530,369 A | 11/1950 | Simons et al. ............... 260/621 |
| 2,760,992 A | 8/1956 | Schoeffel et al. ........... 260/628 |
| 4,554,101 A | 11/1985 | Hopp ....................... 260/112.5 |
| 4,868,116 A | 9/1989 | Morgan et al. ........... 435/240.2 |
| 4,980,286 A | 12/1990 | Morgan et al. ........... 435/172.3 |
| 5,082,670 A | 1/1992 | Gage et al. .................. 424/520 |
| 5,166,320 A | 11/1992 | Wu et al. .................... 530/395 |
| 5,350,836 A | 9/1994 | Kopchick et al. |
| 5,399,346 A | 3/1995 | Anderson et al. ........ 424/93.21 |
| 5,401,651 A | 3/1995 | Walz |
| 5,563,048 A | 10/1996 | Honjo et al. ................ 435/69.1 |
| 5,756,084 A | 5/1998 | Honjo et al. ................ 424/85.1 |
| 5,807,744 A | 9/1998 | Berneman et al. .......... 435/372 |
| 5,856,301 A | 1/1999 | Craig et al. .................... 514/12 |
| 5,871,723 A | 2/1999 | Strieter et al. ............. 424/85.1 |
| 5,919,776 A | 7/1999 | Hagmann et al. ........... 514/159 |
| 5,962,462 A | 10/1999 | Mills et al. .................. 514/278 |
| 5,990,163 A | 11/1999 | Evans et al. ................. 514/549 |
| 6,013,644 A | 1/2000 | Mills et al. .................. 514/210 |
| 6,022,848 A | 2/2000 | Kozlov et al. .................. 541/6 |
| 6,046,185 A | 4/2000 | Burgoyne et al. ........... 514/178 |
| 6,124,319 A | 9/2000 | MacCoss et al. ........... 514/318 |
| 6,132,987 A | 10/2000 | Charo et al. ................ 435/69.1 |
| 6,133,319 A | 10/2000 | Widdowson ................. 514/598 |
| 6,136,827 A | 10/2000 | Caldwell et al. ............ 514/329 |
| 6,140,349 A | 10/2000 | Caldwell et al. ............ 514/326 |
| 6,166,037 A | 12/2000 | Budhu et al. ................ 514/326 |
| 6,204,294 B1 | 3/2001 | Bryan et al. ................. 514/609 |
| 6,356,887 B1 | 3/2002 | Berenson et al. |
| 6,515,001 B2 | 2/2003 | Saxena et al. |
| 6,613,742 B1 | 9/2003 | Huang et al. |

(Continued)

FOREIGN PATENT DOCUMENTS

WO    WO 89/02468    3/1989

(Continued)

OTHER PUBLICATIONS

Tudan et al. C-terminal cyclization of an SDF-1 small peptide analogue dramatically increases receptor affinity and activation of the CXCR4 receptor. J Med Chem. 45(10):2024-2031, 2002.*

(Continued)

*Primary Examiner*—Bridget Bunner
(74) *Attorney, Agent, or Firm*—Brian S. Boyer; TIPS Group

(57) ABSTRACT

In accordance with various aspects of the invention, CXCR4 agonists, including SDF-1 polypeptides and SDF-1 polypeptide homologues, may be used in reducing the rate of hematopoietic cell multiplication. Methods of the invention may comprise administration of an effective amount of an CXCR4 agonist to cells selected from the group consisting of hematopoietic stem cells and hematopoietic progenitor cells. Cells may be treated in vitro or in vivo in a patient. A therapeutically effective amount of the CXCR4 agonist may be administered to a patient in need of such treatment. Patients in need of such treatments may include, for example patients requiring bone marrow or peripheral blood stem cell transplantation.

6 Claims, 13 Drawing Sheets

U.S. PATENT DOCUMENTS

| | | |
|---|---|---|
| 6,693,134 B2 | 2/2004 | Saxena et al. |
| 6,875,738 B1 | 4/2005 | Clark-Lewis et al. |
| 6,946,445 B1 | 9/2005 | Clark-Lewis et al. |
| 2002/0156034 A1 | 10/2002 | Tudan et al. |
| 2002/0165123 A1 | 11/2002 | Tudan et al. |
| 2003/0004136 A1 | 1/2003 | Saxena et al. |
| 2003/0045550 A1 | 3/2003 | Saxena et al. |
| 2003/0092674 A1 | 5/2003 | Saxena et al. |
| 2003/0125380 A1 | 7/2003 | Saxena et al. |
| 2005/0059584 A1 | 3/2005 | Merzouk et al. |
| 2005/0164935 A1 | 7/2005 | Clarke Lewis et al. |
| 2005/0265969 A1 | 12/2005 | Clarke Lewis et al. |
| 2006/0014682 A1 | 1/2006 | Clarke Lewis et al. |

FOREIGN PATENT DOCUMENTS

| | | |
|---|---|---|
| WO | WO 89/05345 | 6/1989 |
| WO | WO 89/07136 | 8/1989 |
| WO | WO 90/06757 | 6/1990 |
| WO | WO 91/04274 | 4/1991 |
| WO | WO 92/07573 | 5/1992 |
| WO | WO 93/10234 | 5/1993 |
| WO | WO 93/13206 | 7/1993 |
| WO | WO 95/05452 | 2/1995 |
| WO | WO 95/09236 | 4/1995 |
| WO | WO 96/40772 | 12/1996 |
| WO | WO 97/28257 | 8/1997 |
| WO | WO 97/28258 | 8/1997 |
| WO | WO 98/04684 | 2/1998 |
| WO | WO 98/04698 | 2/1998 |
| WO | WO 98/09642 | 3/1998 |
| WO | WO 98/51705 | 11/1998 |
| WO | WO 99/47158 | 9/1999 |
| WO | WO 00/09152 | 2/2000 |
| WO | WO 00/66112 | 9/2000 |
| WO | WO 01/76615 | 10/2001 |

OTHER PUBLICATIONS

Perez et al. Increased plasma levels of stromal-derived factor-1 enhance human thrombopoiesis and mobilize human CFC in NOD/SCID mice. Exp Hematol 32: 300-307, 2004.*
Zhong et al. Small peptide analogs to stromal derived factor-1 enhance chemotactic migration of human and mouse hematopoietic cells. Exp Hematol 32: 470-475, 2004.*
Li et al. Identification of the CD8 loop as a surface functional epitope. J Biol Chem 273(26): 16442-16445, 1998.*
Skolnick et al. From genes to protein structure and function: novel applications of computational approaches in the genomic era. Trends in Biotech 18(1): 34-39, 2000.*
Bork, A. Powers and pitfalls in sequence analysis: the 70% hurdle. Genome Res. 10: 398-400, 2000.*
Doerks et al. Protein annotation: detective work for function prediction. Trends in Genetics 14(6): 248-250, 1998.*
Smith et al. The challenges of genome sequence annotation or "The devil is in the details". Nature Biotech 15: 1222-1223, 1997.*
Brenner, S.E. Errors in genome function. Trends in Genetics 15(4): 132-133, 1999.*
Bork et al. Go hunting in sequence databases but watch out for the traps. Trends in Genetics. 12(10): 425-427, 1996.*
Wells, J.A. Additivity of mutational effects in proteins. Biochemistry 29 (37): 8509-8517, 1990.*
Ngo et al. Computational complexity, protein structure prediction, and the Levinthal paradox. The Protein Folding Problem and Tertiary Structure Prediction, pp. 492-495, 1994.*
Ikebe et al. A hinge at the central helix of the regulatory light chain of myosin is critical for phosphorylation-dependent regulation of smooth muscle myosin motor activity. J Biol Chem. 273(28):17702-17707, 1998.*
Nett et al. Changes to the length of the flexible linker region of the Rieske protein impair the interaction of ubiquinol with the cytochrome bc1 complex. Eur J Biochem. 267(18):5777-5782, 2000.*
van Leeuwen et al. Linker length and composition influence the flexibility of Oct. 1 DNA binding. EMBO J. 15;16(8):2043-2053, 1997.*
Robinson et al. Optimizing the stability of single-chain proteins by linker length and composition mutagenesis. Proc Natl Acad Sci USA. 95(11):5929-5934, 1998.*
Acsadi, G. et al, (1991) *Nature* vol. 352, 815-818.
Aiuti, A. et al, (1997) *J. Exp. Med.* vol. 185-1, 111-120.
Aiuti, A. et al, (1999) *Eur. J. Immunol.* vol. 29, 1823-1831.
Alkhatib, G et al, (1996) *Science* vol. 272, 1955-1958.
Allen, M. et al, (2000) *J. Biomolecular Screening* vol. 5 No. 2, 63-69.
Alleva, D. et al, (1998) *J. Immunol.* vol. 161-12, 6878-6884.
Anderlini, P. et al, (1997) *Blood* vol. 90 No. 3, 903-908.
Anderson, W., et al, (2000) *Science* vol. 288, 627-629.
Arenzana-Selsdedos, F. et al, (1996) *Nature* vol. 383, 400.
Armentano, D., et al, (1990) *Proc. Natl. Acad. Sci.* vol. 87, 6141-6145.
Ausubel et al, (1995) *Current Protocols in Mol. Biol. Supp.* vol. 36, 9.10.1-9.14.6.
Avenarius, H. et al, (1993) *Inter. J. Hematology* vol. 58, 189-196.
Baggiolini, M. (1998) *Nature* vol. 392, 565-568.
Baird, A. et al, (1999) *Current Opinion in Immunology* vol. 11, 157-166.
Balasa, B. et al, (1997) *J. Exp. Med.* vol. 186, 385-391.
Baldari, J. et al (1987) *EMBO Journal* vol. 6 No. 1, 229-234.
Barbier, J. et al, (1997) *J. Med. Chem.* vol. 40 No. 9, 1373-1380.
Barbier, J. et al, (2000) *Biochemistry 2000* vol. 39 No. 47, 14522-14530.
Barnes, D. et al, (1998) *J. Clin. Invest.* vol. 101 No. 12, 2910-2919.
Berkner, K., (1988) *Biotechniques* vol. 6 No. 7, 616-628.
Blease, K. et al, (2000) *J. Immunol.* vol. 165, 1564-1572.
Bleul, C. et al, (1996) *J. Exp. Med.* vol. 184, 1101-1109.
Bleul, C. et al, (1996) *Nature* vol. 382, 829-832.
Brandt, J. et al, (1990) *J. Clin. Invest.*, vol. 86, 932-941.
Brandt, J. et al, (1992) *Blood* vol. 79 No. 3, 634-641.
Brandt, J. et al, (1998) *J. Clin. Invest.* vol. 82, 1017-1027.
Buckley, C. et al, (2000) *J. Immunol.* vol. 165, 3423-3429.
Burt, R., (1999) *Stem Cells* vol. 17, No. 6, 366-372.
Campbell, J. et al, (1998) *Science* vol. 279, 381-383.
Carr, M. et al, (1994) *Proc. Natl. Acad. Sci.* vol. 91, 3652-3656.
Cashman, J. et al, (1999) *Blood* vol. 94 No. 11, 3722-3729.
Cavazzana-Calvo, M. et al, (2000) *Science* vol. 288, 669-672.
Charo, I. et al, (1994) *Proc. Natl. Acad. Sci.* vol. 91, 2752-2756.
Choe, H. et al, (1996) *Cell* vol. 85, 1135-1148.
Chowdhury, J. et al, (1991) *Science* vol. 254, 1802-1805.
Clapp, W. et al, (1991) *Blood* vol. 78 No. 4, 1132-1139.
Clark-Lewis, I. et al, (1994) *J. Biol. Chem.* vol. 269 No. 23, 16075-16081.
Cocchi, F. et al (1995) *Science* vol. 270, 1811-1815.
Combadiere, C. et al, (1995) *J. Biol. Chem.* vol. 270, 16491-16494.
Conti, J. et al, (1992) *Cancer* vol. 70 No. 11, 2699-2702.
Cristiano, R. et al, (1993) *Proc. Natl. Acad. Sci.* vol. 90, 2122-2126.
Crump, M. et al, (1997) *EMBO Journal* vol. 16 No. 23, 6996-7007.
Curiel, D. et al, (1991) *Proc. Natl. Acad. Sci.* vol. 88, 8850-8854.
Cushing, S. et al, (1990) *Proc. Natl. Acad. Sci.* vol. 87, 5134-5138.
Cwirla, S. et al, (1997) *Science* vol. 276, 1696-1699.
Dai, Y. et al, (1992) *Proc. Natl. Acad. Sci.* vol. 89, 10892-10895.
Danos, O. et al, (1998) *Proc. Natl. Acad. Sci.* vol. 85, 6460-6464.
Demirer, T. et al, (1996) *Stem Cells* vol. 14, 106-116.
Deng, H. et al, (1996) *Nature* vol. 381, 661-666.
Dhib-Jalbut, S. et al (1996) *Journal of Interferon and Cytokine Research* vol. 16, 195-200.
Di Salvo, J. et al, (2000) *Eur. J. Pharm.* vol. 409, 143-154.
Doranz, B. et al (1996) *Cell* vol. 85, 1149-1158.
Dragic, T. et al, (1996) *Nature* vol. 381, 667-673.
Dunican, A. et al, (2000) *Shock* vol. 13 No. 3, 244-250.
Durig, J. et al, (2000) *Leukemia* vol. 14, 1652-1660.
Eglitis, M. et al, (1985) *Science* vol. 230, 1395-1398.

Elisseeva, E. et al, (2000) *J. Biol. Chem.* vol. 275 No. 35, 26799-26805.
Elseviers, M. et al, (1998) *Biochem. and Biophys. Research Comm.* vol. 154 No. 2, 515-521.
Federsppiel, B. et al, (1993) *Genomics* vol. 16, 707-712.
Feng, Y. et al, (1996) *Science* vol. 272, 872-877.
Ferry, N. et al, (1991) *Proc. Natl. Acad. Sci.* vol. 88, 8377-8381.
Fletcher, F. et al, (1990) *Blood* vol. 76 No. 6, 1098-1103.
Flotte, T. et al, (1992) *Am. J. Respir. Cell Mol. Biol.* vol. 7, 349-356.
Flotte, T. et al, (1993) *J. Biol. Chem.* vol. 268 No. 5, 3781-3790.
Furuichi, K. et al, (2000) *Am. J. Nephrol.* vol. 20, 291-299.
Gimbrone, M. et al, (1989) *Science* vol. 246, 1601-1603.
Giralt, S. et al, (1997) *Blood* vol. 89 No. 12, 4531-4536.
Gong, J. et al, (1996) *J. Biol. Chem.* vol. 271 No. 18, 10521-10527.
Gupta, S. et al, (1998) *J. Biol. Chem.* vol. 273 No. 7, 4282-4287.
Haas, R. et al, (1992) *Bone Marrow Transplantation* vol. 9, 459-465.
Hamada, T. et al, (1998) *J. Exp. Med.* vol. 188 No. 3, 539-548.
Hartung, H. et al, (1990) *Ann. Neurol.* vol. S57, S57-S63.
Hermonat, P. et al, (1984) *Proc. Natl. Acad. Sci.* vol. 81, 6466-6470.
Herz, J. et al, (1993) *Proc. Natl. Acad. Sci.* vol. 90, 2812-2816.
Heveker, N. et al, (1998) *Current Biology* vol. 8, 369-376.
Ho, A. et al, (1993) *Leukemia,* vol. 7 No. 11, 1738-1746.
Hodohara, K. et al, (2000) *Blood* vol. 95 No. 3, 769-775.
Heveker, N. et al. (1998) Current Biology vol. 8, 369-376.
Holmes, W. et al, (1991) *Science* vol. 253 No. 50, 1278-1280.
Hooper, D. et al, (1998) *Proc. Natl. Acad. Sci.* vol. 95, 675-680.
Horuk, R. et al, (2001) *J. Biol. Chem.* vol. 276 No. 6, 4199-4204.
Huang, S. et al, (1992) *Nature* vol. 360, 745-749.
Huber, A. et al, (1991) *Science* vol. 254, 99-102.
Huber, B. et al, (1991) *Proc. Natl. Acad. Sci.* vol. 88, 8039-8043.
Hwu, P. et al, (1993) *J. Immunol.* vol. 150, 4104-4115.
IFNB Multiple Sclerosis Study Group, (1993) *Neurology* vol. 43, 655-661.
Ikebuchi, K. et al, (2001) *Nat. Acad. Sci.* vol. 85, No. 10, 3445-3449.
Imai, T. et al, (1997) *J. Biol. Chem.* vol. 272 No. 23, 15036-15042.
Imai, T. et al, (1998) *J. Biol. Chem.* vol. 273 No. 3, 1764-1768.
Jones, S. et al, (1997) *J. Biol. Chem.* vol. 272 No. 26, 16166-16169.
Kates, S. et al, (1993) *Analytical Biochemistry* vol. 212, 303-310.
Kaufman R. et al, (1987) *EMBO Journal* vol. 6 No. 1, 187-193.
Kawachi, Y, et al, (1996) *Brit. J. Hematology* vol. 94, 413-416.
Kay, M. et al, (1992) *Human Gene Therapy* vol. 3, 647-647.
Kessinger, A. et al, (1989) *Bone Marrow Transplantation* No. 4, 643-646.
Kim, C. et al, (1999) *J. Leukocyte Biology* vol. 65, 6-15.
Kitaura, M. et al, (1996) *J. Biol. Chem.* vol. 271 No. 13, 7725-7730.
Koch, A. et al, (1992) *Science* vol. 258, 1798-1801.
Kowalska, M. et al, (2000) *Blood* vol. 96, No. 1, 50-57.
Kramer, W. et al, (1992) *J. Biol. Chem.* vol. 267 No. 26, 18598-18604.
Kume, A. et al, (1999) *Int. J. Hematology* vol. 69, 227-233.
Kurjan, J. et al, (1982) *Cell* vol. 30, 933-943.
Kuroiwa, M. et al, (1996) *Int. J. Hematology* vol. 63, 311-316.
Lasky, L. et al, (1981) *Transfusion* vol. 21 No. 3, 247-260.
Lataillade, J. et al, (2000) *Blood* vol. 95 No. 3, 756-768.
Law. P., (1983) *Exp. Hematol.* vol. 11 No. 5, 351-357.
Le Chevalier, T., (1994) *Eur. J. Cancer* vol. 30A No. 3, 410-412.
Leary, A. et al, (1988) *Blood* vol. 71 No. 6, 1759-1763.
Lemarchand, P. et al, (1992) *Nat. Acad. Sci.* vol. 89 No. 4, 6482-6486.
Lemarchand, P. et al, (1992) *Proc. Natl. Acad. Sci.* vol. 89, 6482-6486.
Lin, T. et al, (2000) *J. Immunol.* vol. 165, 211-220.
Loetscher, M. et al, (1994) *J. Biol. Chem.* vol. 269 No. 1, 232-237.
Loetscher, P. et al, (1994) *FASEB J.* vol. 8, 1055-1060.
Loetscher, P. et al, (1998) *J. Biol. Chem* vol. 273 No. 35, 22279-22283.
Lohrmann, H. et al, (1978) *B. J. Haematol.* vol. 40, 369-381.
Lombart, H. et al, (1994) *J. Org. Chem.* vol. 59, 6147-6149.
Luckow, V. et al, (1989) *Virology* vol. 170, 31-39.
Lukacs, N. et al, (1997) *J. Immunol* vol. 158, 4398-4404.
Luo, J. et al, (1999) *Biochemical and Biophysical Research Communications* vol. 264, 42-47.
Marshall, G. et al, (1993) *Tetrahedron* vol. 49 No. 17, 3547-3558.
McLaughlin, S. et al, (1988) *J. Virology* vol. 62 No. 6, 1963-1973.
Miller, D., (1990) *Blood* vol. 76 No. 2, 271-278.
Moss, J., (1995) *American Chem. Soc.* Chapter 18, 423-448.
Moss, T. et al, (1990) *Blood* vol. 76 No. 9, 1879-1883.
Murphy, P. et al, (1991) *Science* vol. 258, 1280-1283.
Muzyczka, N., (1992) *Current Topics in Microbiol. and Immunol.* vol. 158, 98-129.
Myers, S. et al, (1995) *J. Biol. Chem.* vol. 270 No. 11, 5786-5792.
Nagai, U. et al, (1993) *Tetrahedron* vol. 49 No. 17, 3577-3592.
Nagasawa, T. et al, (1994) *Proc. Natl. Acad. Sci.,* vol. 91, 2305-2309.
Nagasawa, T. et al, (1996) *Nature* vol. 382, 635-638.
Nagasawa, T. et al, (1996) *Proc. Natl. Acad. Sci.* vol. 93, 14726-14729.
Neote, K. et al, (1993) *Cell* vol. 72, 415-425.
Ng, H. et al, (1999) *J. Med. Chem.* vol. 42, 4680-4694.
Oberlin, E. et al, (1996) *Nature* vol. 382, 833-835.
Peled, A. et al, (1999) *Science* vol. 283, 845-848.
Pettengell, R. et al, (1993) *Blood* vol. 82 No. 7, 2239-2248.
Quantin, B. et al, (1992) *Proc. Natl. Acad. Sci.* vol. 89, 2581-2584.
Richman, C. et al, (1976) *Blood* vol. 47 No. 6, 1031-1039.
Richmond, A. et al, (1986) *J. Cell Phys.* vol. 129, 375-384.
Ripka, W. et al, (1993) *Tetrahedron* vol. 49 No. 17, 3593-3608.
Rosenfeld, M. et al, (1991) *Science* vol. 252, 431-434.
Rosenfeld, M. et al, (1992) *Cell* vol. 68, 143-155.
Rudick, R. et al, (1998) *Neurology* vol. 50 No. 5, 1294-1300.
Sabers, A.. et al, (1995) *Acta. Neurol. Scand.* vol. 92, 19-27.
Sambrook, J. et al, (1989) *Cold Spring Harbor Laboratory Press.*
Samulski, R. et al, (1989) *J. Virology* vol. 63 No. 9, 3822-3828.
Schiffer, C. et al, (1983) *Ann. N.Y. Acad. Sci.,* 161-169.
Schultz, L. et al, (1987) *Gene* vol. 54, 113-123.
Schwarting, A. et al, (1998) *J. Immunol.* vol. 161, 494-503.
Seed, B., (1987) *Nature* vol. 329, 840-842.
Shimoda, K. et al, (1993) *J. Clin. Invest.* vol. 91 No. 4, 1310-1313.
Shirozu, M. et al, (1995) *Genomics* vol. 28, 495-500.
Siena, S. et al, (1989) *Blood* vol. 74 No. 6, 1905-1914.
Smith, G. et al, (1983) *Mol. Cell Biol.* vol. 3 No. 12, 2156-2165.
Stiff, P. et al, (1983) *Transfusion* vol. 23, 500-503.
Strieter, M. et al, (1989) *Science* vol. 253, 1467-1469.
Strieter, R. et al, (1989) *J. Biol. Chem.* vol. 264 No. 18, 10621-10626.
Tashiro, K. et al, (1993) *Science* vol. 261, 600-603.
Thelen, M. et al, (1988) *FASEB J.* vol. 2, 2702-2706.
To, L. et al, (1992) *Bone Marrow Transplantation* vol. 9, 277-284.
Tokuda, A. et al, (2000) *J. Immunol.* vol. 164, 2745-2751.
Tratschin, J. et al, (1984) *J. Virology* vol. 51 No. 3, 611-619.
Tratschin, J. et al, (1984) *Mol. Cell Biol.* vol. 4 No. 10, 2072-2081.
Tratschin, J. et al, (1985) *Mol. Cell Biol.* vol. 5 No. 11, 3251-3260.
Tsuji, T. et al, (1990) *Proc. Natl. Acad. Sci.* vol. 87, 8835-8839.
Unemori, E. et al, (1992) *J. Biol. Chem* vol. 268 No. 2, 1338-1342.
van Beuschem, V. et al, (1992) *Proc. Natl. Acad. Sci.* vol. 89, 7640-7644.
Verfaillie, C. et al, (1990) *J. Exp. Med.* vol. 172, 509-520.
von Tscharner, V. et al, (1986) *Nature* vol. 324, 369-372.
Wang, J. et al, (1998) *Blood* vol. 92 No. 3, 756-764.
Warringa, R. et al, (1991) Blood vol. 77 No. 12, 2694-2700.
Weber, F. et al, (1998) *Annals Neur.* vol. 44 No. 1, 27-34.
Wess, G. et al, (1992) *Tetrahedron Letters* vol. 33 No. 2, 195-198.
Wess, G. et al, (1993) *Tetrahedron Letters* vol. 34 No. 5, 817-818.
Wilson, J. et al, (1988) *Proc. Natl. Acad. Sci.* vol. 85, 3014-3018.
Wilson, J. et al, (1992) *J. Biol. Chem.* vol. 267 No. 2, 963-967.
Wolfe, J. et al, (1990) *Science* vol. 247, 1465-1468.
Wondisford, F. et al, (1988) *Molecular Endocrinology* vol. 2 No. 1, 32-39.
Wu., G. et al, (1988) *J. Biol. Chem.* vol. 263 No. 29, 14621-14624.
Ying, S. et al, (1999) *J. Immunol.* vol. 163, 6321-6329.
Yla-Herttuala, S. et al, (1991) *Proc. Natl. Acad. Sci.* vol. 88, 5252-5256.
Yu, C. et al, (1998) *Immunology* vol. 95, 480-487.
Zhou, N. et al, (2000) *Biochemistry 2000,* vol. 39, 3782-3787.

Zsebo, K. et al, (1990) *Cell* vol. 63, 195-201.
Batory, Don, et al., "The Design and Implementation of Hierarchical Software Systems with Reusable Components," ACM Transactions on Software Engineering and Methodology, (Oct. 1992), pp. 355-398, vol. 1, No. 4.
Graefe, Goetz, "Query Evaluation Techniques for Large Databases," ACM Computing Surveys, (Jun. 1993), pp. 73-170, vol. 25, No. 2.
Hindmarsh, Jon, et al., "Fragmented Interaction: Establishing mutual orientation in virtual environments," Proceedings of the 1998 ACM conference on Computer supported cooperative work, (Nov. 1998), pp. 217-226.
Michael, Maged M., "High Performance Dynamic Lock-Free Hash Tables and List-Based Sets," Proceedings of the fourteenth annual ACM symposium on Parallel algorithms and architectures (Aug. 2002), pp. 73-82.
Michael, Maged M., "Safe Memory Reclamation for Dynamic Lock-Free Objects Using Atomic Reads and Writes," Proceedings of the twenty-first annual symposium on Principles of distributed computing (Jul. 2002), pp. 21-30.
Ramduny, Devina, et al., "Exploring the design space for notification servers," Proceedings of the 1998 ACM conference on Computer supported cooperative work, (1998), pp. 227-236.
Viera, Humberto, et al., "XVerter: Querying XML Data with ORDBMS," Proceedings of the fifth ACM international workshop on Web Information and data management, (Nov. 2003), pp. 37-44.
Zhu, Yali, et al., "Dynamic Plan Migration for Continuous Queries Over Data Streams," SIGMOD Conference (2004), pp. 431-442.
Anonymous, "Oracle 8l Designing and Tuning for Performace," Release 2 (8.1.6), (Dec. 1999), Chapter 19, pp. 12-18; http://download-west.oracle.com/docs/cd/A81042_01DOC/server.816/a76992/ch19_mem.htm and Chapter 127, pp. 26, http://downloat_west.oracle.com/docs/cd/A81042_01/DOC/server.816/a76961/ch127.htm..
Buser, et al., *Methods in Molecular Biology*, 138:143-148 (2000).
Eck et al., Goodman & Gilman's The Phrmacological Basis of Theapeutics, 9$^{th}$ Edition, Chapter 5, McGraw-Hill, NY (1996).
Emanueli et al., *Br. J. Pharmacol.*, 133(7):951-958 (2001).
Gonzalo et al., *J. Immunology*, 165(1):499-508 (2000).
Hessing et al., *Blood*, 94(1o Suppl.): p. 100A (1999).
Li, et al., *J. Biol. Chem.*, 273(26):16442-16445 (1998).
Maniatis, *Cell Biology*, 3:564-608 (1980).
Marshall et al., *Science*, 269(5227):1050, 1052-1055 (1995).
Nanki et al., *J. Immunology*, 165(11):6590-6598 (2000).
Orkin et al., Report and Recommendations of the Panel to assess the NIH Investment in Research on Gene Therapy, available through NIH or at http://www.nih.gov/news/panelrep (1995).
Perez, et al., *Exp. Hematol.*, 32:300-307 (2004).
Rissanen et al., Gene Therapy for Therapeutic Angiogenesis in Critically Ischaemic Lower Limb-on the way to the clinic, *Eur. J. Clin Invest.*, 31(8):651-666 (2001).
Ross, Gene Therapy in the United States: A Five-Year Status Report, *Hum. Gene Ther.*, 7(14):1781-1790 (1996).
Rubanyi, The Future of Human Gene Therapy, *Mol. Aspects Med.*, 22(3):113-142 (2001).
Schwaab et al., *Semin Thromb. Hemostat.*, 27(4):417-424 (2001).
Tudan, et al., *J. Med. Chem.*, 45(10):2024-2031 (2002).
Zhong, et al., *Exp. Hematol.*, 32:470-475 (2004).
Barnerji, et al., *Cell*, 33:729-740 (1983).
Belperio, et al., *J. Leukoc. Biol.*, 68:1-8 (2000).
Benoist, et al., *Nature*, 290:304-310 (1981).
Bollon, et al., *J. of Clinical Hemotology and Oncology*, 10:39-48 (1980).

Botstein, et al., "Making Mutations in Vitro and Putting them Back into Yeast", Dept. of Biol. Massachusetts Institute of Technology, 265-274 (1982).
Broach, J.R., *The Molecular Biology of the Yeast Saccharomyces*, 445-470 (1981).
Broach, J.R., *Cell* 28:203-204 (1982).
Calame, et al., *Advances in Immunology*, 43:236-275 (1988).
Camper, et al., *Genes & Development*, 43:236-275 (1989).
Cenatiempo, Y., *Biochemie*, 68:505-515 (1986).
Colosimo, et al., *BioTechniques*, 29:314-331 (2000).
Daugherty, et al., *Chemokine Protocols*, 138:129-148 (2000).
Daugherty, et al., *Methods in Molecular Biology*, 138:129-134 (2000).
DeNardo, et al., *Cancer*, 94:1275-1286 (2002).
Dufour, J.H., et al., *The Journal of Immunology*, 167(7077-7083):3195-3204 (2001).
Edlund, et al., *Science*, 28:912-916 (1985).
"Expression in E. Coli", Methods in Enzymology, 185:119-129 (1990).
Francis, et al., *International Journal of Hematology*, 68:1-18 (1998).
Gazitt, *J. Hematother. Stem Cell. Res.*, 10:229-236 (2001).
Glick, et al., *J. of Industrial Microbiology*, 1:277-282 (1987).
Glimm, et al., *Blood*, 99(9):3454-3457 (2002).
Gold, et al., *Ann Rev. Microbiol.*, 35:365-403 (1981).
Gottesman, S., *Ann. Rev. Genet.*, 18:415-441 (1984).
Hamer, et al., *J. of Molecular and Applied Genetics*, 1:273-288 (1982).
Hattori, et al., *Blood*, 97:3354-3359 (2001).
Hébert, et al., *The J. Of Biological Chemistry*, 266(28):18989-18994 (1991).
Hunter et al., *Blood*, 86(12):4400-4408 (1995).
John Jr., et al., *Reviews of Infectious Diseases*, 8(5):693-704. (1986).
Johnston, et al., *Proc. Natl. Acad. Sci. USA* 79:6971-6975 (1982).
Kaltsas, et al., *Ann. Oncol.*, 12(Supp. 2)S47-50 (2001).
Kessel, et al., *Science*, 249:374-379 (1990).
Kieseier, et al., *Brain*, 125:823-824 (2002).
Lane, et al., *Blood*, 96:4152-4159 (2000).
Lejeune, et al., *Cancer Immunol. Immunother.*, 38:167-170 (1994).
Mach, et al., *Curr. Opin. Immunol.* 12:571-575 (2000).
McKnight, S.L., *Cell*, 31:355-365 (1982).
McLaughlin, S., et al., *J. Virology*, 62(6):1963-1973 (1988).
Miller et al., "An Insect Baculovirus Host-Vector System for High-Level Expression of Foreign Genes," 277-297 (1986).
Miller, et al., *J. Immunol.* 143(9):2907-2916, (1989).
Moss, J., *American Chem. Soc.* 18:423-448, (1995).
Nagasawa, *Int. J. Hematol.* 72:408-411, (2000).
Nomura, et al., *Int. J. Cancer*, 91:597-606 (2001).
Pinkert, et al., *Genes & Development*, 1:268-276 (1987).
Ponath, et al., *Methods in Molecular Biology*, 138:113-120 (2000).
Queen, et al., *Cell*, 33:741-748 (1983).
Rubin, G.M., *Science*, 240:1453-1459 (1988).
Schwarz, et al., *Nat. Rev. Drug Discov.*, 1:347-358 (2002).
Silver, et al., *Proc. Natl. Acad. Sci. USA*, 81:5951-5955 (1984).
Smith, et al., *Gene*, 67:31-40 (1988).
Wada, et al., *Nucleic Acids Research*, 20:2111-2118 (1992).
Wang, W., et al., *The Journal of Biological Chemistry*, 275(29):22313-22323 (2000).
Winoto, et al., *The EMBO J.*, 8(3):729-733 (1989).

\* cited by examiner

Seq. ID NO: 1 (SDF-1α; Human)
    a) LENGTH: 67 amino acids
    b) TYPE: amino acid
    c) TOPOLOGY: linear
    d) MOLECULE TYPE: protein (recombinant and/or pegylated)

KPVSL SYRCP CRFFE SHVAR ANVKH LKILN TPNCA LQIVA RLKNN
1      6      11     16     21     26     31     36     41

NRQVC IDPKL KWIQE YLEKA LN
46    51    56    61    66

Seq. ID NO: 3 (SDF-1 Precursor, PBSF; Human)

a) LENGTH: 93 amino acids
    b) TYPE: amino acid
    c) TOPOLOGY: linear
    d) MOLECULE TYPE: protein (recombinant and or pegylated)

MNAKV VVVLV LVLTA LCLSD GKPVS LSYRC PCRFF ESHVA RANVK
1      6      11     16     21     26     31     36     41

HLKIL NTPNC ALQIV ARLKN NNRQV CIDPK LKWIQ EYLEK ALNKR
46    51    56    61    66    71    76    81    86

FKM
91

Seq. ID NO: 4 (SDF-1β; Human)

a) LENGTH: 93 amino acids
    b) TYPE: amino acid
    c) TOPOLOGY: linear
    d) MOLECULE TYPE: protein (recombinant and or pegylated)

MNAKV VVVLV LVLTA LCLSD GKPVS LSYRC PCRFF ESHVA RANVK
1      6      11     16     21     26     31     36     41

HLKIL NTPNC ALQIV ARLKN NNRQV CIDPK LKWIQ EYLEK ALNKR
46    51    56    61    66    71    76    81    86

FKM
91

Fig. 13

CXC CHEMOKINE RECEPTOR 4 AGONIST PEPTIDES

CROSS-REFERENCE TO RELATED APPLICATIONS

This application is a continuation-in-part of U.S. application Ser. No. 09/835,107, filed Apr. 12, 2001, which claims the benefit of provisional U.S. application Ser. No. 60/232,425, filed Sep. 14, 2000, and Canadian Application Nos. 2,335,109, filed Feb. 23, 2001, and 2,305,036, filed Apr. 12, 2000.

FIELD OF THE INVENTION

In one aspect, the invention relates to therapeutic uses of chemokine receptor agonists, including peptide agonists of CXC chemokine receptor 4 (CXCR4) for use in the treatment of hematopoietic cells in vitro and in vivo.

BACKGROUND OF THE INVENTION

Hematopoiesis consists of developmental cascades in which the hematopoietic stem cells generate lineage-committed cells and repeat the process of self-renewal. Hematopoietic stem cells are typically cells that have dual capacity for self-renewal and multilineage differentiation.

Cytokines are soluble proteins secreted by a variety of cells including monocytes or lymphocytes that regulate immune responses. Chemokines are a superfamily of chemoattractant proteins that may be classified into four groups, characterized by the nature of cysteine residues that are involved in disulfide bond formation. Chemokines regulate a variety of biological responses and they promote the recruitment of multiple lineages of leukocytes and lymphocytes to a body organ tissue. Chemokines may be classified into two families according to the relative position of the first two cysteine residues in the protein. In CC chemokines, which include beta chemokine the first two cysteines are adjacent to each other. In CXC chemokines, which include alpha chemokine, the first two cysteines are separated by one amino acid residue. Two minor subgroups contain only one of the two cysteines (C) or have three amino acids between the cysteines ($CX_3C$). In humans, the genes of the CXC chemokines are clustered on chromosome 4 (with the exception of SDF-1 gene, which has been localized to chromosome 10) and those of the CC chemokines on chromosome 17.

The molecular targets for chemokines are cell surface receptors. One such receptor is CXC chemokine receptor 4 (CXCR4), which is a G-protein coupled seven transmembrane protein, and was previously called LESTR (Loetscher, M., Geiser, T., O'Reilly, T., Zwahlen, R., Baggionlini, M., and Moser, B., (1994) J. Biol. Chem, 269, 232-237), HUMSTR (Federsppiel, B., Duncan, A. M. V., Delaney, A., Schappert, K., Clark-Lewis, I., and Jirik, F. R. (1993) Genomics 16, 707-712) and Fusin (Feng, Y., Broeder, C. C., Kennedy, P. E., and Berger, E. A. (1996) Science 272, 872-877). CXCR4 is widely expressed on cells of hemopoietic origin, and is a major co-receptor with $CD4^+$ for human immunodeficiency virus 1 (HIV-1) (Feng, Y., Broeder, C. C., Kennedy, P. E., and Berger, E. A. (1996) HIV-1 entry cofactor: Functional cDNA cloning of a seven-transmembrane G-protein-coupled receptor, Science 272, 872-877).

Chemokines are thought to mediate their effect by binding to seven-transmembrane G protein-coupled receptors, and to attract leukocyte subsets to sites of inflammation (Baglionini et al. (1998) Nature 392: 565-568). Many of the chemokines have been shown to be constitutively expressed in lymphoid tissues, indicating that they may have a homeostatic function in regulating lymphocyte trafficking between and within lymphoid organs (Kim and Broxmeyer (1999) J. Leuk. Biol. 56: 6-15).

Stromal cell derived factor one (SDF-1) is a member of the CXC family of chemokines that has been found to be constitutively secreted from the bone marrow stroma (Tashiro, (1993) Science 261, 600-602). The human and mouse SDF-1 predicted protein sequences are approximately 92% identical. Stromal cell derived factor-1a (SDF-1a) and stromal cell derived factor-1β (SDF-1β) are closely related (together referred to herein as SDF-1). The native amino acid sequences of SDF-1α and SDF-1β are known, as are the genomic sequences encoding these proteins (see U.S. Pat. No. 5,563,048 issued 8 Oct. 1996, and U.S. Pat. No. 5,756,084 issued 26 May 1998). Identification of genomic clones has shown that the alpha and beta isoforms are a consequence of alternative splicing of a single gene. The alpha form is derived from exons 1-3 while the beta form contains an additional sequence from exon 4. The entire human gene is approximately 10 Kb. SDF-1 was initially characterized as a pre-B cell-stimulating factor and as a highly efficient chemotactic factor for T cells and monocytes (Bieul et al. (1996) J. Exp. Med. 184:1101-1110).

Biological effects of SDF-1 may be mediated by the chemokine receptor CXCR4 (also known as fusin or LESTR), which is expressed on mononuclear leukocytes including hematopoietic stem cells. SDF-1 is thought to be the natural ligand for CXCR4, and CXCR4 is thought to be the natural receptor for SDF-1 (Nagasawza et al. (1997) Proc. Natl. Acad. Sci. USA 93:726-732). Genetic elimination of SDF-1 is associated with parinatal lethality, including abnormalities in cardiac development, B-cell lymphopoiesis, and bone marrow myelopoiesis (Nagasawa et al. (1996) Nature 382:635-637).

SDF-1 is functionally distinct from other chemokines in that it is reported to have a fundamental role in the trafficking, export and homing of bone marrow progenitor cells (Aiuti, A., Webb, I. J., Bleul, C., Springer, T., and Guierrez-Ramos, J. C., (1996) J. Exp. Med. 185, 111-120 and Nagasawa, T., Hirota, S., Tachibana, K., Takakura N., Nishikawa, S.-I., Kitamura, Y., Yoshida, N., Kikutani, H., and Kishimoto, T., (1996) Nature 382, 635-638). SDF-1 is also structurally distinct in that it has only about 22% amino acid sequence identity with other CXC chemokines (Bleul, C. C., Fuhlbrigge, R. C., Casasnovas, J. M., Aiuti, A., and Springer, T. A., (1996) J. Exp. Med. 184, 1101-1109). SDF-1 appears to be produced constitutively by several cell types, and particularly high levels are found in bone-marrow stromal cells (Shirozu, M., Nakano, T., Inazawa, J., Tashiro, K., Tada, H. Shinohara, T., and Honjo, T., (1995) Genomics, 28, 495-500 and Bleul, C. C., Fuhlbrigge, R. C., Casasnovas, J. M., Aiuti, A., and Springer, T. A., (1996) J. Exp. Med. 184, 1101-1109). A basic physiological role for SDF-1 is implied by the high level of conservation of the SDF-1 sequence between species. In vitro, SDF-1 stimulates chemotaxis of a wide range of cells including monocytes and bone marrow derived progenitor cells (Aiuti, A., Webb, I. J., Bleul, C., Springer, T., and Guierrez-Ramos, J. C., (1996) J. Exp. Med. 185, 111-120 and Bleul, C. C., Fuhlbrigge, R. C., Casasnovas, J. M., Aiuti, A., and Springer, T. A., (1996) J. Exp. Med. 184, 1101-1109). SDF-1 also stimulates a high percentage of resting and activated T-lymphocytes (Bleul, C. C., Fuhlbrigge, R. C., Casasnovas, J. M., Aiuti, A., and Springer, T. A., (1996) J. Exp. Med. 184, 1101-1109 and Campbell, J. J., Hendrick, J., Zlotnik, A., Siani, M. A., Thompson, D. A., and Butcher, E. C., (1998) Science, 279 381-383).

A variety of diseases require treatment with agents which are preferentially cytotoxic to dividing cells. Cancer cells, for example, may be targeted with cytotoxic doses of radiation or chemotherapeutic agents. A significant side-effect of this approach to cancer therapy is the pathological impact of such treatments on rapidly dividing normal cells. These normal cells may for example include hair follicles, mucosal cells and the hematopoietic cells, such as primitive bone marrow progenitor cells and stem cells. The indiscriminate destruction of hematopoietic stem, progenitor or precursor cells can lead to a reduction in normal mature blood cell counts, such as leukocytes, lymphocytes and red blood cells. A major impact on mature cell numbers may be seen particularly with neutrophils (neutropaenia) and platelets (thrombocytopenia), cells which naturally have relatively short half-lives. A decrease in leukocyte count, with concomitant loss of immune system function, may increase a patient's risk of opportunistic infection. Neutropaenia resulting from chemotherapy may for example occur within two or three days of cytotoxic treatments, and may leave the patient vulnerable to infection for up to 2 weeks until the hematopoietic system has recovered sufficiently to regenerate neutrophil counts. A reduced leukocyte count (leukopenia) as a result of cancer therapy may become sufficiently serious that therapy must be interrupted to allow the white blood cell count to rebuild. Interruption of cancer therapy can in turn lead to survival of cancer cells, an increase in the incidence of drug resistance in cancer cells, and ultimately in cancer relapse. There is accordingly a need for therapeutic agents and treatments which facilitate the preservation of hematopoietic progenitor or stem cells in patients subject to treatment with cytotoxic agents.

Bone marrow transplantation has been used in the treatment of a variety of hematological, autoimmune and malignant diseases. In conjunction with bone marrow transplantation, ex vivo hematopoietic (bone marrow) cell culture may be used to expand the population of hematopoietic progenitor or stem cells. It may be desirable to purge an ex vivo hematopoietic cell culture of cancer cells with cytotoxic treatments, while preserving the viability of the hematopoietic progenitor or stem cells. There is accordingly a need for agents and methods, which facilitate the preservation of hematopoietic progenitor or stem cells in ex vivo cell cultures exposed to cytotoxic agents.

A number of proteins have been identified as inhibitors of hematopoietic progenitor cell development, with potential therapeutic usefulness as inhibitors of hematopoeitic cell multiplication: macrophage inflammatory protein 1-alpha (MIP-1-alpha) and LD78 (see U.S. Pat. No. 5,856,301); the alpha globin chain of hemoglobin and beta globin chain of hemoglobin (see U.S. Pat. No. 6,022,848); and, interferon gamma (see U.S. Pat. No. 5,807,744).

Permanent marrow recovery after cytotoxic drug and radiation therapy depends on the survival of hematopoietic stem cells having long term reconstituting (LTR) potential. The major dose limiting sequelae consequent to chemotherapy and/or radiation therapy are neutropenia and thrombocytopenia. Protocols involving dose intensification (i.e., to increase the log-kill of the respective tumour therapy) or schedule compression will exacerbate the degree and duration of myelosuppression associated with the standard chemotherapy and/or radiation therapy. For instance, in the adjuvant setting, repeated cycles of doxorubicin-based treatment have been shown to produce cumulative and long-lasting damage in the bone marrow progenitor cell populations (Lorhrman et al. (1978) Br. J. Haematol. 40:369). The effects of short-term hematopoietic cell damage resulting from chemotherapy has been overcome to some extent by the concurrent use of G-CSF (Neupogen®), used to accelerate the regeneration of neutrophils (Le Chevalier (1994) Eur. J. Cancer 30A:410). This approach has been met with limitations also, as it is accompanied by progressive thrombocytopenia and cumulative bone marrow damage as reflected by a reduction in the quality of mobilized progenitor cells over successive cycles of treatment. Because of the current interest in chemotherapy dose intensification as a means of improving tumour response rates and perhaps patient survival, the necessity for alternative therapies to either improve or replace current treatments to rescue the myeloablative effects of chemotherapy and/or radiation therapy has escalated, and is currently one of the major rate limiting factors for tumour therapy dose escalations.

Transplanted peripheral blood stem cells (PBSC, or autologous PBSC) may provide a rapid and sustained hematopoietic recovery after the administration of high-dose chemotherapy or radiation therapy in patients with hematological malignancies and solid tumours. PBSC transplantation has become the preferred source of stem cells for autologous transplantation because of the shorter time to engraftment and the lack of a need for surgical procedure necessary for bone marrow harvesting (Demirer et al. (1996) Stem Cells 14:106-116; Pettengel et al. (1992) Blood 82:2239-2248). Although the mechanism of stem cell release into the peripheral blood from the bone marrow is not well understood, agents that augment the mobilization of $CD34^+$ cells may prove to be effective in enhancing autologous PBSC transplantation. G-CSF and GM-CSF are currently the most commonly used Ihematopoietic growth factors for PBSC mobilization, although the mobilized cellular profiles can differ significantly from patient to patient. Therefore, other agents are required for this clinical application.

It is generally accepted that stem cell transplants for autoimmune disease should be initiated using autologous or allogenic grafts, where the former would be preferable since they may bear less risk of complication (Burt and Taylor (1999) Stem Cells 17:366-372). Lymphocyte depletion has also been recommended, where lymphocyte depletion is a form of purging autoreactive cells from the graft. In practice, aggressive lymphocyte depletion of an allograft can prevent alloreactivity (i.e., graft-versus-host disease (GVHD)) even without immunosuppressive prophylaxis. Therefore, a lymphocyte-depleted autograft may prevent recurrence of autoreactivity. As a consequence, any concurrent therapy that may enhance the survival of the CFU-GEMM myeloid stem cells, or BFU-E and CFU-GM myelomonocytic stem cells may be beneficial in therapies for autoimmune diseases where hematopoietic stem cells could be compromised.

Retrovirus-mediated gene transfer into murine hematopoietic stem cells and reconstitution of syngeneic mice have demonstrated persistence and functioning of the transgenes over extended period of time (Kume et al. (1999) 69:227-233). Terminally differentiated cells are relatively short-lived, except for memory B and T lymphocytes, and a large number of blood cells are replaced daily. Therefore, when long-term functional correction of blood cells by gene transfer is required, the target cells may be hematopoietic stem cells (Kume et al. (1999) 69:227-233). Compounds that can maintain the survival of the progenitor stem cells may therefore increase the efficiency of the gene transfer in that a greater population of hematopoietic stems cells are available.

A number of proteins have been identified and are currently being utilized clinically as inhibitors of hematopoietic progenitor cell development and hematopoietic cell proliferation (multiplication). These include recombinant-methionyl human G-CSF (Neupogen®, Filgastim; Amgen), GM-CSF (Leukine®, Sargramostim; Immunex), erythropoietin (rhEPO, Epogen®; Amgen), thrombopoietin (rhTPO; Genentech), interleukin-11 (rhIL-11, Neumega®; American Home Products), Flt3 ligand (Mobista; Immunex), multilineage hematopoietic factor (MARstem™; Maret Pharm.), myelopoietin (Leridistem; Searle), IL-3, myeloid progenitor inhibitory factor-1 (Mirostipen; Human Genome Sciences), stem cell factor (rhSCF, Stemgen®; Amgen).

BRIEF DESCRIPTION OF THE DRAWINGS

FIG. 13 shows the sequences of human SDF-1alpha (SEQ ID NO:1), SDF-1 Precursor (PBSF) (SEQ ID NO:2) and SDF-1beta (SEQ ID NO:3).

SUMMARY OF THE INVENTION

Figure 1:
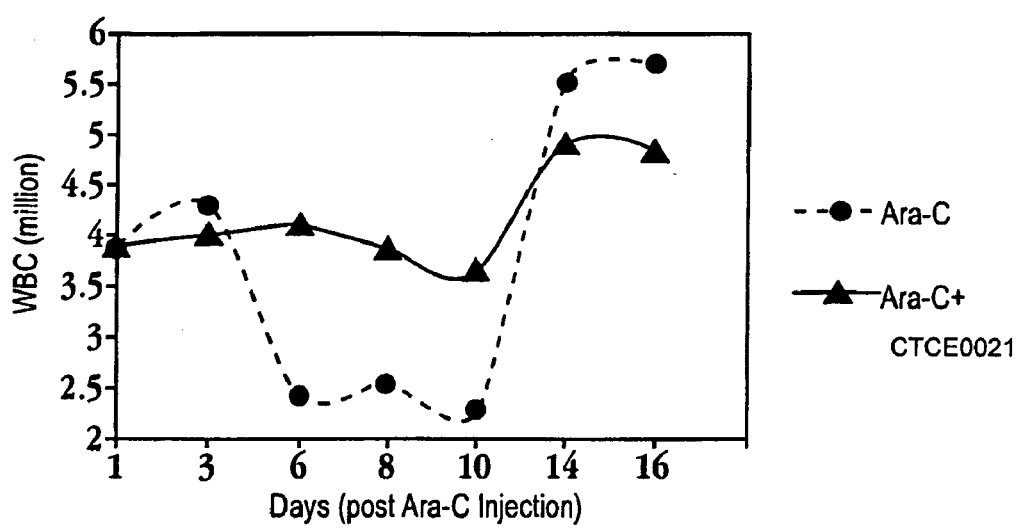
FIG. 1 shows the effect of Ara-C (350 mg/kg) on White Blood Cell Count (WBC) in mice in the presence (triangular data points, solid line, designated Ara-C+CTCE0021 (SEQ ID NO:23) in the legend) and absence (circular data points, dashed line, designated Ara-C in the legend) of a peptide of the invention (designated CTCE0021 (SEQ ID NO:23) and described in Examples 1 and 3).

In accordance with various aspects of the invention, CXCR4 agonists may be used to treat bone marrow progenitor or stem cells to reduce the susceptibility of the cells to cytotoxic agents. CXCR4 agonists may be used to treat bone marrow progenitor cells or stem cells to reduce the rate of cellular multiplication. CXCR4 agonists may for example be used in vivo or ex vivo in bone marrow or peripheral blood stem cell transplantation procedures to treat bone marrow progenitor or stem cells. CXCR4 agonists may be used to treat cancer in a mammal in conjunction with one or more cytotoxic agents. Cytotoxic agents may for example include chemotheraputic agents or radiation. CXCR4 agonists may be used therapeutically to regulate bone marrow progenitor or stem cell growth in vivo, ex vivo and in human diseases, such as cancer.

DETAILED DESCRIPTION OF THE INVENTION

In accordance with some aspects of the invention, hematopoietic stem cells may be affected by CXCR4 agonists via a mechanism of cell growth repression. Since cytotoxic therapies utilized to kill proliferating cancerous cells, such as chemotherapeutic and/or radiation therapy, target proliferating cells, the CXCR4 agonists in accordance with various aspects of this invention may be utilized to reduce cytotoxin mediated destruction of hematopoietic cells, such as primitive bone marrow and peripheral blood progenitor and stem cells, and thereby to enhance recovery of mature blood cell counts, such as leukocytes, lymphocytes and red blood cells, following cytotoxin treatments. In various aspects of the invention, CXCR4 agonists may be given to the patient prior to, during or both prior to and during cytotoxin treatments, such as myeloablative chemotherapy and/or radiation therapy, in order to suppress the growth of the progenitor cells, and thus rescue them from destruction by the therapeutic regimen that the patient is being treated with, for example to treat a cancer. Therefore, cancers susceptible to treatment with CXCR4 agonists in accordance with various aspects of the invention may include both primary and metastatic tumors, and solid tumors, including carcinomas of breast, colon, rectum, lung, oropharynx, hypopharynx, esophagus, stomach, pancreas, liver, gallbladder and bile ducts, small intestine, urinary tract (including kidney, bladder and urothelium), female genital tract, (including cervix, uterus, and ovaries as well as choriocarcinoma and gestational trophoblastic disease), male genital tract (including prostate, seminal vesicles, testes and germ cell tumors), endocrine glands (including the thyroid, adrenal, and pituitary glands), and skin, as well as hemangiomas, melanomas, sarcomas (including those arising from bone and soft tissues as well as Kaposi's sarcoma) and tumors of the brain, nerves, eyes, and meninges (including astrocytomas, gliomas, glioblastomas, retinoblastomas, neuromas, neuroblastomas, Schwannomas, and meningiomas). In some aspects of the invention, CXCR4 agonists may also be useful in treating tumors, such as solid tumors, arising from hematopoietic malignancies such as leukemias (i.e. chloromas, plasmacytomas and the plaques and tumors of mycosis fungoides and cutaneous T-cell lymphoma/leukemia) as well as in the treatment of lymphomas (both Hodgkin's and non-Hodgkin's lymphomas). In addition, CXCR4 agonists may be useful in the prevention of metastases from the tumors described above either when used alone or in combination with cytotoxic agents such as radiotherapy or chemotherapeutic agents.

In alternative aspects of the invention, CXCR4 agonists may be used to enrich populations of $CD34^+$ progenitor cells. Such cells may for example be enriched by CXCR4 agonists in bone marrow (BM) and peripheral blood (PB) stem cell transplantation procedures. Such procedures may be used to treat a variety of diseases (see for example Ball, E. D., Lister, J., and Law, P. Hematopoietic Stem Cell Therapy, Chruchill Livingston (of Harcourt Inc.), New York (2000)). CXCR4 agonists may accordingly be used in such hematopoietic stem cell transplantation (HSCT) protocols for the purposed of treating diseases, such as the following diseases that may be treated with CXCR4 agonists:

Aplastic Anemia;
Acute Lymphoblastic Anemia.;
Acute Myelogenous Leukemia;
Myelodysplasia;
Multiple Myeloma;
Chronic Lymphocytic Leukemia;
Congenital Immunodeficiencies (such as Autoimmune Lymphoproliferative disease, Wiscott-Aldrich Syndrome, X-linked Lymphoproliferative disease, Chronic Granulamatous disease, Kostmann Neutropenia, Leukocyte Adhesion Deficiency);
Metabolic Diseases (for instance those which have been HSCT indicated such as Hurler Syndrome (MPS I/II), Sly Syndrome (MPS VII), Chilhood onset cerebral X-adrenoleukodystrophy, Globard_cell Leukodystrophy), In alternative embodiments, CXCR4 agonists may be used to treat a variety of hematopoietic cells, and such cells may be isolated or may form only part of a treated cell population in vivo or in vitro. Cells amenable to treatment with CXCR4 agonists may for example include cells in the hematopoietic lineage, beginning with pluripotent stem cells, such as bone marrow stem or progenitor cells, lymphoid stem or progenitor cells, myeloid stem cells, CFU-GEMM cells (colony-forming-unit granulocyte, erythroid, macrophage, megakaryocye), B stem cells, T stem cells, DC stem cells, pre-B cells, prothymocytes, BFU-E cells (burst-forming unit—erythroid), BFU-MK cells (burst-forming unit—megakaryocytes), CFU-GM cells (colony-forming unit—granulocyte-macrophage), CFU-bas cells (colony-forming unit—basophil), CFU-Mast cells (colony forming unit—mast cell), CFU-G cells (colony forming unit granulocyte), CFU-M/DC cells (colony forming unit monocyte/dendritic cell), CFU-Eo cells (colony forming unit eosinophil), CFU-E cells (colony forming unit erythroid), CFU-MK cells (colony forming unit megakaryocyte), myeloblasts, monoblasts, B-lymphoblasts, T-lymphoblasts, proerythroblasts, neutrophillic myelocytes, promonocytes, or other hematopoietic cells that differentiate to give rise to mature cells such as macrophages, myeloid related dendritic cells, mast cells, plasma cells, erythrocytes, platelets, neutrophils, monocytes, eosinophils, basophils, B-cells, T-cells or lymphoid related dendritic cells.

In some embodiments, the present invention is concerned with polypeptides having the amino acid sequences shown in SEQ ID NOS:1, 2 or 3 (FIG. 13). In some embodiments, a pegylation moiety may be provided at any position on the sequence. The polypeptides of the present invention may include polypeptides in which part of the amino acid sequence is omitted, or polypeptides that consist of sequences containing additional or replaced amino acids, or spliced forms of the sequences, yet induce activation of the CXCR4. In some embodiments, polypeptides of the invention may be at least 70%, 80% 90% or 95% identical to the polypeptides of SEQ ID NOS:1, 2 or 3, when optimally aligned, over a region of at least 10, 15, 20, 30, 40, 50, 60 or 80 or more, contiguous amino acids. In alternative embodiments, SDF-1 polypeptides of the invention may consist of amino acid sequences that are less than 70% identical to portions of SEQ ID NOS:1, 2 or 3, where a polypeptide demonstrates CXCR4 agonist activity, such as activity that is comparable (such as within 0.01-, 0.1-, 1.0-, 10-, or 100-fold) to that obtained with the SDF-1 polypeptides of SEQ ID NOS:1, 2 or 3.

In one aspect of the invention, a putative SDF-1 polypeptide having some similarity to SEQ ID NOS:1, 2 or 3 may be assessed for CXCR4 agonist activity. Putative SDF-1 polypeptides of the invention may for example be assayed for CXCR4 receptor binding as determined by receptor binding assays, such as radiolabeled ligand receptor competition assays. Activation of CXCR4 by an SDF-1 polypeptide may be determined through assaying activation of the receptor through standard biochemical techniques including intracellular calcium mobilization, cellular chemotaxis, chemiluminescence, degranulation assays, measurement of NADPH-dependent formation of reactive oxygen species, activation of secondary messenger enzymes such as G proteins, phospholipase C (PLC), protein kinase C (PKC), or of Src and Src family kinases (i.e., Fyn). In some embodiments, CXCR4 agonist activity, CXCR4 receptor binding or CXCR4 receptor activation of a putative CXCR4 agonist of the invention may be at least 0.01-, 0.1-, 1.0-, 10-, or 100-fold of the corresponding parameter of a polypeptides of SEQ ID NOS:1, 2 or 3.

In alternative embodiments, a variety of small SDF-1 peptide analogues may be used as CXCR4 agonists. One such peptide is a dimer of amino acids 1-9, in which the amino acid chains are joined by a disulphide bond between each of the cysteines at position 9 in each sequence (designated SDF-1(1-9)$_2$ or (SEQ ID NO:7) KPVSLSYRC-CRYSLSVPK (SEQ ID NO:7)). An alternative peptide is a dimer of amino acids 1-8, (SEQ ID NO:10) KPVSLSYR-X-RYSLSVPK (SEQ ID NO:11), in which the amino acid chains are joined by a linking moiety X between each of the arginines at position 8 in each sequence (designated SDF-1(1-8)$_2$). CXCR4 agonist 1peptides may for example be selected from the group consisting of peptides having the following sequences: KPVSLSYRCPCRFFESHVARAN-VKHLKILNTPNCALQIVARLKNNNRQVCID PKLK-WIQEYLEKALN (SEQ ID NO:1); KPVSLSYRCPCR-FFESH (SEQ ID NO:4); KPVSLSYRC (SEQ ID NO:6); (SEQ ID NO:7) KPVSLSYRC-CRYSLSVPK (SEQ ID NO:7); (SEQ ID NO:8) KPVSLSYRC-X-CRYSLSVPK (SEQ ID NO:9); and, (SEQ ID NO:10) KPVSLSYR-X-RYSLSVPK (SEQ ID NO:11). In the foregoing peptides X may be lysine with both the α (alpha) and ε (epsilon) amino groups of the lysine being associated with covalent (amide) bond formation and the lysyl carboxyl group being protected. The last two compounds in the forgoing list may, for example, be represented as follows, showing the peptide sequences in the standard amino-to-carboxyl orientation:

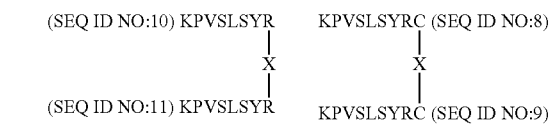

In various alternative embodiments, such SDF-1 peptide analogs, along with SDF-1 polypeptides, are included amongst CXCR4 agonists of the invention.

In some embodiments, CXCR4 agonist peptides may for example also be selected from the group consisting of peptides having the following sequences:

a) SDF-1-derived cyclic amide (E24/K28) agonists (such as CTCE0021 (SEQ ID NO:23)) having the formula:

[RNH-Lys]XaaVSXbbSYRCPCRFF[linker]LK-
    WIQEYLEKALN-NH$_2$    (SEQ ID NOS:35, 204 and 205);

and b) SDF-1-derived cyclic acid (K20/E24) agonists (such as CTCE0022 SEQ ID NO:22)) having the formula:

[RCONH-Lys]XaaVSXbbSYRCPCRFF[linker]LK-
    WIQEYLEKALN-NH$_2$    (SEQ ID NOS:36, 206 and 207);

wherein, R is a substituent that may for example be a hydrogen, alkyl, aryl or polyethyleneglycol (PEG) moiety; Xaa is an amino acid that may for example be either an L-Proline or a D-Proline moiety; Xbb is an amino acid that may for example be either a L-Leucine or a D-Leucine moiety; and [linker] is a moiety providing a covalent attachment between the N and C terminal portions of the peptides, such as a linking moiety having 4 glycines (SEQ ID NO:211) or NH$_2$—(CH$_2$)$_n$—COOH (n=0-20).

In some embodiments, the CXCR4 agonists for use in the invention may be substantially purified peptide fragments, modified peptide fragments, analogues or pharmacologically acceptable salts of either SDF-1α or SDF-1β. SDF-1 derived peptide agonists of CXCR4 may be identified by known biological assays and a variety of techniques such as the aforementioned or as discussed in Crump et al., 1997, The EMBO Journal 16(23) 6996-7007; and Heveker et al., 1998, Current Biology 8(7): 369-376; each of which are incorporated herein by reference. Such SDF-1 derived peptides may include homologs of native SDF-1, such as naturally occurring isoforms or genetic variants, or polypeptides having substantial sequence similarity to SDF-1, such as 40%, 50%, 60%, 70%, 80%, 90%, 95% or 99% sequence identity to at least a portion of the native SDF-1 sequence, the portion of native SDF-1 being any contiguous sequence of 10, 15, 20, 30, 40, 50 or more amino acids, provided the peptides have CXCR4 agonist activity. In some embodiments, chemically similar amino acids may be substituted for amino acids in the native SDF-1 sequence (to provide conservative amino acid substitutions). In some embodiments, peptides having an N-terminal LSY sequence motif within 10, or 7, amino acids of the N-terminus, and/or an N-terminal RFFESH (SEQ ID NO:5) sequence motif within 20 amino acids of the N-terminus may be used provided they have CXCR4 agonistic activity. One family of such peptide agonist candidates has an LSY motif at amino acids 5-7. Alternative peptides further include the RFFESH (SEQ ID NO:5) motif at amino acids 12-17. In alternative embodiments, the LSY motif is located at positions 3-5 of a peptide. The invention also provides peptide dimers having two amino acid sequences, which may each have the foregoing sequence elements, attached by a disulfide bridge within 20, or preferably within 10, amino acids of the N terminus, linking cysteine residues or α-aminobutric acid residues.

The invention further provides pharmaceutical compositions containing CXCR4 agonists. In one embodiment, such compositions include a CXCR4 agonist compound in a therapeutically or prophylactically effective amount sufficient to alter bone marrow and/or peripheral progenitor or stem cell growth, maturation and/or mobilization, and a pharmaceutically acceptable carrier. In another embodiment, the composition includes a CXCR4 agonist compound in a therapeutically or prophylactically effective amount sufficient to inhibit a cytotoxic effect of a cytotoxic agent, such as cytotoxic agents used in chemotherapy or radiation treatment of cancer, and a pharmaceutically acceptable carrier.

An "effective amount" of a compound of the invention includes a therapeutically effective amount or a prophylatically effective amount. A "therapeutically effective amount" refers to an amount effective, at dosages and for periods of time necessary, to achieve the desired therapeutic result, !such as reduction of bone marrow progenitor or stem cell multiplication, or reduction or inhibition of a cytotoxic effect of a cytotoxic agent. A therapeutically effective amount of CXCR4 agonist may vary according to factors such as the disease state, age, sex, and weight of the individual, and the ability of the CXCR4 agonist to elicit a desired response in the individual. Dosage regimens may be adjusted to provide the optimum therapeutic response. A therapeutically effective amount is also one in which any toxic or detrimental effects of the CXCR4 agonist are outweighed by the therapeutically beneficial effects.

A "prophylactically effective amount" refers to an amount effective, at dosages and for periods of time necessary, to achieve the desired prophylactic result, such as preventing or inhibiting a cytotoxic effect of a cytotoxic agent. Typically, a prophylactic dose is used in subjects prior to or at an earlier stage of disease, so that a prophylactically effective amount may be less than a therapeutically effective amount.

In particular embodiments, a preferred range for therapeutically or prophylactically effective amounts of CXCR4 agonists may be 0.1 nM-0.1M, 0.1 nM-0.05M, 0.05 nM-15 µM or 0.01 nM-10 µM. It is to be noted that dosage values may vary with the severity of the condition to be alleviated. For any particular subject, specific dosage regimens may be adjusted over time according to the individual need and the professional judgement of the person administering or supervising the administration of the compositions. Dosage ranges set forth herein are exemplary only and do not limit the dosage ranges that may be selected by medical practitioners.

The amount of active compound in the composition may vary according to factors such as the disease state, age, sex, and weight of the individual. Dosage regimens may be adjusted to provide the optimum therapeutic response. For example, a single bolus may be administered, several divided doses may be administered over time or the dose may be proportionally reduced or increased as indicated by the exigencies of the therapeutic situation. It may be advantageous to formulate parenteral compositions in dosage unit form for ease of administration and uniformity of dosage. "Dosage unit form" as used herein refers to physically discrete units suited as unitary dosages for subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

As used herein "pharmaceutically acceptable carrier" or "exipient" includes any and all solvents, dispersion media, coatings, antibacterial and antifungal agents, isotonic and absorption delaying agents, and the like that are physiologically compatible. In one embodiment, the carrier is suitable for parenteral administration. Alternatively, the carrier can be suitable for intravenous, intraperitoneal, intramuscular, sublingual or oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

In some embodiments, CXCR4 agonists may be formulated in pharmaceutical compositions with additional active ingredients, or administered in methods of treatment in conjunction with treatment with one or more additional medications, such as a medicament selected from the following: recombinant-methionyl human G-CSF (Neupogen®, Filgastim; Amgen), GM-CSF (Leukine®, Sargramostim; Immunex), erythropoietin (rhEPO, Epogen®; Amgen), thrombopoietin (rhTPO; Genentech), interleukin-11 (rhIL-11, Neumega®; American Home Products), Flt3 ligand (Mobista; Immunex), multilineage hematopoietic factor (MARstem™; Maret Pharm.), myelopoietin (Leridistem; Searle), IL-3, myeloid progenitor inhibitory factor-1 (Mirostipen; Human Genome Sciences), and stem cell factor (rhSCF, Stemgen®; Amgen).

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin. Moreover, the CXCR4 agonists may be administered in a time release formulation, for example in a composition which includes a slow release polymer. The active compounds can be prepared with carriers that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods For the preparation of such formulations are patented or generally known to those skilled in the art.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof. In accordance with an alternative aspect of the invention, a CXCR4 agonist may be formulated with one or more additional compounds that enhance the solubility of the CXCR4 agonist.

CXCR4 antagonist compounds of the invention may include SDF-1 derivatives, such as C-terminal hydroxymethyl derivatives, O-modified derivatives (e.g., C-terminal hydroxymethyl benzyl ether), N-terminally modified derivatives including substituted amides such as alkylamides and hydrazides and compounds in which a C-terminal phenylalanine residue is replaced with a phenethylamide analogue (e.g., Ser-Ile-phenethylamide as an analogue of the tripeptide Ser-Ile-Phe).

Within a CXCR4 agonist of the invention, a peptidic structure (such as. an SDF-1 derived peptide) maybe coupled directly or indirectly to at least one modifying group. The term "modifying group" is intended to include structures that are directly attached to the peptidic structure (e.g., by covalent bonding or covalent coupling), as well as those that are indirectly attached to the peptidic structure (e.g., by a stable non-covalent bond association or by covalent coupling to additional amino acid residues, or mimetics, analogues or derivatives thereof, which may flank the SDF-1 core peptidic structure). For example, the modifying group can be coupled to the amino-terminus or carboxy-terminus of an SDF-1 peptidic structure, or to a peptidic or peptidomimetic region flanking the core domain. Alternatively, the modifying group can be coupled to a side chain of at least one amino acid residue of a SDF-1 peptidic structure, or to a peptidic or peptido-mimetic region flanking the core domain (e.g., through the epsilon amino group of a lysyl residue(s), through the carboxyl group of an aspartic acid residue(s) or a glutamic acid residue(s), through a hydroxy group of a tyrosyl residue(s), a serine residue(s) or a threonine residue(s) or other suitable reactive group on an amino acid side chain). Modifying groups covalently coupled to the peptidic structure can be attached by means and using methods well known in the art for linking chemical structures, including, for example, amide, alkylamino, sulphide, carbamate or urea bonds.

In some embodiments, the modifying group may comprise a cyclic, heterocyclic or polycyclic group. The term "cyclic group", as used herein, includes cyclic saturated or unsaturated (i.e., aromatic) group having from 3 to 10, 4 to 8, or 5 to 7 carbon atoms. Exemplary cyclic groups include cyclopropyl, cyclobutyl, cyclopentyl, cyclohexyl, and cyclooctyl. Cyclic groups may be unsubstituted or substituted at one or more ring positions. A cyclic group may for example be substituted with halogens, alkyls, cycloalkyls, alkenyls, alkynyls, aryls, heterocycles, hydroxyls, aminos, nitros, thiols amines, imines, amides, phosphonates, phosphines, carbonyls, carboxyls, silyls, ethers, thioethers, sulfonyls, sulfonates, selenoethers, ketones, aldehydes, esters, —$CF_3$, —CN.

The term "heterocyclic group" includes cyclic saturated, unsaturated and aromatic groups having from 3 to 10, 4 to 8, or 5 to 7 carbon atoms, wherein the ring structure includes about one or more heteroatoms. Heterocyclic groups include pyrrolidine, oxolane, thiolane, imidazole, oxazole, piperidine, piperazine, morpholine. The heterocyclic ring may be substituted at one or more positions with such substituents as, for example, halogens, alkyls, cycloalkyls, alkenyls, alkynyls, aryls, other heterocycles, hydroxyl, amino, nitro, thiol, amines, imines, amides, phosphonates, phosphines, carbonyls, carboxyls, silyls, ethers, thioethers, sulfonyls, selenoethers, ketones, aldehydes, esters, —$CF_3$, —CN. Heterocycles may also be bridged or fused to other cyclic groups as described below.

The term "polycyclic group" as used herein is intended to refer to two or more saturated, unsaturated or aromatic cyclic rings in which two or more carbons are common to two adjoining rings, so that the rings are "fused rings". Rings that are joined through non-adjacent atoms are termed "bridged" rings. Each of the rings of the polycyclic group may be substituted with such substituents as described above, as for example, halogens, alkyls, cycloalkyls, alkenyls, alkynyls, hydroxyl, amino, nitro, thiol, amines, imines, amides, phosphonates, phosphines, carbonyls, carboxyls, silyls, ethers, thioethers, sulfonyls, selenoethers, ketones, aldehydes, esters, —$CF_3$, or —CN.

The term "alkyl" refers to the radical of saturated aliphatic groups, including straight chain alkyl groups, branched-chain alkyl groups, cycloalkyl (alicyclic) groups, alkyl substituted cycloalkyl groups, and cycloalkyl substituted alkyl groups. In some embodiments, a straight chain or branched chain alkyl has 20 or fewer carbon atoms in its backbone ($C_1$-$C_{20}$ for straight chain, $C_3$-$C_{20}$ for branched chain), or 10 or fewer carbon atoms. In some embodiments, cycloalkyls may have from 4-10 carbon atoms in their ring structure, such as 5, 6 or 7 carbon rings. Unless the number of carbons is otherwise specified, "lower alkyl" as used herein means an alkyl group, as defined above, having from one to ten carbon atoms in its backbone structure. Likewise, "lower alkenyl" and "lower alkynyl" have chain lengths of ten or less carbons.

The term "alkyl" (or "lower alkyl") as used throughout the specification and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, halogen, hydroxyl, carbonyl (such as carboxyl, ketones (including alkylcarbonyl and arylcarbonyl groups), and esters (including alkyloxycarbonyl and aryloxycarbonyl groups), thiocarbonyl, acyloxy, alkoxyl, phosphoryl, phosphonate, phosphinate, amino, acylamino, amido, amidine, imino, cyano, nitro, azido, sulfhydryl, alkylthio, sulfate, sulfonate, sulfamoyl, sulfonamido, heterocyclyl, aralkyl, or an aromatic or heteroaromatic moiety. The moieties substituted on the hydrocarbon chain can themselves be substituted, if appropriate. For instance, the substituents of a substituted alkyl may include substituted and unsubstituted forms of aminos, azidos, iminos, amidos, phosphoryls (including phosphonates and phosphinates), sulfonyls (including sulfates, sulfonamidos, sulfamoyls and sulfonates), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —CF$_3$, —CN, and the like.

The terms "alkenyl" and "alkynyl" refer to unsaturated aliphatic groups analogous in length and possible substitution to the alkyls described above, but that contain at least one double or triple bond respectively.

The term "aralkyl", as used herein, refers to an alkyl or alkylenyl group substituted with at least one aryl group. Exemplary aralkyls include benzyl (i.e., phenylmethyl), 2-naphthylethyl, 2-(2-pyridyl)propyl, 5-dibenzosuberyl, and the like.

The term "alkylcarbonyl", as used herein, refers to —C(O)-alkyl. Similarly, the term "arylcarbonyl" refers to —C(O)-aryl. The term "alkyloxycarbonyl", as used herein, refers to the group —C(O)—O-alkyl, and the term "aryloxycarbonyl" refers to —C(O)—O-aryl. The term "acyloxy" refers to —O—C(O)—R$_7$, in which R$_7$ is alkyl, alkenyl, alkynyl, aryl, aralkyl or heterocyclyl.

The term "amino", as used herein, refers to —N(R$_\alpha$)(R$_\beta$), in which R$_\alpha$ and R$_\beta$ are each independently hydrogen, alkyl, alkyenyl, alkynyl, aralkyl, aryl, or in which R$_\alpha$ and R$_\beta$ together with the nitrogen atom to which they are attached form a ring having 4-8 atoms. Thus, the term "amino", as used herein, includes unsubstituted, monosubstituted (e.g., monoalkylamino or monoarylamino), and disubstituted (e.g., dialkylamino or alkylarylamino) amino groups. The term "amido" refers to —C(O)—N(R$_8$)(R$_9$), in which R$_8$ and R$_9$ are as defined above. The term "acylamino" refers to —N(R'$_8$)C(O)—R$_7$, in which R$_7$ is as defined above and R'$_8$ is alkyl.

As used herein, the term "nitro" means —NO$_2$; the term "halogen" designates —F, —Cl, —Br or —I; the term "sulfhydryl" means —SH; and the term "hydroxyl" means —OH.

The term "aryl" as used herein includes 5-, 6- and 7-membered aromatic groups that may include from zero to four heteroatoms in the ring, for example, phenyl, pyrrolyl, furyl, thiophenyl, imidazolyi, oxazole, thiazolyl, triazolyl, pyrazolyl, pyridyl, pyrazinyl, pyridazinyl and pyrimidinyl, and the like. Those aryl groups having heteroatoms in the ring structure may also be referred to as "aryl heterocycles" or "heteroaromatics". The aromatic ring can be substituted at one or more ring positions with such substituents as described above, as for example, halogen, azide, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, sulfonamido, ketone, aldehyde, ester, a heterocyclyl, an aromatic or heteroaromatic moiety, —CF$_3$, —CN, or the like. Aryl groups can also be part of a polycyclic group. For example, aryl groups include fused aromatic moieties such as naphthyl, anthracenyl, quinolyl, indolyl, and the like.

Modifying groups may include groups comprising biotinyl structures, fluorescein-containing groups, a diethylene-triaminepentaacetyl group, a (O)-menthoxyacetyl group, a N-acetylneuraminyl group, a cholyl structure or an iminiobiotinyl group. A CXCR4 agonist compound may be modified at its carboxy terminus with a cholyl group according to methods known in the art (see e.g., Wess, G. et al. (1993) Tetrahedron Letters, 34:817-822; Wess, G. et al. (1992) Tetrahedron Letters 33:195-198; and Kramer, W. et al. (1992) J. Biol. Chem. 267:18598-18604). Cholyl derivatives and analogues may also be used as modifying groups. For example, a preferred cholyl derivative is Aic (3-(O-amino-ethyl-iso)-cholyl), which has a free amino group that can be used to further modify the CXCR4 agonist compound. A modifying group may be a "biotinyl structure", which includes biotinyl groups and analogues and derivatives thereof (such as a 2-iminobiotinyl group). In another embodiment, the modifying group may comprise a "fluorescein-containing group", such as a group derived from reacting an SDF-1 derived peptidic structure with 5-(and 6-)-carboxyfluorescein, succinimidyl ester or fluorescein isothiocyanate. In various other embodiments, the modifying group(s) may comprise an N-acetylneuraminyl group, a trans-4-cotininecarboxyl group, a 2-imino-1-imidazolidineacetyl group, an (S)-(–)-indoline-2-carboxyl group, a (–)-menthoxyacetyl group, a 2-norbornaneacetyl group, a γ-oxo-5-acenaphthenebutyryl, a (–)-2-oxo-4-thiazolidinecarboxyl group, a tetrahydro-3-furoyl group, a 2-iminobiotinyl group, a diethylenetriaminepentaacetyl group, a 4-morpholinecarbonyl group, a 2-thiopheneacetyl group or a 2-thiophenesulfonyl group.

A CXCR4 agonist compound of the invention may be further modified to alter the specific properties of the compound while retaining the desired functionality of the compound. For example, in one embodiment, the compound may be modified to alter a pharmacokinetic property of the compound, such as in vivo stability, bioavailability or half-life. The compound may be modified to label the compound with a detectable substance. The compound may be modified to couple the compound to an additional therapeutic moiety. To further chemically modify the compound, such as to alter its pharmacokinetic properties, reactive groups can be derivatized. For example, when the modifying group is attached to the amino-terminal end of the SDF-1 core domain, the carboxy-terminal end of the compound may be further modified. Potential C-terminal modifications include those that reduce the ability of the compound to act as a substrate for carboxypeptidases. Examples of C-terminal modifiers include an amide group, an ethylamide group and various non-natural amino acids, such as D-amino acids and β-alanine. Alternatively, when the modifying group is attached to the carboxy-terminal end of the aggregation core domain, the amino-terminal end of the compound may be further modified, for example, to reduce the ability of the compound to act as a substrate for aminopeptidases.

A CXCR4 agonist compound can be further modified to label the compound by reacting the compound with a detectable substance. Suitable detectable substances include various enzymes, prosthetic groups, fluorescent materials, luminescent materials and radioactive materials. Examples of suitable enzymes include horseradish peroxidase, alkaline phosphatase, □-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include $^{14}$C, $^{123}$I, $^{124}$I, $^{125}$I, $^{131}$I, $^{99m}$Tc, $^{35}$S or $^{3}$H. A CXCR4 agonist compound may be radioactively labeled with $^{14}$C, either by incorporation of $^{14}$C into the modifying group or one or more amino acid structures in the CXCR4 agonist compound. Labeled CXCR4 agonist compounds may be used to assess the in vivo pharmacokinetics of the compounds, as well as to detect disease progression or propensity of a subject to develop a disease, for example for diagnostic purposes. Tissue distribution CXCR4 receptors can be detected using a labeled CXCR4 agonist compound either in vivo or in an in vitro sample derived from a subject. For use as an in vivo diagnostic agent, a CXCR4 antagonist compound of the invention may be labeled with radioactive technetium or iodine. A modifying group can be chosen that provides a site at which a chelation group for the label can be introduced, such as the Aic derivative of cholic acid, which has a free amino group. For example, a phenylalanine residue within the SDF-1 sequence (such as aminoacid residue 13) may be substituted with radioactive iodotyrosyl. Any of the various isotopes of radioactive iodine may be incorporated to create a diagnostic agent. $^{123}$I (half-life=13.2 hours) may be used for whole body scintigraphy, $^{124}$I (half life=4 days) may be used for positron emission tomography (PET), $^{125}$I (half life=60 days) may be used for metabolic turnover studies and $^{131}$I (half life=8 days) may be used for whole body counting and delayed low resolution imaging studies.

In an alternative chemical modification, a CXCR4 agonist compound of the invention may be prepared in a "prodrug" form, wherein the compound itself does not act as a CXCR4 agonist, but rather is capable of being transformed, upon metabolism in vivo, into a CXCR4 agonist compound as defined herein. For example, in this type of compound, the modifying group can be present in a prodrug form that is capable of being converted upon metabolism into the form of an active CXCR4 agonist. Such a prodrug form of a modifying group is referred to herein as a "secondary modifying group." A variety of strategies are known in the art for preparing peptide prodrugs that limit metabolism in order to optimise delivery of the active form of the peptide-based drug (see e.g., Moss, J. (1995) in Peptide-Based Drug Design: Controlling Transport and Metabolism, Taylor, M. D. and Amidon, G. L. (eds), Chapter 18.

CXCR4 agonist compounds of the invention may be prepared by standard techniques known in the art. A peptide or polypeptide component of a CXCR4 agonist may be composed, at least in part, of a peptide synthesized using standard techniques (such as those described in Bodansky, M. Principles of Peptide Synthesis, Springer Verlag, Berlin (1993); Grant, G. A. (ed.). Synthetic Peptides: A User's Guide, W. H. Freeman and Company, New York (1992); or Clark-Lewis, I., Dewald, B., Loetscher, M., Moser, B., and Baggiolini, M., (1994) J. Biol. Chem., 269, 16075-16081). Automated peptide synthesizers are commercially available (e.g., Advanced ChemTech Model 396; Milligen/Biosearch 9600). Peptides and polypeptides may be assayed for CXCR4 agonist activity in accordance with standard methods. Peptides and polypeptides may be purified by HPLC and analyzed by mass spectrometry. Peptides and polypeptides may be dimerized via a disulfide bridge formed by gentle oxidation of the cysteines using 10% DMSO in water. Following HPLC purification dimer formation may be verified, by mass spectrometry. One or more modifying groups may be attached to a SDF-1 derived peptidic component by standard methods, for example using methods for reaction through an amino group (e.g., the alpha-amino group at the amino-terminus of a peptide), a carboxyl group (e.g., at the carboxy terminus of a peptide), a hydroxyl group (e.g., on a tyrosine, serine or threonine residue) or other suitable reactive group on an amino acid side chain (see e.g., Greene, T. W. and Wuts, P. G. M. Protective Groups in Organic Synthesis, John Wiley and Sons, Inc., New York (1991)).

In another aspect of the invention, CXCR4 agonist peptides may be prepared according to standard recombinant DNA techniques using a nucleic acid molecule encoding the peptide. A nucleotide sequence encoding the peptide or polypeptide may be determined using the genetic code and an oligonucleotide molecule having this nucleotide sequence may be synthesized by standard DNA synthesis methods (e.g., using an automated DNA synthesizer). Alternatively, a DNA molecule encoding a peptide compound may be derived from the natural precursor protein gene or cDNA (e.g., using the polymerase chain reaction (PCR) and/or restriction enzyme digestion) according to standard molecular biology techniques.

The invention also provides an isolated nucleic acid molecule comprising a nucleotide sequence encoding a peptide of the invention. In some embodiments, the peptide may comprise an amino acid sequence having at least one amino acid deletion compared to native SDF-1. The term "nucleic acid molecule" is intended to include DNA molecules and RNA molecules and may be single-stranded or double-stranded. In alternative embodiments, the isolated nucleic acid encodes a peptide wherein one or more amino acids are deleted from the N-terminus, C-terminus and/or an internal site of SDF-1.

To facilitate expression of a peptide compound in a host cell by standard recombinant DNA techniques, the isolated nucleic acid encoding the peptide may be incorporated into a recombinant expression vector. Accordingly, the invention also provides recombinant expression vectors comprising the nucleic acid molecules of the invention. As used herein, ,the term "vector" refers to a nucleic acid molecule capable of transporting another nucleic acid to which it has been operatively linked. Vectors may include circular double stranded DNA plasmids and/or viral vectors. Certain vectors are capable of autologous replication in a host cell into which they are introduced (such as bacterial vectors having a bacterial origin of replication and episomal mammalian vectors). Other vectors (such as non-episomal mammalian vectors) may be integrated into the genome of a host cell upon introduction into the host cell, and thereby may be replicated along with the host genome. Certain vectors may be capable of directing the expression of genes to which they are operatively linked. Such vectors are referred to herein as "recombinant expression vectors" or "expression vectors".

In recombinant expression vectors of the invention, the nucleotide sequence encoding a peptide may be operatively linked to one or more regulatory sequences, selected on the basis of the host cells to be used for expression. The terms "operatively linked" or "operably" linked mean that the sequences encoding the peptide are linked to the regulatory sequence(s) in a manner that allows for expression of the peptide compound. The term "regulatory sequence" includes promoters, enhancers, polyadenylation signals and other expression control elements. Such regulatory sequences are described, for example, in Goeddel; Gene Expression Technology: Methods in Enzymology 185, Academic Press, San Diego, Calif. (1990) (incorporated herein be reference). Regulatory sequences include those that direct constitutive expression of a nucleotide sequence in many types of host cell, those that direct expression of the nucleotide sequence only in certain host cells (such as tissue-specific regulatory sequences) and those that direct expression in a regulatable manner (such as only in the presence of an inducing agent). The design of the expression vector may depend on such factors as the choice of the host cell to be transformed and the level of expression of peptide compound desired.

The recombinant expression vectors of the invention may be designed for expression of peptide compounds in prokaryotic or eukaryotic cells. For example, peptide compounds may be expressed in bacterial cells such as E. coli, insect cells (using baculovirus expression vectors) yeast cells or mammalian cells. Suitable host cells are discussed further in Goeddel, Gene Expression Technology: Methods in Enzymology 185, Academic Press, San Diego, Calif.

(1990). Alternatively, the recombinant expression vector may be transcribed and translated in vitro, for example using T7 promoter regulatory sequences and T7 polymerase. Examples of vectors for expression in yeast *S. cerivisae* include pYepSec1 (Baldari et al., (1987) EMBO J. 6:229-234), pMFa (Kurjan and Herskowitz, (1982) Cell 30:933-943), pJRY88 (Schultz et al., (1987) Gene 54:113-123), and pYES2 (Invitrogen Corporation, San Diego, Calif.). Baculovirus vectors available for expression of proteins or peptides in cultured insect cells (e.g., Sf 9 cells) include the pAc series (Smith et al., (1983) Mol. Cell. Biol. 3:2156-2165) and the pVL series (Lucklow, V. A., and Summers, M. D., (1989) Virology 170:31-39). Examples of mammalian expression vectors include pCDM8 (Seed, B., (1987) Nature 329:840) and pMT2PC (Kaufman et al. (1987), EMBO J. 6:187-195). When used in mammalian cells, the expression vector's control functions are often provided by viral regulatory elements. For example, commonly used promoters are derived from polyoma, Adenovirus 2, cytomegalovirus and Simian Virus 40.

In addition to regulatory control sequences, recombinant expression vectors may contain additional nucleotide sequences, such as a selectable marker gene to identify host cells that have incorporated the vector. Selectable marker genes are well known in the art. To facilitate secretion of the peptide compound from a host cell, in particular mammalian host cells, the recombinant expression vector preferably encodes a signal sequence operatively linked to sequences encoding the amino-terminus of the peptide compound, such that upon expression, the peptide compound is synthesized with the signal sequence fused to its amino terminus. This signal sequence directs the peptide compound into the secretory pathway of the cell and is then cleaved, allowing for release of the mature peptide compound (i.e., the peptide compound without the signal sequence) from the host cell. Use of a signal sequence to facilitate secretion of proteins or peptides from mammalian host cells is well known in the art.

A recombinant expression vector comprising a nucleic acid encoding a peptide compound may be introduced into a host cell to produce the peptide compound in the host cell. Accordingly, the invention also provides host cells containing the recombinant expression vectors of the invention. The terms "host cell" and "recombinant host cell" are used interchangeably herein. Such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein. A host cell may be any prokaryotic or eukaryotic cell. For example, a peptide compound may be expressed in bacterial cells such as *E. coli*, insect cells, yeast or mammalian cells. The peptide compound may be expressed in vivo in a subject to the subject by gene therapy (discussed further below).

Vector DNA can be introduced into prokaryotic or eukaryotic cells via conventional transformation, transfection or infection techniques. The terms "transformation", "transfection" or "infection" refer to techniques for introducing foreign nucleic acid into a host cell, including calcium phosphate or calcium chloride co-precipitation, DEAE-dextran-mediated transfection, lipofection, electroporation, microinjection and viral-mediated infection. Suitable methods for transforming, transfecting or infecting host cells may for example be found in Sambrook et al. (Molecular Cloning: A Laboratory Manual, 2nd Edition, Cold Spring Harbor Laboratory press (1989)), and other laboratory manuals.

Methods for introducing DNA into mammalian cells in vivo are also known, and may be used to deliver the vector DNA of the invention to a subject for gene therapy.

For stable transfection of mammalian cells, it is known that, depending upon the expression vector and transfection technique used, only a small fraction of cells may integrate the foreign DNA into their genome. In order to identify and select these integrants, a gene that encodes a selectable marker (such as resistance to antibiotics) may be introduced into the host cells along with the gene of interest. Preferred selectable markers include those that confer resistance to drugs, such as G418, hygromycin and methotrexate. Nucleic acids encoding a selectable marker may be introduced into a host cell on the same vector as that encoding the peptide compound or may be introduced on a separate vector. Cells stably transfected with the introduced nucleic acid may be identified by drug selection (cells that have incorporated the selectable marker gene will survive, while the other cells die).

A nucleic acid of the invention may be delivered to cells in vivo using methods such as direct injection of DNA, receptor-mediated DNA uptake or viral-mediated infection. Direct injection has been used to introduce naked DNA into cells in vivo (see e.g., Acsadi et al. (1991) Nature 332:815-818; Wolff et al. (1990) Science 247:1465-1468). A delivery apparatus (e.g., a "gene gun") for injecting DNA into cells in vivo may be used. Such an apparatus may be commercially available (e.g., from BioRad). Naked DNA may also be introduced into cells by complexing the DNA to a cation, such as polylysine, which is coupled to a ligand for a cell-surface receptor (see for example Wu, G. and Wu, C. H. (1988) J. Biol. Chem. 263:14621; Wilson el al. (1992) J. Biol. Chem. 267:963-967; and U.S. Pat. No. 5,166,320). Binding of the DNA-ligand complex to the receptor may facilitate uptake of the DNA by receptor-mediated endocytosis. A DNA-ligand complex linked to adenovirus capsids that disrupt endosomes, thereby releasing material into the cytoplasm, may be used to avoid degradation of the complex by intracellular lysosomes (see for example Curiel et al. (1991) Proc. Natl. Acad. Sci. USA 88:8850; Cristiano et al. (1993) Proc. Natl. Acad. Sci. USA 90:2122-2126).

Defective retroviruses are well characterized for use in gene transfer for gene therapy purposes (for reviews see Miller, A. D. (1990) Blood 76:271, Kume et al. (1999) International. J. Hematol. 69:227-233). Protocols for producing recombinant retroviruses and for infecting cells in vitro or in vivo with such viruses can be found in Current Protocols in Molecular Biology, Ausubel, F. M. et al. (eds.) Greene Publishing Associates, (1989), Sections 9.10-9.14 and other standard laboratory manuals. Examples of suitable retroviruses include pLJ, pZIP, pWE and pEM which are well known to those skilled in the art. Examples of suitable packaging virus lines include .pψi.Crip, .pψi.Cre, .pψi.2 and .pψi.Am. Retroviruses have been used to introduce a variety of genes into many different cell types, including epithelial cells, endothelial cells, lymphocytes, myoblasts, hepatocytes, bone marrow cells, in vitro and/or in vivo (see for example Eglitis, et al. (1985) Science 230:1395-1398; Danos and Mulligan (1988) Proc. Natl. Acad. Sci. USA 85:6460-6464; Wilson et al. (1988) Proc. Natl. Acad. Sci. USA 85:3014-3018; Armentano et al. (1990) Proc. Natl. Acad. Sci. USA 87:6141-6145; Huber et al. (1991) Proc. Natl. Acad. Sci. USA 88:8039-8043; Ferry et al. (1991) Proc. Natl. Acad. Sci. USA 88:8377-8381; Chowdhury et al. (1991) Science 254:1802-1805; van Beusechem et al. (1992)

Proc. Natl. Acad. Sci. USA 89:7640-7644; Kay et al. (1992) Human Gene Therapy 3:641-647; Dai et al. (1992) Proc. Natl. Acad. Sci. USA 89:10892-10895; Hwu et al. (1993) J. Immunol. 150:4104-4115; U.S. Pat. No. 4,868,116; U.S. Pat. No. 4,980,286; PCT Application WO 89/07136; PCT Application WO 89/02468; PCT Application WO 89/05345; and PCT Application WO 92/07573). In various embodiments, a genome of a retrovirus that encodes and expresses a polypeptide compound of the invention, may be utilized for the propagation and/or survival of cells, such as hematopoietic progenitor stem cells, for the purposes of maintaining and/or growing cells for the clinical purposes of blood transfusion or engraftment, host conditioning or applications relevant to chemotherapy, radiation therapy or myeloablative therapy.

For use as a gene therapy vector, the genome of an adenovirus may be manipulated so that it encodes and expresses a peptide compound of the invention, but is inactivated in terms of its ability to replicate in a normal lytic viral life cycle. See for example Berkner et al. (1988) BioTechniques 6:616; Rosenfeld et al. (1991) Science 252: 431-434; and Rosenfeld et al. (1992) Cell (38:143-155. Suitable adenoviral vectors derived from the adenovirus strain Ad type 5 dl324 or other strains of adenovirus (e.g., Ad2, Ad3, Ad7 etc.) are well known to those skilled in the art. Recombinant adenoviruses are advantageous in that they do not require dividing cells to be effective gene delivery vehicles and can be used to infect a wide variety of cell types, including airway epithelium (Rosenfeld et al. (1992) cited supra), endothelial cells (Lemarchand et al. (1992) Proc. Natl. Acad. Sci. USA 89:6482-6486), hepatocytes (Herz and Gerard (1993) Proc. Natl. Acad. Sci. USA 90:2812-2816) and muscle cells (Quantin el al. (1992) Proc. Natl. Acad. Sci. USA 89:2581-2584). In various embodiments, a genome of an adenovirus that encodes and expresses a polypeptide compound of the invention, may be utilized for the propagation and/or survival of cells, such as hematopoietic progenitor stem cells, stromal cells, or mesenchymal cells, for the purposes of maintaining and/or growing cells for the clinical purposes of blood transfusion or engraftment, host conditioning or applications relevant to chemotherapy, radiation therapy or myeloablative therapy.

In some embodiments, adeno-associated virus (AAV) may be used as a gene therapy vector for delivery of DNA for gene therapy purposes. AAV is a naturally occurring defective virus that requires another virus, such as an adenovirus or a herpes virus, as a helper virus for efficient replication and a productive life cycle (Muzyczka et al. Curr. Topics in Micro. and Immunol. (1992) 158:97-129). MV may be used to integrate DNA into non-dividing cells (see for example Flotte et al. (1992) Am. J. Respir. Cell. Mol. Biol. 7:349-356; Samulski et al. (1989) J. Virol. 63:3822-3828; and McLaughlin et al. (1989) J. Virol. 62:1963-1973). An AAV vector such as that described in Tratschin et al. (1985) Mol. Cell. Biol. 5:3251-3260 may be used to introduce DNA into cells (see for example Hermonat et al. (1984) Proc. Natl. Acad. Sci. USA 81:6466-6470; Tratschin et al. (1985) Mol. Cell. Biol. 4:2072-2081; Wondisford et al. (1988) Mol. Endocrinol. 2:32-39; Tratschin et al. (1984) J. Virol. 51:611-619; and Flotte et al. (1993) J. Biol. Chem. 268:3781-3790). In some embodiments, a genome of an AAV that encodes and expresses a polypeptide compound of the invention, may be utilized for the propagation and/or survival of cells, such as hematopoietic progenitor stem cells, stromal cells or mesenchymal cells, for the purposes of maintaining and/or growing cells for the clinical purposes of blood transfusion or engraftment, host conditioning or applications relevant to chemotherapy, radiation therapy or myeloablative therapy.

General methods for gene therapy are known in the art. See for example, U.S. Pat. No. 5,399,346 by Anderson et al. A biocompatible capsule for delivering genetic material is described in PCT Publication WO 95/05452 by Baetge et al. Methods for grafting genetically modified cells to treat central nervous system disorders are described in U.S. Pat. No. 5,082,670 and in PCT Publications WO 90/06757 and WO 93/10234, all by Gage et al. Methods of gene transfer into hematopoietic cells have also previously been reported (see Clapp, D. W., et al., Blood 78: 1132-1139 (1991); Anderson, Science 288:627-9 (2000); and , Cavazzana-Calvo et al., Science 288:669-72 (2000), all of which are incorporated herein by reference).

Cancers susceptible to treatment with CXCR4 agonists in accordance with various aspects of the invention may include both primary and metastatic tumors, such as solid tumors, including carcinomas of the breast, colon, rectum, oropharynx, hypopharynx, esophagus, stomach, pancreas, liver, gall bladder and bile ducts, small intestine, urinary tract (including kidney, bladder, and urothelium), female genital tract (including cervix, uterus, and ovaries as well as choriocarcinoma and gestational trophoblast disease), male genital tract (including prostate, seminal vesicles, testes, and germ cell tumors), endocrine glands (including the thyroid, adrenal and pituitary glands), and skin, as well as hemangiomas, melanomas, sarcomas (including those arising from bone and soft tissues as well as Kaposi's sarcoma) and tumors of the brain, nerves, eyes, and meninges (including astrocytomas, gliomas, retinoblastomas, neuromas, neuroblastomas, Schwannomas, and meningiomas). In some aspects of the invention, CXCR4 agonists may also serve in treating solid tumors arising from hematopoietic malignancies such as leukemias (i.e., chloromas, plasmacytomas and the plaques and tumors of mycosis fungoides and cutaneous T-cell lymphoma/leukemia) as well as in the treatment of lymphoma (both Hodgkin's and non-Hodgkin's lymphomas). in addition, CDCX4 agonists may be therapeutic in the prevention of metastasis from the tumors described above either when used alone or in combination with cytotoxic agents such as radiotherapy or chemotherapeutic agents.

In alternative aspects of the invention, CXCR4 agonists such as SDF-1 polypeptides may target CD34$^+$ cells to mediate release of CD34$^+$ cells to the peripheral blood. In these aspects of the invention, CXCR4 agonists such as SDF-1 may enhance circulating CD34$^+$ cell proliferation and hematopoietic stem or progenitor cell survival or levels, which may for example be useful in stem cell transplantation.

In various aspects of the invention, CXCR4 agonists may be used in reducing the rate of hematopoietic cell multiplication. Method of the invention may comprise administration of an effective amount of CXCR4 agonists to cells selected from the group consisting of hematopoietic stem cells and hematopoietic progenitor cells, stromal cells or mesenchymal cells. In alternative embodiments, a therapeutically effective amount of the CXCR4 agonist may be administered to a patient in need of such treatment. Patients in need of such treatments may include, for example: patients having cancer, patients having an autoimmune disease, patients requiring functional gene transfer into hematopoietic stems cells, stromal cells or mesenchymal cells (such as for the dysfunction of any tissue or organ into which a stem cell may differentiate), patients requiring lymphocyte depletion, patients requiring depletion of a blood cancer in the form of purging autoreactive or cancerous cells using autologous or aligenic grafts, or patients requiring autologous peripheral blood stem cell transplantation. A patient in need of treatment in accordance with the invention may also be receiving cytotoxic treatments such as chemotherapy or radiation therapy. In some embodiments, CXCR4 agonists may be used in treatment to purge an ex vivo hematopoietic stem cell culture of cancer cells with cytotoxic treatment, while preserving the viability of the hematopoietic progenitor or stem cells.

In alternative embodiments, CXCR4 agonists may be used in accordance with the invention to treat hematopoietic cells, in patients in need of such treatment, for example:

i) In hematopoietic recovery and bone marrow regeneration following irradiation;

ii) To ameliorate the myelosuppression associated with dose intensive chemotherapy;

iii) In maintenance of high quality mobilized progenitor cells for harvesting and peripheral blood stem cells transplantation;

iv) To enhance hematopoietic recovery after autologous stem cell transplantation;

v) In immunotherapy of cancer and infectious disease;

vi) In solid organ regeneration (Silberstein and Toy, 2001, JAMA Vol 285, 577-580);

vii) In stem cell gene therapy and retro-virus gene transfer into hematopoietic progenitor cells (Hacein-Bey, 2001, Hum. Gene Ther. Vol 12, 291-301; Kaji and Leiden, 2001, JAMA Vol 285, 545-550), stromal cells, or mesenchymal cells;

viii) In bone development, bone repair, and skeletal regeneration therapy.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. In the claims, the word "comprising" is used as an open-ended term, substantially equivalent to the phrase "including, but not limited to".

EXAMPLES

The following examples illustrate, but do not limit, the present invention.

Example 1

Peptides of the invention may be synthesized chemically using the Fmoc/tBu strategy on a continuous flow peptide synthesizer, as for example has been carried out using the following protocols:

A) Reagents (Solvents, Support, Chemicals)

Main Solvent: N,N-Dimethylformamide (DMF): certified ACS spectroanalyzed from Fisher (D131-4) M.W=73.10. The DMF is treated with activated molecular sieves, type 4A (from BDH: B54005) for at least two weeks then tested with FDNB (2,4-Dinitrofluorobenzene from Eastman).

Procedure: Mix equal volumes of FDNB solution (1 mg/ml in 95% EtOH) and DMF; Let stand 30 minutes; read the absorbance at 381 nm over a FDNB blank (0.5 ml FDNB+0.5 ml 95% EtOH). If the absorbance ~0.2, the DMF is suitable to be used for the synthesis.

Deblocking Agent: 20% Piperidine (from Aldrich Chemical company, catalog No: 10,409-4) in DMF containing 0.5% triton X100 v/v (from Sigma, catalg No: T-9284).

Activating Agents: 2-(H-benzotriazol-lyl) 1,1,3,3-tetramethyluronium tetrafluoroborate (TBTU: M.W.=321.09. from Quantum Richilieu, catalog No: R0139)/Hydroxybenzotriazole (HOBt M.W.=135.1 from Quantum Richilieu, catalog No.: R0166-100) respectively, 0.52 M in DMF and 4-Methylmorpholine (NMM ; M.W.=101.15, d=0.926 from Aldrich, catalog No.: M5,655-7): 0.9 M in DMF or in the case of sensitive amino acids to racemization like Cys, we use 2,4,6-Collidine, 99% (M.W.=121.18,d=0.917, from Aldrich, catalog No: 14,238-7): 0.78M in DMF/DCM, 1/1 v/v.

Support: TentaGel R RAM (90 µm), RinK-type Fmoc (from Peptides International, catalog No.: RTS-9995-PI): 0.21 mmol/g, 0.5 g for 0.1 mmol of peptide.

Fmoc-L-amino derivative, side-chains protected with: Boc; tBu; Trt groups: with 4 fold excess (from Peptides International, Bachem, Novabiochem, Chem-Impex Inc). Glu24 and Lys24 are Allyl-protected (from Millipore/Perseptive Biosystems).

B) Initial Amino Loading and Peptide Synthesis Procedure

The first amino acid Asn31 and the remaining residues are doable coupled at 450° C. automatically with 4-fold excess in each coupling. The synthesis is interrupted after residue Leu19. The peptide-bound support is removed from the synthesizer column and placed in a react-vial containing a small magnetic bar for gentle stirring.

C) Removal of the Allyl Groups

A solution of tetrakis(triphenylphosphine)Palladium(0) $Pd(PPh3)_4$ (from Sigma-Aldrich, catalog No: 21,666-6); M.W.=1155.58×0.1 mmol peptide×3 fold=347 mg dissolved in 5% Acetic Acid; 2.5% NMM in $CHCl_3$ to 0.14 M, under argon. The solution is added to the support-bound peptide previously removed from the column in a reactvial containing a small magnetic bar for gentle stirring. The mixture is flushed with argon, sealed and stirred at room temperature for 6 hours. The support-bound peptide is transferred to a filter funnel, washed with 30 ml of a solution made of 0.5% Sodium Diethyldithiocarbonate/in DMF the DCM; DCM/DMF (1:1) and DMF. A positive Kaiser test indicate the deprotection of the amino side chain of the Lys20.

D) Lactam Formation:

Activating agent: 7-Azabenztriazol-1-yloxytris (pyrrolindino) phosphonium-hexafluorophosphate (PyAOP: M.W.=521.7 from PerSeptive Biosystems GmbH, catalog No: GEN076531), 1.4-fold: 0.105 mmol×1.4×521.7=76.6 mg and NMM 1.5-fold: 0.105×1.4×1.5=0.23 mmol v=0.23/0.9 M NMM solution=263 µl)

The cyclisation may be carried out in an amino acid vial at room temperature overnight (~16 hours) with gentle agitation. The completion of cyclization may be indicated by a negative kaiser test. The support-bound peptide may be poured into the column, washed with DMF and the synthesis continues to completion, with a cyclic amide bridge thereby introduced into the peptide.

E) Final Product Removal from the Support:

The support-bound peptide is removed from the synthesizer in to a medium filter funnel, washed with DCM to replace the non-volatile DMF and thoroughly dried under high vacuum from at least two hours, or preferably, overnight.

Cleavage Mixture (reagent K):
TFA/Phenol/Water/Thio-Anisol/EDT (82/5/5/5/2.5); 7.5 ml
Support: 0.5 g resin-peptide.

| | |
|---|---|
| TFA | 6.15 ml (Biograde from Halocarbon) |
| Phenol | 0.375 ml (Aldrich) |
| Water | 0.375 ml (MillQ) |
| Thio-Anisol | 0.375 ml (Aldrich) |
| EDT | 0.187 ml (Aldrich) |
| Total | 7.5 ml |

The cleavage may be performed at room temperature for 4 hours with gentle agitation on a rocker.

F) Precipitation of the Peptide

The cleaved peptide solution is filtered through a filter funnel in a 50 ml round bottom flask. The support is rinsed twice with 4 ml TFA. The TFA solution is concentrated on a rotavap and added drop wise into a cold diethyl ether previously treated with activated neutral aluminum oxide to make it free of peroxide. Approximately 10-fold excess of ether are used. The beads are stored until the yield is determined a peptide characterized. The precipitate is collected at room temperature in screw capped 50 ml polypropylene vial by centrifugation at 2K rpm, using a top bench centrifuge (4 minutes run time). The pellet is washed 3× with cold ether, centrifuged and dried with a flow of argon. The precipitate is dissolved in 20% acetonitrile 0.1% TFA and lyophilized.

G) Crude Product Characterization:

The product is characterized by analytical HPLC.
Experimental conditions: Column: Vydac 218TP54: C18 reversed-phase 5 μm, 4.6 mm ID×150 mL.
Eluants: 0.1% TFA/H$_2$O (solvant A); 0.1% TFA/acetonitrile (solvant B)
Elution Conditions: 20-50% B (40 min ); 60-90% B (5 min); 90-20% B (5 min); 20% B (10 min). At 1.0 ml/min and A214 nm=0.5 absorbance unit full scale.

H) Sample Preparation:

An aliquot of the product is weighed and dissolved in 20% acetonitrile 0.1% TFA at a concentration of 2 mg/ml. The solution is microfuged and 20 μl is applied onto the column. The main peak or the major peaks are collected, SpeedVac dried and molecular weight determined by mass spectrometry.

In accordance with various aspects of the invention, a wide variety of peptide sequences may be prepared, for which the following nomenclature may be used. The portions of the peptide corresponding to a chemokine sequence, such as an SDF-1 sequence may be identified by specifying the corresponding portion of the chemokine, wherein for example a reference to an SDF-1 sequence refers to a sequence having substantial identity to a portion of the sequence of SEQ ID NO:1. For example, the nomenclature SDF-1(1-14) connotes the first fourteen amino acids of the N-terminal sequence of SDF-1 of SEQ ID NO:1. In some embodiments, N-terminal and C-terminal portions of an SDF-1 sequence may be linked by various amino acids, or other linking moieties, denoted by a formula (L)n, wherein "L" is a linking moiety which may for example be an amino acid and n is zero or an integer. The carboxy terminal of the peptide may be modified to be an amide rather than a carboxylic acid. In some embodiments, polypeptides of the invention may be of the following formula:

SDF-1(1-X)-(L)n-SDF-1(Y-Z)

wherein:

X is an integer from 5 to 20;

L is a linking moiety having at least one carbon atom, such as a substituted or unsubstituted alkyl moiety, or an amino acid;

n is an integer from 1 to 50

Y is an integer from 50 to 60

Z is an integer from 60 to 67.

In some embodiments, (CH$_2$)n may for example be used as a linker (L) between N- and C-terminal, where n is an integer and may for example be less than 20, 30, 40, 50 or 100.

Exemplary embodiments of linear polypeptide sequences are as follows:

```
SDF-1(1-14)-(G)₃-SDF-1(55-67) acid:
                                      (SEQ ID NO:12)
H₂NKPVSLSYRCPCRFFGGGLKWIQEYLEKALNCOOH SDF-1(1-14)-(G)₄-SDF-1(55-67) acid:
                                      (SEQ ID NO:13)
H₂NKPVSLSYRCPCRFFGGGGLKWIQEYLEKALNCOOH SDF-1(1-14)-(G)₃-SDF-1(55-67) amide:
                                      (SEQ ID NO:14)
H₂NKPVSLSYRCPCRFFGGGLKWIQEYLEKALNCONH₂

SDF-1(1-14)-(G)₄-SDF-1(55-67) amide:
                                      (SEQ ID NO:15)
H₂NKPVSLSYRCPCRFFGGGGLKWIQEYLEKALNCONH₂

SDF-1(1-17)-(G)₃-SDF-1(55-67) acid:
                                      (SEQ ID NO:16)
H₂NKPVSLSYRCPCRFFESHGGGLKWIQEYLEKALNCOOH SDF-1(1-17)-(G)₄-SDF-1(55-67) acid:
                                      (SEQ ID NO:17)
H₂NKPVSLSYRCPCRFFESHGGGGLKWIQEYLEKALNCOOH SDF-1(1-17)-(G)₃-SDF-1(55-67) amide:
                                      (SEQ ID NO:18)
H₂NKPVSLSYRCPCRFFESHGGGLKWIQEYLEKALNCONH₂

SDF-1(1-17)-(G)₄-SDF-1(55-67) amide:
                                      (SEQ ID NO:19)
H₂NKPVSLSYRCPCRFFESHGGGGLKWIQEYLEKALNCONH₂
```

In alternative embodiments, peptides of the invention may be cyclized, for example glutamate (E) and lysine (K) residues may be joined by side chain cyclization using a lactam formation procedure, as indicated in the following sequences by double underlining of linked residues. Lactams may for example be formed between glutamic acid (E) at amino acid residue 24 and lysine (K) at either position 20 or 28 in the polypeptide (which does not correspond necessarily with the numbering of that residue in the native sequence). In further alternatives, a lysine (K) may be substituted by leucine (L), ornithine (O) or other hydrophobic residues, such as isoleucine (I), norleucine (Nle), methionine (M), valine (V), alanine (A), tryptophan (W) or Phenylalanine (F). Similarly, glutamate (E) may for example be substituted with aspartate (D), denoted by nomenclature such as (E24->D) indicating a substitution at position 24 in the peptide wherein aspartate replaces glutamate.

```
SDF-1(1-14)-(G)4-SDF-1(55-67)-E24/K28-cyclic acid
                                        (SEQ ID NO:20)
H2NKPVSLSYRCPCRFFGGGGLKWIQEYLEKALNCOOH SDF-1(1-14)-(G)4-SDF-1(55-67)-K20/E24-cyclic acid
                                        (SEQ ID NO:21)
H2NKPVSLSYRCPCRFFGGGGLKWIQEYLEKALNCOOH SDF-1(1-14)-(G)4-SDF-1(55-67)-E24/K28-cyclic amide
                                        (SEQ ID NO:22)
H2NKPVSLSYRCPCRFFGGGGLKWIQEYLEKALNCONH2

SDF-1(1-14)-(G)4-SDF-1(55-67) K20/E24-cyclic amide
                                        (SEQ ID NO:23)
H2NKPVSLSYRCPCRFFGGGGLKWIQEYLEKALNCONH2
```

In alternative embodiments of the peptides of the invention, underlined spacer monomers (such as the illustrated glycine G's) may be used in variable numbers, such as 2, 3 or 4 glycines (SEQ ID NO:214).

In alternative embodiments, internal cyclization of peptides of the invention may be in alternative positions, or between substituted amino acids. The nature of the cyclic linkage may also be varied. For example, the linkage may be shortened by replacing the relevant glutamate (E) with an aspartate (D) residue, and/or replacing the lysine (K) with an ornithine (O) residue. Cyclization is for example possible between Aspartic acid 24 (D24) and Lysine 20 or 28 (K20 or K28), as illustrated in some of the exemplified polypeptides.

```
SDF-1(1-14)-(G)4-SDF-1(55-67)-K20/D24-cyclic acid
                                        (SEQ ID NO:24)
H2NKPVSLSYRCPCRFFGGGGLKWIQDYLEKALNCOOH SDF-1(1-14)-(G)4-SDF-1(55-67)-K20/D24-cyclic amide
                                        (SEQ ID NO:25)
H2NKPVSLSYRCPCRFFGGGGLKWIQDYLEKALNCONH2
```

Disulphide or sulphide bridging may be used to produce alternative embodiments of the polypeptides of the invention, in which cysteine residues may for example be involved in bridge formation, as indicated in the following sequences by double underlined residues.

```
SDF-1(1-14)-(G)4-SDF-1(55-67)-C9/C11-cyclic acid
                                        (SEQ ID NO:26)
H2NKPVSLSYRCPCRFFGGGGLKWIQEYLEKALNCOOH SDF-1(1-14)-(G)4-SDF-1(55-67)-C9/C11-cyclic amide
                                        (SEQ ID NO:27)
H2NKPVSLSYRCPCRFFGGGGLKWIQEYLEKALNCONH2
```

In one aspect, polypeptide compounds of the invention may provide a CXCR4 agonist comprising a peptide having: (a) an N-terminal sequence homologous to a chemokine, such as an SDF-1 N-terminal sequence; (b) a C-terminal sequence homologous to a chemokine, such as an SDF-1 C-terminal sequence; (c) a linking moiety joining the N-terminal sequence to the C-terminal sequence, such as a polypeptide linker; and, (d) an internal cyclic bridge formed between portions of the polypeptide, such as an amide linking a carboxylic acid side chain on a first amino acid residue and an amine side chain on a second amino acid residue. In some embodiments, the C-terminal sequence may comprise the internal cyclic bridge.

As shown above, exemplary embodiments of polypeptides of the invention have been synthesized, having N-terminal SDF-1 residues (1-14) or (1-17), linked to C-terminal SDF-1 residues (55-67) by a three or four-glycine linker (SEQ ID NO:212). In some embodiments, peptides are cyclized between glutamic acid (at 24 position) and lysine (at 20 or 28 position). Lactamization may be affected by removing the allylic group from both side chains of lysine and glutamic acid using the palladium technique and then effecting internal amide bond formation between the corresponding lysine and glutamic acid. Selected members of this family of polypeptides showed high affinity in a CXCR4 receptor binding assay (CEM cells) and in activating [$Ca^{2+}$] mobilization (THP-1 cells). Further embodiments of polypeptides are listed below:

SDF-1(1-14)-(G)4-SDF-1(55-67)-K20/D24-(E24 ? D)-cyclic acid or amide (SEQ ID NOS:24 and 25)

SDF-1(1-14)-(G)4-SDF-1(55-67)-K28/D24-(E24 ? D)-cyclic acid or amide (SEQ ID NOS:37 and 38)

Cyclization may also take place between ornithine (O) and glutamic acid (E):

SDF-1(1-14)-(G)4-SDF-1(55-67)-O20/E24-(K20 ? O)-cyclic acid or amide (SEQ ID NOS:39 and 40)

SDF-1(1-14)-(G)4-SDF-1(55-67)-O28/E24-(K28 ? O)-cyclic acid or amide (SEQ ID NOS:41 and 42)

Cyclization may also take place between ornithine (O) and aspartic acid (D):

SDF-1(1-14)-(G)4-SDF-1(55-67)-O20/D24-(K20 ? O & E24 ? D)-cyclic acid or amide (SEQ ID NOS:43 and 44)

SDF-1(1-14)-(G)4-SDF-1(55-67)-O28/D24-(K28 ? O & E24 ? D)-cyclic acid or amide (SEQ ID NOS:45 and 46)

In some embodiments, proline (P) at position 6th may be replaced with serine (S). In some embodiments, lysine (K) and glutamic acid (E) may be replaced by ornithine (O) and aspartic acid (D), respectively. Similarly, substitutions may be made in the LSYR region, replacing lucine (L), serine (S), tyrosine (Y) or arginine (R) by proline (P) or other similarly shaped moiety. Alternatively, proline may be substituted with P*:

Where P*=

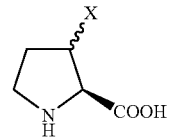

with X=Ar, Ar—OH, alkyl and more

A wide variety of amino acid substitutions may be made in polypeptide sequences, such as K to E, K to D, O to E, O to D. Moieties other than naturally occurring amino acids may also be substituted, such as Btd:

Where Btd*=

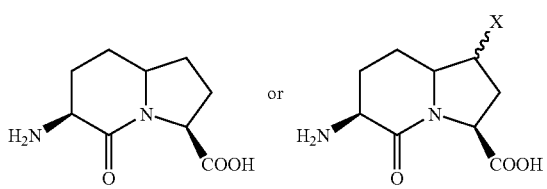

or

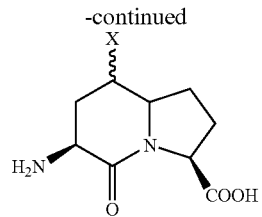

X=Alkyl, Ar, Ar—OH and more

Similarly, polypeptides may be prepared using sequences from chemokines other than SDF-1. Such as residues 36-50, 10-50 or 55-70 of MIP-1α:

```
SDF-1(1-14)-(G)4-MIP-1α(36-50)-acid or amide
H2N-KPVSLSYRCPCRFFGGGGSKPGVIFLTKRSRQV-CONH2          (SEQ ID NOS:28 and 47)

SDF-1(1-14)-(G)4-MIP-1α(11-50)-acid or amide
H2N-KPVSLSYRCPCRFFGGGGCCFSYTSRQIPQNFIADYFETSSQCSKPGVIFLT    (SEQ ID NOS:29 and 48)
KRSRQV-CONH2

SDF-1(1-14)-(G)4-MIP-1α(56-70)-acid or amide
H2N-KPVSLSYRCPCRFFGGGGEEWVQKYVDDLELSA-CONH2          (SEQ ID NOS:30 and 49)
```

In various Figures, compounds are identified by abbreviations, as follows:

```
Structure of CTCE9901:
SDF-1(1-9)2-C9/C9-cysteine dimer
H2NKPVSLSYRCCOOH                                     (SEQ ID NO:7)
       |
H2NKPVSLSYRCCOOH                                     (SEQ ID NO:7)

Structure of CTCE9902:
SDF-1(1-17)
H2NKPVSLSYRCPCRFFESHCOOH                             (SEQ ID NO:4)

Structure of CTCE9904:
SDF-1(1-8)2-lysine bridge dimer
H2NKPVSLSYR                                          (SEQ ID NO:31)
       |
       K-CONH2
       |
H2NKPVSLSYR                                          (SEQ ID NO:32)

Structure of CTCE0013:
SDF-1(1-14)-(G)4-SDF-1(55-67) acid
H2NKPVSLSYRCPCRFFGGGGLKWIQEYLEKALNCOOH               (SEQ ID NO:13)

Structure of CTCE0017:
SDF-1(1-14)-(G)4-SDF-1(55-67) amide
H2NKPVSLSYRCPCRFFGGGGLKWIQEYLEKALNCONH2              (SEQ ID NO:15)

Structure of CTCE0022:
SDF-1(1-14)-(G)4-SDF-1(55-67)-E24/K28-cyclic amide
H2NKPVSLSYRCPCRFFGGGGLKWIQEYLEKALNCONH2              (SEQ ID NO:22)

Structure of CTCE0021:
SDF-1(1-14)-(G)4-SDF-1(55-67)-K20/E24-cyclic amide
H2NKPVSLSYRCPCRFFGGGGLKWIQEYLEKALNCONH2              (SEQ ID NO:23)
```

Example 2

Tables 1 and 2 show the effect of CXCR4 agonists on bone marrow progenitor cells, particularly primitive erythroide cells and primitive granulocytes, compared to mature granulocytes. To obtain the data in Tables 1 and 2, cells were pre-incubated with each of the compounds or saline alone ('no drug' as control). The cells were then exposed to high dose $H^3$-thymidine, a cytotoxic agent. Rapidly dividing cells accumulate proportionally more of the cytotoxic radioactive thymidine and as a result are preferentially killed. The relative proportion of cells killed by the thymidine treatment compared to the control is indicative of the relative effectiveness of the compounds in reducing cellular multiplication, i.e. decreasing the rate of cell cycle progression. A higher (or unchanged) proportion of killed cells compared to the control is indicative that a compound does not reduce cellular multiplication of the given cell type.

TABLE 1

Effect of CXCR4 Agonists on Bone Marrow Progenitor Cells Exposed to $H^3$-Thymidine.

| | % CELL KILLED | | |
|---|---|---|---|
| | No drug (control) | SDF-1 | SDF-1(1-9)$_2$ |
| Primitive Erythroide | 71 | 2 | 9 |
| Primitive Granulocyte | 46 | 1 | 1 |
| Mature Granulocyte | 39 | 45 | 42 |

In Table 1, SDF-1 polypeptide (KPVSL SYRCP CRFFE SHVAR ANVKH LKILN TPNCA LQIVA RLKNN NRQVC IDPKL KWIQE YLEKA LN (SEQ ID NO:1)) is used at 100 ng/ml on a human bone marrow cell culture. SDF-1(1-9)$_2$ ((SEQ ID NO:8) KPVSLSYRC-X-CRYSLS-VPK (SEQ ID NO:9)) is used at 50 ug/ml on a human bone marrow cell culture.

Table 2 further demonstrates that SDF-1 (1-14)-(G)$_4$-SDF-1(55-67)-amide (SEQ ID NO:15) and SDF-1(1-14)-(G)$_4$-SDF-1(55-67)-K20/E24-cyclic amide (SEQ ID NO:23) are both able to inhibit cell cycling in human positive erythroid and primitive granulopoietic cells, but not in mature granulopoietic cells, in the assay as described above in this Example.

TABLE 2

| | % CELL KILLED | | |
|---|---|---|---|
| | No drug (control) | Compound A | Compound B |
| Primitive Erythroide | 47 +/− 4 | 5 +/− 3 | −7 +/− 6 |
| Primitive Granulocyte | 42 +/− 3 | 1 +/− 6 | −11 +/− 7 |
| Mature Granulocyte | 48 +/− 3 | 39 +/− 5 | 44 +/− 6 |

Where: Compound A is SDF-1(1-14)-(G)$_4$-SDF-1(55-67)-amide (SEQ ID NO:15);
Compound B is SDF-1(1-14)-(G)$_4$-SDF-1(55-67)-K20/E24-cyclic amide (SEQ ID NO:23).

Example 3

The present example demonstrates the therapeutic effectiveness of CXCR4 agonists in an animal model, showing protection of hematopoietic cells from cytotoxic treatments with CXCR4 agonists. In these animal studies, normal mice were treated with the cytotoxic chemotherapeutic agent arabinose-cytosine (Ara-C), which are known to deleteriously affect cells with high rates of DNA synthesis (reflecting rapid cell cycling).

As shown in the graph of FIG. 1, in mice given a single dose of Arabinose Cytosine (Ara-C) at 350 mg/kg at day zero intravenously, white blood cell count (WBC) decreases (due to the cytotoxic action of Ara-C). In contrast, in mice given the peptide SDF-1(1-14)-(G)$_4$-SDF-1(55-67)-K20/E24-cyclic amide (SEQ ID NO:23) (designated CTC in the graph legend) in combination with Ara-C, the extent of white blood cell count decrease is significantly ameliorated. In the graph, circular data points correspond to the white blood cell count in animals that received Ara-C but did not receive the peptide, and triangular data points are for animals that received Ara-C and SDF-1(1-14)-(G)$_4$-SDF-1(55-67)-K20/E24-cyclic amide (SEQ ID NO:23). The data clearly demonstrated the protective action of the peptide of the invention against the cyctotoxic action of Ara-C.

Example 4

Figure 2A:
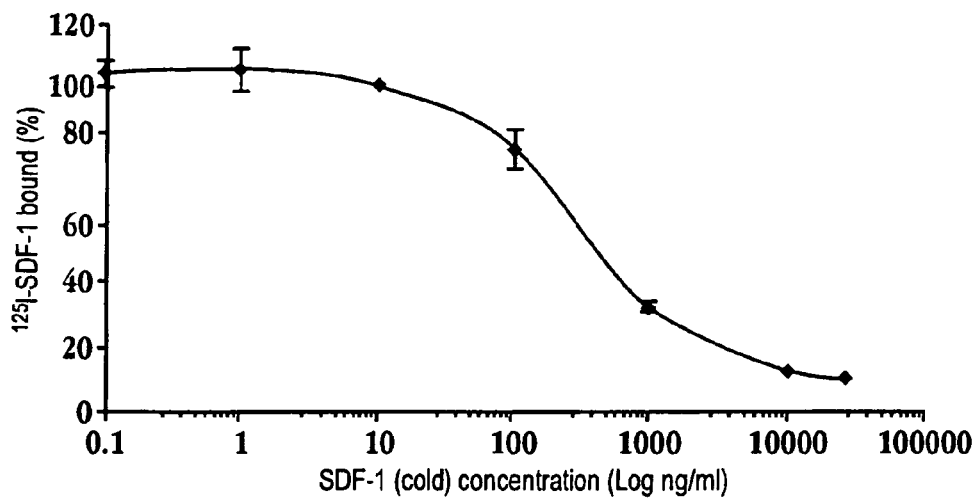
FIGS. 2A and 2B show a concentration-dependant inhibition of $^{125}$I-SDF-1 binding to CXCR4 by SDF-1 (SEQ ID NO:1), obtained as described for the data shown in FIGS. 2A and 2B, indicating the affinity of SDF-1 SEQ ID NO:1) for the CXCR4 receptor.
Figure 2B:
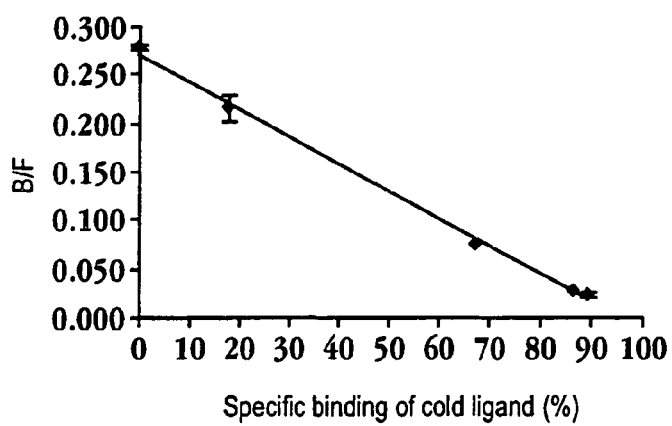
Figure 2C:
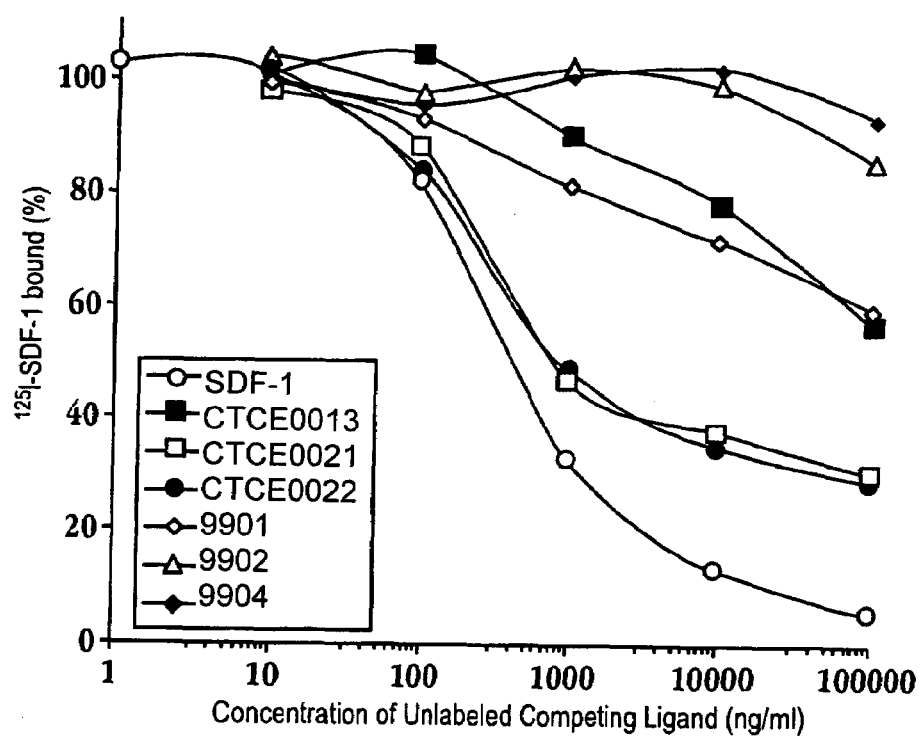
FIG. 2C shows the CXCR4 receptor binding of SDF-1 (SEQ ID NO:1) and the SDF-1 peptide agonist analogs. SDF-1 (SEQ ID NO:1) and the indicated analogs (competing ligands, described in Examples) were added at the concentrations illustrated in the presence of 4 nM $^{125}$I-SDF-1. CEM cells were assessed for $^{125}$I-SDF-1 binding following 2 hr of incubation. The results are expressed as percentages of the maximal specific binding that was determined without competing ligand, and are the mean of three independent experiments.

The efficacy of SDF-1 and SDF-1 peptide analogs as CXCR4 agonists was demonstrated through CXCR4 receptor binding assays. A competitive dose response for binding to the SDF-1 receptor by native SDF-1 and the CXCR4 agonists against $^{125}$I-SDF-1 is shown in FIGS. 2A, 2B, and 2C. A concentration-dependent inhibition of $^{125}$I-SDF-1 is illustrated in FIGS. 2A and 2B, indicating the affinity of SDF-1 for the receptor. A Scartchard plot is illustrated, and the $K_D$ was determined to be 26 nM. SDF-1 and the indicated analogs (competing ligands) were added at the concentrations illustrated in the presence of 4 nM $^{125}$I-SDF-1. CEM cells were assessed for $^{125}$I-SDF-1 binding following 2 hr of incubation. The results are expressed as percentages of the maximal specific binding that was determined without competing ligand, and are the mean of three independent experiments. The inhibition of $^{125}$I-SDF-1 by SDF-1 and the SDF-1 analogs is indicative of CXCR4 receptor binding. The compounds illustrated in the figure are as follows: SDF-1(1-14)-(G)$_4$-SDF-1(55-67)-K20/E24-cyclic amide (CTCE0021), SDF-1(1-14)-(G)$_4$-SDF-1(55-67)-E24/K28-cyclic amide (CTCE0022), SDF-1 (1-9)$_2$-C9/C9-cysteine dimer (CTCE9901), SDF-1(1-17) (CTCE9902), SDF-1 (1-8)$_2$-lysine bridge dimer (CTCE9904) and 32) and SDF-1(1-14)-(G)$_4$-SDF-1(55-67) amide (CTCE0017).

Example 5

Figure 3:
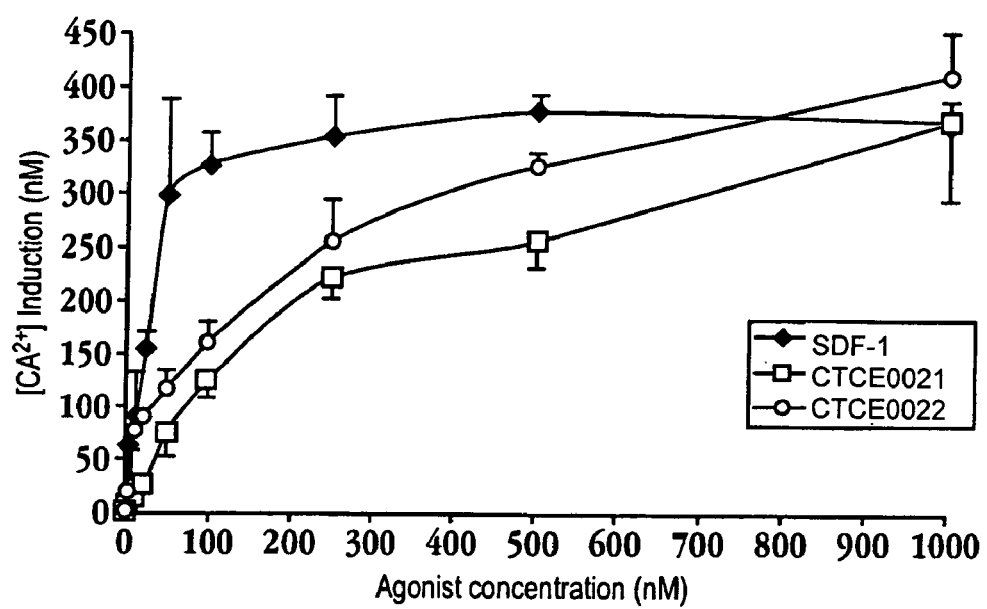
FIG. 3 shows the induction of $[Ca^{2+}]_i$ mobilization by SDF-1 (SEQ ID NO:1) and SDF-1 receptor analogs (described in Examples). Fura-2,AM loaded THP-1 cells ($1\times10^6$/ml) were stimulated with SDF-1 (SEQ ID NO:1) CTCE0021 (SEQ ID NO:23) or CTCE0022 (SEQ ID NO:22) at the concentrations indicated. The values represent the mean +/− one S.D. of n=3 experiments.

This example illustrates the efficacy of SDF-1 and SDF-1 peptide analogs in mediating intracellular calcium mobilization ($[Ca^{2+}]_i$). To illustrate that the binding of SDF-1 and SDF-1 peptide analogs results in the agonistic induction of the CXCR4 receptor, $[Ca^{2+}]_i$ mobilization assays were conducted, the results of which are shown in FIG. 3. To obtain the data shown in FIG. 3, fura-2,AM loaded THP-1 cells (1×10$^6$/ml) were stimulated with SDF-1 (SEQ ID NO:1), SDF-1(1-14)-(G)$_4$-SDF-1(55-67) K20/E24-cyclic amide (SEQ ID NO:23) or SDF-1(1-14)-(G)$_4$-SDF-1(55-67)-E24/K28-cyclic amide (SEQ ID NO:22) at the concentrations indicated (the values represent the mean +/− one S.D. of n=3 experiments). As shown by the data in FIG. 3, incubation of THP-1 cells with SDF-1 (SEQ ID NO:1), SDF-1(1-14)-(G)$_4$-SDF-1(55-67) K20/E24-cyclic amide (SEQ ID NO:23) or SDF-1(1-14)-(G)$_4$-SDF-1(55-67)-E24/K28-cyclic amide (SEQ ID NO:22) resulted in the receptor-mediated induction of [Ca$^{2+}$]$_i$ mobilization. The EC$_{50}$ values (the concentration of ligand necessary to effectively induce 50% of the full [Ca$^{2+}$]$_i$ mobilization potential) for SDF-1(1-14)-(G)$_4$-SDF-1(55-67) acid (SEQ ID NO:13), SDF-1(1-14)-(G)$_4$-SDF-1(55-67)-K20/E24-cyclic amide (SEQ ID NO:23) or SDF-1(1-14)-(G)$_4$-SDF-1(55-67)-E24/K28-cyclic amide (SEQ ID NO:22) and native SDF-1 (SEQ ID NO:1) is shown in Table 3:

TABLE 3

| Compound | EC$_{50}$ (nM) |
|---|---|
| SDF-1 (SEQ ID NO:1) | 26.56 |
| SDF-1(1-14)-(G)$_4$-SDF-1(55-67)-E24/K28-cyclic amide (SEQ ID NO:22) | 106.25 |
| SDF-1(1-14)-(G)$_4$-SDF-1(55-67)-K20/E24-cyclic amide (SEQ ID NO:23) | 147.94 |
| SDF-1(1-14)-(G)$_4$-SDF-1(55-67) acid (SEQ ID NO:13) | 188.30 |

Figure 4:
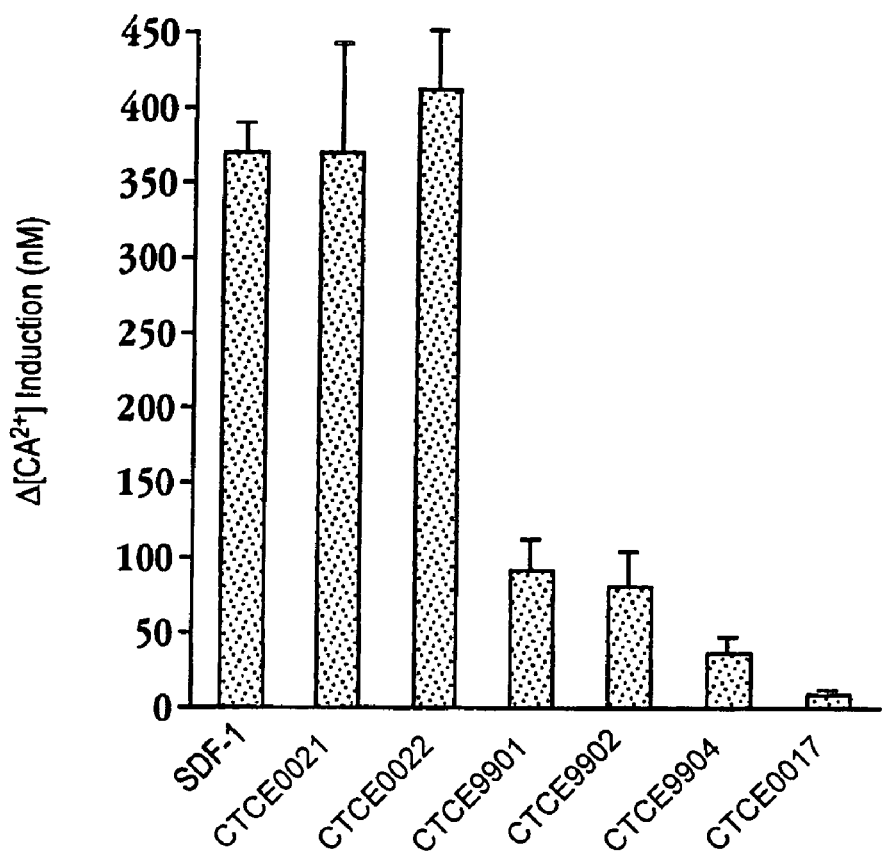
FIG. 4 shows the induction of $[Ca^{2+}]_i$ mobilization by SDF-1 (SEQ ID NO:1) and SDF-1 analogs. Fura-2,AM loaded THP-1 cells ($1\times10^6$/ml) were stimulated with native SDF-1 (SEQ ID NO:1) and the SDF-1 peptide analogs at the concentration of native SDF-1 concentration that gave the maximum $[Ca^{2+}]_i$ stimulation (1 μM). The values represent the mean +/− one S.D. of n=3 experiments. The designated compounds are as follows: SDF-1 (SEQ ID NO:1), SDF-1 (1-14)-(G)$_4$-SDF-1(55-67)-K20/E24-cyclic amide (CTCE0021) (SEQ ID NO:23), SDF-1(1-14)-(G)$_4$-SDF-1 (55-67)-E24/K28-cyclic amide (CTCE0022) (SEQ ID NO:22), SDF-1(1-9)$_2$-C9/C9-cysteine dimer (CTCE9901) (SEQ ID NO:7), SDF-1(1-17) (CTCE9902) (SEQ ID NO:4), SDF-1(1-8)$_2$-lysine bridge dimer (CTCE9904) (SEQ ID NOS:31 and 32) and SDF-1(1-14)-(G)$_4$-SDF-1(55-67) amide (CTCE0017) (SEQ ID NO:15).

The comparative ability of SDF-1 (SEQ ID NO:1), SDF-1(1-14)-(G)$_4$-SDF-1(55-67)-K20/E24-cyclic amide (CTCE0021) (SEQ ID NO:23), SDF-1(1-14)-(G)$_4$-SDF-1(55-67)-E24/K28-cyclic amide (CTCE0022) (SEQ ID NO:22), SDF-1 (1-9)$_2$-C9/C9-cysteine dimer (CTCE9901) (SEQ ID NO:7), SDF-1(1-17) (CTCE9902) (SEQ ID NO:4), SDF-1 (1-8)$_2$lysine bridge dimer (CTCE9904) (SEQ ID NOS:31 and 32) and SDF-1(1-14)-(G)$_4$-SDF-1(55-67) amide (CTCE0017) (SEQ ID NO:15) to induce [Ca$^{2+}$]$_i$ mobilization at the ligand concentration that the native SDF-1 gave maximal [Ca$^{2+}$]$_i$ mobilization (1 µM, refer to FIG. 3) is illustrated in FIG. 4. Fura-2,AM loaded THP-1 cells (1×10$^6$/ml) were stimulated with native SDF-1 and the SDF-1 peptide agonist analogs at the concentration of native SDF-1 that gave the maximum [Ca$^{2+}$]$_i$ stimulation (1 µM) (the values represent the mean +/− one S.D. of n=3 experiments).

Example 6

Primitive high proliferative potential colony forming cells (HHP-CFC) in an adherent layer in culture are usually in a quiescent state. This long term culture (LTC) is established seven to ten days after initiation of the LTC. The cells may be stimulated to proliferate by the addition of fresh medium. Both BFU-E (burst forming unit—erythroid precursor) cells and CFU-GM (colony forming unit—granulocyte-monocyte common precursor) cells of LTC may be maintained in a quiescent state by the mesenchymally derived stromal cells in an adherent layer, but can be reversibly stimulated into the cycle by the addition of fresh media. The ability of CXCR4 agonists such as SDF-1 and SDF-1 polypeptides to overcome this activation may be determined by adding it to the LTC during the medium change. Rapidly dividing cells will accumulate proportionally more of a cytotoxic agent, such as radioactive thymidine, and as a result are preferentially killed.

The results depicted in Table 4 illustrate the ability of SDF-1 (SEQ ID NO:1), and SDF-1(1-14)-(G)$_4$-SDF-1(55-67)-K20/E24-cyclic amide (CTCE0021) (SEQ ID NO:23) and SDF-1(1-14)-(G)$_4$-SDF-1(55-67) acid (CTCE0013) (SEQ ID NO:13) to repress the proliferation of clonogenic erythroid and granulopoitic progenitors (which differentiate into erythrocytes, platelets, monocytes/macrophages and neutrophils) in an in vitro LTC-IC (long-term culture-initiating cells) assay.

TABLE 4

Effect of SDF-1 and SDF-1 agonists on the cycling of primitive progenitors in the adherent layer of human LTC.

| | | % Kill after $^3$H-Thymidine | |
|---|---|---|---|
| Treatment | Dose | Primitive BFU-E | Primitive CFU-GM |
| None | | 48 +/− 4 | 44 +/− 3 |
| CTCE0013 (SEQ ID NO:13) | 1 µg/ml | 24 +/− 6 | 22 +/− 7 |
| | 10 µg/ml | 0 +/− 2 | 0 +/− 0 |
| SDF-1 (SEQ ID NO:1) | 1 µg/ml | 4 +/− 3 | 5 +/− 4 |
| CTCE0021 (SEQ ID NO:23) | 1 µg/ml | 2 +/− 4 | 0 +/− 3 |

To obtain the results set out in Table 4, clonogenic erythroid (BFU-E) and granulopoietic (CFU-GM) progenitors were assayed in methylcellulose cultures. Adherent cells were treated with fresh medium alone (as control) or with the indicated CXCR4 agonist (10 µg/ml SDF-1, CTCE0021 or CTCE0013). Dishes were harvested three days later and $^3$H-thymidine suicide assays performed on the progenitor cells in the adherent layer to determine the proportion of cells killed as a result of accumulation of cytotoxic $^3$H-thymidine, where the difference between the cells in the control and the nuber of cells remaining represent the cells killed.

Figure 5:
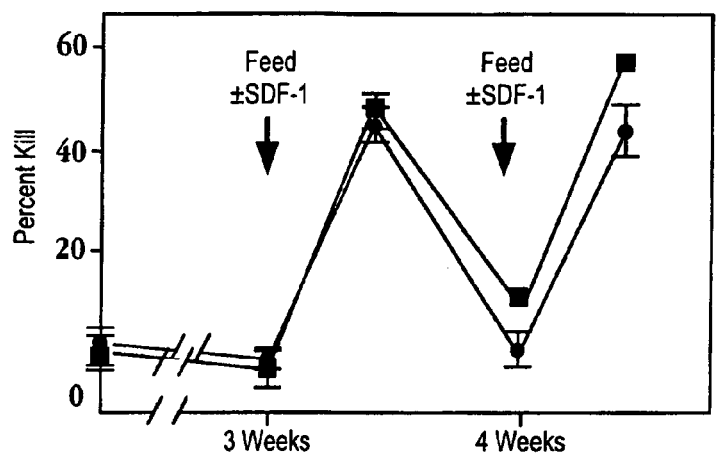
FIG. 5 shows cyclic proliferative activity of primitive normal colony forming cells (CFC) in the adherent layer of a standard long term culture (LTC), in which circles represent BFU-E cells (burst forming unit-erythroid precursors), and squares represent CFU-GM cells (colony forming unit-granulocyte-monocyte common precursor), illustrating the inhibitory effect of SDF-1 on cellular proliferation as measured by the susceptibility of the cells to an agent preferentially cytotoxic to proliferating cells.
Figure 6:
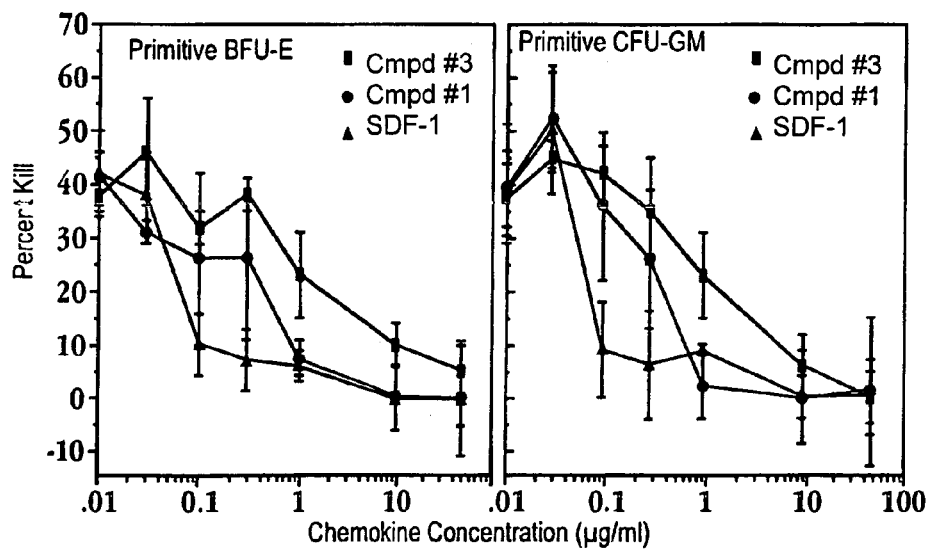
FIG. 6 shows cyclic proliferative activity of primitive normal CFC in the adherent layer of standard LTC, when treated with SDF-1 (SEQ ID NO:1), SDF-1(1-14)-(G)$_4$-SDF-1(55-67)-K20/D24-cyclic amide (Compound #1) (SEQ ID NO:24), SDF-1(1-9)$_2$ (Compound #3) (SEQ ID NOS:8 and 9), as measured by the susceptibility of the cells to an agent preferentially cytotoxic to dividing cells.

FIG. 5 illustrates that feeding cultures SDF-1 in conjunction with media changes results in significantly reduced cell mortality of hematopoietic cells when the cells are challenged with an agent that is preferentially cytotoxic to dividing cells, in which circles represent BFU-E cells (burst forming unit-erythroid precursors), and squares represent CFU-GM cells (colony forming unit-granulocyte-monocyte common precursor). FIG. 6 shows that a similar concentration dependent effect may be obtained with SDF-1(1-14)-(G)$_4$-SDF-1(55-67)-K20/D24-cyclic amide (Compound #1) (SEQ ID NO:25) and SDF-1(1-9)$_2$ (Compound #3) (SEQ ID NOS:8 and 9). Together, FIGS. 5 and 6 illustrate that the SDF-1 (SEQ ID NO:1) polypeptide and SDF-1 peptide analogs repress the cyclic activation of the BFU-E and CFU-GM progenitor stem cells in the adherent layer of LTC.

Example 7

Figure 7:
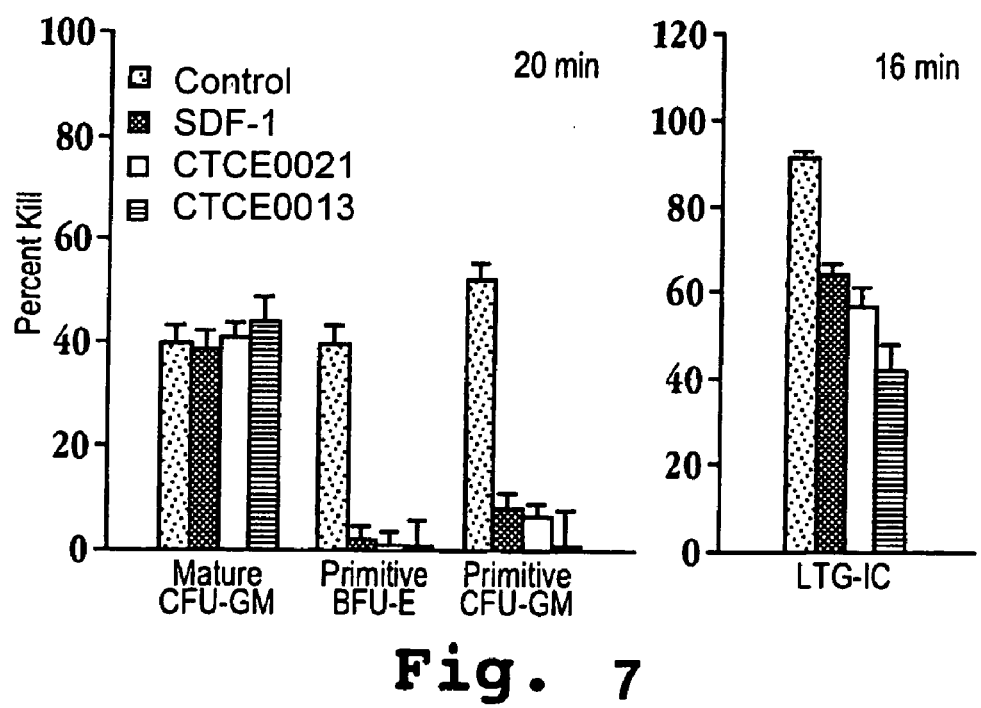
FIG. 7 shows the effect of SDF-1 (SEQ ID NO:1) and SDF-1 analogs (defined in Examples) on the cycling of human progenitors from fetal liver transplanted NOD/SOlD mice. The cycling status of mature and primitive colony forming cells (CFU-GM; colony forming unit-granulocyte-monocyte precursor, BFU-E; burst forming unit-erythroid precursor) in the suspension of CD34$^+$ cells isolated from the marrow of transplanted NOD/SOlD mice was determined by assessing the proportion of these progenitors that were inactivated (killed) by short term (20 min) or overnight (LTC-IC; long-term culture initiating cell) exposure of the cells to 20 μg/ml of high specific activity $^3$H-thymidine. Values represent the mean +/− the S.D. of data from up to four experiments with up to four mice per point in each.
Figure 9:
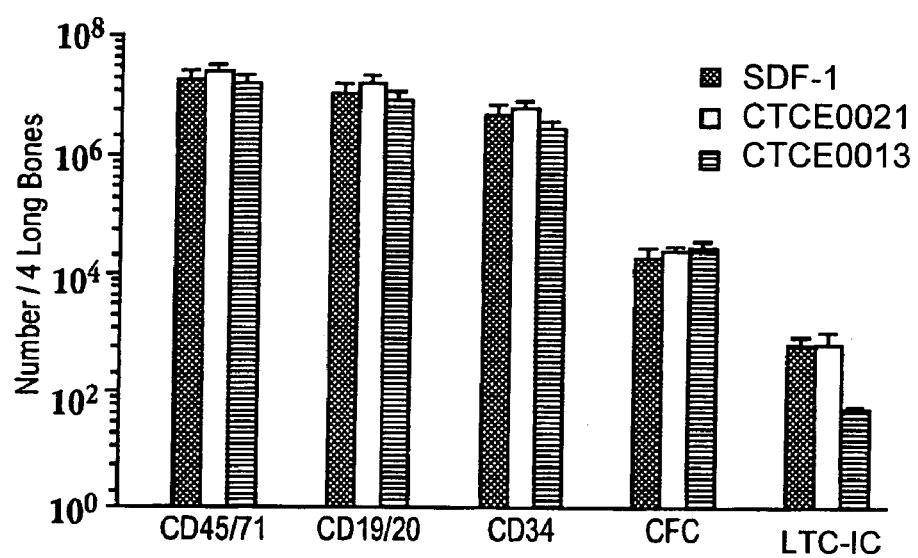
FIG. 9 shows the effect of SDF-1 (SEQ ID NO:1) and SDF-1 Agonists (defined in Examples) on the engraftment of human cells in human fetal liver transplanted NOD/SCID mice. A comparison of the number of phenotypically defined hematopoietic cells detected in the long bones (tibias and femurs) of mice four weeks after being transplanted with 10$^7$ light-density human fetal liver blood cells and then administered SDF-1 (SEQ ID NO:1), CTCE0021 (SEQ ID NO:23) or CTCE0013 (SEQ ID NO:13) (0.5 mg/kg) three times per week for two weeks before sacrifice. Values represent the mean +/− one S.D. of results obtained from three to seven individual mice in three experiments.

FIGS. 7 and 9 show the efficacy of CXCR4 agonists such as SDF-1 and SDF-1 analogues in repressing the proliferation of human progenitor cells in an in vivo engraftment model.

In FIG. 7, the cycling status of mature and primitive colony forming cells (CFU-GM; colony forming unit-granulocyte-monocyte precursor, BFU-E; burst forming unit-erythroid precursor; LTC-IC, long-term culture initiating cell) in the suspension of CD34$^+$ cells isolated from the marrow of transplanted NOD/SCID mice was determined by assessing the proportion of these progenitors that were inactivated (killed) by short term (20 min) or overnight (16 hour) exposure of the cells to 20 µg/ml of high specific activity $^3$H-thymidine (values represent the mean +/− the S.D. of data from up to four experiments with up to four mice per point in each). Significant in the results described in FIG. 4 is the observation that the analogs SDF-1(1-14)-

(G)₄-SDF-1(55-67)-K20/E24-cyclic amide (CTCE0021) (SEQ ID NO:23) and SDF-1 (1-14)-(G)₄-SDF-1(55-67) acid (CTCE0013) (SEQ ID NO:13) are as effective as native SDF-1 (SEQ ID NO:1) at inhibiting the proliferation of "primitive" human progenitor cells, as measured by the reduction of cells killed by exposure to high specific activity ³H-thymidine (which only affects proliferating cells).

Example 8

Figure 8:
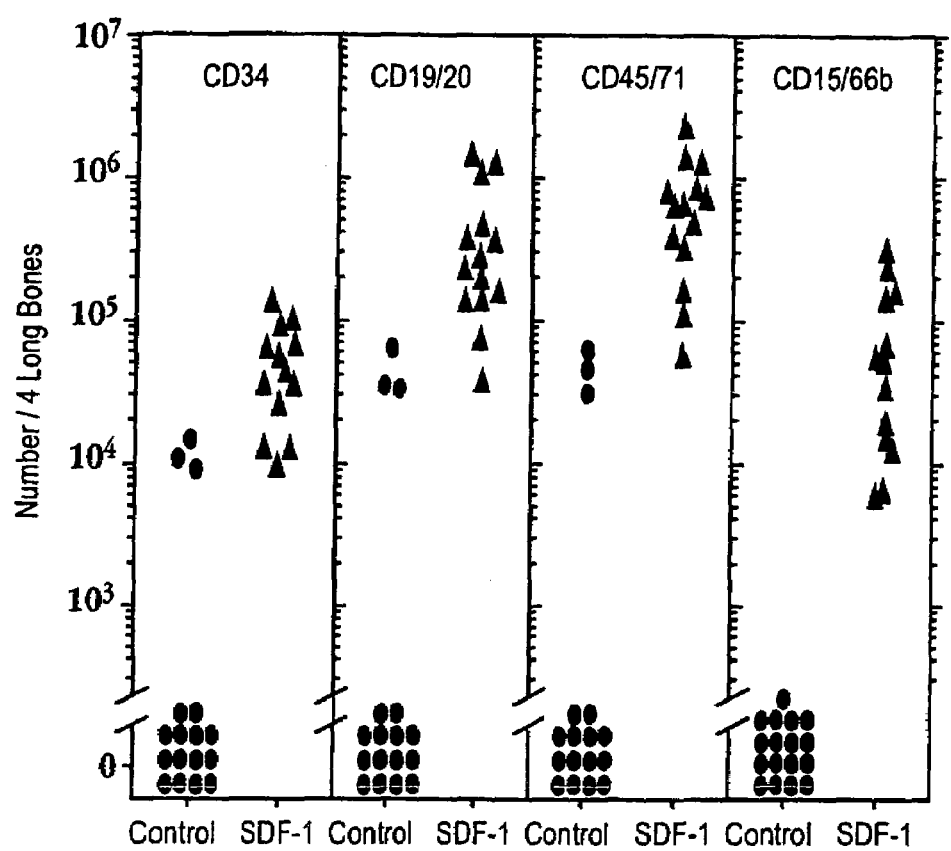
FIG. 8 shows data indicating that SDF-1 enhances the detectability of CRU (colony regenerating units) regenerated in NOD/SCID Mice transplanted with human fetal liver.

SDF-1 enhances the delectability of colony regenerating units (CRU) regenerated in NOD/SCID mice transplanted with human fetal liver cells (FIG. 8). Three to four NOD/SCID mice per group were sublethally irradiated and injected with human cells, in this case 10⁷ light density fetal liver cells, and the mice then maintained for an interval of 2.5-3 weeks. As indicated, each group was then given 2 daily injections of either 10 μg of SDF-1, or an equivalent volume of control medium, and all mice were then sacrificed one day after the second injection. The bone marrow cells from each group were then pooled, and an aliquot removed for FACS analysis and overnight ³H-thymidine suicide assays to measure the cycling activity of the human CFC and LTC-IC (long term culture initiating culture) present. The remainder of the cells were injected into groups of 3-6 secondary recipients. These animals were then sacrificed 6 to 8 weeks later and their bone marrow removed and analysed for the presence of human cells.

This example describes a secondary engraftment. When the bone marrow of the secondary recipients was evaluated, a considerable difference was observed in the level of human cells present in recipients of cells from the different groups of primary mice. As shown in FIG. 8, for SDF-1-injected mice a far greater number of all types of human cells assessed was found in the marrow of the secondary recipients that had received marrow from primary mice treated with either SDF-1 by comparison to recipients of cells from media injected control primary mice.

Example 9

This example illustrates the effect of CXCR4 agonists such as SDF-1 (SEQ ID NO:1) and SDF-1 polypeptide analogs on the engraftment of human cells in human fetal liver transplanted NOD/SCID mice (FIG. 9). As shown in this figure, there was a lack of short-term effect of CXCR4 agonists on the frequency of different human cells present in NOD/SCID mice. In these experiments, 6 to 8 weeks post-transplanted mice were injected two times, one day apart with the test compound (SDF-1 (SEQ ID NO:1), SDF-1(1-14)-(G)₄-SDF-1(55-67)-K20/E24-cyclic amide (CTCE0021) (SEQ ID NO:23) or SDF-1(1-14)-(G)₄-SDF-1(55-67) acid (CTCE013) SEQ ID NO:13)) and sacrificed one day later. The frequency of the phenotypically defined human hematopoietic cells detected in the long bones (tibias and femurs) of mice was determined. Administration of 0.5 mg/kg of SDF-1 had no significant effect on the number of CD45/71, CD19/20, or CD34 cells, nor on the CFC or LTC-IC. In addition, none of the human cell types were detectably affected by this schedule of CXCR4 agonist administration. This data, coupled with that of FIGS. 7 and 8, indicates that SDF-1 (SEQ ID NO:1), SDF-1 analogs and other CXCR4 agonists may effectively augment secondary engraftment of human progenitor cells.

Example 10

Figure 10:
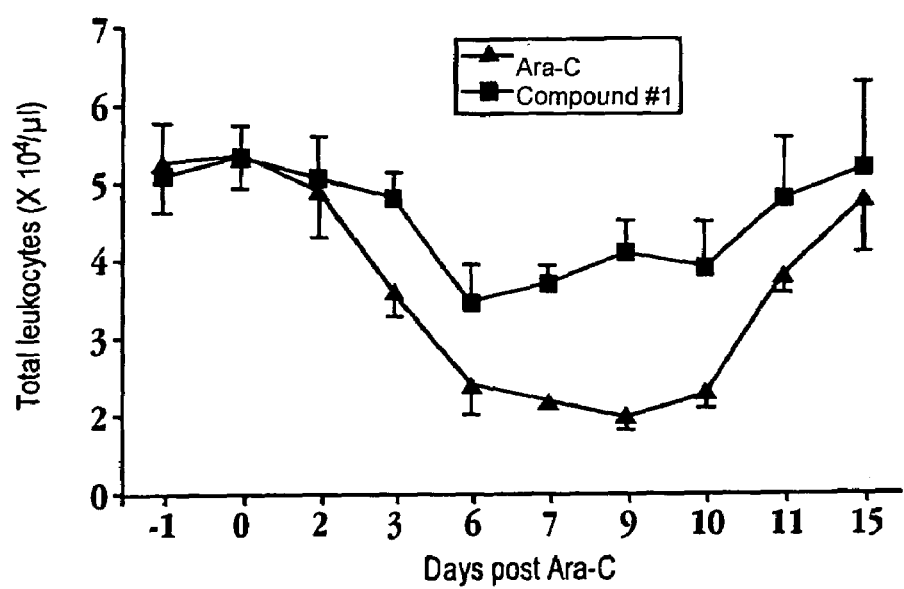
FIG. 10 shows the effect of CTCE0021 (SEQ ID NO:23) (1 mg/kg, defined in the Examples) on the recovery of leukocytes following myeloablative chemotherapy with Ara-C (300 mg/kg). Mice were treated with Ara-C alone (Ara-C) or in combination with CTCE0021 (SEQ ID NO:23). The results represent the mean +/− one S.D. of 6 animals/group.

This example illustrates the effect of an SDF-1 polypeptide analog CTCE0021 (SEQ ID NO:23) (10 mg/kg, identified as Compound #1 in FIG. 12) on the recovery of leukocytes following myeloablative chemotherapy with Ara-C (300 mg/kg). In the experiment described in the example, C3Hhen mice (female) were treated with 500 mg/kg Ara-C for two cycles—on days 0 and 10. During the second cycle of Ara-C dosing, Ara-C treated mice were injected with 10 mg/kg CTCE0021 (SEQ ID NO:23) each day. A control was conducted with animals treated with Ara-C alone. Blood was collected from the tail vein into heparin-containing tubes at the onset of the experiment, and one day before every day following the second Ara-C dose. A total leukocyte count was determined. As shown in the graph of FIG. 10, the CXCR4 agonist CTCE0021 (SEQ ID NO:23) acted to inhibit the cytotoxic effects of Ara-C and to sustain a higher level of leukocytes, illustrating the reversal of myelosuppressive effects of a chemotherapeutic regimen in vivo.

Example 11

Figure 11:
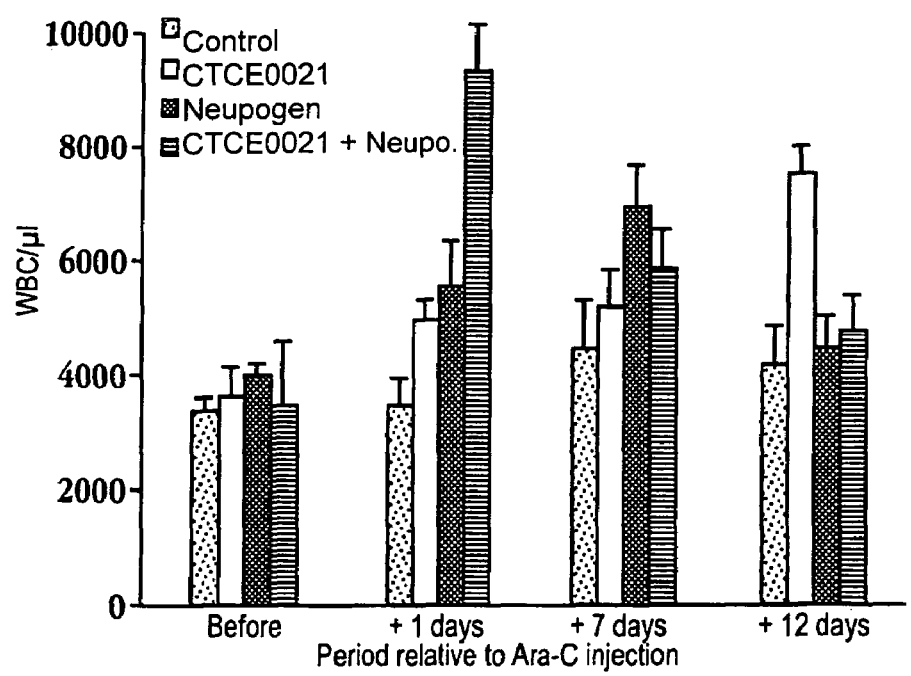
FIG. 11 shows the effect of CTCE0021 (SEQ ID NO:23) (defined in Examples) and Neupogen® (G-CSF) on the growth of white blood cells in Ara-C treated mice. C3Hhen mice (female) were treated with 500 mg/kg Ara-C for two cycles—on days 0 and 10. During the second cycle of Ara-C dosing, Ara-C treated mice were injected with 10 mg/kg CTCE0021 (SEQ ID NO:23), 10 mg/kg Neupogen®, alone or together (on days −1, 0, and 1 to 3). Control represents animals treated with Ara-C alone. Blood was collected from the tail vein into heparin-containing tubes at the onset of the experiment, and one day before and 1, 7 and 12 days following the second Ara-C dose. A total white blood cell count was obtained. The results represent the mean +/− one S.D. of 6 animals/group.

This example illustrates the effect of an SDF-1 polypeptide analog SDF-1(1-14)-(G)4-SDF-1(55-67)-K20/E24-cyclic amide (CTCE0021 (SEQ ID NO:23) 1 mg/kg) on the recovery of leukocytes following myeloablative chemotherapy with Ara-C (500 mg/kg) compared to G-CSF (Neupogen®) (FIG. 11). C3Hhen mice (female) were treated with 500 mg/kg Ara-C for two cycles—on days 0 and 10. During the second cycle of Ara-C dosing, Ara-C treated mice were injected with 10 mg/kg CTCE0021 (SEQ ID NO:23), 10 mg/kg Neupogen®, alone or together (on days -1, 0, and 1 to 3), with controls receiving no drug. Blood was collected from the tail vein into heparin-containing tubes at the onset of the experiment, and one day before and 1, 7 and 12 days following the second Ara-C dose. A total white blood cell count was obtained. The results in this example indicates that not only does treatment with CTCE0021 (SEQ ID NO:23) enhance the recovery of white blood cells following myeloablative chemotherapy with Ara-C, co-treatment with the SDF-1 polypeptide analog and G-CSF (Neupogen®) resulted in a greater recovery compared the animals treated with G-CSF alone during the early treatment phase. Furthermore, the recovery following treatment with the SDF-1 polypeptide analog was sustained compared to the G-CSF treated animals.

Figure 12:
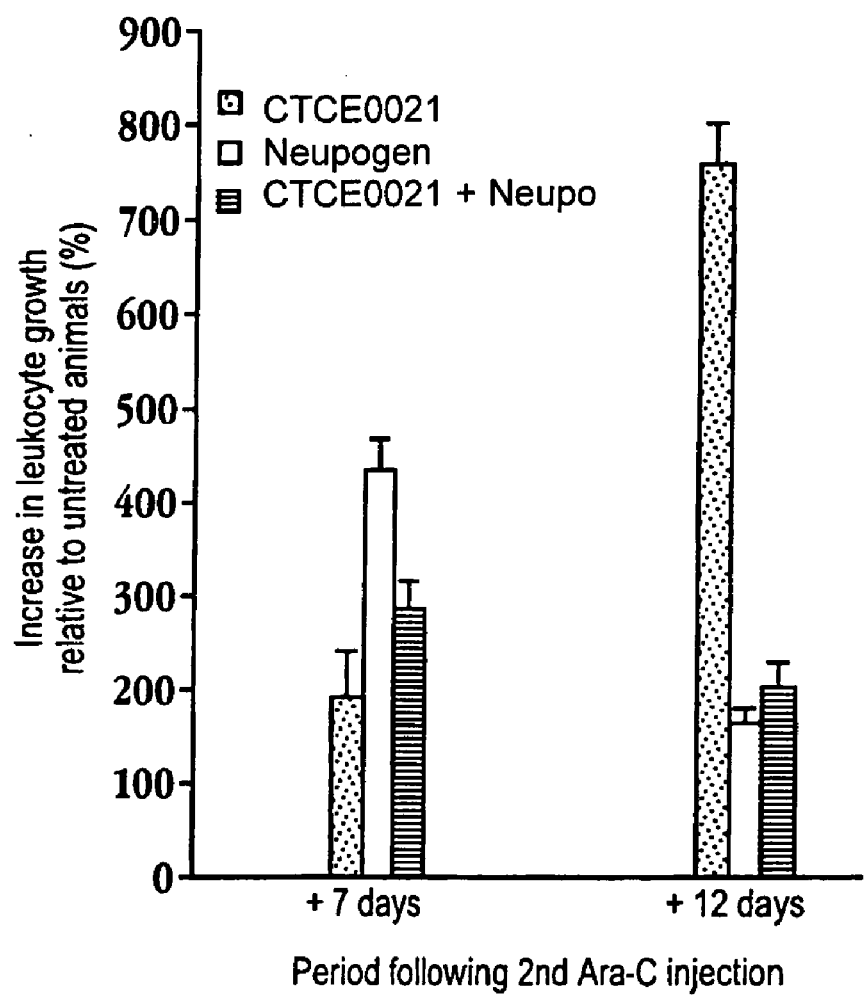
FIG. 12 shows the effect of CTCE0021 (SEQ ID NO:23) and Neupogen® on the relative growth of white blood cells in Ara-C treated mice. C3Hhen mice (female) were treated with 500 mg/kg Ara-C for two cycles—on days 0 and 10. During the second cycle of Ara-C dosing, Ara-C treated mice were injected with 10 mg/kg CTCE0021 (SEQ ID NO:23) (defined in Examples), 10 mg/kg Neupogen®, alone or together (on days −1, 0, and 1 to 3). Control represents animals treated with Ara-C alone. Blood was collected from the tail vein into heparin-containing tubes at the onset of the experiment, and one day before 7 and 12 days following the second Ara-C dose. A total white blood cell count was obtained. The increase in leukocytes (white blood cells) was determined relative to the number of cells counted the day before the second cycle Ara-C dose was administered. The results represent the mean +/− one S.D. of 6 animals/group.

FIG. 12 depicts the results of an experiment conducted under identical conditions, but the growth (increase in leukocyte count) relative to the number of cells counted in animals treated with Ara-C alone is illustrated. By twelve days following Ara-C administration, an approximately 7.5-fold increase in leukocytes was observed in mice treated with CTCE0021 (SEQ ID NO:23) relative to animals treated with Ara-C alone, compared to 180% obtained in animals treated with Neupogen®.

Example 12

Table 5 shows the effect of the CXCR4 agonist, CTCE-0021 (SEQ ID NO:23), on the mobilization of leukocytes (neutrophils) in mice injected intravenously. CTCE-0021 (SEQ ID NO:23) was injected intravenously into Balb/C mice at 25 mg/kg. To obtain the data in Table 4, blood was collected through cardiac puncture and counted for the increase in white blood cells, and platelets.

TABLE 5

Effect of the SDF-1 agonist, CTCE-0021, on the mobilization of leukocytes (neutrophils) in mice.

| Treatment day | Neutrophils ($10^9$/l) | Lymphocytes ($10^9$/l) | Platelets ($10^9$/l) |
|---|---|---|---|
| Day 0 (untreated) | 0.968 +/− 0.311 | 4.78 +/− 0.88 | 1099 +/− 50 |
| Day 2 (CTCE-0021 (SEQ ID NO:23) treated) | 3.159 +/− 0.761 | 3.15 +/− 1.075 | 1044 +/− 65 |
| Day 3 (CTCE-0021 (SEQ ID NO:23) treated) | 3.209 +/− 0.735 | 3.371 +/− 1.113 | 977 +/− 152 |
| Day 5 (CTCE-0021 (SEQ ID NO:23) treated) | 1.592 +/− 0.961 | 5.325 +/− 0.771 | 882 +/− 88 |
| Day 5 (untreated) | 0.893 +/− 0.371 | 6.540 +/− 0.970 | 937 +/− 169 |
| Day 8 (CTCE-0021 (SEQ ID NO:23) treated) | 2.513 +/− 2.733 | 4.072 +/− 1.386 | 1111 +/− 124 |

In Table 5, CTCE-0021 peptide is represented by the following structure: SDF-1(1-31 K20/E24-cyclic amide) Agonist (SEQ ID NO:23).

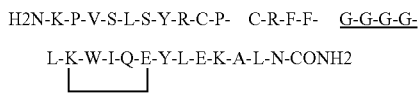

H2N-K-P-V-S-L-S-Y-R-C-P- C-R-F-F- G-G-G-G-L-K-W-I-Q-E-Y-L-E-K-A-L-N-CONH2

These results demonstrate that CXCR-4 agonists, such as CTCE-0021 (SEQ ID NO:23), may be used to mobilize neutrophils (for example in patients undergoing chemotherapy to facilitate blood cell recovery). In this example, intravenous injection of the CXCR-agonist may facilitate the creation of an artificial chemotactic gradient, which may facilitate an immune response in the target tissue (in this case blood). The gradient is established when the active therapeutic compound has pharmacokinetic characteristics that facilitate an appropriate residence time in the tissue into which the compound is administered, coupled with an appropriate susceptibility to degradation in vivo so that the concentration of the compound decreases away from the target tissue. In alternative embodiments, the invention therefore provides methods of treating a subject comprising administering to a target tissue a labile chemokine receptor agonist or antagonist so as to create an artificial chemotactic gradient. The agonist or antagonist may for example have a plasma half life of not more than 2 hours, as is the case with CTCE-0021, or not more than 1, 3, 4, or 5 hours in alternative embodiments. One aspect of the invention provides a route of therapeutic chemokine administration which establishes an essentially uniform dosage of the chemokine receptor ligand in the target tissue, with a decreasing dosage of the chemokine radiating from the target tissue. For example, an inhaled aerosol formulation may be used to administer a labile chemokine receptor agonist or antagonist to the lung epithelium.

Example 13

Alternative embodiments of CTCE0021-like and CTCE0022-like SDF-1 analogs may include CXCR4 agonist peptides such as:

SDF-1-derived E24/K28-cyclic amide (CTCE0021-like) compounds having the formula

[RNH-Lys]XaaVSXbbSYRCPCRFF[linker]LK-WIQEYLEKALN-NH$_2$ (SEQ ID NOS:50-52);

and

SDF-1-derived K20/E24-cyclic amides (CTCE0022-like) compounds having the formula

[RCONH-Lys]XaaVSXbbSYRCPCRFF[linker]LK-WIQEYLEKALN-NH$_2$ (SEQ ID NOS:53-55).

In the foregoing peptides, R is a substituent that may for example be a hydrogen, alkyl, aryl or polyethyleneglycol (PEG) moiety; Xaa is an amino acid that may for example be either an L-Proline or a D-Proline moiety; Xbb is an amino acid that may for example be either a L-Leucine or a D-Leucine moiety; and [linker] is a moiety providing a covalent attachment between the N and C terminal portions of the peptides, such as a linking moiety having 4 glycines (SEQ ID NO:211) or NH$_2$—(CH$_2$)$_n$—COOH (n=0-20).

Alternative embodiments of the forgoing peptides are as follows:

CTCE-0021-like Analogs

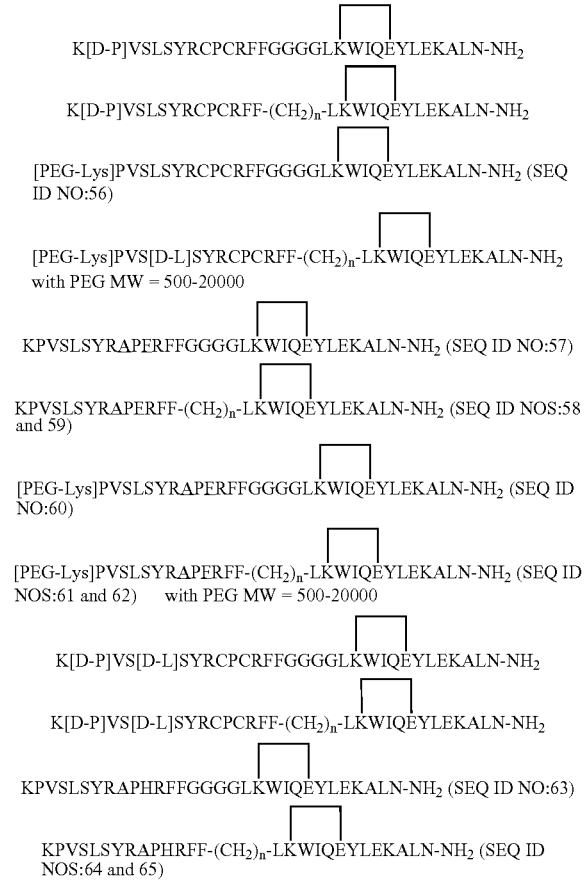

-continued

[PEG-Lys]PVSLSYRAPHRFFGGGGLKWIQEYLEKALN-NH₂ (SEQ ID NO:66)

[PEG-Lys]PVSLSYRAPHRFF-(CH₂)ₙ-LKWIQEYLEKALN-NH₂ (SEQ ID NO:67 and 68) with PEG(Polyethyleneglycol chain) MW = 500-20000

K[D-P]VS[D-L]SYRAPHRFFGGGGLKWIQEYLEKALN-NH₂

K[D-P]VS[D-L]SYRAPHRFF-(CH₂)ₙ-LKWIQEYLEKALN-NH₂

KPVSLSYRAPWRFFGGGGLKWIQEYLEKALN-NH₂ (SEQ ID NO:69)

KPVSLSYRAPWRFF-(CH₂)ₙ-LKWIQEYLEKALN-NH₂ (SEQ ID NOS:70 and 71)

[PEG-Lys]PVSLSYRAPWRFFGGGGLKWIQEYLEKALN-NH₂ (SEQ ID NO:72)

[PEG-Lys]PVSLSYRAPWRFF-(CH₂)ₙ-LKWIQEYLEKALN-NH₂ (SEQ ID NOS:73 and 74) with PEG(Polyethyleneglycol chain) MW = 500-20000

K[D-P]VS[D-L]SYRAPWRFFGGGGLKWIQEYLEKALN-NH₂

K[D-P]VS[D-L]SYRAPWRFF-(CH₂)ₙ-LKWIQEYLEKALN-NH₂

KPVSLSYREPARFFGGGGLKWIQEYLEKALN-NH₂ (SEQ ID NO:75)

KPVSLSYREPARFF-(CH₂)ₙ-LKWIQEYLEKALN-NH₂ (SEQ ID NOS:76 and 77)

[PEG-Lys]PVSLSYREPARFFGGGGLKWIQEYLEKALN-NH₂ (SEQ ID NO:78)

[PEG-Lys]PVSLSYREPARFF-(CH₂)ₙ-LKWIQEYLEKALN-NH₂ (SEQ ID NOS:79 and 80) with PEG(Polyethyleneglycol chain) MW = 500-20000

K[D-P]VS[D-L]SYREPARFFGGGGLKWIQEYLEKALN-NH₂

K[D-P]VS[D-L]SYREPARFF-(CH₂)ₙLKWIQEYLEKALN-NH₂

KPVSLSYRHPARFFGGGGLKWIQEYLEKALN-NH₂ (SEQ ID NO:81)

KPVSLSYRHPARFF-(CH₂)ₙ-LKWIQEYLEKALN-NH₂ (SEQ ID NOS:82 and 83)

[PEG-Lys]PVSLSYRHPARFFGGGGLKWIQEYLEKALN-NH₂ (SEQ ID NO:84)

[PEG-Lys]PVSLSYRHPARFF-(CH₂)ₙ-LKWIQEYLEKALN-NH₂ (SEQ ID NOS:85 and 86) with PEG(Polyethyleneglycol chain) MW = 500-20000

K[D-P]VS[D-L]SYRHPARFFGGGGLKWIQEYLEKALN-NH₂

K[D-P]VS[D-L]SYRHPARFF-(CH₂)ₙ-LKWIQEYLEKALN-NH₂

KPVSLSYRWPARFFGGGGLKWIQEYLEKALN-NH₂ (SEQ ID NO:87)

KPVSLSYRWPARFF-(CH₂)ₙ-LKWIQEYLEKALN-NH₂ (SEQ ID NOS:88 and 89)

[PEG-Lys]PVSLSYRWPARFFGGGGLKWIQEYLEKALN-NH₂ (SEQ ID NO:90)

[PEG-Lys]PVSLSYRWPARFF-(CH₂)ₙ-LKWIQEYLEKALN-NH₂ (SEQ ID NOS:91 and 92) with PEG(Polyethyleneglycol chain) MW = 500-20000

K[D-P]VS[D-L]SYRWPARFFGGGGLKWIQEYLEKALN-NH₂

K[D-P]VS[D-L]SYRWPARFF-(CH₂)ₙ-LKWIQEYLEKALN-NH₂

KPVSLSYRAPYRFFGGGGLKWIQEYLEKALN-NH₂ (SEQ ID NO:93)

KPVSLSYRWPYRFF-(CH₂)ₙ-LKWIQEYLEKALN-NH₂ (SEQ ID NOS: 94 and 95)

[PEG-Lys]PVSLSYRAPYRFFGGGGLKWIQEYLEKALN-NH₂ (SEQ ID NO:96)

[PEG-Lys]PVSLSYRAPYRFF-(CH₂)ₙ-LKWIQEYLEKALN-NH₂ (SEQ ID NOS:97 and 98) with PEG(Polyethyleneglycol chain) MW = 500-20000

K[D-P]VS[D-L]SYRAPYRFFGGGGLKWIQEYLEKALN-NH₂

K[D-P]VS[D-L]SYRAPYRFF-(CH₂)ₙ-LKWIQEYLEKALN-NH₂

KPVSLSYRYPYRFFGGGGLKWIQEYLEKALN-NH₂ (SEQ ID NO:99)

KPVSLSYRYPYRFF-(CH₂)ₙ-LKWIQEYLEKALN-NH₂ (SEQ ID NOS:100 and 101)

[PEG-Lys]PVSLSYRYPYRFFGGGGLKWIQEYLEKALN-NH₂ (SEQ ID NO:102)

[PEG-Lys]PVSLSYRYPYRFF-(CH₂)ₙ-LKWIQEYLEKALN-NH₂ (SEQ ID NOS:103 and 104) with PEG(Polyethyleneglycol chain) MW = 500-20000

K[D-P]VS[D-L]SYRYPYRFFGGGGLKWIQEYLEKALN-NH₂

K[D-P]VS[D-L]SYRYPYRFF-(CH₂)ₙ-LKWIQEYLEKALN-NH₂

KPVSLSYRYPARFFGGGGLKWIQEYLEKALN-NH₂ (SEQ ID NO:105)

KPVSLSYRYPARFF-(CH₂)ₙ-LKWIQEYLEKALN-NH₂ (SEQ ID NOS:106 and 107)

[PEG-Lys]PVSLSYRYPARFFGGGGLKWIQEYLEKALN-NH₂ (SEQ ID NO:108)

[PEG-Lys]PVSLSYRYPARFF-(CH₂)ₙ-LKWIQEYLEKALN-NH₂ (SEQ ID NOS:109 and 110) with PEG(Polyethyleneglycol chain) MW = 500-20000

K[D-P]VS[D-L]SYRYPARFFGGGGLKWIQEYLEKALN-NH₂

-continued

K[D-P]VS[D-L]SYRYPARFF-(CH₂)ₙ-LKWIQEYLEKALN-NH₂

KPVSLSYREPERFFGGGGLKWIQEYLEKALN-NH₂ (SEQ ID NO:111)

KPVSLSYREPERFF-(CH₂)ₙ-LKWIQEYLEKALN-NH₂ (SEQ ID NOS:112 and 113)

[PEG-Lys]PVSLSYREPERFFGGGGLKWIQEYLEKALN-NH₂ (SEQ ID NO:114)

[PEG-Lys]PVSLSYREPERFF-(CH₂)ₙ-LKWIQEYLEKALN-NH₂ (SEQ ID NOS:115 and 116) with PEG(Polyethyleneglycol chain) MW = 500-20000

K[D-P]VS[D-L]SYREPERFFGGGGLKWIQEYLEKALN-NH₂

K[D-P]VS[D-L]SYREPERFF-(CH₂)ₙ-LKWIQEYLEKALN-NH₂

KPVSLSYRHPHRFFGGGGLKWIQEYLEKALN-NH₂ (SEQ ID NO:117)

KPVSLSYRHPHRFF-(CH₂)ₙ-LKWIQEYLEKALN-NH₂ (SEQ ID NOS:118 and 119)

[PEG-Lys]PVSLSYRHPHRFFGGGGLKWIQEYLEKALN-NH₂ (SEQ ID NO:120)

[PEG-Lys]PVSLSYRHPHRFF-(CH₂)ₙ-LKWIQEYLEKALN-NH₂ (SEQ ID NOS:121 and 122) with PEG(Polyethyleneglycol chain) MW = 500-20000

K[D-P]VS[D-L]SYRHPHRFFGGGGLKWIQEYLEKALN-NH₂

K[D-P]VS[D-L]SYRHPHRFF-(CH₂)ₙ-LKWIQEYLEKALN-NH₂

KPVSLSYRWPWRFFGGGGLKWIQEYLEKALN-NH₂ (SEQ ID NO:123)

KPVSLSYRWPWRFF-(CH₂)ₙ-LKWIQEYLEKALN-NH₂(SEQ ID NOS:124 and 125)

[PEG-Lys]PVSLSYRWPWRFFGGGGLKWIQEYLEKALN-NH₂ (SEQ ID NO:126)

[PEG-Lys]PVSLSYRWPWRFF-(CH₂)ₙ-LKWIQEYLEKALN-NH₂ (SEQ ID NOS:127 and 128) with PEG(Polyethyleneglycol chain) MW = 500-20000

K[D-P]VS[D-L]SYRWPWRFFGGGGLKWIQEYLEKALN-NH₂

K[D-P]VS[D-L]SYRWPWRFF-(CH₂)ₙ-LKWIQEYLEKALN-NH₂

CTCE-0022-like Analogs

K[D-P]VS[D-L]SYRCPCRFFGGGGLKWIQEYLEKALN-NH₂

K[D-P]VS[D-L]SYRCPCRFF-(CH₂)ₙ-LKWIQEYLEKALN-NH₂

[PEG-Lys]PVSLSYRCPCRFFGGGGLKWIQEYLEKALN-NH₂ (SEQ ID NO:129)

[PEG-Lys]PVSLSYRCPCRFF-(CH₂)ₙ-LKWIQEYLEKALN-NH₂ (SEQ ID NOS:130 and 131) with PEG(Polyethyleneglycol chain) MW = 500-20000

KPVSLSYRAPERFFGGGGLKWIQEYLEKALN-NH₂ (SEQ ID NO:132)

KPVSLSYRAPERFF-(CH₂)ₙ-LKWIQEYLEKALN-NH₂ (SEQ ID NOS:133 and 134)

[PEG-Lys]PVSLSYRAPERFFGGGGLKWIQEYLEKALN-NH₂ (SEQ ID NO:135)

[PEG-Lys]PVSLSYRAPERFF-(CH₂)ₙ-LKWIQEYLEKALN-NH₂ (SEQ ID NOS:136 and 137) with PEG(Polyethyleneglycol chain) MW = 500-20000

K[D-P]VS[D-L]SYRCPCRFFGGGGLKWIQEYLEKALN-NH₂

K[D-P]VS[D-L]SYRCPCRFF-(CH₂)ₙ-LKWIQEYLEKALN-NH₂

KPVSLSYRAPHRFFGGGGLKWIQEYLEKALN-NH₂ (SEQ ID NO:138)

KPVSLSYRAPHRFF-(CH₂)ₙ-LKWIQEYLEKALN-NH₂ (SEQ ID NO:139 and 140)

[PEG-Lys]PVSLSYRAPHRFFGGGGLKWIQEYLEKALN-NH₂ (SEQ ID NO:141)

[PEG-Lys]PVSLSYRAPHRFF-(CH₂)ₙ-LKWIQEYLEKALN-NH₂ (SEQ ID NOS:142 and 143) with PEG(Polyethyleneglycol chain) MW = 500-20000

K[D-P]VS[D-L]SYRAPHRFFGGGGLKWIQEYLEKALN-NH₂

K[D-P]VS[D-L]SYRAPHRFF-(CH₂)ₙ-LKWIQEYLEKALN-NH₂

KPVSLSYRAPWRFFGGGGLKWIQEYLEKALN-NH₂ (SEQ ID NO:144)

KPVSLSYRAPWRFF-(CH₂)ₙ-LKWIQEYLEKALN-NH₂ (SEQ ID NOS:145 and 146)

[PEG-Lys]PVSLSYRAPWRFFGGGGLKWIQEYLEKALN-NH₂ (SEQ ID NO:147)

[PEG-Lys]PVSLSYRAPWRFF-(CH₂)ₙ-LKWIQEYLEKALN-NH₂ (SEQ ID NO:148 and 149) with PEG(Polyethyleneglycol chain) MW = 500-20000

K[D-P]VS[D-L]SYRAPWRFFGGGGLKWIQEYLEKALN-NH₂

K[D-P]VS[D-L]SYRAPWRFF-(CH₂)ₙ-LKWIQEYLEKALN-NH₂

KPVSLSYREPARFFGGGGLKWIQEYLEKALN-NH₂ (SEQ ID NO:150)

KPVSLSYREPARFF-(CH₂)ₙ-LKWIQEYLEKALN-NH₂ (SEQ ID NOS:151 and 152)

[PEG-Lys]PVSLSYREPARFFGGGGLKWIQEYLEKALN-NH₂ (SEQ ID NO:153)

-continued

[PEG-Lys]PVSLSYREPARFF-(CH₂)ₙ-LKWIQEYLEKALN-NH₂ (SEQ ID NOS:154 and 155) with PEG(Polyethyleneglycol chain) MW = 500-20000

K[D-P]VS[D-L]SYREPARFFGGGGLKWIQEYLEKALN-NH₂

K[D-P]VS[D-L]SYREPARFF-(CH₂)ₙ-LKWIQEYLEKALN-NH₂

KPVSLSYRHPARFFGGGGLKWIQEYLEKALN-NH₂ (SEQ ID NO:156)

KPVSLSYRHPARFF-(CH₂)ₙ-LKWIQEYLEKALN-NH₂ (SEQ ID NOS:157 and 158)

[PEG-Lys]PVSLSYRHPARFFGGGGLKWIQEYLEKALN-NH₂ (SEQ ID NO:159)

[PEG-Lys]PVSLSYRHPARFF-(CH₂)ₙ-LKWIQEYLEKALN-NH₂ (SEQ ID NOS:160 and 161) with PEG(Polyethyleneglycol chain) MW = 500-20000

K[D-P]VS[D-L]SYRHPARFFGGGGLKWIQEYLEKALN-NH₂

K[D-P]VS[D-L]SYRHPARFF-(CH₂)ₙ-LKWIQEYLEKALN-NH₂

KPVSLSYRWPARFFGGGGLKWIQEYLEKALN-NH₂ (SEQ ID NO:162)

KPVSLSYRWPARFF-(CH₂)ₙ-LKWIQEYLEKALN-NH₂ (SEQ ID NOS:163 and 164)

[PEG-Lys]PVSLSYRWPARFFGGGGLKWIQEYLEKALN-NH₂ (SEQ ID NO:165)

[PEG-Lys]PVSLSYRWPARFF-(CH₂)ₙ-LKWIQEYLEKALN-NH₂ (SEQ ID NOS:166 and 167) with PEG(Polyethyleneglycol chain) MW = 500-20000

K[D-P]VS[D-L]SYRWPARFFGGGGLKWIQEYLEKALN-NH₂

K[D-P]VS[D-L]SYRWPARFF-(CH₂)ₙ-LKWIQEYLEKALN-NH₂

KPVSLSYRAPYRFFGGGGLKWIQEYLEKALN-NH₂ (SEQ ID NO:168)

KPVSLSYRAPYRFF-(CH₂)ₙ-LKWIQEYLEKALN-NH₂ (SEQ ID NOS:169 and 170)

[PEG-Lys]PVSLSYRAPYRFFGGGGLKWIQEYLEKALN-NH₂ (SEQ ID NO:171)

[PEG-Lys]PVSLSYRAPYRFF-(CH₂)ₙ-LKWIQEYLEKALN-NH₂ (SEQ ID NOS:172 and 173) with PEG(Polyethyleneglycol chain) MW = 500-20000

K[D-P]VS[D-L]SYRAPYRFFGGGGLKWIQEYLEKALN-NH₂

K[D-P]VS[D-L]SYRAPYRFF-(CH₂)ₙ-LKWIQEYLEKALN-NH₂

KPVSLSYRYPYRFFGGGGLKWIQEYLEKALN-NH₂ (SEQ ID NO:174)

KPVSLSYRYPYRFF-(CH₂)ₙ-LKWIQEYLEKALN-NH₂ (SEQ ID NOS:175 and 176)

[PEG-Lys]PVSLSYRYPYRFFGGGGLKWIQEYLEKALN-NH₂ (SEQ ID NO:177)

[PEG-Lys]PVSLSYRYPYRFF-(CH₂)ₙ-LKWIQEYLEKALN-NH₂ (SEQ ID NOS:178 and 179) with PEG(Polyethyleneglycol chain) MW = 500-20000

K[D-P]VS[D-L]SYRYPYRFFGGGGLKWIQEYLEKALN-NH₂

K[D-P]VS[D-L]SYRYPYRFF-(CH₂)ₙ-LKWIQEYLEKALN-NH₂

KPVSLSYRYPARFFGGGGLKWIQEYLEKALN-NH₂ (SEQ ID NO:180)

KPVSLSYRYPARFF-(CH₂)ₙ-LKWIQEYLEKALN-NH₂ (SEQ ID NOS: 181 and 182)

[PEG-Lys]PVSLSYRYPARFFGGGGLKWIQEYLEKALN-NH₂ (SEQ ID NO:183)

[PEG-Lys]PVSLSYRYPARFF-(CH₂)ₙ-LKWIQEYLEKALN-NH₂ (SEQ ID NOS:184 and 185) with PEG(Polyethyleneglycol chain) MW = 500-20000

K[D-P]VS[D-L]SYRYPARFFGGGGLKWIQEYLEKALN-NH₂

K[D-P]VS[D-L]SYRYPARFF-(CH₂)ₙ-LKWIQEYLEKALN-NH₂

KPVSLSYREPERFFGGGGLKWIQEYLEKALN-NH₂ (SEQ ID NO:186)

KPVSLSYREPERFF-(CH₂)ₙ-LKWIQEYLEKALN-NH₂ (SEQ ID NOS: 187 and 188)

[PEG-Lys]PVSLSYREPERFFGGGGLKWIQEYLEKALN-NH₂ (SEQ ID NO:189)

[PEG-Lys]PVSLSYREPERFF-(CH₂)ₙ-LKWIQEYLEKALN-NH₂ (SEQ ID NOS:190 and 191) with PEG(Polyethyleneglycol chain) MW = 500-20000

K[D-P]VS[D-L]SYREPERFFGGGGLKWIQEYLEKALN-NH₂

K[D-P]VS[D-L]SYREPERFF-(CH₂)ₙ-LKWIQEYLEKALN-NH₂

KPVSLSYRHPHRFFGGGGLKWIQEYLEKALN-NH₂ (SEQ ID NO:192)

KPVSLSYRHPHRFF-(CH₂)ₙ-LKWIQEYLEKALN-NH₂ (SEQ ID NOS:193 and 194)

[PEG-Lys]PVSLSYRHPHRFFGGGGLKWIQEYLEKALN-NH₂ (SEQ ID NO:195)

[PEG-Lys]PVSLSYRHPHRFF-(CH₂)ₙ-LKWIQEYLEKALN-NH₂ (SEQ ID NOS:196 and 197) with PEG(Polyethyleneglycol chain) MW = 500-20000

-continued

K[D-P]VS[D-L]SYRHPHRFFGGGGLKWIQEYLEKALN-NH₂

K[D-P]VS[D-L]SYRHPHRFF-(CH₂)ₙ-LKWIQEYLEKALN-NH₂

KPVSLSYRWPWRFFGGGGLKWIQEYLEKALN-NH₂ (SEQ ID NO:198)

KPVSLSYREPERFF-(CH₂)ₙ-LKWIQEYLEKALN-NH₂ (SEQ ID NOS:199 and 200)

[PEG-Lys]PVSLSYRWPWRFFGGGGLKWIQEYLEKALN-NH₂ (SEQ ID NO:201)

[PEG-Lys]PVSLSYRWPWRFF-(CH₂)ₙ-LKWIQEYLEKALN-NH₂ (SEQ ID NOS:202 and 203) with PEG(Polyethyleneglycol chain) MW = 500-20000

K[D-P]VS[D-L]SYRWPWRFFGGGGLKWIQEYLEKALN-NH₂

K[D-P]VS[D-L]SYRWPWRFF-(CH₂)ₙ-LKWIQEYLEKALN-NH₂

Structure Legend
Structure of CTCE9901:
SDF-1 (1-9)2-cysteine dimer

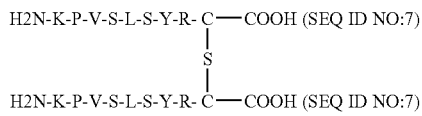

Structure of CTCE9902:
SDF-1 (1-17) mer
H2N- K- P- V- S- L- S- Y- R- C- P- C- R- F- F-E-S-H-COOH (SEQ ID NO:4)

Structure of CTCE9904:
SDF-1 (1-8)₂-lysine dimer

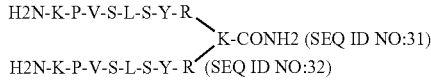

Structure of CTCE0013:
H2N- K- P- V- S- L- S- Y- R- C- P- C- R- F- F- G-G-G-G-L- K- W- I- Q- E- Y- L- E- K- A- L- N- COOH (SEQ ID NO:13)

Structure of CTCE0017:
H2N- K- P- V- S- L- S- Y- R- C- P- C- R- F- F- G-G-G-G-L- K- W- I- Q- E- Y- L- E- K-A- L-N- CONH2 (SEQ ID NO:15)

Structure of CTCE0022:
SDF-1 (1-31 E24/K28-cyclic amide) Agonist

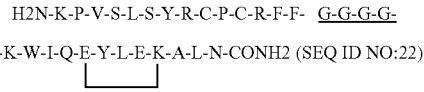

Structure of CTCE0021:
SDF-1 (1-31 K20E24-cyclic amide) Agonist

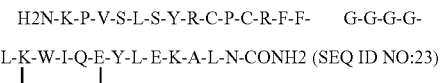

What is claimed is:

1. A CXC chemokine receptor 4 (CXCR4) agonist comprising the sequence:

KPVSLSYRAPFRFF-[LINKER]-LKWIQEYLEKALN-NH$_2$ (residue positions 1-14 of SEQ ID NO: 208 linked to residue positions 19-31 of SEQ ID NO:208)

wherein, the LINKER consist of 4 glycines.

2. A pharmaceutical composition comprising the agonist of claim 1 wherein the agonist comprises the formula:

KPVSLSYRAPFRFFGGGGLKWIQEYLEKALN-NH$_2$ (SEQ ID NO:57)

in a pharmaceutically acceptable carrier.

3. A variant of the CXCR4 agonist of claim 1, wherein said variant differs from said agonist by the following:
   a) the variant has an N-terminal 14 amino acids that is at least 95% identical to amino acids 1-14 of SEQ ID NO: 208; or
   b) the variant has a C-terminal 13 amino acids that is at least 95% identical to amino acids 19-31 of SEQ ID NO: 208.

4. A pharmaceutical composition comprising the CXCR4 agonist variant of claim 3.

5. A composition comprising a CXC chemokine receptor 4 (CXCR4) agonist wherein the agonist comprises the formula:

KPVSLSYRAPFRFFGGGGLKWIQEYLEKALN-NH$_2$ (SEQ ID NO:132)

in a pharmaceutically acceptable carrier.

6. A variant of the CXCR4 agonist of claim 5, wherein said variant differs from said agonist by the following:
   a) the variant has an N-terminal 14 amino acids that is at least 95% identical to amino acids 1-14 of SEQ ID NO: 208; or
   b) the variant has a C-terminal 13 amino acids that is at least 95% identical to amino acids 19-31 of SEQ ID NO: 208.

* * * * *

SEQUENCE LISTING

```
<160> NUMBER OF SEQ ID NOS: 214

<210> SEQ ID NO 1
<211> LENGTH: 67
<212> TYPE: PRT
<213> ORGANISM: Homo sapiens
<220> FEATURE:
<223> OTHER INFORMATION: human SDF-1alpha

<400> SEQUENCE: 1

Lys Pro Val Ser Leu Ser Tyr Arg Cys Pro Cys Arg Phe Phe Glu Ser
1               5                   10                  15

His Val Ala Arg Ala Asn Val Lys His Leu Lys Ile Leu Asn Thr Pro
            20                  25                  30

Asn Cys Ala Leu Gln Ile Val Ala Arg Leu Lys Asn Asn Asn Arg Gln
        35                  40                  45

Val Cys Ile Asp Pro Lys Leu Lys Trp Ile Gln Glu Tyr Leu Glu Lys
    50                  55                  60
```

-continued

Ala Leu Asn
65

<210> SEQ ID NO 2
<211> LENGTH: 93
<212> TYPE: PRT
<213> ORGANISM: Homo sapiens
<220> FEATURE:
<223> OTHER INFORMATION: human SDF-1 precursor, PBSF

<400> SEQUENCE: 2

Met Asn Ala Lys Val Val Val Leu Val Leu Val Leu Thr Ala Leu
1               5                   10                  15

Cys Leu Ser Asp Gly Lys Pro Val Ser Leu Ser Tyr Arg Cys Pro Cys
                20                  25                  30

Arg Phe Phe Glu Ser His Val Ala Arg Ala Asn Val Lys His Leu Lys
                35                  40                  45

Ile Leu Asn Thr Pro Asn Cys Ala Leu Gln Ile Val Ala Arg Leu Lys
                50                  55                  60

Asn Asn Asn Arg Gln Val Cys Ile Asp Pro Lys Leu Lys Trp Ile Gln
65                  70                  75                  80

Glu Tyr Leu Glu Lys Ala Leu Asn Lys Arg Phe Lys Met
                85                  90

<210> SEQ ID NO 3
<211> LENGTH: 93
<212> TYPE: PRT
<213> ORGANISM: Homo sapiens
<220> FEATURE:
<223> OTHER INFORMATION: human SDF-1beta

<400> SEQUENCE: 3

Met Asn Ala Lys Val Val Val Leu Val Leu Val Leu Thr Ala Leu
1               5                   10                  15

Cys Leu Ser Asp Gly Lys Pro Val Ser Leu Ser Tyr Arg Cys Pro Cys
                20                  25                  30

Arg Phe Phe Glu Ser His Val Ala Arg Ala Asn Val Lys His Leu Lys
                35                  40                  45

Ile Leu Asn Thr Pro Asn Cys Ala Leu Gln Ile Val Ala Arg Leu Lys
                50                  55                  60

Asn Asn Asn Arg Gln Val Cys Ile Asp Pro Lys Leu Lys Trp Ile Gln
65                  70                  75                  80

Glu Tyr Leu Glu Lys Ala Leu Asn Lys Arg Phe Lys Met
                85                  90

<210> SEQ ID NO 4
<211> LENGTH: 17
<212> TYPE: PRT
<213> ORGANISM: Artificial Sequence
<220> FEATURE:
<223> OTHER INFORMATION: synthetic CXCR4 agonist SDF-1(1-17), CTCE9902

<400> SEQUENCE: 4

Lys Pro Val Ser Leu Ser Tyr Arg Cys Pro Cys Arg Phe Phe Glu Ser
1               5                   10                  15

His

<210> SEQ ID NO 5
<211> LENGTH: 6
<212> TYPE: PRT
<213> ORGANISM: Artificial Sequence

```
<220> FEATURE:
<223> OTHER INFORMATION: CXCR4 agonist sequence motif within 20 amino
      acids of the N-terminus

<400> SEQUENCE: 5

Arg Phe Phe Glu Ser His
1               5

<210> SEQ ID NO 6
<211> LENGTH: 9
<212> TYPE: PRT
<213> ORGANISM: Artificial Sequence
<220> FEATURE:
<223> OTHER INFORMATION: synthetic SDF-1 peptide analogue CXCR4 agonist

<400> SEQUENCE: 6

Lys Pro Val Ser Leu Ser Tyr Arg Cys
1               5

<210> SEQ ID NO 7
<211> LENGTH: 9
<212> TYPE: PRT
<213> ORGANISM: Artificial Sequence
<220> FEATURE:
<223> OTHER INFORMATION: synthetic CXCR4 agonist
      SDF-1(1-9)-2-C9/C9-cysteine dimer, CTCE9901
<220> FEATURE:
<221> NAME/KEY: MISC_FEATURE
<222> LOCATION: (7)..(7)
<223> OTHER INFORMATION: dimerised by formation of a disulfide bond
      between two Cys residues in position 7 of two SEQ ID NO:7 peptides

<400> SEQUENCE: 7

Lys Pro Val Ser Leu Ser Tyr Arg Cys
1               5

<210> SEQ ID NO 8
<211> LENGTH: 10
<212> TYPE: PRT
<213> ORGANISM: Artificial Sequence
<220> FEATURE:
<223> OTHER INFORMATION: portion of synthetic CXCR4 agonist SDF-1(1-9)-2
      (Compound #3)
<220> FEATURE:
<221> NAME/KEY: MOD_RES
<222> LOCATION: (10)..(10)
<223> OTHER INFORMATION: Xaa = Lys whose epsilon amino group forms a
      covalent amide bond with the alpha amino group of Cys at position
      9 of KPVSLSYRC (SEQ ID NO:9), thereby forming a dimer

<400> SEQUENCE: 8

Lys Pro Val Ser Leu Ser Tyr Arg Cys Xaa
1               5                   10

<210> SEQ ID NO 9
<211> LENGTH: 9
<212> TYPE: PRT
<213> ORGANISM: Artificial Sequence
<220> FEATURE:
<223> OTHER INFORMATION: portion of synthetic CXCR4 agonist SDF-1(1-9)-2
      (Compound #3)
<220> FEATURE:
<221> NAME/KEY: MOD_RES
<222> LOCATION: (9)..(9)
<223> OTHER INFORMATION: Xaa = Cys whose alpha amino group forms a
      covalent amide bond with the epsilon amino group of Lys at
      position 10 of KPVSLSYRCX (SEQ ID NO:8), thereby forming a dimer

<400> SEQUENCE: 9

Lys Pro Val Ser Leu Ser Tyr Arg Xaa
```

<210> SEQ ID NO 10
<211> LENGTH: 9
<212> TYPE: PRT
<213> ORGANISM: Artificial Sequence
<220> FEATURE:
<223> OTHER INFORMATION: portion of synthetic CXCR4 agonist dimer of
      SDF-1 amino acids 1-8
<220> FEATURE:
<221> NAME/KEY: MOD_RES
<222> LOCATION: (9)..(9)
<223> OTHER INFORMATION: Xaa = Lys whose epsilon amino group forms a
      covalent amide bond with the alpha amino group of Arg at position
      8 of KPVSLSYX (SEQ ID NO:11), thereby forming a dimer

<400> SEQUENCE: 10

Lys Pro Val Ser Leu Ser Tyr Arg Xaa
1               5

<210> SEQ ID NO 11
<211> LENGTH: 8
<212> TYPE: PRT
<213> ORGANISM: Artificial Sequence
<220> FEATURE:
<223> OTHER INFORMATION: portion of synthetic CXCR4 agonist dimer of
      SDF-1 amino acids 1-8
<220> FEATURE:
<221> NAME/KEY: MOD_RES
<222> LOCATION: (8)..(8)
<223> OTHER INFORMATION: Xaa = Arg whose alpha amino group forms a
      covalent amide bond with the epsilon amino group of Lys at
      position 9 of KPVSLSYRX (SEQ ID NO:10), thereby forming a dimer

<400> SEQUENCE: 11

Lys Pro Val Ser Leu Ser Tyr Xaa
1               5

<210> SEQ ID NO 12
<211> LENGTH: 30
<212> TYPE: PRT
<213> ORGANISM: Artificial Sequence
<220> FEATURE:
<223> OTHER INFORMATION: synthetic CXCR4 agonist
      SDF-1(1-14)-(G)-3-SDF-1(55-67) acid
<220> FEATURE:
<221> NAME/KEY: MISC_FEATURE
<222> LOCATION: (17)..(17)
<223> OTHER INFORMATION: Gly in position 17 may be present or absent

<400> SEQUENCE: 12

Lys Pro Val Ser Leu Ser Tyr Arg Cys Pro Cys Arg Phe Phe Gly Gly
1               5                   10                  15

Gly Leu Lys Trp Ile Gln Glu Tyr Leu Glu Lys Ala Leu Asn
            20                  25                  30

<210> SEQ ID NO 13
<211> LENGTH: 31
<212> TYPE: PRT
<213> ORGANISM: Artificial Sequence
<220> FEATURE:
<223> OTHER INFORMATION: synthetic CXCR4 agonist
      SDF-1(1-14)-(G)-4-SDF-1(55-67) acid, CTCE0013
<220> FEATURE:
<221> NAME/KEY: MISC_FEATURE
<222> LOCATION: (17)..(18)
<223> OTHER INFORMATION: Gly in positions 17 and/or 18 may independently
      be present or absent

<400> SEQUENCE: 13

```
Lys Pro Val Ser Leu Ser Tyr Arg Cys Pro Cys Arg Phe Phe Gly Gly
1               5                   10                  15

Gly Gly Leu Lys Trp Ile Gln Glu Tyr Leu Glu Lys Ala Leu Asn
            20                  25                  30

<210> SEQ ID NO 14
<211> LENGTH: 30
<212> TYPE: PRT
<213> ORGANISM: Artificial Sequence
<220> FEATURE:
<223> OTHER INFORMATION: synthetic CXCR4 agonist
      SDF-1(1-14)-(G)-3-SDF-1(55-67) amide
<220> FEATURE:
<221> NAME/KEY: MISC_FEATURE
<222> LOCATION: (17)..(17)
<223> OTHER INFORMATION: Gly in position 17 may be present or absent
<220> FEATURE:
<221> NAME/KEY: MOD_RES
<222> LOCATION: (30)..(30)
<223> OTHER INFORMATION: AMIDATION

<400> SEQUENCE: 14

Lys Pro Val Ser Leu Ser Tyr Arg Cys Pro Cys Arg Phe Phe Gly Gly
1               5                   10                  15

Gly Leu Lys Trp Ile Gln Glu Tyr Leu Glu Lys Ala Leu Asn
            20                  25                  30

<210> SEQ ID NO 15
<211> LENGTH: 31
<212> TYPE: PRT
<213> ORGANISM: Artificial Sequence
<220> FEATURE:
<223> OTHER INFORMATION: synthetic CXCR4 agonist
      SDF-1(1-14)-(G)-4-SDF-1(55-67) amide, CTCE0017, Compound A
<220> FEATURE:
<221> NAME/KEY: MISC_FEATURE
<222> LOCATION: (17)..(18)
<223> OTHER INFORMATION: Gly in positions 17 and/or 18 may independently
      be present or absent
<220> FEATURE:
<221> NAME/KEY: MOD_RES
<222> LOCATION: (31)..(31)
<223> OTHER INFORMATION: AMIDATION

<400> SEQUENCE: 15

Lys Pro Val Ser Leu Ser Tyr Arg Cys Pro Cys Arg Phe Phe Gly Gly
1               5                   10                  15

Gly Gly Leu Lys Trp Ile Gln Glu Tyr Leu Glu Lys Ala Leu Asn
            20                  25                  30

<210> SEQ ID NO 16
<211> LENGTH: 33
<212> TYPE: PRT
<213> ORGANISM: Artificial Sequence
<220> FEATURE:
<223> OTHER INFORMATION: synthetic CXCR4 agonist
      SDF-1(1-17)-(G)-3-SDF-1(55-67) acid
<220> FEATURE:
<221> NAME/KEY: MISC_FEATURE
<222> LOCATION: (20)..(20)
<223> OTHER INFORMATION: Gly in position 20 may be present or absent

<400> SEQUENCE: 16

Lys Pro Val Ser Leu Ser Tyr Arg Cys Pro Cys Arg Phe Phe Glu Ser
1               5                   10                  15

His Gly Gly Gly Leu Lys Trp Ile Gln Glu Tyr Leu Glu Lys Ala Leu
            20                  25                  30

Asn
```

<210> SEQ ID NO 17
<211> LENGTH: 34
<212> TYPE: PRT
<213> ORGANISM: Artificial Sequence
<220> FEATURE:
<223> OTHER INFORMATION: synthetic CXCR4 agonist
      SDF-1(1-17)-(G)-4-SDF-1(55-67) acid
<220> FEATURE:
<221> NAME/KEY: MISC_FEATURE
<222> LOCATION: (20)..(21)
<223> OTHER INFORMATION: Gly in positions 20 and/or 21 may independently
      be present or absent

<400> SEQUENCE: 17

Lys Pro Val Ser Leu Ser Tyr Arg Cys Pro Cys Arg Phe Phe Glu Ser
1               5                   10                  15

His Gly Gly Gly Gly Leu Lys Trp Ile Gln Glu Tyr Leu Glu Lys Ala
            20                  25                  30

Leu Asn

<210> SEQ ID NO 18
<211> LENGTH: 33
<212> TYPE: PRT
<213> ORGANISM: Artificial Sequence
<220> FEATURE:
<223> OTHER INFORMATION: synthetic CXCR4 agonist
      SDF-1(1-17)-(G)-3-SDF-1(55-67) amide
<220> FEATURE:
<221> NAME/KEY: MISC_FEATURE
<222> LOCATION: (20)..(20)
<223> OTHER INFORMATION: Gly in position 20 may be present or absent
<220> FEATURE:
<221> NAME/KEY: MOD_RES
<222> LOCATION: (33)..(33)
<223> OTHER INFORMATION: AMIDATION

<400> SEQUENCE: 18

Lys Pro Val Ser Leu Ser Tyr Arg Cys Pro Cys Arg Phe Phe Glu Ser
1               5                   10                  15

His Gly Gly Gly Leu Lys Trp Ile Gln Glu Tyr Leu Glu Lys Ala Leu
            20                  25                  30

Asn

<210> SEQ ID NO 19
<211> LENGTH: 34
<212> TYPE: PRT
<213> ORGANISM: Artificial Sequence
<220> FEATURE:
<223> OTHER INFORMATION: synthetic CXCR4 agonist
      SDF-1(1-17)-(G)-4-SDF-1(55-67) amide
<220> FEATURE:
<221> NAME/KEY: MISC_FEATURE
<222> LOCATION: (20)..(21)
<223> OTHER INFORMATION: Gly in positions 20 and/or 21 may be
      independently present or absent
<220> FEATURE:
<221> NAME/KEY: MOD_RES
<222> LOCATION: (34)..(34)
<223> OTHER INFORMATION: AMIDATION

<400> SEQUENCE: 19

Lys Pro Val Ser Leu Ser Tyr Arg Cys Pro Cys Arg Phe Phe Glu Ser
1               5                   10                  15

His Gly Gly Gly Gly Leu Lys Trp Ile Gln Glu Tyr Leu Glu Lys Ala
            20                  25                  30

Leu Asn

```
<210> SEQ ID NO 20
<211> LENGTH: 31
<212> TYPE: PRT
<213> ORGANISM: Artificial Sequence
<220> FEATURE:
<223> OTHER INFORMATION: synthetic CXCR4 agonist
      SDF-1(1-14)-(G)-4-SDF-1(55-67)-E24/K28-cyclic acid
<220> FEATURE:
<221> NAME/KEY: MISC_FEATURE
<222> LOCATION: (17)..(18)
<223> OTHER INFORMATION: Gly in positions 17 and/or 18 may be
      independently present or absent
<220> FEATURE:
<221> NAME/KEY: MISC_FEATURE
<222> LOCATION: (24)..(28)
<223> OTHER INFORMATION: side chain cyclized using lactam formation

<400> SEQUENCE: 20

Lys Pro Val Ser Leu Ser Tyr Arg Cys Pro Cys Arg Phe Phe Gly Gly
1               5                   10                  15

Gly Gly Leu Lys Trp Ile Gln Glu Tyr Leu Glu Lys Ala Leu Asn
            20                  25                  30

<210> SEQ ID NO 21
<211> LENGTH: 31
<212> TYPE: PRT
<213> ORGANISM: Artificial Sequence
<220> FEATURE:
<223> OTHER INFORMATION: synthetic CXCR4 agonist
      SDF-1(1-14)-(G)-4-SDF-1(55-67)-K20/E24-cyclic acid
<220> FEATURE:
<221> NAME/KEY: MISC_FEATURE
<222> LOCATION: (17)..(18)
<223> OTHER INFORMATION: Gly in positions 17 and/or 18 may be
      independently present or absent
<220> FEATURE:
<221> NAME/KEY: MISC_FEATURE
<222> LOCATION: (20)..(24)
<223> OTHER INFORMATION: side chain cyclized using lactam formation

<400> SEQUENCE: 21

Lys Pro Val Ser Leu Ser Tyr Arg Cys Pro Cys Arg Phe Phe Gly Gly
1               5                   10                  15

Gly Gly Leu Lys Trp Ile Gln Glu Tyr Leu Glu Lys Ala Leu Asn
            20                  25                  30

<210> SEQ ID NO 22
<211> LENGTH: 31
<212> TYPE: PRT
<213> ORGANISM: Artificial Sequence
<220> FEATURE:
<223> OTHER INFORMATION: synthetic CXCR4 agonist
      SDF-1(1-14)-(G)-4-SDF-1(55-67)-E24/K28-cyclic amide,
      CTCE0022
<220> FEATURE:
<221> NAME/KEY: MISC_FEATURE
<222> LOCATION: (17)..(18)
<223> OTHER INFORMATION: Gly in positions 17 and/or 18 may be
      independently present or absent
<220> FEATURE:
<221> NAME/KEY: MISC_FEATURE
<222> LOCATION: (24)..(28)
<223> OTHER INFORMATION: side chain cyclized using lactam formation
<220> FEATURE:
<221> NAME/KEY: MOD_RES
<222> LOCATION: (31)..(31)
<223> OTHER INFORMATION: AMIDATION

<400> SEQUENCE: 22

Lys Pro Val Ser Leu Ser Tyr Arg Cys Pro Cys Arg Phe Phe Gly Gly
```

```
                1               5                  10                  15
Gly Gly Leu Lys Trp Ile Gln Glu Tyr Leu Glu Lys Ala Leu Asn
            20                  25                  30

<210> SEQ ID NO 23
<211> LENGTH: 31
<212> TYPE: PRT
<213> ORGANISM: Artificial Sequence
<220> FEATURE:
<223> OTHER INFORMATION: synthetic CXCR4 agonist
      SDF-1(1-14)-(G)-4-SDF-1(55-67)-K20/E24-cyclic amide,
      CTCE0021, Compound B
<220> FEATURE:
<221> NAME/KEY: MISC_FEATURE
<222> LOCATION: (17)..(18)
<223> OTHER INFORMATION: Gly in positions 17 and/or 18 may be
      independently present or absent
<220> FEATURE:
<221> NAME/KEY: MISC_FEATURE
<222> LOCATION: (20)..(24)
<223> OTHER INFORMATION: side chain cyclized using lactam formation
<220> FEATURE:
<221> NAME/KEY: MOD_RES
<222> LOCATION: (31)..(31)
<223> OTHER INFORMATION: AMIDATION

<400> SEQUENCE: 23

Lys Pro Val Ser Leu Ser Tyr Arg Cys Pro Cys Arg Phe Phe Gly Gly
1               5                  10                  15

Gly Gly Leu Lys Trp Ile Gln Glu Tyr Leu Glu Lys Ala Leu Asn
            20                  25                  30

<210> SEQ ID NO 24
<211> LENGTH: 31
<212> TYPE: PRT
<213> ORGANISM: Artificial Sequence
<220> FEATURE:
<223> OTHER INFORMATION: synthetic CXCR4 agonist
      SDF-1(1-14)-(G)-4-SDF-1(55-67)-K20/D24-(E24->D)-cyclic
      acid
<220> FEATURE:
<221> NAME/KEY: MISC_FEATURE
<222> LOCATION: (17)..(18)
<223> OTHER INFORMATION: Gly in positions 17 and/or 18 may be
      independently present or absent
<220> FEATURE:
<221> NAME/KEY: MISC_FEATURE
<222> LOCATION: (20)..(24)
<223> OTHER INFORMATION: side chain cyclized using lactam formation

<400> SEQUENCE: 24

Lys Pro Val Ser Leu Ser Tyr Arg Cys Pro Cys Arg Phe Phe Gly Gly
1               5                  10                  15

Gly Gly Leu Lys Trp Ile Gln Asp Tyr Leu Glu Lys Ala Leu Asn
            20                  25                  30

<210> SEQ ID NO 25
<211> LENGTH: 31
<212> TYPE: PRT
<213> ORGANISM: Artificial Sequence
<220> FEATURE:
<223> OTHER INFORMATION: synthetic CXCR4 agonist
      SDF-1(1-14)-(G)-4-SDF-1(55-67)-K20/D24-(E24->D)-cyclic
      amide
<220> FEATURE:
<221> NAME/KEY: MISC_FEATURE
<222> LOCATION: (17)..(18)
<223> OTHER INFORMATION: Gly in positions 17 and/or 18 may be
      independently present or absent
<220> FEATURE:
<221> NAME/KEY: MISC_FEATURE
```

```
<222> LOCATION: (20)..(24)
<223> OTHER INFORMATION: side chain cyclized using lactam formation
<220> FEATURE:
<221> NAME/KEY: MOD_RES
<222> LOCATION: (31)..(31)
<223> OTHER INFORMATION: AMIDATION

<400> SEQUENCE: 25

Lys Pro Val Ser Leu Ser Tyr Arg Cys Pro Cys Arg Phe Phe Gly Gly
1               5                   10                  15

Gly Gly Leu Lys Trp Ile Gln Asp Tyr Leu Glu Lys Ala Leu Asn
            20                  25                  30

<210> SEQ ID NO 26
<211> LENGTH: 31
<212> TYPE: PRT
<213> ORGANISM: Artificial Sequence
<220> FEATURE:
<223> OTHER INFORMATION: synthetic CXCR4 agonist
      SDF-1(1-14)-(G)-4-SDF-1(55-67)-C9/C11-cyclic acid
<220> FEATURE:
<221> NAME/KEY: MISC_FEATURE
<222> LOCATION: (9)..(11)
<223> OTHER INFORMATION: cyclized with disulfide bridge
<220> FEATURE:
<221> NAME/KEY: MISC_FEATURE
<222> LOCATION: (17)..(18)
<223> OTHER INFORMATION: Gly in positions 17 and/or 18 may be
      independently present or absent

<400> SEQUENCE: 26

Lys Pro Val Ser Leu Ser Tyr Arg Cys Pro Cys Arg Phe Phe Gly Gly
1               5                   10                  15

Gly Gly Leu Lys Trp Ile Gln Glu Tyr Leu Glu Lys Ala Leu Asn
            20                  25                  30

<210> SEQ ID NO 27
<211> LENGTH: 31
<212> TYPE: PRT
<213> ORGANISM: Artificial Sequence
<220> FEATURE:
<223> OTHER INFORMATION: synthetic CXCR4 agonist
      SDF-1(1-14)-(G)-4-SDF-1(55-67)-C9/C11-cyclic amide
<220> FEATURE:
<221> NAME/KEY: MISC_FEATURE
<222> LOCATION: (9)..(11)
<223> OTHER INFORMATION: cyclized with disulfide bridge
<220> FEATURE:
<221> NAME/KEY: MISC_FEATURE
<222> LOCATION: (17)..(18)
<223> OTHER INFORMATION: Gly in positions 17 and/or 18 may be
      independently present or absent
<220> FEATURE:
<221> NAME/KEY: MOD_RES
<222> LOCATION: (31)..(31)
<223> OTHER INFORMATION: AMIDATION

<400> SEQUENCE: 27

Lys Pro Val Ser Leu Ser Tyr Arg Cys Pro Cys Arg Phe Phe Gly Gly
1               5                   10                  15

Gly Gly Leu Lys Trp Ile Gln Glu Tyr Leu Glu Lys Ala Leu Asn
            20                  25                  30

<210> SEQ ID NO 28
<211> LENGTH: 33
<212> TYPE: PRT
<213> ORGANISM: Artificial Sequence
<220> FEATURE:
<223> OTHER INFORMATION: synthetic CXCR4 agonist
      SDF-1(1-14)-(G)-4-MIP-1alpha(36-50)-acid
```

```
<220> FEATURE:
<221> NAME/KEY: MISC_FEATURE
<222> LOCATION: (17)..(18)
<223> OTHER INFORMATION: Gly in positions 17 and/or 18 may be
      independently present or absent

<400> SEQUENCE: 28

Lys Pro Val Ser Leu Ser Tyr Arg Cys Pro Cys Arg Phe Phe Gly Gly
1               5                   10                  15

Gly Gly Ser Lys Pro Gly Val Ile Phe Leu Thr Lys Arg Ser Arg Gln
            20                  25                  30

Val

<210> SEQ ID NO 29
<211> LENGTH: 58
<212> TYPE: PRT
<213> ORGANISM: Artificial Sequence
<220> FEATURE:
<223> OTHER INFORMATION: synthetic CXCR4 agonist
      SDF-1(1-14)-(G)-4-MIP-1alpha(11-50)-acid
<220> FEATURE:
<221> NAME/KEY: MISC_FEATURE
<222> LOCATION: (17)..(18)
<223> OTHER INFORMATION: Gly in positions 17 and/or 18 may be
      independently present or absent

<400> SEQUENCE: 29

Lys Pro Val Ser Leu Ser Tyr Arg Cys Pro Cys Arg Phe Phe Gly Gly
1               5                   10                  15

Gly Gly Cys Cys Phe Ser Tyr Thr Ser Arg Gln Ile Pro Gln Asn Phe
            20                  25                  30

Ile Ala Asp Tyr Phe Glu Thr Ser Ser Gln Cys Ser Lys Pro Gly Val
        35                  40                  45

Ile Phe Leu Thr Lys Arg Ser Arg Gln Val
    50                  55

<210> SEQ ID NO 30
<211> LENGTH: 33
<212> TYPE: PRT
<213> ORGANISM: Artificial Sequence
<220> FEATURE:
<223> OTHER INFORMATION: synthetic CXCR4 agonist
      SDF-1(1-14)-(G)-4-MIP-1alpha(56-70)-acid
<220> FEATURE:
<221> NAME/KEY: MISC_FEATURE
<222> LOCATION: (17)..(18)
<223> OTHER INFORMATION: Gly in positions 17 and/or 18 may be
      independently present or absent

<400> SEQUENCE: 30

Lys Pro Val Ser Leu Ser Tyr Arg Cys Pro Cys Arg Phe Phe Gly Gly
1               5                   10                  15

Gly Gly Glu Glu Trp Val Gln Lys Tyr Val Asp Asp Leu Glu Leu Ser
            20                  25                  30

Ala

<210> SEQ ID NO 31
<211> LENGTH: 9
<212> TYPE: PRT
<213> ORGANISM: Artificial Sequence
<220> FEATURE:
<223> OTHER INFORMATION: portion of synthetic CXCR4 agonist
      SDF-1(1-8)-2-lysine bridge dimer, CTCE9904
<220> FEATURE:
<221> NAME/KEY: MOD_RES
<222> LOCATION: (9)..(9)
```

```
<223> OTHER INFORMATION: Xaa = lysinamide whose epsilon amino group
      forms a covalent amide bond with the alpha amino group of Arg at
      position 8 of KPVSLSYX (SEQ ID NO:32), thereby forming a
      dimer

<400> SEQUENCE: 31

Lys Pro Val Ser Leu Ser Tyr Arg Xaa
1               5

<210> SEQ ID NO 32
<211> LENGTH: 8
<212> TYPE: PRT
<213> ORGANISM: Artificial Sequence
<220> FEATURE:
<223> OTHER INFORMATION: portion of synthetic CXCR4 agonist
      SDF-1(1-8)-2-lysine bridge dimer, CTCE9904
<220> FEATURE:
<221> NAME/KEY: MOD_RES
<222> LOCATION: (8)..(8)
<223> OTHER INFORMATION: Xaa = Arg whose alpha amino group forms a
      covalent amide bond with the epsilon amino group of lysinamide at
      position 9 of KPVSLSYRX (SEQ ID NO:31), thereby forming a
      dimer

<400> SEQUENCE: 32

Lys Pro Val Ser Leu Ser Tyr Xaa
1               5

<210> SEQ ID NO 33

<400> SEQUENCE: 33

000

<210> SEQ ID NO 34

<400> SEQUENCE: 34

000

<210> SEQ ID NO 35
<211> LENGTH: 31
<212> TYPE: PRT
<213> ORGANISM: Artificial Sequence
<220> FEATURE:
<223> OTHER INFORMATION: synthetic CXCR4 agonist SDF-1-derived cyclic
      amide (E24/K28)
<220> FEATURE:
<221> NAME/KEY: MISC_FEATURE
<222> LOCATION: (1)..(1)
<223> OTHER INFORMATION: Lys may be modified with a substituent that may
      be a hydrogen, alkyl, aryl or polytheleneglycol (PEG) moiety
<220> FEATURE:
<221> NAME/KEY: MISC_FEATURE
<222> LOCATION: (2)..(2)
<223> OTHER INFORMATION: Xaa = an amino acid that may be either an L-Pro
      or a D-Pro moiety
<220> FEATURE:
<221> NAME/KEY: MISC_FEATURE
<222> LOCATION: (5)..(5)
<223> OTHER INFORMATION: Xaa = an amino acid that may be either an L-Leu
      or a D-Leu moiety
<220> FEATURE:
<221> NAME/KEY: MISC_FEATURE
<222> LOCATION: (17)..(18)
<223> OTHER INFORMATION: Gly in positions 17 and/or 18 may be
      independently present or absent
<220> FEATURE:
<221> NAME/KEY: MISC_FEATURE
<222> LOCATION: (24)..(28)
<223> OTHER INFORMATION: side chain cyclized using lactam formation
<220> FEATURE:
<221> NAME/KEY: MOD_RES
```

```
<222> LOCATION: (31)..(31)
<223> OTHER INFORMATION: AMIDATION

<400> SEQUENCE: 35

Lys Xaa Val Ser Xaa Ser Tyr Arg Cys Pro Cys Arg Phe Phe Gly Gly
1               5                   10                  15

Gly Gly Leu Lys Trp Ile Gln Glu Tyr Leu Glu Lys Ala Leu Asn
            20                  25                  30

<210> SEQ ID NO 36
<211> LENGTH: 31
<212> TYPE: PRT
<213> ORGANISM: Artificial Sequence
<220> FEATURE:
<223> OTHER INFORMATION: synthetic CXCR4 agonist SDF-1-derived cyclic
      acid (K20/E24)
<220> FEATURE:
<221> NAME/KEY: MISC_FEATURE
<222> LOCATION: (1)..(1)
<223> OTHER INFORMATION: Lys may be modified with a substituent that may
      be a hydrogen, alkyl, aryl or polytheleneglycol (PEG) moiety
<220> FEATURE:
<221> NAME/KEY: MISC_FEATURE
<222> LOCATION: (2)..(2)
<223> OTHER INFORMATION: Xaa = an amino acid that may be either an L-Pro
      or a D-Pro moiety
<220> FEATURE:
<221> NAME/KEY: MISC_FEATURE
<222> LOCATION: (5)..(5)
<223> OTHER INFORMATION: Xaa = an amino acid that may be either an L-Leu
      or a D-Leu Moiety
<220> FEATURE:
<221> NAME/KEY: MISC_FEATURE
<222> LOCATION: (17)..(18)
<223> OTHER INFORMATION: Gly in positions 17 and/or 18 may be
      independently present or absent
<220> FEATURE:
<221> NAME/KEY: MISC_FEATURE
<222> LOCATION: (20)..(24)
<223> OTHER INFORMATION: side chain cyclized using lactam formation
<220> FEATURE:
<221> NAME/KEY: MOD_RES
<222> LOCATION: (31)..(31)
<223> OTHER INFORMATION: AMIDATION

<400> SEQUENCE: 36

Lys Xaa Val Ser Xaa Ser Tyr Arg Cys Pro Cys Arg Phe Phe Gly Gly
1               5                   10                  15

Gly Gly Leu Lys Trp Ile Gln Glu Tyr Leu Glu Lys Ala Leu Asn
            20                  25                  30

<210> SEQ ID NO 37
<211> LENGTH: 31
<212> TYPE: PRT
<213> ORGANISM: Artificial Sequence
<220> FEATURE:
<223> OTHER INFORMATION: synthetic CXCR4 agonist
      SDF-1(1-14)-(G)-4-SDF-1(55-67)-K28/D24-(E24->D)-cyclic
      acid
<220> FEATURE:
<221> NAME/KEY: MISC_FEATURE
<222> LOCATION: (17)..(18)
<223> OTHER INFORMATION: Gly in positions 17 and/or 18 may be
      independently present or absent
<220> FEATURE:
<221> NAME/KEY: MISC_FEATURE
<222> LOCATION: (24)..(28)
<223> OTHER INFORMATION: side chain cyclized using lactam formation

<400> SEQUENCE: 37

Lys Pro Val Ser Leu Ser Tyr Arg Cys Pro Cys Arg Phe Phe Gly Gly
1               5                   10                  15
```

```
Gly Gly Leu Lys Trp Ile Gln Asp Tyr Leu Glu Lys Ala Leu Asn
            20                  25                  30

<210> SEQ ID NO 38
<211> LENGTH: 31
<212> TYPE: PRT
<213> ORGANISM: Artificial Sequence
<220> FEATURE:
<223> OTHER INFORMATION: synthetic CXCR4 agonist
      SDF-1(1-14)-(G)-4-SDF-1(55-67)-K28/D24-(E24->D)-cyclic
      amide
<220> FEATURE:
<221> NAME/KEY: MISC_FEATURE
<222> LOCATION: (17)..(18)
<223> OTHER INFORMATION: Gly in positions 17 and/or 18 may be
      independently present or absent
<220> FEATURE:
<221> NAME/KEY: MISC_FEATURE
<222> LOCATION: (24)..(28)
<223> OTHER INFORMATION: side chain cyclized using lactam formation
<220> FEATURE:
<221> NAME/KEY: MOD_RES
<222> LOCATION: (31)..(31)
<223> OTHER INFORMATION: AMIDATION

<400> SEQUENCE: 38

Lys Pro Val Ser Leu Ser Tyr Arg Cys Pro Cys Arg Phe Phe Gly Gly
1               5                   10                  15

Gly Gly Leu Lys Trp Ile Gln Asp Tyr Leu Glu Lys Ala Leu Asn
            20                  25                  30

<210> SEQ ID NO 39
<211> LENGTH: 31
<212> TYPE: PRT
<213> ORGANISM: Artificial Sequence
<220> FEATURE:
<223> OTHER INFORMATION: synthetic CXCR4 agonist
      SDF-1(1-14)-(G)-4-SDF-1(55-67)-O20/E24-(K20->O)-cyclic
      acid
<220> FEATURE:
<221> NAME/KEY: MISC_FEATURE
<222> LOCATION: (17)..(18)
<223> OTHER INFORMATION: Gly in positions 17 and/or 18 may be
      independently present or absent
<220> FEATURE:
<221> NAME/KEY: MISC_FEATURE
<222> LOCATION: (20)..(20)
<223> OTHER INFORMATION: Xaa = Orn
<220> FEATURE:
<221> NAME/KEY: MISC_FEATURE
<222> LOCATION: (20)..(24)
<223> OTHER INFORMATION: side chain cyclized using lactam formation

<400> SEQUENCE: 39

Lys Pro Val Ser Leu Ser Tyr Arg Cys Pro Cys Arg Phe Phe Gly Gly
1               5                   10                  15

Gly Gly Leu Xaa Trp Ile Gln Glu Tyr Leu Glu Lys Ala Leu Asn
            20                  25                  30

<210> SEQ ID NO 40
<211> LENGTH: 31
<212> TYPE: PRT
<213> ORGANISM: Artificial Sequence
<220> FEATURE:
<223> OTHER INFORMATION: synthetic CXCR4 agonist
      SDF-1(1-14)-(G)-4-SDF-1(55-67)-O20/E24-(K20->O)-cyclic
      amide
<220> FEATURE:
<221> NAME/KEY: MISC_FEATURE
<222> LOCATION: (17)..(18)
<223> OTHER INFORMATION: Gly in positions 17 and/or 18 may be
```

```
        independently present or absent
<220> FEATURE:
<221> NAME/KEY: MISC_FEATURE
<222> LOCATION: (20)..(20)
<223> OTHER INFORMATION: Xaa = Orn
<220> FEATURE:
<221> NAME/KEY: MISC_FEATURE
<222> LOCATION: (20)..(24)
<223> OTHER INFORMATION: side chain cyclized using lactam formation
<220> FEATURE:
<221> NAME/KEY: MOD_RES
<222> LOCATION: (31)..(31)
<223> OTHER INFORMATION: AMIDATION

<400> SEQUENCE: 40

Lys Pro Val Ser Leu Ser Tyr Arg Cys Pro Cys Arg Phe Phe Gly Gly
1               5                   10                  15

Gly Gly Leu Xaa Trp Ile Gln Glu Tyr Leu Glu Lys Ala Leu Asn
            20                  25                  30

<210> SEQ ID NO 41
<211> LENGTH: 31
<212> TYPE: PRT
<213> ORGANISM: Artificial Sequence
<220> FEATURE:
<223> OTHER INFORMATION: synthetic CXCR4 agonist
      SDF-1(1-14)-(G)-4-SDF-1(55-67)-O28/E24-(K28->O)-cyclic
      acid
<220> FEATURE:
<221> NAME/KEY: MISC_FEATURE
<222> LOCATION: (17)..(18)
<223> OTHER INFORMATION: Gly in positions 17 and/or 18 may be
      independently present or absent
<220> FEATURE:
<221> NAME/KEY: MISC_FEATURE
<222> LOCATION: (24)..(28)
<223> OTHER INFORMATION: side chain cyclized using lactam formation
<220> FEATURE:
<221> NAME/KEY: MISC_FEATURE
<222> LOCATION: (28)..(28)
<223> OTHER INFORMATION: Xaa = Orn

<400> SEQUENCE: 41

Lys Pro Val Ser Leu Ser Tyr Arg Cys Pro Cys Arg Phe Phe Gly Gly
1               5                   10                  15

Gly Gly Leu Lys Trp Ile Gln Glu Tyr Leu Glu Xaa Ala Leu Asn
            20                  25                  30

<210> SEQ ID NO 42
<211> LENGTH: 31
<212> TYPE: PRT
<213> ORGANISM: Artificial Sequence
<220> FEATURE:
<223> OTHER INFORMATION: synthetic CXCR4 agonist
      SDF-1(1-14)-(G)-4-SDF-1(55-67)-O28/E24-(K28->O)-cyclic
      amide
<220> FEATURE:
<221> NAME/KEY: MISC_FEATURE
<222> LOCATION: (17)..(18)
<223> OTHER INFORMATION: Gly in positions 17 and/or 18 may be
      independently present or absent
<220> FEATURE:
<221> NAME/KEY: MISC_FEATURE
<222> LOCATION: (24)..(28)
<223> OTHER INFORMATION: side chain cyclized using lactam formation
<220> FEATURE:
<221> NAME/KEY: MISC_FEATURE
<222> LOCATION: (28)..(28)
<223> OTHER INFORMATION: Xaa = Orn
<220> FEATURE:
<221> NAME/KEY: MOD_RES
<222> LOCATION: (31)..(31)
<223> OTHER INFORMATION: AMIDATION
```

-continued

```
<400> SEQUENCE: 42

Lys Pro Val Ser Leu Ser Tyr Arg Cys Pro Cys Arg Phe Phe Gly Gly
1               5                  10                  15

Gly Gly Leu Lys Trp Ile Gln Glu Tyr Leu Glu Xaa Ala Leu Asn
            20                  25                  30

<210> SEQ ID NO 43
<211> LENGTH: 31
<212> TYPE: PRT
<213> ORGANISM: Artificial Sequence
<220> FEATURE:
<223> OTHER INFORMATION: synthetic CXCR4 agonist
      SDF-1(1-14)-(G)-4-SDF-1(55-67)-O20/D24-(K20->O
      & E24->D)-cyclic acid
<220> FEATURE:
<221> NAME/KEY: MISC_FEATURE
<222> LOCATION: (17)..(18)
<223> OTHER INFORMATION: Gly in positions 17 and/or 18 may be
      independently present or absent
<220> FEATURE:
<221> NAME/KEY: MISC_FEATURE
<222> LOCATION: (20)..(20)
<223> OTHER INFORMATION: Xaa = Orn
<220> FEATURE:
<221> NAME/KEY: MISC_FEATURE
<222> LOCATION: (20)..(24)
<223> OTHER INFORMATION: side chain cyclized using lactam formation

<400> SEQUENCE: 43

Lys Pro Val Ser Leu Ser Tyr Arg Cys Pro Cys Arg Phe Phe Gly Gly
1               5                  10                  15

Gly Gly Leu Xaa Trp Ile Gln Asp Tyr Leu Glu Lys Ala Leu Asn
            20                  25                  30

<210> SEQ ID NO 44
<211> LENGTH: 31
<212> TYPE: PRT
<213> ORGANISM: Artificial Sequence
<220> FEATURE:
<223> OTHER INFORMATION: synthetic CXCR4 agonist
      SDF-1(1-14)-(G)-4-SDF-1(55-67)-O20/D24-(K20->O
      & E24->D)-cyclic amide
<220> FEATURE:
<221> NAME/KEY: MISC_FEATURE
<222> LOCATION: (17)..(18)
<223> OTHER INFORMATION: Gly in positions 17 and/or 18 may be
      independently present or absent
<220> FEATURE:
<221> NAME/KEY: MISC_FEATURE
<222> LOCATION: (20)..(20)
<223> OTHER INFORMATION: Xaa = Orn
<220> FEATURE:
<221> NAME/KEY: MISC_FEATURE
<222> LOCATION: (20)..(24)
<223> OTHER INFORMATION: side chain cyclized using lactam formation
<220> FEATURE:
<221> NAME/KEY: MOD_RES
<222> LOCATION: (31)..(31)
<223> OTHER INFORMATION: AMIDATION

<400> SEQUENCE: 44

Lys Pro Val Ser Leu Ser Tyr Arg Cys Pro Cys Arg Phe Phe Gly Gly
1               5                  10                  15

Gly Gly Leu Xaa Trp Ile Gln Asp Tyr Leu Glu Lys Ala Leu Asn
            20                  25                  30

<210> SEQ ID NO 45
<211> LENGTH: 31
<212> TYPE: PRT
```

```
<213> ORGANISM: Artificial Sequence
<220> FEATURE:
<223> OTHER INFORMATION: synthetic CXCR4 agonist
      SDF-1(1-14)-(G)-4-SDF-1(55-67)-O28/D24-(K28->O
      & E24->D)-cyclic acid
<220> FEATURE:
<221> NAME/KEY: MISC_FEATURE
<222> LOCATION: (17)..(18)
<223> OTHER INFORMATION: Gly in positions 17 and/or 18 may be
      independently present or absent
<220> FEATURE:
<221> NAME/KEY: MISC_FEATURE
<222> LOCATION: (24)..(28)
<223> OTHER INFORMATION: side chain cyclized using lactam formation
<220> FEATURE:
<221> NAME/KEY: MISC_FEATURE
<222> LOCATION: (28)..(28)
<223> OTHER INFORMATION: Xaa = Orn

<400> SEQUENCE: 45

Lys Pro Val Ser Leu Ser Tyr Arg Cys Pro Cys Arg Phe Phe Gly Gly
1               5                   10                  15

Gly Gly Leu Lys Trp Ile Gln Asp Tyr Leu Glu Xaa Ala Leu Asn
            20                  25                  30

<210> SEQ ID NO 46
<211> LENGTH: 31
<212> TYPE: PRT
<213> ORGANISM: Artificial Sequence
<220> FEATURE:
<223> OTHER INFORMATION: synthetic CXCR4 agonist
      SDF-1(1-14)-(G)-4-SDF-1(55-67)-O28/D24-(K28->O
      & E24->D)-cyclic amide
<220> FEATURE:
<221> NAME/KEY: MISC_FEATURE
<222> LOCATION: (17)..(18)
<223> OTHER INFORMATION: Gly in positions 17 and/or 18 may be
      independently present or absent
<220> FEATURE:
<221> NAME/KEY: MISC_FEATURE
<222> LOCATION: (24)..(28)
<223> OTHER INFORMATION: side chain cyclized using lactam formation
<220> FEATURE:
<221> NAME/KEY: MISC_FEATURE
<222> LOCATION: (28)..(28)
<223> OTHER INFORMATION: Xaa = Orn
<220> FEATURE:
<221> NAME/KEY: MOD_RES
<222> LOCATION: (31)..(31)
<223> OTHER INFORMATION: AMIDATION

<400> SEQUENCE: 46

Lys Pro Val Ser Leu Ser Tyr Arg Cys Pro Cys Arg Phe Phe Gly Gly
1               5                   10                  15

Gly Gly Leu Lys Trp Ile Gln Asp Tyr Leu Glu Xaa Ala Leu Asn
            20                  25                  30

<210> SEQ ID NO 47
<211> LENGTH: 33
<212> TYPE: PRT
<213> ORGANISM: Artificial Sequence
<220> FEATURE:
<223> OTHER INFORMATION: synthetic CXCR4 agonist
      SDF-1(1-14)-(G)-4-MIP-1alpha(36-50)-amide
<220> FEATURE:
<221> NAME/KEY: MISC_FEATURE
<222> LOCATION: (17)..(18)
<223> OTHER INFORMATION: Gly in positions 17 and/or 18 may be
      independently present or absent
<220> FEATURE:
<221> NAME/KEY: MOD_RES
<222> LOCATION: (33)..(33)
<223> OTHER INFORMATION: AMIDATION
```

```
<400> SEQUENCE: 47

Lys Pro Val Ser Leu Ser Tyr Arg Cys Pro Cys Arg Phe Phe Gly Gly
1               5                   10                  15

Gly Gly Ser Lys Pro Gly Val Ile Phe Leu Thr Lys Arg Ser Arg Gln
            20                  25                  30

Val

<210> SEQ ID NO 48
<211> LENGTH: 58
<212> TYPE: PRT
<213> ORGANISM: Artificial Sequence
<220> FEATURE:
<223> OTHER INFORMATION: synthetic CXCR4 agonist
      SDF-1(1-14)-(G)-4-MIP-1alpha(11-50)-amide
<220> FEATURE:
<221> NAME/KEY: MISC_FEATURE
<222> LOCATION: (17)..(18)
<223> OTHER INFORMATION: Gly in positions 17 and/or 18 may be
      independently present or absent
<220> FEATURE:
<221> NAME/KEY: MOD_RES
<222> LOCATION: (58)..(58)
<223> OTHER INFORMATION: AMIDATION

<400> SEQUENCE: 48

Lys Pro Val Ser Leu Ser Tyr Arg Cys Pro Cys Arg Phe Phe Gly Gly
1               5                   10                  15

Gly Gly Cys Cys Phe Ser Tyr Thr Ser Arg Gln Ile Pro Gln Asn Phe
            20                  25                  30

Ile Ala Asp Tyr Phe Glu Thr Ser Ser Gln Cys Ser Lys Pro Gly Val
        35                  40                  45

Ile Phe Leu Thr Lys Arg Ser Arg Gln Val
        50                  55

<210> SEQ ID NO 49
<211> LENGTH: 33
<212> TYPE: PRT
<213> ORGANISM: Artificial Sequence
<220> FEATURE:
<223> OTHER INFORMATION: synthetic CXCR4 agonist
      SDF-1(1-14)-(G)-4-MIP-1alpha(56-70)-amide
<220> FEATURE:
<221> NAME/KEY: MISC_FEATURE
<222> LOCATION: (17)..(18)
<223> OTHER INFORMATION: Gly in positions 17 and/or 18 may be
      independently present or absent
<220> FEATURE:
<221> NAME/KEY: MOD_RES
<222> LOCATION: (33)..(33)
<223> OTHER INFORMATION: AMIDATION

<400> SEQUENCE: 49

Lys Pro Val Ser Leu Ser Tyr Arg Cys Pro Cys Arg Phe Phe Gly Gly
1               5                   10                  15

Gly Gly Glu Glu Trp Val Gln Lys Tyr Val Asp Asp Leu Glu Leu Ser
            20                  25                  30

Ala

<210> SEQ ID NO 50
<211> LENGTH: 31
<212> TYPE: PRT
<213> ORGANISM: Artificial Sequence
<220> FEATURE:
<223> OTHER INFORMATION: synthetic CXCR4 agonist SDF-1-derived
      E24/K28-cyclic amide
```

```
<220> FEATURE:
<221> NAME/KEY: MISC_FEATURE
<222> LOCATION: (1)..(1)
<223> OTHER INFORMATION: Lys may be modified with a substituent that may
      be a hydrogen, alkyl, aryl or polyethylene glycol (PEG) moiety
<220> FEATURE:
<221> NAME/KEY: MISC_FEATURE
<222> LOCATION: (2)..(2)
<223> OTHER INFORMATION: Xaa = an amino acid that may be either an L-Pro
      or a D-Pro moiety
<220> FEATURE:
<221> NAME/KEY: MISC_FEATURE
<222> LOCATION: (5)..(5)
<223> OTHER INFORMATION: Xaa = an amino acid that may be either an L-Leu
      or a D-Leu moiety
<220> FEATURE:
<221> NAME/KEY: MISC_FEATURE
<222> LOCATION: (17)..(18)
<223> OTHER INFORMATION: Gly in positions 17 and/or 18 may be
      independently present or absent
<220> FEATURE:
<221> NAME/KEY: MISC_FEATURE
<222> LOCATION: (24)..(28)
<223> OTHER INFORMATION: side chain cyclized using lactam formation
<220> FEATURE:
<221> NAME/KEY: MOD_RES
<222> LOCATION: (31)..(31)
<223> OTHER INFORMATION: AMIDATION

<400> SEQUENCE: 50

Lys Xaa Val Ser Xaa Ser Tyr Arg Cys Pro Cys Arg Phe Phe Gly Gly
1               5                   10                  15

Gly Gly Leu Lys Trp Ile Gln Glu Tyr Leu Glu Lys Ala Leu Asn
            20                  25                  30

<210> SEQ ID NO 51
<211> LENGTH: 14
<212> TYPE: PRT
<213> ORGANISM: Artificial Sequence
<220> FEATURE:
<223> OTHER INFORMATION: portion of synthetic CXCR4 agonist
      SDF-1-derived E24/K28-cyclic amide
<220> FEATURE:
<221> NAME/KEY: MISC_FEATURE
<222> LOCATION: (1)..(1)
<223> OTHER INFORMATION: Lys may be modified with a substituent that may
      be a hydrogen, alkyl, aryl or polyethylene glycol (PEG) moiety
<220> FEATURE:
<221> NAME/KEY: MISC_FEATURE
<222> LOCATION: (2)..(2)
<223> OTHER INFORMATION: Xaa = an amino acid that may be either an L-Pro
      or a D-Pro moiety
<220> FEATURE:
<221> NAME/KEY: MISC_FEATURE
<222> LOCATION: (5)..(5)
<223> OTHER INFORMATION: Xaa = an amino acid that may be either an L-Leu
      or a D-Leu moiety
<220> FEATURE:
<221> NAME/KEY: MOD_RES
<222> LOCATION: (14)..(14)
<223> OTHER INFORMATION: Xaa = Phe linked to Leu at position 1 of
      XKWIQEYLEKALN (SEQ ID NO:52) via a moiety providing covalent
      attachment between N and C terminal portions of the peptides, such
      as NH-2-(CH-2)-n-COOH (n = 0-20)

<400> SEQUENCE: 51

Lys Xaa Val Ser Xaa Ser Tyr Arg Cys Pro Cys Arg Phe Xaa
1               5                   10

<210> SEQ ID NO 52
<211> LENGTH: 13
<212> TYPE: PRT
<213> ORGANISM: Artificial Sequence
<220> FEATURE:
```

```
<223> OTHER INFORMATION: portion of synthetic CXCR4 agonist
      SDF-1-derived E24/K28-cyclic amide
<220> FEATURE:
<221> NAME/KEY: MOD_RES
<222> LOCATION: (1)..(1)
<223> OTHER INFORMATION: Xaa = Leu linked to Phe at position 14 of
      KXVSXSYRCPCRFX (SEQ ID NO:51) via a moiety providing covalent
      attachment between N and C terminal portions of the peptides, such
      as NH-2-(CH-2)-n-COOH (n = 0-20)
<220> FEATURE:
<221> NAME/KEY: MISC_FEATURE
<222> LOCATION: (6)..(10)
<223> OTHER INFORMATION: side chain cyclized using lactam formation
<220> FEATURE:
<221> NAME/KEY: MOD_RES
<222> LOCATION: (13)..(13)
<223> OTHER INFORMATION: AMIDATION

<400> SEQUENCE: 52

Xaa Lys Trp Ile Gln Glu Tyr Leu Glu Lys Ala Leu Asn
1               5                   10

<210> SEQ ID NO 53
<211> LENGTH: 31
<212> TYPE: PRT
<213> ORGANISM: Artificial Sequence
<220> FEATURE:
<223> OTHER INFORMATION: synthetic CXCR4 agonist SDF-1-derived
      K20/E24-cyclic amide
<220> FEATURE:
<221> NAME/KEY: MISC_FEATURE
<222> LOCATION: (1)..(1)
<223> OTHER INFORMATION: Lys may be modified with a substituent that may
      be a hydrogen, alkyl, aryl or polyethylene glycol (PEG) moiety
<220> FEATURE:
<221> NAME/KEY: MISC_FEATURE
<222> LOCATION: (2)..(2)
<223> OTHER INFORMATION: Xaa = an amino acid that may be either an L-Pro
      or a D-Pro moiety
<220> FEATURE:
<221> NAME/KEY: MISC_FEATURE
<222> LOCATION: (5)..(5)
<223> OTHER INFORMATION: Xaa = an amino acid that may be either an L-Leu
      or a D-Leu moiety
<220> FEATURE:
<221> NAME/KEY: MISC_FEATURE
<222> LOCATION: (17)..(18)
<223> OTHER INFORMATION: Gly in positions 17 and/or 18 may be
      independently present or absent
<220> FEATURE:
<221> NAME/KEY: MISC_FEATURE
<222> LOCATION: (20)..(24)
<223> OTHER INFORMATION: side chain cyclized using lactam formation
<220> FEATURE:
<221> NAME/KEY: MOD_RES
<222> LOCATION: (31)..(31)
<223> OTHER INFORMATION: AMIDATION

<400> SEQUENCE: 53

Lys Xaa Val Ser Xaa Ser Tyr Arg Cys Pro Cys Arg Phe Phe Gly Gly
1               5                   10                  15

Gly Gly Leu Lys Trp Ile Gln Glu Tyr Leu Glu Lys Ala Leu Asn
            20                  25                  30

<210> SEQ ID NO 54
<211> LENGTH: 14
<212> TYPE: PRT
<213> ORGANISM: Artificial Sequence
<220> FEATURE:
<223> OTHER INFORMATION: portion of synthetic CXCR4 agonist
      SDF-1-derived K20/E24-cyclic amide
<220> FEATURE:
<221> NAME/KEY: MISC_FEATURE
<222> LOCATION: (1)..(1)
```

```
<223> OTHER INFORMATION: Lys may be modified with a substituent that may
      be a hydrogen, alkyl, aryl or polyethylene glycol (PEG) moiety
<220> FEATURE:
<221> NAME/KEY: MISC_FEATURE
<222> LOCATION: (2)..(2)
<223> OTHER INFORMATION: Xaa = an amino acid that may be either an L-Pro
      or a D-Pro moiety
<220> FEATURE:
<221> NAME/KEY: MISC_FEATURE
<222> LOCATION: (5)..(5)
<223> OTHER INFORMATION: Xaa = an amino acid that may be either an L-Leu
      or a D-Leu moiety
<220> FEATURE:
<221> NAME/KEY: MOD_RES
<222> LOCATION: (14)..(14)
<223> OTHER INFORMATION: Xaa = Phe linked to Leu at position 1 of
      XKWIQEYLEKALN (SEQ ID NO:55) via a moiety providing covalent
      attachment between N and C terminal portions of the peptides, such
      as NH-2-(CH-2)-n-COOH (n = 0-20)

<400> SEQUENCE: 54

Lys Xaa Val Ser Xaa Ser Tyr Arg Cys Pro Cys Arg Phe Xaa
1               5                   10

<210> SEQ ID NO 55
<211> LENGTH: 13
<212> TYPE: PRT
<213> ORGANISM: Artificial Sequence
<220> FEATURE:
<223> OTHER INFORMATION: portion of synthetic CXCR4 agonist
      SDF-1-derived K20/E24-cyclic amide
<220> FEATURE:
<221> NAME/KEY: MOD_RES
<222> LOCATION: (1)..(1)
<223> OTHER INFORMATION: Xaa = Leu linked to Phe at position 14 of
      KXVSXSYRCPCRFX (SEQ ID NO:54) via a moiety providing covalent
      attachment between N and C terminal portions of the peptides, such
      as NH-2-(CH-2)-n-COOH (n = 0-20)
<220> FEATURE:
<221> NAME/KEY: MISC_FEATURE
<222> LOCATION: (2)..(6)
<223> OTHER INFORMATION: side chain cyclized using lactam formation
<220> FEATURE:
<221> NAME/KEY: MOD_RES
<222> LOCATION: (13)..(13)
<223> OTHER INFORMATION: AMIDATION

<400> SEQUENCE: 55

Xaa Lys Trp Ile Gln Glu Tyr Leu Glu Lys Ala Leu Asn
1               5                   10

<210> SEQ ID NO 56
<211> LENGTH: 31
<212> TYPE: PRT
<213> ORGANISM: Artificial Sequence
<220> FEATURE:
<223> OTHER INFORMATION: synthetic CTCE0021-like analog CXCR4 agonist
<220> FEATURE:
<221> NAME/KEY: MOD_RES
<222> LOCATION: (1)..(1)
<223> OTHER INFORMATION: Lys is modified with polyethylene glycol (PEG)
<220> FEATURE:
<221> NAME/KEY: MISC_FEATURE
<222> LOCATION: (20)..(24)
<223> OTHER INFORMATION: side chain cyclized using lactam formation
<220> FEATURE:
<221> NAME/KEY: MOD_RES
<222> LOCATION: (31)..(31)
<223> OTHER INFORMATION: AMIDATION

<400> SEQUENCE: 56

Lys Pro Val Ser Leu Ser Tyr Arg Cys Pro Cys Arg Phe Phe Gly Gly
1               5                   10                  15
```

```
Gly Gly Leu Lys Trp Ile Gln Glu Tyr Leu Glu Lys Ala Leu Asn
        20                  25                  30

<210> SEQ ID NO 57
<211> LENGTH: 31
<212> TYPE: PRT
<213> ORGANISM: Artificial Sequence
<220> FEATURE:
<223> OTHER INFORMATION: synthetic CTCE0021-like analog CXCR4 agonist
<220> FEATURE:
<221> NAME/KEY: MISC_FEATURE
<222> LOCATION: (20)..(24)
<223> OTHER INFORMATION: side chain cyclized using lactam formation
<220> FEATURE:
<221> NAME/KEY: MOD_RES
<222> LOCATION: (31)..(31)
<223> OTHER INFORMATION: AMIDATION

<400> SEQUENCE: 57

Lys Pro Val Ser Leu Ser Tyr Arg Ala Pro Phe Arg Phe Gly Gly
1               5                   10                  15

Gly Gly Leu Lys Trp Ile Gln Glu Tyr Leu Glu Lys Ala Leu Asn
        20                  25                  30

<210> SEQ ID NO 58
<211> LENGTH: 14
<212> TYPE: PRT
<213> ORGANISM: Artificial Sequence
<220> FEATURE:
<223> OTHER INFORMATION: portion of synthetic CTCE0021-like analog CXCR4
      agonist
<220> FEATURE:
<221> NAME/KEY: MOD_RES
<222> LOCATION: (14)..(14)
<223> OTHER INFORMATION: Xaa = Phe linked to Leu at position 1 of
      XKWIQEYLEKALN (SEQ ID NO:59) via a moiety providing covalent
      attachment between N and C terminal portions of the peptides, such
      as NH-2-(CH-2)-n-COOH (n = 0-20)

<400> SEQUENCE: 58

Lys Pro Val Ser Leu Ser Tyr Arg Ala Pro Phe Arg Phe Xaa
1               5                   10

<210> SEQ ID NO 59
<211> LENGTH: 13
<212> TYPE: PRT
<213> ORGANISM: Artificial Sequence
<220> FEATURE:
<223> OTHER INFORMATION: portion of synthetic CTCE0021-like analog CXCR4
      agonist
<220> FEATURE:
<221> NAME/KEY: MOD_RES
<222> LOCATION: (1)..(1)
<223> OTHER INFORMATION: Xaa = Leu linked to Phe at position 14 of
      KXVSXSYRCPCRFX (SEQ ID NO:58) via a moiety providing covalent
      attachment between N and C terminal portions of the peptides, such
      as NH-2-(CH-2)-n-COOH (n = 0-20)
<220> FEATURE:
<221> NAME/KEY: MISC_FEATURE
<222> LOCATION: (2)..(6)
<223> OTHER INFORMATION: side chain cyclized using lactam formation
<220> FEATURE:
<221> NAME/KEY: MOD_RES
<222> LOCATION: (13)..(13)
<223> OTHER INFORMATION: AMIDATION

<400> SEQUENCE: 59

Xaa Lys Trp Ile Gln Glu Tyr Leu Glu Lys Ala Leu Asn
1               5                   10

<210> SEQ ID NO 60
```

```
<211> LENGTH: 31
<212> TYPE: PRT
<213> ORGANISM: Artificial Sequence
<220> FEATURE:
<223> OTHER INFORMATION: synthetic CTCE0021-like analog CXCR4 agonist
<220> FEATURE:
<221> NAME/KEY: MOD_RES
<222> LOCATION: (1)..(1)
<223> OTHER INFORMATION: Lys is modified with polyethylene glycol (PEG)
<220> FEATURE:
<221> NAME/KEY: MISC_FEATURE
<222> LOCATION: (20)..(24)
<223> OTHER INFORMATION: side chain cyclized using lactam formation
<220> FEATURE:
<221> NAME/KEY: MOD_RES
<222> LOCATION: (31)..(31)
<223> OTHER INFORMATION: AMIDATION

<400> SEQUENCE: 60

Lys Pro Val Ser Leu Ser Tyr Arg Ala Pro Phe Arg Phe Phe Gly Gly
1               5                   10                  15

Gly Gly Leu Lys Trp Ile Gln Glu Tyr Leu Glu Lys Ala Leu Asn
            20                  25                  30

<210> SEQ ID NO 61
<211> LENGTH: 14
<212> TYPE: PRT
<213> ORGANISM: Artificial Sequence
<220> FEATURE:
<223> OTHER INFORMATION: portion of synthetic CTCE0021-like analog CXCR4
      agonist
<220> FEATURE:
<221> NAME/KEY: MOD_RES
<222> LOCATION: (1)..(1)
<223> OTHER INFORMATION: Lys is modified with polyethylene glycol (PEG)
<220> FEATURE:
<221> NAME/KEY: MOD_RES
<222> LOCATION: (14)..(14)
<223> OTHER INFORMATION: Xaa = Phe linked to Leu at position 1 of
      XKWIQEYLEKALN (SEQ ID NO:62) via a moiety providing covalent
      attachment between N and C terminal portions of the peptides, such
      as NH-2-(CH-2)-n-COOH (n = 0-20)

<400> SEQUENCE: 61

Lys Pro Val Ser Leu Ser Tyr Arg Ala Pro Phe Arg Phe Xaa
1               5                   10

<210> SEQ ID NO 62
<211> LENGTH: 13
<212> TYPE: PRT
<213> ORGANISM: Artificial Sequence
<220> FEATURE:
<223> OTHER INFORMATION: portion of synthetic CTCE0021-like analog CXCR4
      agonist
<220> FEATURE:
<221> NAME/KEY: MOD_RES
<222> LOCATION: (1)..(1)
<223> OTHER INFORMATION: Xaa = Leu linked to Phe at position 14 of
      KXVSXSYRCPCRFX (SEQ ID NO:61) via a moiety providing covalent
      attachment between N and C terminal portions of the peptides, such
      as NH-2-(CH-2)-n-COOH (n = 0-20)
<220> FEATURE:
<221> NAME/KEY: MISC_FEATURE
<222> LOCATION: (2)..(6)
<223> OTHER INFORMATION: side chain cyclized using lactam formation
<220> FEATURE:
<221> NAME/KEY: MOD_RES
<222> LOCATION: (13)..(13)
<223> OTHER INFORMATION: AMIDATION

<400> SEQUENCE: 62

Xaa Lys Trp Ile Gln Glu Tyr Leu Glu Lys Ala Leu Asn
1               5                   10
```

<210> SEQ ID NO 63
<211> LENGTH: 31
<212> TYPE: PRT
<213> ORGANISM: Artificial Sequence
<220> FEATURE:
<223> OTHER INFORMATION: synthetic CTCE0021-like analog CXCR4 agonist
<220> FEATURE:
<221> NAME/KEY: MISC_FEATURE
<222> LOCATION: (20)..(24)
<223> OTHER INFORMATION: side chain cyclized using lactam formation
<220> FEATURE:
<221> NAME/KEY: MOD_RES
<222> LOCATION: (31)..(31)
<223> OTHER INFORMATION: AMIDATION

<400> SEQUENCE: 63

Lys Pro Val Ser Leu Ser Tyr Arg Ala Pro His Arg Phe Phe Gly Gly
1               5                   10                  15

Gly Gly Leu Lys Trp Ile Gln Glu Tyr Leu Glu Lys Ala Leu Asn
            20                  25                  30

<210> SEQ ID NO 64
<211> LENGTH: 14
<212> TYPE: PRT
<213> ORGANISM: Artificial Sequence
<220> FEATURE:
<223> OTHER INFORMATION: portion of synthetic CTCE0021-like analog CXCR4
      agonist
<220> FEATURE:
<221> NAME/KEY: MOD_RES
<222> LOCATION: (14)..(14)
<223> OTHER INFORMATION: Xaa = Phe linked to Leu at position 1 of
      XKWIQEYLEKALN (SEQ ID NO:65) via a moiety providing covalent
      attachment between N and C terminal portions of the peptides, such
      as NH-2-(CH-2)-n-COOH (n = 0-20)

<400> SEQUENCE: 64

Lys Pro Val Ser Leu Ser Tyr Arg Ala Pro His Arg Phe Xaa
1               5                   10

<210> SEQ ID NO 65
<211> LENGTH: 13
<212> TYPE: PRT
<213> ORGANISM: Artificial Sequence
<220> FEATURE:
<223> OTHER INFORMATION: portion of synthetic CTCE0021-like analog CXCR4
      agonist
<220> FEATURE:
<221> NAME/KEY: MOD_RES
<222> LOCATION: (1)..(1)
<223> OTHER INFORMATION: Xaa = Leu linked to Phe at position 14 of
      KXVSXSYRCPCRFX (SEQ ID NO:64) via a moiety providing covalent
      attachment between N and C terminal portions of the peptides, such
      as NH-2-(CH-2)-n-COOH (n = 0-20)
<220> FEATURE:
<221> NAME/KEY: MISC_FEATURE
<222> LOCATION: (2)..(6)
<223> OTHER INFORMATION: side chain cyclized using lactam formation
<220> FEATURE:
<221> NAME/KEY: MOD_RES
<222> LOCATION: (13)..(13)
<223> OTHER INFORMATION: AMIDATION

<400> SEQUENCE: 65

Xaa Lys Trp Ile Gln Glu Tyr Leu Glu Lys Ala Leu Asn
1               5                   10

<210> SEQ ID NO 66
<211> LENGTH: 31
<212> TYPE: PRT

```
<213> ORGANISM: Artificial Sequence
<220> FEATURE:
<223> OTHER INFORMATION: synthetic CTCE0021-like analog CXCR4 agonist
<220> FEATURE:
<221> NAME/KEY: MOD_RES
<222> LOCATION: (1)..(1)
<223> OTHER INFORMATION: Lys is modified with polyethylene glycol (PEG)
<220>

```
Xaa Lys Trp Ile Gln Glu Tyr Leu Glu Lys Ala Leu Asn
1               5                   10

<210> SEQ ID NO 69
<211> LENGTH: 31
<212> TYPE: PRT
<213> ORGANISM: Artificial Sequence
<220> FEATURE:
<223> OTHER INFORMATION: synthetic CTCE0021-like analog CXCR4 agonist
<220> FEATURE:
<221> NAME/KEY: MISC_FEATURE
<222> LOCATION: (20)..(24)
<223> OTHER INFORMATION: side chain cyclized using lactam formation
<220> FEATURE:
<221> NAME/KEY: MOD_RES
<222> LOCATION: (31)..(31)
<223> OTHER INFORMATION: AMIDATION

<400> SEQUENCE: 69

Lys Pro Val Ser Leu Ser Tyr Arg Ala Pro Trp Arg Phe Phe Gly Gly
1               5                   10                  15

Gly Gly Leu Lys Trp Ile Gln Glu Tyr Leu Glu Lys Ala Leu Asn
            20                  25                  30

<210> SEQ ID NO 70
<211> LENGTH: 14
<212> TYPE: PRT
<213> ORGANISM: Artificial Sequence
<220> FEATURE:
<223> OTHER INFORMATION: portion of synthetic CTCE0021-like analog CXCR4
      agonist
<220> FEATURE:
<221> NAME/KEY: MOD_RES
<222> LOCATION: (14)..(14)
<223> OTHER INFORMATION: Xaa = Phe linked to Leu at position 1 of
      XKWIQEYLEKALN (SEQ ID NO:71) via a moiety providing covalent
      attachment between N and C terminal portions of the peptides, such
      as NH-2-(CH-2)-n-COOH (n = 0-20)

<400> SEQUENCE: 70

Lys Pro Val Ser Leu Ser Tyr Arg Ala Pro Trp Arg Phe Xaa
1               5                   10

<210> SEQ ID NO 71
<211> LENGTH: 13
<212> TYPE: PRT
<213> ORGANISM: Artificial Sequence
<220> FEATURE:
<223> OTHER INFORMATION: portion of synthetic CTCE0021-like analog CXCR4
      agonist
<220> FEATURE:
<221> NAME/KEY: MOD_RES
<222> LOCATION: (1)..(1)
<223> OTHER INFORMATION: Xaa = Leu linked to Phe at position 14 of
      KXVSXSYRCPCRFX (SEQ ID NO:70) via a moiety providing covalent
      attachment between N and C terminal portions of the peptides, such
      as NH-2-(CH-2)-n-COOH (n = 0-20)
<220> FEATURE:
<221> NAME/KEY: MISC_FEATURE
<222> LOCATION: (2)..(6)
<223> OTHER INFORMATION: side chain cyclized using lactam formation
<220> FEATURE:
<221> NAME/KEY: MOD_RES
<222> LOCATION: (13)..(13)
<223> OTHER INFORMATION: AMIDATION

<400> SEQUENCE: 71

Xaa Lys Trp Ile Gln Glu Tyr Leu Glu Lys Ala Leu Asn
1               5                   10

<210> SEQ ID NO 72
```

```
<211> LENGTH: 31
<212> TYPE: PRT
<213> ORGANISM: Artificial Sequence
<220> FEATURE:
<223> OTHER INFORMATION: synthetic CTCE0021-like analog CXCR4 agonist
<220> FEATURE:
<221> NAME/KEY: MOD_RES
<222> LOCATION: (1)..(1)
<223> OTHER INFORMATION: Lys is modified with polyethylene glycol (PEG)
<220> FEATURE:
<221> NAME/KEY: MISC_FEATURE
<222> LOCATION: (20)..(24)
<223> OTHER INFORMATION: side chain cyclized using lactam formation
<220> FEATURE:
<221> NAME/KEY: MOD_RES
<222> LOCATION: (31)..(31)
<223> OTHER INFORMATION: AMIDATION

<400> SEQUENCE: 72

Lys Pro Val Ser Leu Ser Tyr Arg Ala Pro Trp Arg Phe Phe Gly Gly
1               5                   10                  15

Gly Gly Leu Lys Trp Ile Gln Glu Tyr Leu Glu Lys Ala Leu Asn
            20                  25                  30

<210> SEQ ID NO 73
<211> LENGTH: 14
<212> TYPE: PRT
<213> ORGANISM: Artificial Sequence
<220> FEATURE:
<223> OTHER INFORMATION: portion of synthetic CTCE0021-like analog CXCR4
      agonist
<220> FEATURE:
<221> NAME/KEY: MOD_RES
<222> LOCATION: (1)..(1)
<223> OTHER INFORMATION: Lys is modified with polyethylene glycol (PEG)
<220> FEATURE:
<221> NAME/KEY: MOD_RES
<222> LOCATION: (14)..(14)
<223> OTHER INFORMATION: Xaa = Phe linked to Leu at position 1 of
      XKWIQEYLEKALN (SEQ ID NO:74) via a moiety providing covalent
      attachment between N and C terminal portions of the peptides, such
      as NH-2-(CH-2)-n-COOH (n = 0-20)

<400> SEQUENCE: 73

Lys Pro Val Ser Leu Ser Tyr Arg Ala Pro Trp Arg Phe Xaa
1               5                   10

<210> SEQ ID NO 74
<211> LENGTH: 13
<212> TYPE: PRT
<213> ORGANISM: Artificial Sequence
<220> FEATURE:
<223> OTHER INFORMATION: portion of synthetic CTCE0021-like analog CXCR4
      agonist
<220> FEATURE:
<221> NAME/KEY: MOD_RES
<222> LOCATION: (1)..(1)
<223> OTHER INFORMATION: Xaa = Leu linked to Phe at position 14 of
      KXVSXSYRCPCRFX (SEQ ID NO:73) via a moiety providing covalent
      attachment between N and C terminal portions of the peptides, such
      as NH-2-(CH-2)-n-COOH (n = 0-20)
<220> FEATURE:
<221> NAME/KEY: MISC_FEATURE
<222> LOCATION: (2)..(6)
<223> OTHER INFORMATION: side chain cyclized using lactam formation
<220> FEATURE:
<221> NAME/KEY: MOD_RES
<222> LOCATION: (13)..(13)
<223> OTHER INFORMATION: AMIDATION

<400> SEQUENCE: 74

Xaa Lys Trp Ile Gln Glu Tyr Leu Glu Lys Ala Leu Asn
1               5                   10
```

```
<210> SEQ ID NO 75
<211> LENGTH: 31
<212> TYPE: PRT
<213> ORGANISM: Artificial Sequence
<220> FEATURE:
<223> OTHER INFORMATION: synthetic CTCE0021-like analog CXCR4 agonist
<220> FEATURE:
<221> NAME/KEY: MISC_FEATURE
<222> LOCATION: (20)..(24)
<223> OTHER INFORMATION: side chain cyclized using lactam formation
<220> FEATURE:
<221> NAME/KEY: MOD_RES
<222> LOCATION: (31)..(31)
<223> OTHER INFORMATION: AMIDATION

<400> SEQUENCE: 75

Lys Pro Val Ser Leu Ser Tyr Arg Phe Pro Ala Arg Phe Phe Gly Gly
1               5                   10                  15

Gly Gly Leu Lys Trp Ile Gln Glu Tyr Leu Glu Lys Ala Leu Asn
            20                  25                  30

<210> SEQ ID NO 76
<211> LENGTH: 14
<212> TYPE: PRT
<213> ORGANISM: Artificial Sequence
<220> FEATURE:
<223> OTHER INFORMATION: portion of synthetic CTCE0021-like analog CXCR4
      agonist
<220> FEATURE:
<221> NAME/KEY: MOD_RES
<222> LOCATION: (14)..(14)
<223> OTHER INFORMATION: Xaa = Phe linked to Leu at position 1 of
      XKWIQEYLEKALN (SEQ ID NO:77) via a moiety providing covalent
      attachment between N and C terminal portions of the peptides, such
      as NH-2-(CH-2)-n-COOH (n = 0-20)

<400> SEQUENCE: 76

Lys Pro Val Ser Leu Ser Tyr Arg Phe Pro Ala Arg Phe Xaa
1               5                   10

<210> SEQ ID NO 77
<211> LENGTH: 13
<212> TYPE: PRT
<213> ORGANISM: Artificial Sequence
<220> FEATURE:
<223> OTHER INFORMATION: portion of synthetic CTCE0021-like analog CXCR4
      agonist
<220> FEATURE:
<221> NAME/KEY: MOD_RES
<222> LOCATION: (1)..(1)
<223> OTHER INFORMATION: Xaa = Leu linked to Phe at position 14 of
      KXVSXSYRCPCRFX (SEQ ID NO:76) via a moiety providing covalent
      attachment between N and C terminal portions of the peptides, such
      as NH-2-(CH-2)-n-COOH (n = 0-20)
<220> FEATURE:
<221> NAME/KEY: MISC_FEATURE
<222> LOCATION: (2)..(6)
<223> OTHER INFORMATION: side chain cyclized using lactam formation
<220> FEATURE:
<221> NAME/KEY: MOD_RES
<222> LOCATION: (13)..(13)
<223> OTHER INFORMATION: AMIDATION

<400> SEQUENCE: 77

Xaa Lys Trp Ile Gln Glu Tyr Leu Glu Lys Ala Leu Asn
1               5                   10

<210> SEQ ID NO 78
<211> LENGTH: 31
<212> TYPE: PRT
```

```
<213> ORGANISM: Artificial Sequence
<220> FEATURE:
<223> OTHER INFORMATION: synthetic CTCE0021-like analog CX

```
<210> SEQ ID NO 81
<211> LENGTH: 31
<212> TYPE: PRT
<213> ORGANISM: Artificial Sequence
<220> FEATURE:
<223> OTHER INFORMATION: synthetic CTCE0021-like analog CXCR4 agonist
<220> FEATURE:
<221> NAME/KEY: MISC_FEATURE
<222> LOCATION: (20)..(24)
<223> OTHER INFORMATION: side chain cyclized using lactam formation
<220> FEATURE:
<221> NAME/KEY: MOD_RES
<222> LOCATION: (31)..(31)
<223> OTHER INFORMATION: AMIDATION

<400> SEQUENCE: 81

Lys Pro Val Ser Leu Ser Tyr Arg His Pro Ala Arg Phe Gly Gly
1               5                   10                  15

Gly Gly Leu Lys Trp Ile Gln Glu Tyr Leu Glu Lys Ala Leu Asn
            20                  25                  30

<210> SEQ ID NO 82
<211> LENGTH: 14
<212> TYPE: PRT
<213> ORGANISM: Artificial Sequence
<220> FEATURE:
<223> OTHER INFORMATION: portion of synthetic CTCE0021-like analog CXCR4
      agonist
<220> FEATURE:
<221> NAME/KEY: MOD_RES
<222> LOCATION: (14)..(14)
<223> OTHER INFORMATION: Xaa = Phe linked to Leu at position 1 of
      XKWIQEYLEKALN (SEQ ID NO:83) via a moiety providing covalent
      attachment between N and C terminal portions of the peptides, such
      as NH-2-(CH-2)-n-COOH (n = 0-20)

<400> SEQUENCE: 82

Lys Pro Val Ser Leu Ser Tyr Arg His Pro Ala Arg Phe Xaa
1               5                   10

<210> SEQ ID NO 83
<211> LENGTH: 13
<212> TYPE: PRT
<213> ORGANISM: Artificial Sequence
<220> FEATURE:
<223> OTHER INFORMATION: portion of synthetic CTCE0021-like analog CXCR4
      agonist
<220> FEATURE:
<221> NAME/KEY: MOD_RES
<222> LOCATION: (1)..(1)
<223> OTHER INFORMATION: Xaa = Leu linked to Phe at position 14 of
      KXVSXSYRCPCRFX (SEQ ID NO:82) via a moiety providing covalent
      attachment between N and C terminal portions of the peptides, such
      as NH-2-(CH-2)-n-COOH (n = 0-20)
<220> FEATURE:
<221> NAME/KEY: MISC_FEATURE
<222> LOCATION: (2)..(6)
<223> OTHER INFORMATION: side chain cyclized using lactam formation
<220> FEATURE:
<221> NAME/KEY: MOD_RES
<222> LOCATION: (13)..(13)
<223> OTHER INFORMATION: AMIDATION

<400> SEQUENCE: 83

Xaa Lys Trp Ile Gln Glu Tyr Leu Glu Lys Ala Leu Asn
1               5                   10

<210> SEQ ID NO 84
<211> LENGTH: 31
<212> TYPE: PRT
<213> ORGANISM: Artificial Sequence
<220> FEATURE:
```

<223> OTHER INFORMATION: synthetic CTCE0021-like analog CXCR4 agonist
<220> FEATURE:
<221> NAME/KEY: MOD_RES
<222> LOCATION: (1)..(1)
<223> OTHER INFORMATION: Lys is modified with polyethylene glycol (PEG)
<220> FEATURE:
<221> NAME/KEY: MISC_FEATURE
<222> LOCATION: (20)..(24)
<223> OTHER INFORMATION: side chain cyclized using lactam formation
<220> FEATURE:
<221> NAME/KEY: MOD_RES
<222> LOCATION: (31)..(31)
<223> OTHER INFORMATION: AMIDATION

<400> SEQUENCE: 84

Lys Pro Val Ser Leu Ser Tyr Arg His Pro Ala Arg Phe Phe Gly Gly
1               5                   10                  15

Gly Gly Leu Lys Trp Ile Gln Glu Tyr Leu Glu Lys Ala Leu Asn
            20                  25                  30

<210> SEQ ID NO 85
<211> LENGTH: 14
<212> TYPE: PRT
<213> ORGANISM: Artificial Sequence
<220> FEATURE:
<223> OTHER INFORMATION: portion of synthetic CTCE0021-like analog CXCR4
      agonist
<220> FEATURE:
<221> NAME/KEY: MOD_RES
<222> LOCATION: (1)..(1)
<223> OTHER INFORMATION: Lys is modified with polyethylene glycol (PEG)
<220> FEATURE:
<221> NAME/KEY: MOD_RES
<222> LOCATION: (14)..(14)
<223> OTHER INFORMATION: Xaa = Phe linked to Leu at position 1 of
      XKWIQEYLEKALN (SEQ ID NO:86) via a moiety providing covalent
      attachment between N and C terminal portions of the peptides, such
      as NH-2-(CH-2)-n-COOH (n = 0-20)

<400> SEQUENCE: 85

Lys Pro Val Ser Leu Ser Tyr Arg His Pro Ala Arg Phe Xaa
1               5                   10

<210> SEQ ID NO 86
<211> LENGTH: 13
<212> TYPE: PRT
<213> ORGANISM: Artificial Sequence
<220> FEATURE:
<223> OTHER INFORMATION: portion of synthetic CTCE0021-like analog CXCR4
      agonist
<220> FEATURE:
<221> NAME/KEY: MOD_RES
<222> LOCATION: (1)..(1)
<223> OTHER INFORMATION: Xaa = Leu linked to Phe at position 14 of
      KXVSXSYRCPCRFX (SEQ ID NO:85) via a moiety providing covalent
      attachment between N and C terminal portions of the peptides, such
      as NH-2-(CH-2)-n-COOH (n = 0-20)
<220> FEATURE:
<221> NAME/KEY: MISC_FEATURE
<222> LOCATION: (2)..(6)
<223> OTHER INFORMATION: side chain cyclized using lactam formation
<220> FEATURE:
<221> NAME/KEY: MOD_RES
<222> LOCATION: (13)..(13)
<223> OTHER INFORMATION: AMIDATION

<400> SEQUENCE: 86

Xaa Lys Trp Ile Gln Glu Tyr Leu Glu Lys Ala Leu Asn
1               5                   10

<210> SEQ ID NO 87
<211> LENGTH: 31

```
<212> TYPE: PRT
<213> ORGANISM: Artificial Sequence
<220> FEATURE:
<223> OTHER INFORMATION: synthetic CTCE0021-like analog CXCR4 agonist
<220> FEATURE:
<221> NAME/KEY: MISC_FEATURE
<222> LOCATION: (20)..(24)
<223> OTHER INFORMATION: side chain cyclized using lactam formation
<220> FEATURE:
<221> NAME/KEY: MOD_RES
<222> LOCATION: (31)..(31)
<223> OTHER INFORMATION: AMIDATION

<400> SEQUENCE: 87

Lys Pro Val Ser Leu Ser Tyr Arg Trp Pro Ala Arg Phe Phe Gly Gly
1               5                   10                  15

Gly Gly Leu Lys Trp Ile Gln Glu Tyr Leu Glu Lys Ala Leu Asn
            20                  25                  30

<210> SEQ ID NO 88
<211> LENGTH: 14
<212> TYPE: PRT
<213> ORGANISM: Artificial Sequence
<220> FEATURE:
<223> OTHER INFORMATION: portion of synthetic CTCE0021-like analog CXCR4
      agonist
<220> FEATURE:
<221> NAME/KEY: MOD_RES
<222> LOCATION: (14)..(14)
<223> OTHER INFORMATION: Xaa = Phe linked to Leu at position 1 of
      XKWIQEYLEKALN (SEQ ID NO:89) via a moiety providing covalent
      attachment between N and C terminal portions of the peptides, such
      as NH-2-(CH-2)-n-COOH (n = 0-20)

<400> SEQUENCE: 88

Lys Pro Val Ser Leu Ser Tyr Arg Trp Pro Ala Arg Phe Xaa
1               5                   10

<210> SEQ ID NO 89
<211> LENGTH: 13
<212> TYPE: PRT
<213> ORGANISM: Artificial Sequence
<220> FEATURE:
<223> OTHER INFORMATION: portion of synthetic CTCE0021-like analog CXCR4
      agonist
<220> FEATURE:
<221> NAME/KEY: MOD_RES
<222> LOCATION: (1)..(1)
<223> OTHER INFORMATION: Xaa = Leu linked to Phe at position 14 of
      KXVSXSYRCPCRFX (SEQ ID NO:88) via a moiety providing covalent
      attachment between N and C terminal portions of the peptides, such
      as NH-2-(CH-2)-n-COOH (n = 0-20)
<220> FEATURE:
<221> NAME/KEY: MISC_FEATURE
<222> LOCATION: (2)..(6)
<223> OTHER INFORMATION: side chain cyclized using lactam formation
<220> FEATURE:
<221> NAME/KEY: MOD_RES
<222> LOCATION: (13)..(13)
<223> OTHER INFORMATION: AMIDATION

<400> SEQUENCE: 89

Xaa Lys Trp Ile Gln Glu Tyr Leu Glu Lys Ala Leu Asn
1               5                   10

<210> SEQ ID NO 90
<211> LENGTH: 31
<212> TYPE: PRT
<213> ORGANISM: Artificial Sequence
<220> FEATURE:
<223> OTHER INFORMATION: synthetic CTCE0021-like analog CXCR4 agonist
<220> FEATURE:
```

```
<221> NAME/KEY: MOD_RES
<222> LOCATION: (1)..(1)
<223> OTHER INFORMATION: Lys is modified with polyethylene glycol (PEG)
<220> FEATURE:
<221> NAME/KEY: MISC_FEATURE
<222> LOCATION: (20)..(24)
<223> OTHER INFORMATION: side chain cyclized using lactam formation
<220> FEATURE:
<221> NAME/KEY: MOD_RES
<222> LOCATION: (31)..(31)
<223> OTHER INFORMATION: AMIDATION

<400> SEQUENCE: 90

Lys Pro Val Ser Leu Ser Tyr Arg Trp Pro Ala Arg Phe Phe Gly Gly
1               5                   10                  15

Gly Gly Leu Lys Trp Ile Gln Glu Tyr Leu Glu Lys Ala Leu Asn
            20                  25                  30

<210> SEQ ID NO 91
<211> LENGTH: 14
<212> TYPE: PRT
<213> ORGANISM: Artificial Sequence
<220> FEATURE:
<223> OTHER INFORMATION: portion of synthetic CTCE0021-like analog CXCR4
      agonist
<220> FEATURE:
<221> NAME/KEY: MOD_RES
<222> LOCATION: (1)..(1)
<223> OTHER INFORMATION: Lys is modified with polyethylene glycol (PEG)
<220> FEATURE:
<221> NAME/KEY: MOD_RES
<222> LOCATION: (14)..(14)
<223> OTHER INFORMATION: Xaa = Phe linked to Leu at position 1 of
      XKWIQEYLEKALN (SEQ ID NO:92) via a moiety providing covalent
      attachment between N and C terminal portions of the peptides, such
      as NH-2-(CH-2)-n-COOH (n = 0-20)

<400> SEQUENCE: 91

Lys Pro Val Ser Leu Ser Tyr Arg Trp Pro Ala Arg Phe Xaa
1               5                   10

<210> SEQ ID NO 92
<211> LENGTH: 13
<212> TYPE: PRT
<213> ORGANISM: Artificial Sequence
<220> FEATURE:
<223> OTHER INFORMATION: portion of synthetic CTCE0021-like analog CXCR4
      agonist
<220> FEATURE:
<221> NAME/KEY: MOD_RES
<222> LOCATION: (1)..(1)
<223> OTHER INFORMATION: Xaa = Leu linked to Phe at position 14 of
      KXVSXSYRCPCRFX (SEQ ID NO:91) via a moiety providing covalent
      attachment between N and C terminal portions of the peptides, such
      as NH-2-(CH-2)-n-COOH (n = 0-20)
<220> FEATURE:
<221> NAME/KEY: MISC_FEATURE
<222> LOCATION: (2)..(6)
<223> OTHER INFORMATION: side chain cyclized using lactam formation
<220> FEATURE:
<221> NAME/KEY: MOD_RES
<222> LOCATION: (13)..(13)
<223> OTHER INFORMATION: AMIDATION

<400> SEQUENCE: 92

Xaa Lys Trp Ile Gln Glu Tyr Leu Glu Lys Ala Leu Asn
1               5                   10

<210> SEQ ID NO 93
<211> LENGTH: 31
<212> TYPE: PRT
<213> ORGANISM: Artificial Sequence
```

```
<220> FEATURE:
<223> OTHER INFORMATION: synthetic CTCE0021-like analog CXCR4 agonist
<220> FEATURE:
<221> NAME/KEY: MISC_FEATURE
<222> LOCATION: (20)..(24)
<223> OTHER INFORMATION: side chain cyclized using lactam formation
<220> FEATURE:
<221> NAME/KEY: MOD_RES
<222> LOCATION: (31)..(31)
<223> OTHER INFORMATION: AMIDATION

<400> SEQUENCE: 93

Lys Pro Val Ser Leu Ser Tyr Arg Ala Pro Tyr Arg Phe Phe Gly Gly
1               5                   10                  15

Gly Gly Leu Lys Trp Ile Gln Glu Tyr Leu Glu Lys Ala Leu Asn
            20                  25                  30

<210> SEQ ID NO 94
<211> LENGTH: 14
<212> TYPE: PRT
<213> ORGANISM: Artificial Sequence
<220> FEATURE:
<223> OTHER INFORMATION: portion of synthetic CTCE0021-like analog CXCR4
      agonist
<220> FEATURE:
<221> NAME/KEY: MOD_RES
<222> LOCATION: (14)..(14)
<223> OTHER INFORMATION: Xaa = Phe linked to Leu at position 1 of
      XKWIQEYLEKALN (SEQ ID NO:95) via a moiety providing covalent
      attachment between N and C terminal portions of the peptides, such
      as NH-2-(CH-2)-n-COOH (n = 0-20)

<400> SEQUENCE: 94

Lys Pro Val Ser Leu Ser Tyr Arg Ala Pro Tyr Arg Phe Xaa
1               5                   10

<210> SEQ ID NO 95
<211> LENGTH: 13
<212> TYPE: PRT
<213> ORGANISM: Artificial Sequence
<220> FEATURE:
<223> OTHER INFORMATION: portion of synthetic CTCE0021-like analog CXCR4
      agonist
<220> FEATURE:
<221> NAME/KEY: MOD_RES
<222> LOCATION: (1)..(1)
<223> OTHER INFORMATION: Xaa = Leu linked to Phe at position 14 of
      KXVSXSYRCPCRFX (SEQ ID NO:94) via a moiety providing covalent
      attachment between N and C terminal portions of the peptides, such
      as NH-2-(CH-2)-n-COOH (n = 0-20)
<220> FEATURE:
<221> NAME/KEY: MISC_FEATURE
<222> LOCATION: (2)..(6)
<223> OTHER INFORMATION: side chain cyclized using lactam formation
<220> FEATURE:
<221> NAME/KEY: MOD_RES
<222> LOCATION: (13)..(13)
<223> OTHER INFORMATION: AMIDATION

<400> SEQUENCE: 95

Xaa Lys Trp Ile Gln Glu Tyr Leu Glu Lys Ala Leu Asn
1               5                   10

<210> SEQ ID NO 96
<211> LENGTH: 31
<212> TYPE: PRT
<213> ORGANISM: Artificial Sequence
<220> FEATURE:
<223> OTHER INFORMATION: synthetic CTCE0021-like analog CXCR4 agonist
<220> FEATURE:
<221> NAME/KEY: MOD_RES
<222> LOCATION: (1)..(1)
```

```
<223> OTHER INFORMATION: Lys is modified with polyethylene glycol (PEG)
<220> FEATURE:
<221> NAME/KEY: MISC_FEATURE
<222> LOCATION: (20)..(24)
<223> OTHER INFORMATION: side chain cyclized using lactam formation
<220> FEATURE:
<221> NAME/KEY: MOD_RES
<222> LOCATION: (31)..(31)
<223> OTHER INFORMATION: AMIDATION

<400> SEQUENCE: 96

Lys Pro Val Ser Leu Ser Tyr Arg Ala Pro Tyr Arg Phe Phe Gly Gly
1               5                   10                  15

Gly Gly Leu Lys Trp Ile Gln Glu Tyr Leu Glu Lys Ala Leu Asn
            20                  25                  30

<210> SEQ ID NO 97
<211> LENGTH: 14
<212> TYPE: PRT
<213> ORGANISM: Artificial Sequence
<220> FEATURE:
<223> OTHER INFORMATION: portion of synthetic CTCE0021-like analog CXCR4
      agonist
<220> FEATURE:
<221> NAME/KEY: MOD_RES
<222> LOCATION: (1)..(1)
<223> OTHER INFORMATION: Lys is modified with polyethylene glycol (PEG)
<220> FEATURE:
<221> NAME/KEY: MOD_RES
<222> LOCATION: (14)..(14)
<223> OTHER INFORMATION: Xaa = Phe linked to Leu at position 1 of
      XKWIQEYLEKALN (SEQ ID NO:98) via a moiety providing covalent
      attachment between N and C terminal portions of the peptides, such
      as NH-2-(CH-2)-n-COOH (n = 0-20)

<400> SEQUENCE: 97

Lys Pro Val Ser Leu Ser Tyr Arg Ala Pro Tyr Arg Phe Xaa
1               5                   10

<210> SEQ ID NO 98
<211> LENGTH: 13
<212> TYPE: PRT
<213> ORGANISM: Artificial Sequence
<220> FEATURE:
<223> OTHER INFORMATION: portion of synthetic CTCE0021-like analog CXCR4
      agonist
<220> FEATURE:
<221> NAME/KEY: MOD_RES
<222> LOCATION: (1)..(1)
<223> OTHER INFORMATION: Xaa = Leu linked to Phe at position 14 of
      KXVSXSYRCPCRFX (SEQ ID NO:97) via a moiety providing covalent
      attachment between N and C terminal portions of the peptides, such
      as NH-2-(CH-2)-n-COOH (n = 0-20)
<220> FEATURE:
<221> NAME/KEY: MISC_FEATURE
<222> LOCATION: (2)..(6)
<223> OTHER INFORMATION: side chain cyclized using lactam formation
<220> FEATURE:
<221> NAME/KEY: MOD_RES
<222> LOCATION: (13)..(13)
<223> OTHER INFORMATION: AMIDATION

<400> SEQUENCE: 98

Xaa Lys Trp Ile Gln Glu Tyr Leu Glu Lys Ala Leu Asn
1               5                   10

<210> SEQ ID NO 99
<211> LENGTH: 31
<212> TYPE: PRT
<213> ORGANISM: Artificial Sequence
<220> FEATURE:
<223> OTHER INFORMATION: synthetic CTCE0021-like analog CXCR4 agonist
```

```
<220> FEATURE:
<221> NAME/KEY: MISC_FEATURE
<222> LOCATION: (20)..(24)
<223> OTHER INFORMATION: side chain cyclized using lactam formation
<220> FEATURE:
<221> NAME/KEY: MOD_RES
<222> LOCATION: (31)..(31)
<223> OTHER INFORMATION: AMIDATION

<400> SEQUENCE: 99

Lys Pro Val Ser Leu Ser Tyr Arg Tyr Pro Tyr Arg Phe Phe Gly Gly
1               5                   10                  15

Gly Gly Leu Lys Trp Ile Gln Glu Tyr Leu Glu Lys Ala Leu Asn
            20                  25                  30

<210> SEQ ID NO 100
<211> LENGTH: 14
<212> TYPE: PRT
<213> ORGANISM: Artificial Sequence
<220> FEATURE:
<223> OTHER INFORMATION: portion of synthetic CTCE0021-like analog CXCR4
      agonist
<220> FEATURE:
<221> NAME/KEY: MOD_RES
<222> LOCATION: (14)..(14)
<223> OTHER INFORMATION: Xaa = Phe linked to Leu at position 1 of
      XKWIQEYLEKALN (SEQ ID NO:101) via a moiety providing covalent
      attachment between N and C terminal portions of the peptides, such
      as NH-2-(CH-2)-n-COOH (n = 0-20)

<400> SEQUENCE: 100

Lys Pro Val Ser Leu Ser Tyr Arg Tyr Pro Tyr Arg Phe Xaa
1               5                   10

<210> SEQ ID NO 101
<211> LENGTH: 13
<212> TYPE: PRT
<213> ORGANISM: Artificial Sequence
<220> FEATURE:
<223> OTHER INFORMATION: portion of synthetic CTCE0021-like analog CXCR4
      agonist
<220> FEATURE:
<221> NAME/KEY: MOD_RES
<222> LOCATION: (1)..(1)
<223> OTHER INFORMATION: Xaa = Leu linked to Phe at position 14 of
      KXVSXSYRCPCRFX (SEQ ID NO:100) via a moiety providing covalent
      attachment between N and C terminal portions of the
      peptides, such as NH-2-(CH-2)-n-COOH (n = 0-20)
<220> FEATURE:
<221> NAME/KEY: MISC_FEATURE
<222> LOCATION: (2)..(6)
<223> OTHER INFORMATION: side chain cyclized using lactam formation
<220> FEATURE:
<221> NAME/KEY: MOD_RES
<222> LOCATION: (13)..(13)
<223> OTHER INFORMATION: AMIDATION

<400> SEQUENCE: 101

Xaa Lys Trp Ile Gln Glu Tyr Leu Glu Lys Ala Leu Asn
1               5                   10

<210> SEQ ID NO 102
<211> LENGTH: 31
<212> TYPE: PRT
<213> ORGANISM: Artificial Sequence
<220> FEATURE:
<223> OTHER INFORMATION: synthetic CTCE0021-like analog CXCR4 agonist
<220> FEATURE:
<221> NAME/KEY: MOD_RES
<222> LOCATION: (1)..(1)
<223> OTHER INFORMATION: Lys is modified with polyethylene glycol (PEG)
<220> FEATURE:
```

```
<221> NAME/KEY: MISC_FEATURE
<222> LOCATION: (20)..(24)
<223> OTHER INFORMATION: side chain cyclized using lactam formation
<220> FEATURE:
<221> NAME/KEY: MOD_RES
<222> LOCATION: (31)..(31)
<223> OTHER INFORMATION: AMIDATION

<400> SEQUENCE: 102

Lys Pro Val Ser Leu Ser Tyr Arg Tyr Pro Tyr Arg Phe Phe Gly Gly
1               5                   10                  15

Gly Gly Leu Lys Trp Ile Gln Glu Tyr Leu Glu Lys Ala Leu Asn
            20                  25                  30

<210> SEQ ID NO 103
<211> LENGTH: 14
<212> TYPE: PRT
<213> ORGANISM: Artificial Sequence
<220> FEATURE:
<223> OTHER INFORMATION: portion of synthetic CTCE0021-like analog CXCR4
      agonist
<220> FEATURE:
<221> NAME/KEY: MOD_RES
<222> LOCATION: (1)..(1)
<223> OTHER INFORMATION: Lys is modified with polyethylene glycol (PEG)
<220> FEATURE:
<221> NAME/KEY: MOD_RES
<222> LOCATION: (14)..(14)
<223> OTHER INFORMATION: Xaa = Phe linked to Leu at position 1 of
      XKWIQEYLEKALN (SEQ ID NO:104) via a moiety providing covalent
      attachment between N and C terminal portions of the
      peptides, such as NH-2-(CH-2)-n-COOH (n = 0-20)

<400> SEQUENCE: 103

Lys Pro Val Ser Leu Ser Tyr Arg Tyr Pro Tyr Arg Phe Xaa
1               5                   10

<210> SEQ ID NO 104
<211> LENGTH: 13
<212> TYPE: PRT
<213> ORGANISM: Artificial Sequence
<220> FEATURE:
<223> OTHER INFORMATION: portion of synthetic CTCE0021-like analog CXCR4
      agonist
<220> FEATURE:
<221> NAME/KEY: MOD_RES
<222> LOCATION: (1)..(1)
<223> OTHER INFORMATION: Xaa = Leu linked to Phe at position 14 of
      KXVSXSYRCPCRFX (SEQ ID NO:103) via a moiety providing covalent
      attachment between N and C terminal portions of the
      peptides, such as NH-2-(CH-2)-n-COOH (n = 0-20)
<220> FEATURE:
<221> NAME/KEY: MISC_FEATURE
<222> LOCATION: (2)..(6)
<223> OTHER INFORMATION: side chain cyclized using lactam formation
<220> FEATURE:
<221> NAME/KEY: MOD_RES
<222> LOCATION: (13)..(13)
<223> OTHER INFORMATION: AMIDATION

<400> SEQUENCE: 104

Xaa Lys Trp Ile Gln Glu Tyr Leu Glu Lys Ala Leu Asn
1               5                   10

<210> SEQ ID NO 105
<211> LENGTH: 31
<212> TYPE: PRT
<213> ORGANISM: Artificial Sequence
<220> FEATURE:
<223> OTHER INFORMATION: synthetic CTCE0021-like analog CXCR4 agonist
<220> FEATURE:
<221> NAME/KEY: MISC_FEATURE
```

```
<222> LOCATION: (20)..(24)
<223> OTHER INFORMATION: side chain cyclized using lactam formation
<220> FEATURE:
<221> NAME/KEY: MOD_RES
<222> LOCATION: (31)..(31)
<223> OTHER INFORMATION: AMIDATION

<400> SEQUENCE: 105

Lys Pro Val Ser Leu Ser Tyr Arg Tyr Pro Ala Arg Phe Phe Gly Gly
1               5                   10                  15

Gly Gly Leu Lys Trp Ile Gln Glu Tyr Leu Glu Lys Ala Leu Asn
            20                  25                  30

<210> SEQ ID NO 106
<211> LENGTH: 14
<212> TYPE: PRT
<213> ORGANISM: Artificial Sequence
<220> FEATURE:
<223> OTHER INFORMATION: portion of synthetic CTCE0021-like analog CXCR4
      agonist
<220> FEATURE:
<221> NAME/KEY: MOD_RES
<222> LOCATION: (14)..(14)
<223> OTHER INFORMATION: Xaa = Phe linked to Leu at position 1 of
      XKWIQEYLEKALN (SEQ ID NO:107) via a moiety providing covalent
      attachment between N and C terminal portions of the
      peptides, such as NH-2-(CH-2)-n-COOH (n = 0-20)

<400> SEQUENCE: 106

Lys Pro Val Ser Leu Ser Tyr Arg Tyr Pro Ala Arg Phe Xaa
1               5                   10

<210> SEQ ID NO 107
<211> LENGTH: 13
<212> TYPE: PRT
<213> ORGANISM: Artificial Sequence
<220> FEATURE:
<223> OTHER INFORMATION: portion of synthetic CTCE0021-like analog CXCR4
      agonist
<220> FEATURE:
<221> NAME/KEY: MOD_RES
<222> LOCATION: (1)..(1)
<223> OTHER INFORMATION: Xaa = Leu linked to Phe at position 14 of
      KXVSXSYRCPCRFX (SEQ ID NO:106) via a moiety providing covalent
      attachment between N and C terminal portions of the
      peptides, such as NH-2-(CH-2)-n-COOH (n = 0-20)
<220> FEATURE:
<221> NAME/KEY: MISC_FEATURE
<222> LOCATION: (2)..(6)
<223> OTHER INFORMATION: side chain cyclized using lactam formation
<220> FEATURE:
<221> NAME/KEY: MOD_RES
<222> LOCATION: (13)..(13)
<223> OTHER INFORMATION: AMIDATION

<400> SEQUENCE: 107

Xaa Lys Trp Ile Gln Glu Tyr Leu Glu Lys Ala Leu Asn
1               5                   10

<210> SEQ ID NO 108
<211> LENGTH: 31
<212> TYPE: PRT
<213> ORGANISM: Artificial Sequence
<220> FEATURE:
<223> OTHER INFORMATION: synthetic CTCE0021-like analog CXCR4 agonist
<220> FEATURE:
<221> NAME/KEY: MOD_RES
<222> LOCATION: (1)..(1)
<223> OTHER INFORMATION: Lys is modified with polyethylene glycol (PEG)
<220> FEATURE:
<221> NAME/KEY: MISC_FEATURE
<222> LOCATION: (20)..(24)
```

```
<223> OTHER INFORMATION: side chain cyclized using lactam formation
<220> FEATURE:
<221> NAME/KEY: MOD_RES
<222> LOCATION: (31)..(31)
<223> OTHER INFORMATION: AMIDATION

<400> SEQUENCE: 108

Lys Pro Val Ser Leu Ser Tyr Arg Tyr Pro Ala Arg Phe Phe Gly Gly
1               5                   10                  15

Gly Gly Leu Lys Trp Ile Gln Glu Tyr Leu Glu Lys Ala Leu Asn
            20                  25                  30

<210> SEQ ID NO 109
<211> LENGTH: 14
<212> TYPE: PRT
<213> ORGANISM: Artificial Sequence
<220> FEATURE:
<223> OTHER INFORMATION: portion of synthetic CTCE0021-like analog CXCR4
      agonist
<220> FEATURE:
<221> NAME/KEY: MOD_RES
<222> LOCATION: (1)..(1)
<223> OTHER INFORMATION: Lys is modified with polyethylene glycol (PEG)
<220> FEATURE:
<221> NAME/KEY: MOD_RES
<222> LOCATION: (14)..(14)
<223> OTHER INFORMATION: Xaa = Phe linked to Leu at position 1 of
      XKWIQEYLEKALN (SEQ ID NO:110) via a moiety providing covalent
      attachment between N and C terminal portions of the
      peptides, such as NH-2-(CH-2)-n-COOH (n = 0-20)

<400> SEQUENCE: 109

Lys Pro Val Ser Leu Ser Tyr Arg Tyr Pro Ala Arg Phe Xaa
1               5                   10

<210> SEQ ID NO 110
<211> LENGTH: 13
<212> TYPE: PRT
<213> ORGANISM: Artificial Sequence
<220> FEATURE:
<223> OTHER INFORMATION: portion of synthetic CTCE0021-like analog CXCR4
      agonist
<220> FEATURE:
<221> NAME/KEY: MOD_RES
<222> LOCATION: (1)..(1)
<223> OTHER INFORMATION: Xaa = Leu linked to Phe at position 14 of
      KXVSXSYRCPCRFX (SEQ ID NO:109) via a moiety providing covalent
      attachment between N and C terminal portions of the
      peptides, such as NH-2-(CH-2)-n-COOH (n = 0-20)
<220> FEATURE:
<221> NAME/KEY: MISC_FEATURE
<222> LOCATION: (2)..(6)
<223> OTHER INFORMATION: side chain cyclized using lactam formation

<400> SEQUENCE: 110

Xaa Lys Trp Ile Gln Glu Tyr Leu Glu Lys Ala Leu Asn
1               5                   10

<210> SEQ ID NO 111
<211> LENGTH: 31
<212> TYPE: PRT
<213> ORGANISM: Artificial Sequence
<220> FEATURE:
<223> OTHER INFORMATION: synthetic CTCE0021-like analog CXCR4 agonist
<220> FEATURE:
<221> NAME/KEY: MISC_FEATURE
<222> LOCATION: (20)..(24)
<223> OTHER INFORMATION: side chain cyclized using lactam formation
<220> FEATURE:
<221> NAME/KEY: MOD_RES
<222> LOCATION: (31)..(31)
<223> OTHER INFORMATION: AMIDATION
```

<400> SEQUENCE: 111

Lys Pro Val Ser Leu Ser Tyr Arg Phe Pro Phe Arg Phe Phe Gly Gly
1               5                   10                  15

Gly Gly Leu Lys Trp Ile Gln Glu Tyr Leu Glu Lys Ala Leu Asn
            20                  25                  30

<210> SEQ ID NO 112
<211> LENGTH: 14
<212> TYPE: PRT
<213> ORGANISM: Artificial Sequence
<220> FEATURE:
<223> OTHER INFORMATION: portion of synthetic CTCE0021-like analog CXCR4
      agonist
<220> FEATURE:
<221> NAME/KEY: MOD_RES
<222> LOCATION: (14)..(14)
<223> OTHER INFORMATION: Xaa = Phe linked to Leu at position 1 of
      XKWIQEYLEKALN (SEQ ID NO:113) via a moiety providing covalent
      attachment between N and C terminal portions of the
      peptides, such as NH-2-(CH-2)-n-COOH (n = 0-20)

<400> SEQUENCE: 112

Lys Pro Val Ser Leu Ser Tyr Arg Phe Pro Phe Arg Phe Xaa
1               5                   10

<210> SEQ ID NO 113
<211> LENGTH: 13
<212> TYPE: PRT
<213> ORGANISM: Artificial Sequence
<220> FEATURE:
<223> OTHER INFORMATION: portion of synthetic CTCE0021-like analog CXCR4
      agonist
<220> FEATURE:
<221> NAME/KEY: MOD_RES
<222> LOCATION: (1)..(1)
<223> OTHER INFORMATION: Xaa = Leu linked to Phe at position 14 of
      KXVSXSYRCPCRFX (SEQ ID NO:112) via a moiety providing covalent
      attachment between N and C terminal portions of the
      peptides, such as NH-2-(CH-2)-n-COOH (n = 0-20)
<220> FEATURE:
<221> NAME/KEY: MISC_FEATURE
<222> LOCATION: (2)..(6)
<223> OTHER INFORMATION: side chain cyclized using lactam formation
<220> FEATURE:
<221> NAME/KEY: MOD_RES
<222> LOCATION: (13)..(13)
<223> OTHER INFORMATION: AMIDATION

<400> SEQUENCE: 113

Xaa Lys Trp Ile Gln Glu Tyr Leu Glu Lys Ala Leu Asn
1               5                   10

<210> SEQ ID NO 114
<211> LENGTH: 31
<212> TYPE: PRT
<213> ORGANISM: Artificial Sequence
<220> FEATURE:
<223> OTHER INFORMATION: synthetic CTCE0021-like analog CXCR4 agonist
<220> FEATURE:
<221> NAME/KEY: MOD_RES
<222> LOCATION: (1)..(1)
<223> OTHER INFORMATION: Lys is modified with polyethylene glycol (PEG)
<220> FEATURE:
<221> NAME/KEY: MISC_FEATURE
<222> LOCATION: (20)..(24)
<223> OTHER INFORMATION: side chain cyclized using lactam formation
<220> FEATURE:
<221> NAME/KEY: MOD_RES
<222> LOCATION: (31)..(31)
<223> OTHER INFORMATION: AMIDATION

```
<400> SEQUENCE: 114

Lys Pro Val Ser Leu Ser Tyr Arg Phe Pro Phe Arg Phe Phe Gly Gly
1               5                   10                  15

Gly Gly Leu Lys Trp Ile Gln Glu Tyr Leu Glu Lys Ala Leu Asn
            20                  25                  30

<210> SEQ ID NO 115
<211> LENGTH: 14
<212> TYPE: PRT
<213> ORGANISM: Artificial Sequence
<220> FEATURE:
<223> OTHER INFORMATION: portion of synthetic CTCE0021-like analog CXCR4
      agonist
<220> FEATURE:
<221> NAME/KEY: MOD_RES
<222> LOCATION: (1)..(1)
<223> OTHER INFORMATION: Lys is modified with polyethylene glycol (PEG)
<220> FEATURE:
<221> NAME/KEY: MOD_RES
<222> LOCATION: (14)..(14)
<223> OTHER INFORMATION: Xaa = Phe linked to Leu at position 1 of
      XKWIQEYLEKALN (SEQ ID NO:116) via a moiety providing covalent
      attachment between N and C terminal portions of the
      peptides, such as NH-2-(CH-2)-n-COOH (n = 0-20)

<400> SEQUENCE: 115

Lys Pro Val Ser Leu Ser Tyr Arg Phe Pro Phe Arg Phe Xaa
1               5                   10

<210> SEQ ID NO 116
<211> LENGTH: 13
<212> TYPE: PRT
<213> ORGANISM: Artificial Sequence
<220> FEATURE:
<223> OTHER INFORMATION: portion of synthetic CTCE0021-like analog CXCR4
      agonist
<220> FEATURE:
<221> NAME/KEY: MOD_RES
<222> LOCATION: (1)..(1)
<223> OTHER INFORMATION: Xaa = Leu linked to Phe at position 14 of
      KXVSXSYRCPCRFX (SEQ ID NO:115) via a moiety providing covalent
      attachment between N and C terminal portions of the
      peptides, such as NH-2-(CH-2)-n-COOH (n = 0-20)
<220> FEATURE:
<221> NAME/KEY: MISC_FEATURE
<222> LOCATION: (2)..(6)
<223> OTHER INFORMATION: side chain cyclized using lactam formation
<220> FEATURE:
<221> NAME/KEY: MOD_RES
<222> LOCATION: (13)..(13)
<223> OTHER INFORMATION: AMIDATION

<400> SEQUENCE: 116

Xaa Lys Trp Ile Gln Glu Tyr Leu Glu Lys Ala Leu Asn
1               5                   10

<210> SEQ ID NO 117
<211> LENGTH: 31
<212> TYPE: PRT
<213> ORGANISM: Artificial Sequence
<220> FEATURE:
<223> OTHER INFORMATION: synthetic CTCE0021-like analog CXCR4 agonist
<220> FEATURE:
<221> NAME/KEY: MISC_FEATURE
<222> LOCATION: (20)..(24)
<223> OTHER INFORMATION: side chain cyclized using lactam formation
<220> FEATURE:
<221> NAME/KEY: MOD_RES
<222> LOCATION: (31)..(31)
<223> OTHER INFORMATION: AMIDATION

<400> SEQUENCE: 117
```

```
Lys Pro Val Ser Leu Ser Tyr Arg His Pro His Arg Phe Phe Gly Gly
1               5                   10                  15

Gly Gly Leu Lys Trp Ile Gln Glu Tyr Leu Glu Lys Ala Leu Asn
            20                  25                  30

<210> SEQ ID NO 118
<211> LENGTH: 14
<212> TYPE: PRT
<213> ORGANISM: Artificial Sequence
<220> FEATURE:
<223> OTHER INFORMATION: portion of synthetic CTCE0021-like analog CXCR4
      agonist
<220> FEATURE:
<221> NAME/KEY: MOD_RES
<222> LOCATION: (14)..(14)
<223> OTHER INFORMATION: Xaa = Phe linked to Leu at position 1 of
      XKWIQEYLEKALN (SEQ ID NO:119) via a moiety providing covalent
      attachment between N and C terminal portions of the
      peptides, such as NH-2-(CH-2)-n-COOH (n = 0-20)

<400> SEQUENCE: 118

Lys Pro Val Ser Leu Ser Tyr Arg His Pro His Arg Phe Xaa
1               5                   10

<210> SEQ ID NO 119
<211> LENGTH: 13
<212> TYPE: PRT
<213> ORGANISM: Artificial Sequence
<220> FEATURE:
<223> OTHER INFORMATION: portion of synthetic CTCE0021-like analog CXCR4
      agonist
<220> FEATURE:
<221> NAME/KEY: MOD_RES
<222> LOCATION: (1)..(1)
<223> OTHER INFORMATION: Xaa = Leu linked to Phe at position 14 of
      KXVSXSYRCPCRFX (SEQ ID NO:118) via a moiety providing covalent
      attachment between N and C terminal portions of the
      peptides, such as NH-2-(CH-2)-n-COOH (n = 0-20)
<220> FEATURE:
<221> NAME/KEY: MISC_FEATURE
<222> LOCATION: (2)..(6)
<223> OTHER INFORMATION: side chain cyclized using lactam formation
<220> FEATURE:
<221> NAME/KEY: MOD_RES
<222> LOCATION: (13)..(13)
<223> OTHER INFORMATION: AMIDATION

<400> SEQUENCE: 119

Xaa Lys Trp Ile Gln Glu Tyr Leu Glu Lys Ala Leu Asn
1               5                   10

<210> SEQ ID NO 120
<211> LENGTH: 31
<212> TYPE: PRT
<213> ORGANISM: Artificial Sequence
<220> FEATURE:
<223> OTHER INFORMATION: synthetic CTCE0021-like analog CXCR4 agonist
<220> FEATURE:
<221> NAME/KEY: MOD_RES
<222> LOCATION: (1)..(1)
<223> OTHER INFORMATION: Lys is modified with polyethylene glycol (PEG)
<220> FEATURE:
<221> NAME/KEY: MISC_FEATURE
<222> LOCATION: (20)..(24)
<223> OTHER INFORMATION: side chain cyclized using lactam formation
<220> FEATURE:
<221> NAME/KEY: MOD_RES
<222> LOCATION: (31)..(31)
<223> OTHER INFORMATION: AMIDATION

<400> SEQUENCE: 120
```

```
Lys Pro Val Ser Leu Ser Tyr Arg His Pro His Arg Phe Phe Gly Gly
1               5                   10                  15

Gly Gly Leu Lys Trp Ile Gln Glu Tyr Leu Glu Lys Ala Leu Asn
            20                  25                  30
```

<210> SEQ ID NO 121
<211> LENGTH: 14
<212> TYPE: PRT
<213> ORGANISM: Artificial Sequence
<220> FEATURE:
<223> OTHER INFORMATION: portion of synthetic CTCE0021-like analog CXCR4
      agonist
<220> FEATURE:
<221> NAME/KEY: MOD_RES
<222> LOCATION: (1)..(1)
<223> OTHER INFORMATION: Lys is modified with polyethylene glycol (PEG)
<220> FEATURE:
<221> NAME/KEY: MOD_RES
<222> LOCATION: (14)..(14)
<223> OTHER INFORMATION: Xaa = Phe linked to Leu at position 1 of
      XKWIQEYLEKALN (SEQ ID NO:122) via a moiety providing covalent
      attachment between N and C terminal portions of the
      peptides, such as NH-2-(CH-2)-n-COOH (n = 0-20)

<400> SEQUENCE: 121

```
Lys Pro Val Ser Leu Ser Tyr Arg His Pro His Arg Phe Xaa
1               5                   10
```

<210> SEQ ID NO 122
<211> LENGTH: 13
<212> TYPE: PRT
<213> ORGANISM: Artificial Sequence
<220> FEATURE:
<223> OTHER INFORMATION: portion of synthetic CTCE0021-like analog CXCR4
      agonist
<220> FEATURE:
<221> NAME/KEY: MOD_RES
<222> LOCATION: (1)..(1)
<223> OTHER INFORMATION: Xaa = Leu linked to Phe at position 14 of
      KXVSXSYRCPCRFX (SEQ ID NO:121) via a moiety providing covalent
      attachment between N and C terminal portions of the
      peptides, such as NH-2-(CH-2)-n-COOH (n = 0-20)
<220> FEATURE:
<221> NAME/KEY: MISC_FEATURE
<222> LOCATION: (2)..(6)
<223> OTHER INFORMATION: side chain cyclized using lactam formation
<220> FEATURE:
<221> NAME/KEY: MOD_RES
<222> LOCATION: (13)..(13)
<223> OTHER INFORMATION: AMIDATION

<400> SEQUENCE: 122

```
Xaa Lys Trp Ile Gln Glu Tyr Leu Glu Lys Ala Leu Asn
1               5                   10
```

<210> SEQ ID NO 123
<211> LENGTH: 31
<212> TYPE: PRT
<213> ORGANISM: Artificial Sequence
<220> FEATURE:
<223> OTHER INFORMATION: synthetic CTCE0021-like analog CXCR4 agonist
<220> FEATURE:
<221> NAME/KEY: MISC_FEATURE
<222> LOCATION: (20)..(24)
<223> OTHER INFORMATION: side chain cyclized using lactam formation
<220> FEATURE:
<221> NAME/KEY: MOD_RES
<222> LOCATION: (31)..(31)
<223> OTHER INFORMATION: AMIDATION

<400> SEQUENCE: 123

```
Lys Pro Val Ser Leu Ser Tyr Arg Trp Pro Trp Arg Phe Phe Gly Gly
```

|       |       |       |       |       |       |       |       |       |       |       |       |       |       |       |
|-------|-------|-------|-------|-------|-------|-------|-------|-------|-------|-------|-------|-------|-------|-------|
| 1     |       |       |       | 5     |       |       |       |       | 10    |       |       |       |       | 15    |

Gly Gly Leu Lys Trp Ile Gln Glu Tyr Leu Glu Lys Ala Leu Asn
            20                  25                  30

<210> SEQ ID NO 124
<211> LENGTH: 14
<212> TYPE: PRT
<213> ORGANISM: Artificial Sequence
<220> FEATURE:
<223> OTHER INFORMATION: portion of synthetic CTCE0021-like analog CXCR4
      agonist
<220> FEATURE:
<221> NAME/KEY: MOD_RES
<222> LOCATION: (14)..(14)
<223> OTHER INFORMATION: Xaa = Phe linked to Leu at position 1 of
      XKWIQEYLEKALN (SEQ ID NO:125) via a moiety providing covalent
      attachment between N and C terminal portions of the
      peptides, such as NH-2-(CH-2)-n-COOH (n = 0-20)

<400> SEQUENCE: 124

Lys Pro Val Ser Leu Ser Tyr Arg Trp Pro Trp Arg Phe Xaa
1               5                   10

<210> SEQ ID NO 125
<211> LENGTH: 13
<212> TYPE: PRT
<213> ORGANISM: Artificial Sequence
<220> FEATURE:
<223> OTHER INFORMATION: portion of synthetic CTCE0021-like analog CXCR4
      agonist
<220> FEATURE:
<221> NAME/KEY: MOD_RES
<222> LOCATION: (1)..(1)
<223> OTHER INFORMATION: Xaa = Leu linked to Phe at position 14 of
      KXVSXSYRCPCRFX (SEQ ID NO:124) via a moiety providing covalent
      attachment between N and C terminal portions of the
      peptides, such as NH-2-(CH-2)-n-COOH (n = 0-20)
<220> FEATURE:
<221> NAME/KEY: MISC_FEATURE
<222> LOCATION: (2)..(6)
<223> OTHER INFORMATION: side chain cyclized using lactam formation
<220> FEATURE:
<221> NAME/KEY: MOD_RES
<222> LOCATION: (13)..(13)
<223> OTHER INFORMATION: AMIDATION

<400> SEQUENCE: 125

Xaa Lys Trp Ile Gln Glu Tyr Leu Glu Lys Ala Leu Asn
1               5                   10

<210> SEQ ID NO 126
<211> LENGTH: 31
<212> TYPE: PRT
<213> ORGANISM: Artificial Sequence
<220> FEATURE:
<223> OTHER INFORMATION: synthetic CTCE0021-like analog CXCR4 agonist
<220> FEATURE:
<221> NAME/KEY: MOD_RES
<222> LOCATION: (1)..(1)
<223> OTHER INFORMATION: Lys is modified with polyethylene glycol (PEG)
<220> FEATURE:
<221> NAME/KEY: MISC_FEATURE
<222> LOCATION: (20)..(24)
<223> OTHER INFORMATION: side chain cyclized using lactam formation
<220> FEATURE:
<221> NAME/KEY: MOD_RES
<222> LOCATION: (31)..(31)
<223> OTHER INFORMATION: AMIDATION

<400> SEQUENCE: 126

Lys Pro Val Ser Leu Ser Tyr Arg Trp Pro Trp Arg Phe Phe Gly Gly
1               5                   10                  15

```
Gly Gly Leu Lys Trp Ile Gln Glu Tyr Leu Glu Lys Ala Leu Asn
        20                  25                  30

<210> SEQ ID NO 127
<211> LENGTH: 14
<212> TYPE: PRT
<213> ORGANISM: Artificial Sequence
<220> FEATURE:
<223> OTHER INFORMATION: portion of synthetic CTCE0021-like analog CXCR4
      agonist
<220> FEATURE:
<221> NAME/KEY: MOD_RES
<222> LOCATION: (1)..(1)
<223> OTHER INFORMATION: Lys is modified with polyethylene glycol (PEG)
<220> FEATURE:
<221> NAME/KEY: MOD_RES
<222> LOCATION: (14)..(14)
<223> OTHER INFORMATION: Xaa = Phe linked to Leu at position 1 of
      XKWIQEYLEKALN (SEQ ID NO:128) via a moiety providing covalent
      attachment between N and C terminal portions of the
      peptides, such as NH-2-(CH-2)-n-COOH (n = 0-20)

<400> SEQUENCE: 127

Lys Pro Val Ser Leu Ser Tyr Arg Trp Pro Trp Arg Phe Xaa
1               5                   10

<210> SEQ ID NO 128
<211> LENGTH: 13
<212> TYPE: PRT
<213> ORGANISM: Artificial Sequence
<220> FEATURE:
<223> OTHER INFORMATION: portion of synthetic CTCE0021-like analog CXCR4
      agonist
<220> FEATURE:
<221> NAME/KEY: MOD_RES
<222> LOCATION: (1)..(1)
<223> OTHER INFORMATION: Xaa = Leu linked to Phe at position 14 of
      KXVSXSYRCPCRFX (SEQ ID NO:127) via a moiety providing covalent
      attachment between N and C terminal portions of the
      peptides, such as NH-2-(CH-2)-n-COOH (n = 0-20)
<220> FEATURE:
<221> NAME/KEY: MISC_FEATURE
<222> LOCATION: (2)..(6)
<223> OTHER INFORMATION: side chain cyclized using lactam formation
<220> FEATURE:
<221> NAME/KEY: MOD_RES
<222> LOCATION: (13)..(13)
<223> OTHER INFORMATION: AMIDATION

<400> SEQUENCE: 128

Xaa Lys Trp Ile Gln Glu Tyr Leu Glu Lys Ala Leu Asn
1               5                   10

<210> SEQ ID NO 129
<211> LENGTH: 31
<212> TYPE: PRT
<213> ORGANISM: Artificial Sequence
<220> FEATURE:
<223> OTHER INFORMATION: synthetic CTCE0022-like analog CXCR4 agonist
<220> FEATURE:
<221> NAME/KEY: MOD_RES
<222> LOCATION: (1)..(1)
<223> OTHER INFORMATION: Lys is modified with polyethylene glycol (PEG)
<220> FEATURE:
<221> NAME/KEY: MISC_FEATURE
<222> LOCATION: (24)..(28)
<223> OTHER INFORMATION: side chain cyclized using lactam formation
<220> FEATURE:
<221> NAME/KEY: MOD_RES
<222> LOCATION: (31)..(31)
<223> OTHER INFORMATION: AMIDATION

<400> SEQUENCE: 129
```

```
Lys Pro Val Ser Leu Ser Tyr Arg Cys Pro Cys Arg Phe Phe Gly Gly
1               5                   10                  15

Gly Gly Leu Lys Trp Ile Gln Glu Tyr Leu Glu Lys Ala Leu Asn
            20                  25                  30
```

<210> SEQ ID NO 130
<211> LENGTH: 14
<212> TYPE: PRT
<213> ORGANISM: Artificial Sequence
<220> FEATURE:
<223> OTHER INFORMATION: portion of synthetic CTCE0022-like analog CXCR4
      agonist
<220> FEATURE:
<221> NAME/KEY: MOD_RES
<222> LOCATION: (1)..(1)
<223> OTHER INFORMATION: Lys is modified with polyethylene glycol (PEG)
<220> FEATURE:
<221> NAME/KEY: MOD_RES
<222> LOCATION: (14)..(14)
<223> OTHER INFORMATION: Xaa = Phe linked to Leu at position 1 of
      XKWIQEYLEKALN (SEQ ID NO:131) via a moiety providing covalent
      attachment between N and C terminal portions of the
      peptides, such as NH-2-(CH-2)-n-COOH (n = 0-20)

<400> SEQUENCE: 130

```
Lys Pro Val Ser Leu Ser Tyr Arg Cys Pro Cys Arg Phe Xaa
1               5                   10
```

<210> SEQ ID NO 131
<211> LENGTH: 13
<212> TYPE: PRT
<213> ORGANISM: Artificial Sequence
<220> FEATURE:
<223> OTHER INFORMATION: portion of synthetic CTCE0022-like analog CXCR4
      agonist
<220> FEATURE:
<221> NAME/KEY: MOD_RES
<222> LOCATION: (1)..(1)
<223> OTHER INFORMATION: Xaa = Leu linked to Phe at position 14 of
      KXVSXSYRCPCRFX (SEQ ID NO:130) via a moiety providing covalent
      attachment between N and C terminal portions of the
      peptides, such as NH-2-(CH-2)-n-COOH (n = 0-20)
<220> FEATURE:
<221> NAME/KEY: MISC_FEATURE
<222> LOCATION: (6)..(10)
<223> OTHER INFORMATION: side chain cyclized using lactam formation
<220> FEATURE:
<221> NAME/KEY: MOD_RES
<222> LOCATION: (13)..(13)
<223> OTHER INFORMATION: AMIDATION

<400> SEQUENCE: 131

```
Xaa Lys Trp Ile Gln Glu Tyr Leu Glu Lys Ala Leu Asn
1               5                   10
```

<210> SEQ ID NO 132
<211> LENGTH: 31
<212> TYPE: PRT
<213> ORGANISM: Artificial Sequence
<220> FEATURE:
<223> OTHER INFORMATION: synthetic CTCE0022-like analog CXCR4 agonist
<220> FEATURE:
<221> NAME/KEY: MISC_FEATURE
<222> LOCATION: (24)..(28)
<223> OTHER INFORMATION: side chain cyclized using lactam formation
<220> FEATURE:
<221> NAME/KEY: MOD_RES
<222> LOCATION: (31)..(31)
<223> OTHER INFORMATION: AMIDATION

<400> SEQUENCE: 132

```
Lys Pro Val Ser Leu Ser Tyr Arg Ala Pro Phe Arg Phe Phe Gly Gly
1               5                   10                  15

Gly Gly Leu Lys Trp Ile Gln Glu Tyr Leu Glu Lys Ala Leu Asn
            20                  25                  30
```

<210> SEQ ID NO 133
<211> LENGTH: 14
<212> TYPE: PRT
<213> ORGANISM: Artificial Sequence
<220> FEATURE:
<223> OTHER INFORMATION: portion of synthetic CTCE0022-like analog CXCR4
      agonist
<220> FEATURE:
<221> NAME/KEY: MOD_RES
<222> LOCATION: (14)..(14)
<223> OTHER INFORMATION: Xaa = Phe linked to Leu at position 1 of
      XKWIQEYLEKALN (SEQ ID NO:134) via a moiety providing covalent
      attachment between N and C terminal portions of the
      peptides, such as NH-2-(CH-2)-n-COOH (n = 0-20)

<400> SEQUENCE: 133

```
Lys Pro Val Ser Leu Ser Tyr Arg Ala Pro Phe Arg Phe Xaa
1               5                   10
```

<210> SEQ ID NO 134
<211> LENGTH: 13
<212> TYPE: PRT
<213> ORGANISM: Artificial Sequence
<220> FEATURE:
<223> OTHER INFORMATION: portion of synthetic CTCE0022-like analog CXCR4
      agonist
<220> FEATURE:
<221> NAME/KEY: MOD_RES
<222> LOCATION: (1)..(1)
<223> OTHER INFORMATION: Xaa = Leu linked to Phe at position 14 of
      KXVSXSYRCPCRFX (SEQ ID NO:133) via a moiety providing covalent
      attachment between N and C terminal portions of the
      peptides, such as NH-2-(CH-2)-n-COOH (n = 0-20)
<220> FEATURE:
<221> NAME/KEY: MISC_FEATURE
<222> LOCATION: (6)..(10)
<223> OTHER INFORMATION: side chain cyclized using lactam formation
<220> FEATURE:
<221> NAME/KEY: MOD_RES
<222> LOCATION: (13)..(13)
<223> OTHER INFORMATION: AMIDATION

<400> SEQUENCE: 134

```
Xaa Lys Trp Ile Gln Glu Tyr Leu Glu Lys Ala Leu Asn
1               5                   10
```

<210> SEQ ID NO 135
<211> LENGTH: 31
<212> TYPE: PRT
<213> ORGANISM: Artificial Sequence
<220> FEATURE:
<223> OTHER INFORMATION: synthetic CTCE0022-like analog CXCR4 agonist
<220> FEATURE:
<221> NAME/KEY: MOD_RES
<222> LOCATION: (1)..(1)
<223> OTHER INFORMATION: Lys is modified with polyethylene glycol (PEG)
<220> FEATURE:
<221> NAME/KEY: MISC_FEATURE
<222> LOCATION: (24)..(28)
<223> OTHER INFORMATION: side chain cyclized using lactam formation
<220> FEATURE:
<221> NAME/KEY: MOD_RES
<222> LOCATION: (31)..(31)
<223> OTHER INFORMATION: AMIDATION

<400> SEQUENCE: 135

```
Lys Pro Val Ser Leu Ser Tyr Arg Ala Pro Phe Arg Phe Phe Gly Gly
```

```
1               5                   10                  15
Gly Gly Leu Lys Trp Ile Gln Glu Tyr Leu Glu Lys Ala Leu Asn
            20                  25                  30

<210> SEQ ID NO 136
<211> LENGTH: 14
<212> TYPE: PRT
<213> ORGANISM: Artificial Sequence
<220> FEATURE:
<223> OTHER INFORMATION: portion of synthetic CTCE0022-like analog CXCR4
      agonist
<220> FEATURE:
<221> NAME/KEY: MOD_RES
<222> LOCATION: (1)..(1)
<223> OTHER INFORMATION: Lys is modified with polyethylene glycol (PEG)
<220> FEATURE:
<221> NAME/KEY: MOD_RES
<222> LOCATION: (14)..(14)
<223> OTHER INFORMATION: Xaa = Phe linked to Leu at position 1 of
      XKWIQEYLEKALN (SEQ ID NO:137) via a moiety providing covalent
      attachment between N and C terminal portions of the
      peptides, such as NH-2-(CH-2)-n-COOH (n = 0-20)

<400> SEQUENCE: 136

Lys Pro Val Ser Leu Ser Tyr Arg Ala Pro Phe Arg Phe Xaa
1               5                   10

<210> SEQ ID NO 137
<211> LENGTH: 13
<212> TYPE: PRT
<213> ORGANISM: Artificial Sequence
<220> FEATURE:
<223> OTHER INFORMATION: portion of synthetic CTCE0022-like analog CXCR4
      agonist
<220> FEATURE:
<221> NAME/KEY: MOD_RES
<222> LOCATION: (1)..(1)
<223> OTHER INFORMATION: Xaa = Leu linked to Phe at position 14 of
      KXVSXSYRCPCRFX (SEQ ID NO:136) via a moiety providing covalent
      attachment between N and C terminal portions of the
      peptides, such as NH-2-(CH-2)-n-COOH (n = 0-20)
<220> FEATURE:
<221> NAME/KEY: MISC_FEATURE
<222> LOCATION: (6)..(10)
<223> OTHER INFORMATION: side chain cyclized using lactam formation
<220> FEATURE:
<221> NAME/KEY: MOD_RES
<222> LOCATION: (13)..(13)
<223> OTHER INFORMATION: AMIDATION

<400> SEQUENCE: 137

Xaa Lys Trp Ile Gln Glu Tyr Leu Glu Lys Ala Leu Asn
1               5                   10

<210> SEQ ID NO 138
<211> LENGTH: 31
<212> TYPE: PRT
<213> ORGANISM: Artificial Sequence
<220> FEATURE:
<223> OTHER INFORMATION: synthetic CTCE0022-like analog CXCR4 agonist
<220> FEATURE:
<221> NAME/KEY: MISC_FEATURE
<222> LOCATION: (24)..(28)
<223> OTHER INFORMATION: side chain cyclized using lactam formation
<220> FEATURE:
<221> NAME/KEY: MOD_RES
<222> LOCATION: (31)..(31)
<223> OTHER INFORMATION: AMIDATION

<400> SEQUENCE: 138

Lys Pro Val Ser Leu Ser Tyr Arg Ala Pro His Arg Phe Phe Gly Gly
1               5                   10                  15
```

```
Gly Gly Leu Lys Trp Ile Gln Glu Tyr Leu Glu Lys Ala Leu Asn
            20                  25                  30
```

<210> SEQ ID NO 139
<211> LENGTH: 14
<212> TYPE: PRT
<213> ORGANISM: Artificial Sequence
<220> FEATURE:
<223> OTHER INFORMATION: portion of synthetic CTCE0022-like analog CXCR4
      agonist
<220> FEATURE:
<221> NAME/KEY: MOD_RES
<222> LOCATION: (14)..(14)
<223> OTHER INFORMATION: Xaa = Phe linked to Leu at position 1 of
      XKWIQEYLEKALN (SEQ ID NO:140) via a moiety providing covalent
      attachment between N and C terminal portions of the
      peptides, such as NH-2-(CH-2)-n-COOH (n = 0-20)

<400> SEQUENCE: 139

```
Lys Pro Val Ser Leu Ser Tyr Arg Ala Pro His Arg Phe Xaa
1               5                   10
```

<210> SEQ ID NO 140
<211> LENGTH: 13
<212> TYPE: PRT
<213> ORGANISM: Artificial Sequence
<220> FEATURE:
<223> OTHER INFORMATION: portion of synthetic CTCE0022-like analog CXCR4
      agonist
<220> FEATURE:
<221> NAME/KEY: MOD_RES
<222> LOCATION: (1)..(1)
<223> OTHER INFORMATION: Xaa = Leu linked to Phe at position 14 of
      KXVSXSYRCPCRFX (SEQ ID NO:139) via a moiety providing covalent
      attachment between N and C terminal portions of the
      peptides, such as NH-2-(CH-2)-n-COOH (n = 0-20)
<220> FEATURE:
<221> NAME/KEY: MISC_FEATURE
<222> LOCATION: (6)..(10)
<223> OTHER INFORMATION: side chain cyclized using lactam formation
<220> FEATURE:
<221> NAME/KEY: MOD_RES
<222> LOCATION: (13)..(13)
<223> OTHER INFORMATION: AMIDATION

<400> SEQUENCE: 140

```
Xaa Lys Trp Ile Gln Glu Tyr Leu Glu Lys Ala Leu Asn
1               5                   10
```

<210> SEQ ID NO 141
<211> LENGTH: 31
<212> TYPE: PRT
<213> ORGANISM: Artificial Sequence
<220> FEATURE:
<223> OTHER INFORMATION: synthetic CTCE0022-like analog CXCR4 agonist
<220> FEATURE:
<221> NAME/KEY: MOD_RES
<222> LOCATION: (1)..(1)
<223> OTHER INFORMATION: Lys is modified with polyethylene glycol (PEG)
<220> FEATURE:
<221> NAME/KEY: MISC_FEATURE
<222> LOCATION: (24)..(28)
<223> OTHER INFORMATION: side chain cyclized using lactam formation
<220> FEATURE:
<221> NAME/KEY: MOD_RES
<222> LOCATION: (31)..(31)
<223> OTHER INFORMATION: AMIDATION

<400> SEQUENCE: 141

```
Lys Pro Val Ser Leu Ser Tyr Arg Ala Pro His Arg Phe Phe Gly Gly
1               5                   10                  15
```

Gly Gly Leu Lys Trp Ile Gln Glu Tyr Leu Glu Lys Ala Leu Asn
            20                  25                  30

<210> SEQ ID NO 142
<211> LENGTH: 14
<212> TYPE: PRT
<213> ORGANISM: Artificial Sequence
<220> FEATURE:
<223> OTHER INFORMATION: portion of synthetic CTCE0022-like analog CXCR4
      agonist
<220> FEATURE:
<221> NAME/KEY: MOD_RES
<222> LOCATION: (1)..(1)
<223> OTHER INFORMATION: Lys is modified with polyethylene glycol (PEG)
<220> FEATURE:
<221> NAME/KEY: MOD_RES
<222> LOCATION: (14)..(14)
<223> OTHER INFORMATION: Xaa = Phe linked to Leu at position 1 of
      XKWIQEYLEKALN (SEQ ID NO:143) via a moiety providing covalent
      attachment between N and C terminal portions of the
      peptides, such as NH-2-(CH-2)-n-COOH (n = 0-20)

<400> SEQUENCE: 142

Lys Pro Val Ser Leu Ser Tyr Arg Ala Pro His Arg Phe Xaa
1               5                   10

<210> SEQ ID NO 143
<211> LENGTH: 13
<212> TYPE: PRT
<213> ORGANISM: Artificial Sequence
<220> FEATURE:
<223> OTHER INFORMATION: portion of synthetic CTCE0022-like analog CXCR4
      agonist
<220> FEATURE:
<221> NAME/KEY: MOD_RES
<222> LOCATION: (1)..(1)
<223> OTHER INFORMATION: Xaa = Leu linked to Phe at position 14 of
      KXVSXSYRCPCRFX (SEQ ID NO:142) via a moiety providing covalent
      attachment between N and C terminal portions of the
      peptides, such as NH-2-(CH-2)-n-COOH (n = 0-20)
<220> FEATURE:
<221> NAME/KEY: MISC_FEATURE
<222> LOCATION: (6)..(10)
<223> OTHER INFORMATION: side chain cyclized using lactam formation
<220> FEATURE:
<221> NAME/KEY: MOD_RES
<222> LOCATION: (13)..(13)
<223> OTHER INFORMATION: AMIDATION

<400> SEQUENCE: 143

Xaa Lys Trp Ile Gln Glu Tyr Leu Glu Lys Ala Leu Asn
1               5                   10

<210> SEQ ID NO 144
<211> LENGTH: 31
<212> TYPE: PRT
<213> ORGANISM: Artificial Sequence
<220> FEATURE:
<223> OTHER INFORMATION: synthetic CTCE0022-like analog CXCR4 agonist
<220> FEATURE:
<221> NAME/KEY: MISC_FEATURE
<222> LOCATION: (24)..(28)
<223> OTHER INFORMATION: side chain cyclized using lactam formation
<220> FEATURE:
<221> NAME/KEY: MOD_RES
<222> LOCATION: (31)..(31)
<223> OTHER INFORMATION: AMIDATION

<400> SEQUENCE: 144

Lys Pro Val Ser Leu Ser Tyr Arg Ala Pro Trp Arg Phe Phe Gly Gly
1               5                   10                  15

Gly Gly Leu Lys Trp Ile Gln Glu Tyr Leu Glu Lys Ala Leu Asn

<210> SEQ ID NO 145
<211> LENGTH: 14
<212> TYPE: PRT
<213> ORGANISM: Artificial Sequence
<220> FEATURE:
<223> OTHER INFORMATION: portion of synthetic CTCE0022-like analog CXCR4
      agonist
<220> FEATURE:
<221> NAME/KEY: MOD_RES
<222> LOCATION: (14)..(14)
<223> OTHER INFORMATION: Xaa = Phe linked to Leu at position 1 of
      XKWIQEYLEKALN (SEQ ID NO:146) via a moiety providing covalent
      attachment between N and C terminal portions of the
      peptides, such as NH-2-(CH-2)-n-COOH (n = 0-20)

<400> SE

```
<210> SEQ ID NO 148
<211> LENGTH: 14
<212> TYPE: PRT
<213> ORGANISM: Artificial Sequence
<220> FEATURE:
<223> OTHER INFORMATION: portion of synthetic CTCE0022-like analog CXCR4
      agonist
<220> FEATURE:
<221> NAME/KEY: MOD_RES
<222> LOCATION: (1)..(1)
<223> OTHER INFORMATION: Lys is modified with polyethylene glycol (PEG)
<220> FEATURE:
<221> NAME/KEY: MOD_RES
<222> LOCATION: (14)..(14)
<223> OTHER INFORMATION: Xaa = Phe linked to Leu at position 1 of
      XKWIQEYLEKALN (SEQ ID NO:149) via a moiety providing covalent
      attachment between N and C terminal portions of the
      peptides, such as NH-2-(CH-2)-n-COOH (n = 0-20)

<400> SEQUENCE: 148

Lys Pro Val Ser Leu Ser Tyr Arg Ala Pro Trp Arg Phe Xaa
1               5                   10

<210> SEQ ID NO 149
<211> LENGTH: 13
<212> TYPE: PRT
<213> ORGANISM: Artificial Sequence
<220> FEATURE:
<223> OTHER INFORMATION: portion of synthetic CTCE0022-like analog CXCR4
      agonist
<220> FEATURE:
<221> NAME/KEY: MOD_RES
<222> LOCATION: (1)..(1)
<223> OTHER INFORMATION: Xaa = Leu linked to Phe at position 14 of
      KXVSXSYRCPCRFX (SEQ ID NO:148) via a moiety providing covalent
      attachment between N and C terminal portions of the
      peptides, such as NH-2-(CH-2)-n-COOH (n = 0-20)
<220> FEATURE:
<221> NAME/KEY: MISC_FEATURE
<222> LOCATION: (6)..(10)
<223> OTHER INFORMATION: side chain cyclized using lactam formation
<220> FEATURE:
<221> NAME/KEY: MOD_RES
<222> LOCATION: (13)..(13)
<223> OTHER INFORMATION: AMIDATION

<400> SEQUENCE: 149

Xaa Lys Trp Ile Gln Glu Tyr Leu Glu Lys Ala Leu Asn
1               5                   10

<210> SEQ ID NO 150
<211> LENGTH: 31
<212> TYPE: PRT
<213> ORGANISM: Artificial Sequence
<220> FEATURE:
<223> OTHER INFORMATION: synthetic CTCE0022-like analog CXCR4 agonist
<220> FEATURE:
<221> NAME/KEY: MISC_FEATURE
<222> LOCATION: (24)..(28)
<223> OTHER INFORMATION: side chain cyclized using lactam formation
<220> FEATURE:
<221> NAME/KEY: MOD_RES
<222> LOCATION: (31)..(31)
<223> OTHER INFORMATION: AMIDATION

<400> SEQUENCE: 150

Lys Pro Val Ser Leu Ser Tyr Arg Phe Pro Ala Arg Phe Phe Gly Gly
1               5                   10                  15

Gly Gly Leu Lys Trp Ile Gln Glu Tyr Leu Glu Lys Ala Leu Asn
            20                  25                  30
```

```
<210> SEQ ID NO 151
<211> LENGTH: 14
<212> TYPE: PRT
<213> ORGANISM: Artificial Sequence
<220> FEATURE:
<223> OTHER INFORMATION: portion of synthetic CTCE0022-like analog CXCR4
      agonist
<220> FEATURE:
<221> NAME/KEY: MOD_RES
<222> LOCATION: (14)..(14)
<223> OTHER INFORMATION: Xaa = Phe linked to Leu at position 1 of
      XKWIQEYLEKALN (SEQ ID NO:152) via a moiety providing covalent
      attachment between N and C terminal portions of the
      peptides, such as NH-2-(CH-2)-n-COOH (n = 0-20)

<400> SEQUENCE: 151

Lys Pro Val Ser Leu Ser Tyr Arg Phe Pro Ala Arg Phe Xaa
1               5                   10

<210> SEQ ID NO 152
<211> LENGTH: 13
<212> TYPE: PRT
<213> ORGANISM: Artificial Sequence
<220> FEATURE:
<223> OTHER INFORMATION: portion of synthetic CTCE0022-like analog CXCR4
      agonist
<220> FEATURE:
<221> NAME/KEY: MOD_RES
<222> LOCATION: (1)..(1)
<223> OTHER INFORMATION: Xaa = Leu linked to Phe at position 14 of
      KXVSXSYRCPCRFX (SEQ ID NO:151) via a moiety providing covalent
      attachment between N and C terminal portions of the
      peptides, such as NH-2-(CH-2)-n-COOH (n = 0-20)
<220> FEATURE:
<221> NAME/KEY: MISC_FEATURE
<222> LOCATION: (6)..(10)
<223> OTHER INFORMATION: side chain cyclized using lactam formation
<220> FEATURE:
<221> NAME/KEY: MOD_RES
<222> LOCATION: (13)..(13)
<223> OTHER INFORMATION: AMIDATION

<400> SEQUENCE: 152

Xaa Lys Trp Ile Gln Glu Tyr Leu Glu Lys Ala Leu Asn
1               5                   10

<210> SEQ ID NO 153
<211> LENGTH: 31
<212> TYPE: PRT
<213> ORGANISM: Artificial Sequence
<220> FEATURE:
<223> OTHER INFORMATION: synthetic CTCE0022-like analog CXCR4 agonist
<220> FEATURE:
<221> NAME/KEY: MOD_RES
<222> LOCATION: (1)..(1)
<223> OTHER INFORMATION: Lys is modified with polyethylene glycol (PEG)
<220> FEATURE:
<221> NAME/KEY: MISC_FEATURE
<222> LOCATION: (24)..(28)
<223> OTHER INFORMATION: side chain cyclized using lactam formation
<220> FEATURE:
<221> NAME/KEY: MOD_RES
<222> LOCATION: (31)..(31)
<223> OTHER INFORMATION: AMIDATION

<400> SEQUENCE: 153

Lys Pro Val Ser Leu Ser Tyr Arg Phe Pro Ala Arg Phe Phe Gly Gly
1               5                   10                  15

Gly Gly Leu Lys Trp Ile Gln Glu Tyr Leu Glu Lys Ala Leu Asn
            20                  25                  30
```

```
<210> SEQ ID NO 154
<211> LENGTH: 14
<212> TYPE: PRT
<213> ORGANISM: Artificial Sequence
<220> FEATURE:
<223> OTHER INFORMATION: portion of synthetic CTCE0022-like analog CXCR4
      agonist
<220> FEATURE:
<221> NAME/KEY: MOD_RES
<222> LOCATION: (1)..(1)
<223> OTHER INFORMATION: Lys is modified with polyethylene glycol (PEG)
<220> FEATURE:
<221> NAME/KEY: MOD_RES
<222> LOCATION: (14)..(14)
<223> OTHER INFORMATION: Xaa = Phe linked to Leu at position 1 of
      XKWIQEYLEKALN (SEQ ID NO:155) via a moiety providing covalent
      attachment between N and C terminal portions of the
      peptides, such as NH-2-(CH-2)-n-COOH (n = 0-20)

<400> SEQUENCE: 154

Lys Pro Val Ser Leu Ser Tyr Arg Phe Pro Ala Arg Phe Xaa
1               5                   10

<210> SEQ ID NO 155
<211> LENGTH: 13
<212> TYPE: PRT
<213> ORGANISM: Artificial Sequence
<220> FEATURE:
<223> OTHER INFORMATION: portion of synthetic CTCE0022-like analog CXCR4
      agonist
<220> FEATURE:
<221> NAME/KEY: MOD_RES
<222> LOCATION: (1)..(1)
<223> OTHER INFORMATION: Xaa = Leu linked to Phe at position 14 of
      KXVSXSYRCPCRFX (SEQ ID NO:154) via a moiety providing covalent
      attachment between N and C terminal portions of

```
<211> LENGTH: 14
<212> TYPE: PRT
<213> ORGANISM: Artificial Sequence
<220> FEATURE:
<223> OTHER INFORMATION: portion of synthetic CTCE0022-like analog CXCR4
      agonist
<220> FEATURE:
<221> NAME/KEY: MOD_RES
<222> LOCATION: (14)..(14)
<223> OTHER INFORMATION: Xaa = Phe linked to Leu at position 1 of
      XKWIQEYLEKALN (SEQ ID NO:158) via a moiety providing covalent
      attachment between N and C terminal portions of the
      peptides, such as NH-2-(CH-2)-n-COOH (n = 0-20)

<400> SEQUENCE: 157

Lys Pro Val Ser Leu Ser Tyr Arg His Pro Ala Arg Phe Xaa
1               5                   10

<210> SEQ ID NO 158
<211> LENGTH: 13
<212> TYPE: PRT
<213> ORGANISM: Artificial Sequence
<220> FEATURE:
<223> OTHER INFORMATION: portion of synthetic CTCE0022-like analog CXCR4
      agonist
<220> FEATURE:
<221> NAME/KEY: MOD_RES
<222> LOCATION: (1)..(1)
<223> OTHER INFORMATION: Xaa = Leu linked to Phe at position 14 of
      KXVSXSYRCPCRFX (SEQ ID NO:157) via a moiety providing covalent
      attachment between N and C terminal portions of the
      peptides, such as NH-2-(CH-2)-n-COOH (n = 0-20)
<220> FEATURE:
<221> NAME/KEY: MISC_FEATURE
<222> LOCATION: (6)..(10)
<223> OTHER INFORMATION: side chain cyclized using lactam formation
<220> FEATURE:
<221> NAME/KEY: MOD_RES
<222> LOCATION: (13)..(13)
<223> OTHER INFORMATION: AMIDATION

<400> SEQUENCE: 158

Xaa Lys Trp Ile Gln Glu Tyr Leu Glu Lys Ala Leu Asn
1               5                   10

<210> SEQ ID NO 159
<211> LENGTH: 31
<212> TYPE: PRT
<213> ORGANISM: Artificial Sequence
<220> FEATURE:
<223> OTHER INFORMATION: synthetic CTCE0022-like analog CXCR4 agonist
<220> FEATURE:
<221> NAME/KEY: MOD_RES
<222> LOCATION: (1)..(1)
<223> OTHER INFORMATION: Lys is modified with polyethylene glycol (PEG)
<220> FEATURE:
<221> NAME/KEY: MISC_FEATURE
<222> LOCATION: (24)..(28)
<223> OTHER INFORMATION: side chain cyclized using lactam formation
<220> FEATURE:
<221> NAME/KEY: MOD_RES
<222> LOCATION: (31)..(31)
<223> OTHER INFORMATION: AMIDATION

<400> SEQUENCE: 159

Lys Pro Val Ser Leu Ser Tyr Arg His Pro Ala Arg Phe Phe Gly Gly
1               5                   10                  15

Gly Gly Leu Lys Trp Ile Gln Glu Tyr Leu Glu Lys Ala Leu Asn
            20                  25                  30

<210> SEQ ID NO 160
<211> LENGTH: 14
```

```
<212> TYPE: PRT
<213> ORGANISM: Artificial Sequence
<220> FEATURE:
<223> OTHER INFORMATION: portion of synthetic CTCE0022-like analog CXCR4
      agonist
<220> FEATURE:
<221> NAME/KEY: MOD_RES
<222> LOCATION: (1)..(1)
<223> OTHER INFORMATION: Lys is modified with polyethylene glycol (PEG)
<220> FEATURE:
<221> NAME/KEY: MOD_RES
<222> LOCATION: (14)..(14)
<223> OTHER INFORMATION: Xaa = Phe linked to Leu at position 1 of
      XKWIQEYLEKALN (SEQ ID NO:161) via a moiety providing covalent
      attachment between N and C terminal portions of the
      peptides, such as NH-2-(CH-2)-n-COOH (n = 0-20)

<400> SEQUENCE: 160

Lys Pro Val Ser Leu Ser Tyr Arg His Pro Ala Arg Phe Xaa
1               5                   10

<210> SEQ ID NO 161
<211> LENGTH: 13
<212> TYPE: PRT
<213> ORGANISM: Artificial Sequence
<220> FEATURE:
<223> OTHER INFORMATION: portion of synthetic CTCE0022-like analog CXCR4
      agonist
<220> FEATURE:
<221> NAME/KEY: MOD_RES
<222> LOCATION: (1)..(1)
<223> OTHER INFORMATION: Xaa = Leu linked to Phe at position 14 of
      KXVSXSYRCPCRFX (SEQ ID NO:160) via a moiety providing covalent
      attachment between N and C terminal portions of the
      peptides, such as NH-2-(CH-2)-n-COOH (n = 0-20)
<220> FEATURE:
<221> NAME/KEY: MISC_FEATURE
<222> LOCATION: (6)..(10)
<223> OTHER INFORMATION: side chain cyclized using lactam formation
<220> FEATURE:
<221> NAME/KEY: MOD_RES
<222> LOCATION: (13)..(13)
<223> OTHER INFORMATION: AMIDATION

<400> SEQUENCE: 161

Xaa Lys Trp Ile Gln Glu Tyr Leu Glu Lys Ala Leu Asn
1               5                   10

<210> SEQ ID NO 162
<211> LENGTH: 31
<212> TYPE: PRT
<213> ORGANISM: Artificial Sequence
<220> FEATURE:
<223> OTHER INFORMATION: synthetic CTCE0022-like analog CXCR4 agonist
<220> FEATURE:
<221> NAME/KEY: MISC_FEATURE
<222> LOCATION: (24)..(28)
<223> OTHER INFORMATION: side chain cyclized using lactam formation
<220> FEATURE:
<221> NAME/KEY: MOD_RES
<222> LOCATION: (31)..(31)
<223> OTHER INFORMATION: AMIDATION

<400> SEQUENCE: 162

Lys Pro Val Ser Leu Ser Tyr Arg Trp Pro Ala Arg Phe Phe Gly Gly
1               5                   10                  15

Gly Gly Leu Lys Trp Ile Gln Glu Tyr Leu Glu Lys Ala Leu Asn
            20                  25                  30

<210> SEQ ID NO 163
<211> LENGTH: 14
<212> TYPE: PRT
```

```
<213> ORGANISM: Artificial Sequence
<220> FEATURE:
<223> OTHER INFORMATION: portion of synthetic CTCE0022-like analog CXCR4
      agonist
<220> FEATURE:
<221> NAME/KEY: MOD_RES
<222> LOCATION: (14)..(14)
<223> OTHER INFORMATION: Xaa = Phe linked to Leu at position 1 of
      XKWIQEYLEKALN (SEQ ID NO:164) via a moiety providing covalent
      attachment between N and C terminal portions of the
      peptides, such as NH-2-(CH-2)-n-COOH (n = 0-20)

<400> SEQUENCE: 163

Lys Pro Val Ser Leu Ser Tyr Arg Trp Pro Ala Arg Phe Xaa
1               5                   10

<210> SEQ ID NO 164
<211> LENGTH: 13
<212> TYPE: PRT
<213> ORGANISM: Artificial Sequence
<220> FEATURE:
<223> OTHER INFORMATION: portion of synthetic CTCE0022-like analog CXCR4
      agonist
<220> FEATURE:
<221> NAME/KEY: MOD_RES
<222> LOCATION: (1)..(1)
<223> OTHER INFORMATION: Xaa = Leu linked to Phe at position 14 of
      KXVSXSYRCPCRFX (SEQ ID NO:163) via a moiety providing covalent
      attachment between N and C terminal portions of the
      peptides, such as NH-2-(CH-2)-n-COOH (n = 0-20)
<220> FEATURE:
<221> NAME/KEY: MISC_FEATURE
<222> LOCATION: (6)..(10)
<223> OTHER INFORMATION: side chain cyclized using lactam formation
<220> FEATURE:
<221> NAME/KEY: MOD_RES
<222> LOCATION: (13)..(13)
<223> OTHER INFORMATION: AMIDATION

<400> SEQUENCE: 164

Xaa Lys Trp Ile Gln Glu Tyr Leu Glu Lys Ala Leu Asn
1               5                   10

<210> SEQ ID NO 165
<211> LENGTH: 31
<212> TYPE: PRT
<213> ORGANISM: Artificial Sequence
<220> FEATURE:
<223> OTHER INFORMATION: synthetic CTCE0022-like analog CXCR4 agonist
<220> FEATURE:
<221> NAME/KEY: MOD_RES
<222> LOCATION: (1)..(1)
<223> OTHER INFORMATION: Lys is modified with polyethylene glycol (PEG)
<220> FEATURE:
<221> NAME/KEY: MISC_FEATURE
<222> LOCATION: (24)..(28)
<223> OTHER INFORMATION: side chain cyclized using lactam formation
<220> FEATURE:
<221> NAME/KEY: MOD_RES
<222> LOCATION: (31)..(31)
<223> OTHER INFORMATION: AMIDATION

<400> SEQUENCE: 165

Lys Pro Val Ser Leu Ser Tyr Arg Trp Pro Ala Arg Phe Phe Gly Gly
1               5                   10                  15

Gly Gly Leu Lys Trp Ile Gln Glu Tyr Leu Glu Lys Ala Leu Asn
            20                  25                  30

<210> SEQ ID NO 166
<211> LENGTH: 14
<212> TYPE: PRT
<213> ORGANISM: Artificial Sequence
```

```
<220> FEATURE:
<223> OTHER INFORMATION: portion of synthetic CTCE0022-like analog CXCR4
      agonist
<220> FEATURE:
<221> NAME/KEY: MOD_RES
<222> LOCATION: (1)..(1)
<223> OTHER INFORMATION: Lys is modified with polyethylene glycol (PEG)
<220> FEATURE:
<221> NAME/KEY: MOD_RES
<222> LOCATION: (14)..(14)
<223> OTHER INFORMATION: Xaa = Phe linked to Leu at position 1 of
      XKWIQEYLEKALN (SEQ ID NO:167) via a moiety providing covalent
      attachment between N and C terminal portions of the
      peptides, such as NH-2-(CH-2)-n-COOH (n = 0-20)

<400> SEQUENCE: 166

Lys Pro Val Ser Leu Ser Tyr Arg Trp Pro Ala Arg Phe Xaa
1               5                   10

<210> SEQ ID NO 167
<211> LENGTH: 13
<212> TYPE: PRT
<213> ORGANISM: Artificial Sequence
<220> FEATURE:
<223> OTHER INFORMATION: portion of synthetic CTCE0022-like analog CXCR4
      agonist
<220> FEATURE:
<221> NAME/KEY: MOD_RES
<222> LOCATION: (1)..(1)
<223> OTHER INFORMATION: Xaa = Leu linked to Phe at position 14 of
      KXVSXSYRCPCRFX (SEQ ID NO:166) via a moiety providing covalent
      attachment between N and C terminal portions of the
      peptides, such as NH-2-(CH-2)-n-COOH (n = 0-20)
<220> FEATURE:
<221> NAME/KEY: MISC_FEATURE
<222> LOCATION: (6)..(10)
<223> OTHER INFORMATION: side chain cyclized using lactam formation
<220> FEATURE:
<221> NAME/KEY: MOD_RES
<222> LOCATION: (13)..(13)
<223> OTHER INFORMATION: AMIDATION

<400> SEQUENCE: 167

Xaa Lys Trp Ile Gln Glu Tyr Leu Glu Lys Ala Leu Asn
1               5                   10

<210> SEQ ID NO 168
<211> LENGTH: 31
<212> TYPE: PRT
<213> ORGANISM: Artificial Sequence
<220> FEATURE:
<223> OTHER INFORMATION: synthetic CTCE0022-like analog CXCR4 agonist
<220> FEATURE:
<221> NAME/KEY: MISC_FEATURE
<222> LOCATION: (24)..(28)
<223> OTHER INFORMATION: side chain cyclized using lactam formation
<220> FEATURE:
<221> NAME/KEY: MOD_RES
<222> LOCATION: (31)..(31)
<223> OTHER INFORMATION: AMIDATION

<400> SEQUENCE: 168

Lys Pro Val Ser Leu Ser Tyr Arg Ala Pro Tyr Arg Phe Phe Gly Gly
1               5                   10                  15

Gly Gly Leu Lys Trp Ile Gln Glu Tyr Leu Glu Lys Ala Leu Asn
            20                  25                  30

<210> SEQ ID NO 169
<211> LENGTH: 14
<212> TYPE: PRT
<213> ORGANISM: Artificial Sequence
<220> FEATURE:
```

```
<223> OTHER INFORMATION: portion of synthetic CTCE0022-like analog CXCR4
      agonist
<220> FEATURE:
<221> NAME/KEY: MOD_RES
<222> LOCATION: (14)..(14)
<223> OTHER INFORMATION: Xaa = Phe linked to Leu at position 1 of
      XKWIQEYLEKALN (SEQ ID NO:170) via a moiety providing covalent
      attachment between N and C terminal portions of the
      peptides, such as NH-2-(CH-2)-n-COOH (n = 0-20)

<400> SEQUENCE: 169

Lys Pro Val Ser Leu Ser Tyr Arg Ala Pro Tyr Arg Phe Xaa
1               5                   10

<210> SEQ ID NO 170
<211> LENGTH: 13
<212> TYPE: PRT
<213> ORGANISM: Artificial Sequence
<220> FEATURE:
<223> OTHER INFORMATION: portion of synthetic CTCE0022-like analog CXCR4
      agonist
<220> FEATURE:
<221> NAME/KEY: MOD_RES
<222> LOCATION: (1)..(1)
<223> OTHER INFORMATION: Xaa = Leu linked to Phe at position 14 of
      KXVSXSYRCPCRFX (SEQ ID NO:169) via a moiety providing covalent
      attachment between N and C terminal portions of the
      peptides, such as NH-2-(CH-2)-n-COOH (n = 0-20)
<220> FEATURE:
<221> NAME/KEY: MISC_FEATURE
<222> LOCATION: (6)..(10)
<223> OTHER INFORMATION: side chain cyclized using lactam formation
<220> FEATURE:
<221> NAME/KEY: MOD_RES
<222> LOCATION: (13)..(13)
<223> OTHER INFORMATION: AMIDATION

<400> SEQUENCE: 170

Xaa Lys Trp Ile Gln Glu Tyr Leu Glu Lys Ala Leu Asn
1               5                   10

<210> SEQ ID NO 171
<211> LENGTH: 31
<212> TYPE: PRT
<213> ORGANISM: Artificial Sequence
<220> FEATURE:
<223> OTHER INFORMATION: synthetic CTCE0022-like analog CXCR4 agonist
<220> FEATURE:
<221> NAME/KEY: MOD_RES
<222> LOCATION: (1)..(1)
<223> OTHER INFORMATION: Lys is modified with polyethylene glycol (PEG)
<220> FEATURE:
<221> NAME/KEY: MISC_FEATURE
<222> LOCATION: (24)..(28)
<223> OTHER INFORMATION: side chain cyclized using lactam formation
<220> FEATURE:
<221> NAME/KEY: MOD_RES
<222> LOCATION: (31)..(31)
<223> OTHER INFORMATION: AMIDATION

<400> SEQUENCE: 171

Lys Pro Val Ser Leu Ser Tyr Arg Ala Pro Tyr Arg Phe Phe Gly Gly
1               5                   10                  15

Gly Gly Leu Lys Trp Ile Gln Glu Tyr Leu Glu Lys Ala Leu Asn
            20                  25                  30

<210> SEQ ID NO 172
<211> LENGTH: 14
<212> TYPE: PRT
<213> ORGANISM: Artificial Sequence
<220> FEATURE:
<223> OTHER INFORMATION: portion of synthetic CTCE0022-like analog CXCR4
```

```
                            agonist
<220> FEATURE:
<221> NAME/KEY: MOD_RES
<222> LOCATION: (1)..(1)
<223> OTHER INFORMATION: Lys is modified with polyethylene glycol (PEG)
<220> FEATURE:
<221> NAME/KEY: MOD_RES
<222> LOCATION: (14)..(14)
<223> OTHER INFORMATION: Xaa = Phe linked to Leu at position 1 of
      XKWIQEYLEKALN (SEQ ID NO:173) via a moiety providing covalent
      attachment between N and C terminal portions of the
      peptides, such as NH-2-(CH-2)-n-COOH (n = 0-20)

<400> SEQUENCE: 172

Lys Pro Val Ser Leu Ser Tyr Arg Ala Pro Tyr Arg Phe Xaa
1               5                   10

<210> SEQ ID NO 173
<211> LENGTH: 13
<212> TYPE: PRT
<213> ORGANISM: Artificial Sequence
<220> FEATURE:
<223> OTHER INFORMATION: portion of synthetic CTCE0022-like analog CXCR4
      agonist
<220> FEATURE:
<221> NAME/KEY: MOD_RES
<222> LOCATION: (1)..(1)
<223> OTHER INFORMATION: Xaa = Leu linked to Phe at position 14 of
      KXVSXSYRCPCRFX (SEQ ID NO:172) via a moiety providing covalent
      attachment between N and C terminal portions of the
      peptides, such as NH-2-(CH-2)-n-COOH (n = 0-20)
<220> FEATURE:
<221> NAME/KEY: MISC_FEATURE
<222> LOCATION: (6)..(10)
<223> OTHER INFORMATION: side chain cyclized using lactam formation
<220> FEATURE:
<221> NAME/KEY: MOD_RES
<222> LOCATION: (13)..(13)
<223> OTHER INFORMATION: AMIDATION

<400> SEQUENCE: 173

Xaa Lys Trp Ile Gln Glu Tyr Leu Glu Lys Ala Leu Asn
1               5                   10

<210> SEQ ID NO 174
<211> LENGTH: 31
<212> TYPE: PRT
<213> ORGANISM: Artificial Sequence
<220> FEATURE:
<223> OTHER INFORMATION: synthetic CTCE0022-like analog CXCR4 agonist
<220> FEATURE:
<221> NAME/KEY: MISC_FEATURE
<222> LOCATION: (24)..(28)
<223> OTHER INFORMATION: side chain cyclized using lactam formation
<220> FEATURE:
<221> NAME/KEY: MOD_RES
<222> LOCATION: (31)..(31)
<223> OTHER INFORMATION: AMIDATION

<400> SEQUENCE: 174

Lys Pro Val Ser Leu Ser Tyr Arg Tyr Pro Tyr Arg Phe Phe Gly Gly
1               5                   10                  15

Gly Gly Leu Lys Trp Ile Gln Glu Tyr Leu Glu Lys Ala Leu Asn
            20                  25                  30

<210> SEQ ID NO 175
<211> LENGTH: 14
<212> TYPE: PRT
<213> ORGANISM: Artificial Sequence
<220> FEATURE:
<223> OTHER INFORMATION: portion of synthetic CTCE0022-like analog CXCR4
      agonist
```

```
<220> FEATURE:
<221> NAME/KEY: MOD_RES
<222> LOCATION: (14)..(14)
<223> OTHER INFORMATION: Xaa = Phe linked to Leu at position 1 of
      XKWIQEYLEKALN (SEQ ID NO:176) via a moiety providing covalent
      attachment between N and C terminal portions of the
      peptides, such as NH-2-(CH-2)-n-COOH (n = 0-20)

<400> SEQUENCE: 175

Lys Pro Val Ser Leu Ser Tyr Arg Tyr Pro Tyr Arg Phe Xaa
1               5                   10

<210> SEQ ID NO 176
<211> LENGTH: 13
<212> TYPE: PRT
<213> ORGANISM: Artificial Sequence
<220> FEATURE:
<223> OTHER INFORMATION: portion of synthetic CTCE0022-like analog CXCR4
      agonist
<220> FEATURE:
<221> NAME/KEY: MOD_RES
<222> LOCATION: (1)..(1)
<223> OTHER INFORMATION: Xaa = Leu linked to Phe at position 14 of
      KXVSXSYRCPCRFX (SEQ ID NO:175) via a moiety providing covalent
      attachment between N and C terminal portions of the
      peptides, such as NH-2-(CH-2)-n-COOH (n = 0-20)
<220> FEATURE:
<221> NAME/KEY: MISC_FEATURE
<222> LOCATION: (6)..(10)
<223> OTHER INFORMATION: side chain cyclized using lactam formation
<220> FEATURE:
<221> NAME/KEY: MOD_RES
<222> LOCATION: (13)..(13)
<223> OTHER INFORMATION: AMIDATION

<400> SEQUENCE: 176

Xaa Lys Trp Ile Gln Glu Tyr Leu Glu Lys Ala Leu Asn
1               5                   10

<210> SEQ ID NO 177
<211> LENGTH: 31
<212> TYPE: PRT
<213> ORGANISM: Artificial Sequence
<220> FEATURE:
<223> OTHER INFORMATION: synthetic CTCE0022-like analog CXCR4 agonist
<220> FEATURE:
<221> NAME/KEY: MOD_RES
<222> LOCATION: (1)..(1)
<223> OTHER INFORMATION: Lys is modified with polyethylene glycol (PEG)
<220> FEATURE:
<221> NAME/KEY: MISC_FEATURE
<222> LOCATION: (24)..(28)
<223> OTHER INFORMATION: side chain cyclized using lactam formation
<220> FEATURE:
<221> NAME/KEY: MOD_RES
<222> LOCATION: (31)..(31)
<223> OTHER INFORMATION: AMIDATION

<400> SEQUENCE: 177

Lys Pro Val Ser Leu Ser Tyr Arg Tyr Pro Tyr Arg Phe Phe Gly Gly
1               5                   10                  15

Gly Gly Leu Lys Trp Ile Gln Glu Tyr Leu Glu Lys Ala Leu Asn
            20                  25                  30

<210> SEQ ID NO 178
<211> LENGTH: 14
<212> TYPE: PRT
<213> ORGANISM: Artificial Sequence
<220> FEATURE:
<223> OTHER INFORMATION: portion of synthetic CTCE0022-like analog CXCR4
      agonist
<220> FEATURE:
```

```
<221> NAME/KEY: MOD_RES
<222> LOCATION: (1)..(1)
<223> OTHER INFORMATION: Lys is modified with polyethylene glycol (PEG)
<220> FEATURE:
<221> NAME/KEY: MOD_RES
<222> LOCATION: (14)..(14)
<223> OTHER INFORMATION: Xaa = Phe linked to Leu at position 1 of
      XKWIQEYLEKALN (SEQ ID NO:179) via a moiety providing covalent
      attachment between N and C terminal portions of the
      peptides, such as NH-2-(CH-2)-n-COOH (n = 0-20)

<400> SEQUENCE: 178

Lys Pro Val Ser Leu Ser Tyr Arg Tyr Pro Tyr Arg Phe Xaa
1               5                   10

<210> SEQ ID NO 179
<211> LENGTH: 13
<212> TYPE: PRT
<213> ORGANISM: Artificial Sequence
<220> FEATURE:
<223> OTHER INFORMATION: portion of synthetic CTCE0022-like analog CXCR4
      agonist
<220> FEATURE:
<221> NAME/KEY: MOD_RES
<222> LOCATION: (1)..(1)
<223> OTHER INFORMATION: Xaa = Leu linked to Phe at position 14 of
      KXVSXSYRCPCRFX (SEQ ID NO:178) via a moiety providing covalent
      attachment between N and C terminal portions of the
      peptides, such as NH-2-(CH-2)-n-COOH (n = 0-20)
<220> FEATURE:
<221> NAME/KEY: MISC_FEATURE
<222> LOCATION: (6)..(10)
<223> OTHER INFORMATION: side chain cyclized using lactam formation
<220> FEATURE:
<221> NAME/KEY: MOD_RES
<222> LOCATION: (13)..(13)
<223> OTHER INFORMATION: AMIDATION

<400> SEQUENCE: 179

Xaa Lys Trp Ile Gln Glu Tyr Leu Glu Lys Ala Leu Asn
1               5                   10

<210> SEQ ID NO 180
<211> LENGTH: 31
<212> TYPE: PRT
<213> ORGANISM: Artificial Sequence
<220> FEATURE:
<223> OTHER INFORMATION: synthetic CTCE0022-like analog CXCR4 agonist
<220> FEATURE:
<221> NAME/KEY: MISC_FEATURE
<222> LOCATION: (24)..(28)
<223> OTHER INFORMATION: side chain cyclized using lactam formation
<220> FEATURE:
<221> NAME/KEY: MOD_RES
<222> LOCATION: (31)..(31)
<223> OTHER INFORMATION: AMIDATION

<400> SEQUENCE: 180

Lys Pro Val Ser Leu Ser Tyr Arg Tyr Pro Ala Arg Phe Phe Gly Gly
1               5                   10                  15

Gly Gly Leu Lys Trp Ile Gln Glu Tyr Leu Glu Lys Ala Leu Asn
                20                  25                  30

<210> SEQ ID NO 181
<211> LENGTH: 14
<212> TYPE: PRT
<213> ORGANISM: Artificial Sequence
<220> FEATURE:
<223> OTHER INFORMATION: portion of synthetic CTCE0022-like analog CXCR4
      agonist
<220> FEATURE:
<221> NAME/KEY: MOD_RES
```

```
<222> LOCATION: (14)..(14)
<223> OTHER INFORMATION: Xaa = Phe linked to Leu at position 1 of
      XKWIQEYLEKALN (SEQ ID NO:182) via a moiety providing covalent
      attachment between N and C terminal portions of the
      peptides, such as NH-2-(CH-2)-n-COOH (n = 0-20)

<400> SEQUENCE: 181

Lys Pro Val Ser Leu Ser Tyr Arg Tyr Pro Ala Arg Phe Xaa
1               5                   10

<210> SEQ ID NO 182
<211> LENGTH: 13
<212> TYPE: PRT
<213> ORGANISM: Artificial Sequence
<220> FEATURE:
<223> OTHER INFORMATION: portion of synthetic CTCE0022-like analog CXCR4
      agonist
<220> FEATURE:
<221> NAME/KEY: MOD_RES
<222> LOCATION: (1)..(1)
<223> OTHER INFORMATION: Xaa = Leu linked to Phe at position 14 of
      KXVSXSYRCPCRFX (SEQ ID NO:181) via a moiety providing covalent
      attachment between N and C terminal portions of the
      peptides, such as NH-2-(CH-2)-n-COOH (n = 0-20)
<220> FEATURE:
<221> NAME/KEY: MISC_FEATURE
<222> LOCATION: (6)..(10)
<223> OTHER INFORMATION: side chain cyclized using lactam formation
<220> FEATURE:
<221> NAME/KEY: MOD_RES
<222> LOCATION: (13)..(13)
<223> OTHER INFORMATION: AMIDATION

<400> SEQUENCE: 182

Xaa Lys Trp Ile Gln Glu Tyr Leu Glu Lys Ala Leu Asn
1               5                   10

<210> SEQ ID NO 183
<211> LENGTH: 31
<212> TYPE: PRT
<213> ORGANISM: Artificial Sequence
<220> FEATURE:
<223> OTHER INFORMATION: synthetic CTCE0022-like analog CXCR4 agonist
<220> FEATURE:
<221> NAME/KEY: MOD_RES
<222> LOCATION: (1)..(1)
<223> OTHER INFORMATION: Lys is modified with polyethylene glycol (PEG)
<220> FEATURE:
<221> NAME/KEY: MISC_FEATURE
<222> LOCATION: (24)..(28)
<223> OTHER INFORMATION: side chain cyclized using lactam formation
<220> FEATURE:
<221> NAME/KEY: MOD_RES
<222> LOCATION: (31)..(31)
<223> OTHER INFORMATION: AMIDATION

<400> SEQUENCE: 183

Lys Pro Val Ser Leu Ser Tyr Arg Tyr Pro Ala Arg Phe Phe Gly Gly
1               5                   10                  15

Gly Gly Leu Lys Trp Ile Gln Glu Tyr Leu Glu Lys Ala Leu Asn
            20                  25                  30

<210> SEQ ID NO 184
<211> LENGTH: 14
<212> TYPE: PRT
<213> ORGANISM: Artificial Sequence
<220> FEATURE:
<223> OTHER INFORMATION: portion of synthetic CTCE0022-like analog CXCR4
      agonist
<220> FEATURE:
<221> NAME/KEY: MOD_RES
<222> LOCATION: (1)..(1)
```

```
<223> OTHER INFORMATION: Lys is modified with polyethylene glycol (PEG)
<220> FEATURE:
<221> NAME/KEY: MOD_RES
<222> LOCATION: (14)..(14)
<223> OTHER INFORMATION: Xaa = Phe linked to Leu at position 1 of
      XKWIQEYLEKALN (SEQ ID NO:185) via a moiety providing covalent
      attachment between N and C terminal portions of the
      peptides, such as NH-2-(CH-2)-n-COOH (n = 0-20)

<400> SEQUENCE: 184

Lys Pro Val Ser Leu Ser Tyr Arg Tyr Pro Ala Arg Phe Xaa
1               5                   10

<210> SEQ ID NO 185
<211> LENGTH: 13
<212> TYPE: PRT
<213> ORGANISM: Artificial Sequence
<220> FEATURE:
<223> OTHER INFORMATION: portion of synthetic CTCE0022-like analog CXCR4
      agonist
<220> FEATURE:
<221> NAME/KEY: MOD_RES
<222> LOCATION: (1)..(1)
<223> OTHER INFORMATION: Xaa = Leu linked to Phe at position 14 of
      KXVSXSYRCPCRFX (SEQ ID NO:184) via a moiety providing covalent
      attachment between N and C terminal portions of the
      peptides, such as NH-2-(CH-2)-n-COOH (n = 0-20)
<220> FEATURE:
<221> NAME/KEY: MISC_FEATURE
<222> LOCATION: (6)..(10)
<223> OTHER INFORMATION: side chain cyclized using lactam formation
<220> FEATURE:
<221> NAME/KEY: MOD_RES
<222> LOCATION: (13)..(13)
<223> OTHER INFORMATION: AMIDATION

<400> SEQUENCE: 185

Xaa Lys Trp Ile Gln Glu Tyr Leu Glu Lys Ala Leu Asn
1               5                   10

<210> SEQ ID NO 186
<211> LENGTH: 31
<212> TYPE: PRT
<213> ORGANISM: Artificial Sequence
<220> FEATURE:
<223> OTHER INFORMATION: synthetic CTCE0022-like analog CXCR4 agonist
<220> FEATURE:
<221> NAME/KEY: MISC_FEATURE
<222> LOCATION: (24)..(28)
<223> OTHER INFORMATION: side chain cyclized using lactam formation
<220> FEATURE:
<221> NAME/KEY: MOD_RES
<222> LOCATION: (31)..(31)
<223> OTHER INFORMATION: AMIDATION

<400> SEQUENCE: 186

Lys Pro Val Ser Leu Ser Tyr Arg Phe Pro Phe Arg Phe Phe Gly Gly
1               5                   10                  15

Gly Gly Leu Lys Trp Ile Gln Glu Tyr Leu Glu Lys Ala Leu Asn
            20                  25                  30

<210> SEQ ID NO 187
<211> LENGTH: 14
<212> TYPE: PRT
<213> ORGANISM: Artificial Sequence
<220> FEATURE:
<223> OTHER INFORMATION: portion of synthetic CTCE0022-like analog CXCR4
      agonist
<220> FEATURE:
<221> NAME/KEY: MOD_RES
<222> LOCATION: (14)..(14)
<223> OTHER INFORMATION: Xaa = Phe linked to Leu at position 1 of
```

```
              XKWIQEYLEKALN (SEQ ID NO:188) via a moiety providing covalent
              attachment between N and C terminal portions of the
              peptides, such as NH-2-(CH-2)-n-COOH (n = 0-20)

<400> SEQUENCE: 187

Lys Pro Val Ser Leu Ser Tyr Arg Phe Pro Phe Arg Phe Xaa
1               5                   10

<210> SEQ ID NO 188
<211> LENGTH: 13
<212> TYPE: PRT
<213> ORGANISM: Artificial Sequence
<220> FEATURE:
<223> OTHER INFORMATION: portion of synthetic CTCE0022-like analog CXCR4
      agonist
<220> FEATURE:
<221> NAME/KEY: MOD_RES
<222> LOCATION: (1)..(1)
<223> OTHER INFORMATION: Xaa = Leu linked to Phe at position 14 of
      KXVSXSYRCPCRFX (SEQ ID NO:187) via a moiety providing covalent
      attachment between N and C terminal portions of the
      peptides, such as NH-2-(CH-2)-n-COOH (n = 0-20)
<220> FEATURE:
<221> NAME/KEY: MISC_FEATURE
<222> LOCATION: (6)..(10)
<223> OTHER INFORMATION: side chain cyclized using lactam formation
<220> FEATURE:
<221> NAME/KEY: MOD_RES
<222> LOCATION: (13)..(13)
<223> OTHER INFORMATION: AMIDATION

<400> SEQUENCE: 188

Xaa Lys Trp Ile Gln Glu Tyr Leu Glu Lys Ala Leu Asn
1               5                   10

<210> SEQ ID NO 189
<211> LENGTH: 31
<212> TYPE: PRT
<213> ORGANISM: Artificial Sequence
<220> FEATURE:
<223> OTHER INFORMATION: synthetic CTCE0022-like analog CXCR4 agonist
<220> FEATURE:
<221> NAME/KEY: MOD_RES
<222> LOCATION: (1)..(1)
<223> OTHER INFORMATION: Lys is modified with polyethylene glycol (PEG)
<220> FEATURE:
<221> NAME/KEY: MISC_FEATURE
<222> LOCATION: (24)..(28)
<223> OTHER INFORMATION: side chain cyclized using lactam formation
<220> FEATURE:
<221> NAME/KEY: MOD_RES
<222> LOCATION: (31)..(31)
<223> OTHER INFORMATION: AMIDATION

<400> SEQUENCE: 189

Lys Pro Val Ser Leu Ser Tyr Arg Phe Pro Phe Arg Phe Phe Gly Gly
1               5                   10                  15

Gly Gly Leu Lys Trp Ile Gln Glu Tyr Leu Glu Lys Ala Leu Asn
            20                  25                  30

<210> SEQ ID NO 190
<211> LENGTH: 14
<212> TYPE: PRT
<213> ORGANISM: Artificial Sequence
<220> FEATURE:
<223> OTHER INFORMATION: portion of synthetic CTCE0022-like analog CXCR4
      agonist
<220> FEATURE:
<221> NAME/KEY: MOD_RES
<222> LOCATION: (1)..(1)
<223> OTHER INFORMATION: Lys is modified with polyethylene glycol (PEG)
<220> FEATURE:
```

```
<221> NAME/KEY: MOD_RES
<222> LOCATION: (14)..(14)
<223> OTHER INFORMATION: Xaa = Phe linked to Leu at position 1 of
      XKWIQEYLEKALN (SEQ ID NO:191) via a moiety providing covalent
      attachment between N and C terminal portions of the
      peptides, such as NH-2-(CH-2)-n-COOH (n = 0-20)

<400> SEQUENCE: 190

Lys Pro Val Ser Leu Ser Tyr Arg Phe Pro Phe Arg Phe Xaa
1               5                   10

<210> SEQ ID NO 191
<211> LENGTH: 13
<212> TYPE: PRT
<213> ORGANISM: Artificial Sequence
<220> FEATURE:
<223> OTHER INFORMATION: portion of synthetic CTCE0022-like analog CXCR4
      agonist
<220> FEATURE:
<221> NAME/KEY: MOD_RES
<222> LOCATION: (1)..(1)
<223> OTHER INFORMATION: Xaa = Leu linked to Phe at position 14 of
      KXVSXSYRCPCRFX (SEQ ID NO:190) via a moiety providing covalent
      attachment between N and C terminal portions of the
      peptides, such as NH-2-(CH-2)-n-COOH (n = 0-20)
<220> FEATURE:
<221> NAME/KEY: MISC_FEATURE
<222> LOCATION: (6)..(10)
<223> OTHER INFORMATION: side chain cyclized using lactam formation
<220> FEATURE:
<221> NAME/KEY: MOD_RES
<222> LOCATION: (13)..(13)
<223> OTHER INFORMATION: AMIDATION

<400> SEQUENCE: 191

Xaa Lys Trp Ile Gln Glu Tyr Leu Glu Lys Ala Leu Asn
1               5                   10

<210> SEQ ID NO 192
<211> LENGTH: 31
<212> TYPE: PRT
<213> ORGANISM: Artificial Sequence
<220> FEATURE:
<223> OTHER INFORMATION: synthetic CTCE0022-like analog CXCR4 agonist
<220> FEATURE:
<221> NAME/KEY: MISC_FEATURE
<222> LOCATION: (24)..(28)
<223> OTHER INFORMATION: side chain cyclized using lactam formation
<220> FEATURE:
<221> NAME/KEY: MOD_RES
<222> LOCATION: (31)..(31)
<223> OTHER INFORMATION: AMIDATION

<400> SEQUENCE: 192

Lys Pro Val Ser Leu Ser Tyr Arg His Pro His Arg Phe Phe Gly Gly
1               5                   10                  15

Gly Gly Leu Lys Trp Ile Gln Glu Tyr Leu Glu Lys Ala Leu Asn
            20                  25                  30

<210> SEQ ID NO 193
<211> LENGTH: 14
<212> TYPE: PRT
<213> ORGANISM: Artificial Sequence
<220> FEATURE:
<223> OTHER INFORMATION: portion of synthetic CTCE0022-like analog CXCR4
      agonist
<220> FEATURE:
<221> NAME/KEY: MOD_RES
<222> LOCATION: (14)..(14)
<223> OTHER INFORMATION: Xaa = Phe linked to Leu at position 1 of
      XKWIQEYLEKALN (SEQ ID NO:194) via a moiety providing covalent
      attachment between N and C terminal portions of the
``` peptides, such as NH-2-(CH-2)-n-COOH (n = 0-20)

<400> SEQUENCE: 193

Lys Pro Val Ser Leu Ser Tyr Arg His Pro His Arg Phe Xaa
1               5                   10

<210> SEQ ID NO 194
<211> LENGTH: 13
<212> TYPE: PRT
<213> ORGANISM: Artificial Sequence
<220> FEATURE:
<223> OTHER INFORMATION: portion of synthetic CTCE0022-like analog CXCR4
      agonist
<220> FEATURE:
<221> NAME/KEY: MOD_RES
<222> LOCATION: (1)..(1)
<223> OTHER INFORMATION: Xaa = Leu linked to Phe at position 14 of
      KXVSXSYRCPCRFX (SEQ ID NO:193) via a moiety providing covalent
      attachment between N and C terminal portions of the
      peptides, such as NH-2-(CH-2)-n-COOH (n = 0-20)
<220> FEATURE:
<221> NAME/KEY: MISC_FEATURE
<222> LOCATION: (6)..(10)
<223> OTHER INFORMATION: side chain cyclized using lactam formation
<220> FEATURE:
<221> NAME/KEY: MOD_RES
<222> LOCATION: (13)..(13)
<223> OTHER INFORMATION: AMIDATION

<400> SEQUENCE: 194

Xaa Lys Trp Ile Gln Glu Tyr Leu Glu Lys Ala Leu Asn
1               5                   10

<210> SEQ ID NO 195
<211> LENGTH: 31
<212> TYPE: PRT
<213> ORGANISM: Artificial Sequence
<220> FEATURE:
<223> OTHER INFORMATION: synthetic CTCE0022-like analog CXCR4 agonist
<220> FEATURE:
<221> NAME/KEY: MOD_RES
<222> LOCATION: (1)..(1)
<223> OTHER INFORMATION: Lys is modified with polyethylene glycol (PEG)
<220> FEATURE:
<221> NAME/KEY: MISC_FEATURE
<222> LOCATION: (24)..(28)
<223> OTHER INFORMATION: side chain cyclized using lactam formation
<220> FEATURE:
<221> NAME/KEY: MOD_RES
<222> LOCATION: (31)..(31)
<223> OTHER INFORMATION: AMIDATION

<400> SEQUENCE: 195

Lys Pro Val Ser Leu Ser Tyr Arg His Pro His Arg Phe Phe Gly Gly
1               5                   10                  15

Gly Gly Leu Lys Trp Ile Gln Glu Tyr Leu Glu Lys Ala Leu Asn
            20                  25                  30

<210> SEQ ID NO 196
<211> LENGTH: 14
<212> TYPE: PRT
<213> ORGANISM: Artificial Sequence
<220> FEATURE:
<223> OTHER INFORMATION: portion of synthetic CTCE0022-like analog CXCR4
      agonist
<220> FEATURE:
<221> NAME/KEY: MOD_RES
<222> LOCATION: (1)..(1)
<223> OTHER INFORMATION: Lys is modified with polyethylene glycol (PEG)
<220> FEATURE:
<221> NAME/KEY: MOD_RES
<222> LOCATION: (14)..(14)

```
<223> OTHER INFORMATION: Xaa = Phe linked to Leu at position 1 of
      XKWIQEYLEKALN (SEQ ID NO:197) via a moiety providing covalent
      attachment between N and C terminal portions of the
      peptides, such as NH-2-(CH-2)-n-COOH (n = 0-20)

<400> SEQUENCE: 196

Lys Pro Val Ser Leu Ser Tyr Arg His Pro His Arg Phe Xaa
1               5                   10

<210> SEQ ID NO 197
<211> LENGTH: 13
<212> TYPE: PRT
<213> ORGANISM: Artificial Sequence
<220> FEATURE:
<223> OTHER INFORMATION: portion of synthetic CTCE0022-like analog CXCR4
      agonist
<220> FEATURE:
<221> NAME/KEY: MOD_RES
<222> LOCATION: (1)..(1)
<223> OTHER INFORMATION: Xaa = Leu linked to Phe at position 14 of
      KXVSXSYRCPCRFX (SEQ ID NO:196) via a moiety providing covalent
      attachment between N and C terminal portions of the
      peptides, such as NH-2-(CH-2)-n-COOH (n = 0-20)
<220> FEATURE:
<221> NAME/KEY: MISC_FEATURE
<222> LOCATION: (6)..(10)
<223> OTHER INFORMATION: side chain cyclized using lactam formation
<220> FEATURE:
<221> NAME/KEY: MOD_RES
<222> LOCATION: (13)..(13)
<223> OTHER INFORMATION: AMIDATION

<400> SEQUENCE: 197

Xaa Lys Trp Ile Gln Glu Tyr Leu Glu Lys Ala Leu Asn
1               5                   10

<210> SEQ ID NO 198
<211> LENGTH: 31
<212> TYPE: PRT
<213> ORGANISM: Artificial Sequence
<220> FEATURE:
<223> OTHER INFORMATION: synthetic CTCE0022-like analog CXCR4 agonist
<220> FEATURE:
<221> NAME/KEY: MISC_FEATURE
<222> LOCATION: (24)..(28)
<223> OTHER INFORMATION: side chain cyclized using lactam formation

<400> SEQUENCE: 198

Lys Pro Val Ser Leu Ser Tyr Arg Trp Pro Trp Arg Phe Phe Gly Gly
1               5                   10                  15

Gly Gly Leu Lys Trp Ile Gln Glu Tyr Leu Glu Lys Ala Leu Asn
            20                  25                  30

<210> SEQ ID NO 199
<211> LENGTH: 14
<212> TYPE: PRT
<213> ORGANISM: Artificial Sequence
<220> FEATURE:
<223> OTHER INFORMATION: portion of synthetic CTCE0022-like analog CXCR4
      agonist
<220> FEATURE:
<221> NAME/KEY: MOD_RES
<222> LOCATION: (14)..(14)
<223> OTHER INFORMATION: Xaa = Phe linked to Leu at position 1 of
      XKWIQEYLEKALN (SEQ ID NO:200) via a moiety providing covalent
      attachment between N and C terminal portions of the
      peptides, such as NH-2-(CH-2)-n-COOH (n = 0-20)

<400> SEQUENCE: 199

Lys Pro Val Ser Leu Ser Tyr Arg Trp Pro Trp Arg Phe Xaa
1               5                   10
```

<210> SEQ ID NO 200
<211> LENGTH: 13
<212> TYPE: PRT
<213> ORGANISM: Artificial Sequence
<220> FEATURE:
<223> OTHER INFORMATION: portion of synthetic CTCE0022-like analog CXCR4 agonist
<220> FEATURE:
<221> NAME/KEY: MOD_RES
<222> LOCATION: (1)..(1)
<223> OTHER INFORMATION: Xaa = Leu linked to Phe at position 14 of KXVSXSYRCPCRFX (SEQ ID NO:199) via a moiety providing covalent attachment between N and C terminal portions of the peptides, such as NH-2-(CH-2)-n-COOH (n = 0-20)
<220> FEATURE:
<221> NAME/KEY: MISC_FEATURE
<222> LOCATION: (6)..(10)
<223> OTHER INFORMATION: side chain cyclized using lactam formation
<220> FEATURE:
<221> NAME/KEY: MOD_RES
<222> LOCATION: (13)..(13)
<223> OTHER INFORMATION: AMIDATION

<400> SEQUENCE: 200

Xaa Lys Trp Ile Gln Glu Tyr Leu Glu Lys Ala Leu Asn
1               5                   10

<210> SEQ ID NO 201
<211> LENGTH: 31
<212> TYPE: PRT
<213> ORGANISM: Artificial Sequence
<220> FEATURE:
<223> OTHER INFORMATION: synthetic CTCE0022-like analog CXCR4 agonist
<220> FEATURE:
<221> NAME/KEY: MOD_RES
<222> LOCATION: (1)..(1)
<223> OTHER INFORMATION: Lys is modified with polyethylene glycol (PEG)
<220> FEATURE:
<221> NAME/KEY: MISC_FEATURE
<222> LOCATION: (24)..(28)
<223> OTHER INFORMATION: side chain cyclized using lactam formation
<220> FEATURE:
<221> NAME/KEY: MOD_RES
<222> LOCATION: (31)..(31)
<223> OTHER INFORMATION: AMIDATION

<400> SEQUENCE: 201

Lys Pro Val Ser Leu Ser Tyr Arg Trp Pro Trp Arg Phe Phe Gly Gly
1               5                   10                  15

Gly Gly Leu Lys Trp Ile Gln Glu Tyr Leu Glu Lys Ala Leu Asn
            20                  25                  30

<210> SEQ ID NO 202
<211> LENGTH: 14
<212> TYPE: PRT
<213> ORGANISM: Artificial Sequence
<220> FEATURE:
<223> OTHER INFORMATION: portion of synthetic CTCE0022-like analog CXCR4 agonist
<220> FEATURE:
<221> NAME/KEY: MOD_RES
<222> LOCATION: (1)..(1)
<223> OTHER INFORMATION: Lys is modified with polyethylene glycol (PEG)
<220> FEATURE:
<221> NAME/KEY: MOD_RES
<222> LOCATION: (14)..(14)
<223> OTHER INFORMATION: Xaa = Phe linked to Leu at position 1 of XKWIQEYLEKALN (SEQ ID NO:203) via a moiety providing covalent attachment between N and C terminal portions of the peptides, such as NH-2-(CH-2)-n-COOH (n = 0-20)

<400> SEQUENCE: 202

```
Lys Pro Val Ser Leu Ser Tyr Arg Trp Pro Trp Arg Phe Xaa
1               5                   10
```

<210> SEQ ID NO 203
<211> LENGTH: 13
<212> TYPE: PRT
<213> ORGANISM: Artificial Sequence
<220> FEATURE:
<223> OTHER INFORMATION: portion of synthetic CTCE0022-like analog CXCR4
      agonist
<220> FEATURE:
<221> NAME/KEY: MOD_RES
<222> LOCATION: (1)..(1)
<223> OTHER INFORMATION: Xaa = Leu linked to Phe at position 14 of
      KXVSXSYRCPCRFX (SEQ ID NO:202) via a moiety providing covalent
      attachment between N and C terminal portions of the
      peptides, such as NH-2-(CH-2)-n-COOH (n = 0-20)
<220> FEATURE:
<221> NAME/KEY: MISC_FEATURE
<222> LOCATION: (6)..(10)
<223> OTHER INFORMATION: side chain cyclized using lactam formation
<220> FEATURE:
<221> NAME/KEY: MOD_RES
<222> LOCATION: (13)..(13)
<223> OTHER INFORMATION: AMIDATION

<400> SEQUENCE: 203

```
Xaa Lys Trp Ile Gln Glu Tyr Leu Glu Lys Ala Leu Asn
1               5                   10
```

<210> SEQ ID NO 204
<211> LENGTH: 14
<212> TYPE: PRT
<213> ORGANISM: Artificial Sequence
<220> FEATURE:
<223> OTHER INFORMATION: portion of synthetic CXCR4 agonist
      SDF-1-derived cyclic amide (E24/K28)
<220> FEATURE:
<221> NAME/KEY: MISC_FEATURE
<222> LOCATION: (1)..(1)
<223> OTHER INFORMATION: Lys may be modified with a substituent that may
      be a hydrogen, alkyl, aryl or polyethylene glycol (PEG) moiety
<220> FEATURE:
<221> NAME/KEY: MISC_FEATURE
<222> LOCATION: (2)..(2)
<223> OTHER INFORMATION: Xaa = an amino acid that may be either an L-Pro
      or a D-Pro moiety
<220> FEATURE:
<221> NAME/KEY: MISC_FEATURE
<222> LOCATION: (5)..(5)
<223> OTHER INFORMATION: Xaa = an amino acid that may be either an L-Leu
      or a D-Leu moiety
<220> FEATURE:
<221> NAME/KEY: MOD_RES
<222> LOCATION: (14)..(14)
<223> OTHER INFORMATION: Xaa = Phe linked to Leu at position 1 of
      XKWIQEYLEKALN (SEQ ID NO:205) via a moiety providing covalent
      attachment between N and C terminal portions of the
      peptides, such as NH-2-(CH-2)-n-COOH (n = 0-20)

<400> SEQUENCE: 204

```
Lys Xaa Val Ser Xaa Ser Tyr Arg Cys Pro Cys Arg Phe Xaa
1               5                   10
```

<210> SEQ ID NO 205
<211> LENGTH: 13
<212> TYPE: PRT
<213> ORGANISM: Artificial Sequence
<220> FEATURE:
<223> OTHER INFORMATION: portion of synthetic CXCR4 agonist
      SDF-1-derived cyclic amide (E24/K28)
<220> FEATURE:
<221> NAME/KEY: MOD_RES

```
<222> LOCATION: (1)..(1)
<223> OTHER INFORMATION: Xaa = Leu linked to Phe at position 14 of
      KXVSXSYRCPCRFX (SEQ ID NO:204) via a moiety providing covalent
      attachment between N and C terminal portions of the
      peptides, such as NH-2-(CH-2)-n-COOH (n = 0-20)
<220> FEATURE:
<221> NAME/KEY: MISC_FEATURE
<222> LOCATION: (6)..(10)
<223> OTHER INFORMATION: side chain cyclized using lactam formation
<220> FEATURE:
<221> NAME/KEY: MOD_RES
<222> LOCATION: (13)..(13)
<223> OTHER INFORMATION: AMIDATION

<400> SEQUENCE: 205

Xaa Lys Trp Ile Gln Glu Tyr Leu Glu Lys Ala Leu Asn
1               5                   10

<210> SEQ ID NO 206
<211> LENGTH: 14
<212> TYPE: PRT
<213> ORGANISM: Artificial Sequence
<220> FEATURE:
<223> OTHER INFORMATION: portion of synthetic CXCR4 agonist
      SDF-1-derived cyclic acid (K20/E24)
<220> FEATURE:
<221> NAME/KEY: MISC_FEATURE
<222> LOCATION: (1)..(1)
<223> OTHER INFORMATION: Lys may be modified with a substituent that may
      be a hydrogen, alkyl, aryl or polyethylene glycol (PEG) moiety
<220> FEATURE:
<221> NAME/KEY: MISC_FEATURE
<222> LOCATION: (2)..(2)
<223> OTHER INFORMATION: Xaa = an amino acid that may be either an L-Pro
      or a D-Pro moiety
<220> FEATURE:
<221> NAME/KEY: MISC_FEATURE
<222> LOCATION: (5)..(5)
<223> OTHER INFORMATION: Xaa = an amino acid that may be either an L-Leu
      or a D-Leu moiety
<220> FEATURE:
<221> NAME/KEY: MOD_RES
<222> LOCATION: (14)..(14)
<223> OTHER INFORMATION: Xaa = Phe linked to Leu at position 1 of
      XKWIQEYLEKALN (SEQ ID NO:207) via a moiety providing covalent
      attachment between N and C terminal portions of the
      peptides, such as NH-2-(CH-2)-n-COOH (n = 0-20)

<400> SEQUENCE: 206

Lys Xaa Val Ser Xaa Ser Tyr Arg Cys Pro Cys Arg Phe Xaa
1               5                   10

<210> SEQ ID NO 207
<211> LENGTH: 13
<212> TYPE: PRT
<213> ORGANISM: Artificial Sequence
<220> FEATURE:
<223> OTHER INFORMATION: portion of synthetic CXCR4 agonist
      SDF-1-derived cyclic acid (K20/E24)
<220> FEATURE:
<221> NAME/KEY: MOD_RES
<222> LOCATION: (1)..(1)
<223> OTHER INFORMATION: Xaa = Leu linked to Phe at position 14 of
      KXVSXSYRCPCRFX (SEQ ID NO:206) via a moiety providing covalent
      attachment between N and C terminal portions of the
      peptides, such as NH-2-(CH-2)-n-COOH (n = 0-20)
<220> FEATURE:
<221> NAME/KEY: MISC_FEATURE
<222> LOCATION: (6)..(10)
<223> OTHER INFORMATION: side chain cyclized using lactam formation
<220> FEATURE:
<221> NAME/KEY: MOD_RES
<222> LOCATION: (13)..(13)
<223> OTHER INFORMATION: AMIDATION
```

```
<400> SEQUENCE: 207

Xaa Lys Trp Ile Gln Glu Tyr Leu Glu Lys Ala Leu Asn
1               5                   10

<210> SEQ ID NO 208
<211> LENGTH: 31
<212> TYPE: PRT
<213> ORGANISM: Artificial Sequence
<220> FEATURE:
<223> OTHER INFORMATION: synthetic CXCR4 agonist
<220> FEATURE:
<221> NAME/KEY: MISC_FEATURE
<222> LOCATION: (17)..(18)
<223> OTHER INFORMATION: Gly in positions 17 and/or 18 may be
      independently present or absent
<220> FEATURE:
<221> NAME/KEY: MISC_FEATURE
<222> LOCATION: (20)..(24)
<223> OTHER INFORMATION: side chain cyclized using lactam formation
<220> FEATURE:
<221> NAME/KEY: MOD_RES
<222> LOCATION: (31)..(31)
<223> OTHER INFORMATION: AMIDATION

<400> SEQUENCE: 208

Lys Pro Val Ser Leu Ser Tyr Arg Ala Pro Phe Arg Phe Gly Gly
1               5                   10                  15

Gly Gly Leu Lys Trp Ile Gln Glu Tyr Leu Glu Lys Ala Leu Asn
            20                  25                  30

<210> SEQ ID NO 209
<211> LENGTH: 14
<212> TYPE: PRT
<213> ORGANISM: Artificial Sequence
<220> FEATURE:
<223> OTHER INFORMATION: portion of synthetic CXCR4 agonist
<220> FEATURE:
<221> NAME/KEY: MOD_RES
<222> LOCATION: (14)..(14)
<223> OTHER INFORMATION: Xaa = Phe linked to Leu at position 1 of
      XKWIQEYLEKALN (SEQ ID NO:210) via a moiety providing covalent
      attachment between N and C terminal portions of the
      peptides, such as NH-2-(CH-2)-n-COOH (n = 0-20)

<400> SEQUENCE: 209

Lys Pro Val Ser Leu Ser Tyr Arg Ala Pro Phe Arg Phe Xaa
1               5                   10

<210> SEQ ID NO 210
<211> LENGTH: 13
<212> TYPE: PRT
<213> ORGANISM: Artificial Sequence
<220> FEATURE:
<223> OTHER INFORMATION: portion of synthetic CXCR4 agonist
<220> FEATURE:
<221> NAME/KEY: MOD_RES
<222> LOCATION: (1)..(1)
<223> OTHER INFORMATION: Xaa = Leu linked to Phe at position 14 of
      KPVSLSYRAPFRFX (SEQ ID NO:209) via a moiety providing covalent
      attachment between N and C terminal portions of the
      peptides, such as NH-2-(CH-2)-n-COOH (n = 0-20)
<220> FEATURE:
<221> NAME/KEY: MISC_FEATURE
<222> LOCATION: (2)..(6)
<223> OTHER INFORMATION: side chain cyclized using lactam formation
<220> FEATURE:
<221> NAME/KEY: MOD_RES
<222> LOCATION: (13)..(13)
<223> OTHER INFORMATION: AMIDATION

<400> SEQUENCE: 210
```

```
Xaa Lys Trp Ile Gln Glu Tyr Leu Glu Lys Ala Leu Asn
1               5                   10

<210> SEQ ID NO 211
<211> LENGTH: 4
<212> TYPE: PRT
<213> ORGANISM: Artificial Sequence
<220> FEATURE:
<223> OTHER INFORMATION: 4 glycine linking moiety, [linker]

<400> SEQUENCE: 211

Gly Gly Gly Gly
1

<210> SEQ ID NO 212
<211> LENGTH: 4
<212> TYPE: PRT
<213> ORGANISM: Artificial Sequence
<220> FEATURE:
<223> OTHER INFORMATION: three or four glycine linker
<220> FEATURE:
<221> NAME/KEY: MISC_FEATURE
<222> LOCATION: (4)..(4)
<223> OTHER INFORMATION: Gly in position 4 may be present or absent

<400> SEQUENCE: 212

Gly Gly Gly Gly
1

<210> SEQ ID NO 213
<211> LENGTH: 4
<212> TYPE: PRT
<213> ORGANISM: Artificial Sequence
<220> FEATURE:
<223> OTHER INFORMATION: G-1-4 linker
<220> FEATURE:
<221> NAME/KEY: MISC_FEATURE
<222> LOCATION: (2)..(4)
<223> OTHER INFORMATION: Gly in positions 2-4 may be present or absent

<400> SEQUENCE: 213

Gly Gly Gly Gly
1

<210> SEQ ID NO 214
<211> LENGTH: 4
<212> TYPE: PRT
<213> ORGANISM: Artificial Sequence
<220> FEATURE:
<223> OTHER INFORMATION: variable spacer monomer
<220> FEATURE:
<221> NAME/KEY: MISC_FEATURE
<222> LOCATION: (3)..(4)
<223> OTHER INFORMATION: Gly in positions 3-4 may be present or absent

<400> SEQUENCE: 214

Gly Gly Gly Gly
1
```